United States Patent
Kearney et al.

(10) Patent No.: US 10,802,027 B2
(45) Date of Patent: Oct. 13, 2020

(54) COMPOSITIONS, METHODS AND KITS FOR DIAGNOSIS OF LUNG CANCER

(71) Applicant: Biodesix, Inc., Boulder, CO (US)

(72) Inventors: Paul Edward Kearney, Seattle, WA (US); Kenneth Charles Fang, San Francisco, CA (US); Xiao-Jun Li, Bellevue, WA (US); Clive Hayward, Seattle, WA (US)

(73) Assignee: Biodesix, Inc., Boulder, CO (US)

( * ) Notice: Subject to any disclaimer, the term of this patent is extended or adjusted under 35 U.S.C. 154(b) by 0 days.

(21) Appl. No.: 15/587,767

(22) Filed: May 5, 2017

(65) Prior Publication Data
US 2018/0059113 A1 Mar. 1, 2018

Related U.S. Application Data

(60) Provisional application No. 62/332,054, filed on May 5, 2016, provisional application No. 62/430,853, filed on Dec. 6, 2016.

(51) Int. Cl.
| | | |
|---|---|---|
| *G01N 33/574* | (2006.01) | |
| *G01N 33/68* | (2006.01) | |
| *G16H 50/30* | (2018.01) | |
| *G06N 7/00* | (2006.01) | |
| *G16B 20/00* | (2019.01) | |
| *G16H 50/20* | (2018.01) | |
| *G16H 40/63* | (2018.01) | |
| *G06F 19/00* | (2018.01) | |

(52) U.S. Cl.
CPC ....... *G01N 33/57423* (2013.01); *G06N 7/005* (2013.01); *G16H 50/30* (2018.01); *G01N 33/6848* (2013.01); *G01N 2560/00* (2013.01); *G01N 2800/00* (2013.01); *G06F 19/321* (2013.01); *G16B 20/00* (2019.02); *G16H 40/63* (2018.01); *G16H 50/20* (2018.01)

(58) Field of Classification Search
CPC ......... G01N 33/57423; G01N 33/6843; G01N 2800/00
See application file for complete search history.

(56) References Cited

U.S. PATENT DOCUMENTS

| | | | | |
|---|---|---|---|---|
| 2010/0055689 A1* | 3/2010 | Spira | ............. | C12Q 1/6886 435/6.14 |
| 2012/0315641 A1* | 12/2012 | Dubinett | ............. | C12Q 1/6886 435/6.12 |
| 2013/0217057 A1* | 8/2013 | Kearney | ............. | G01N 33/57423 435/23 |
| 2015/0219666 A1 | 8/2015 | Li et al. | | |

FOREIGN PATENT DOCUMENTS

| WO | WO 2013/096845 A2 | 6/2013 |
|---|---|---|
| WO | WO-2015/042353 A1 | 3/2015 |
| WO | WO 2015/042454 A1 | 3/2015 |

OTHER PUBLICATIONS

Kearney P. et al. "An Integrated Risk Predictor for Pulmonary Nodules", bioRxiv, Dec. 17, 2016, pp. 1-17.
International Preliminary Report on Patentability for International Application No. PCT/US2017/031250 dated Nov. 6, 2018.
International Search Report and Written Opinion for International Application No. PCT/US2017/031250 dated Jul. 11, 2017.

* cited by examiner

*Primary Examiner* — Hong Sang
(74) *Attorney, Agent, or Firm* — Foley Hoag LLP

(57) ABSTRACT

Methods are provided for identifying biomarker proteins that exhibit differential expression in subjects with a first lung condition versus healthy subjects or subjects with a second lung condition. Also provided are compositions comprising these biomarker proteins and methods of using these biomarker proteins or panels thereof to diagnose, classify, and monitor various lung conditions. The methods and compositions provided herein may be used to diagnose or classify a subject as having lung cancer or a non-cancerous condition, and to distinguish between different types of cancer (e.g., malignant versus benign, SCLC versus NSCLC).

15 Claims, 41 Drawing Sheets
Specification includes a Sequence Listing.

COMPOSITIONS, METHODS AND KITS FOR DIAGNOSIS OF LUNG CANCER

RELATED APPLICATIONS

This application claims priority to and the benefit of U.S. Ser. No. 62/332,054, filed on May 5, 2016, and U.S. Ser. No. 62/430,853, filed on Dec. 6, 2016, the contents of each of which are incorporated herein by reference in their entireties.

INCORPORATION BY REFERENCE OF SEQUENCE LISTING

The contents of the text file named "IDIA-015-001WO-Seq-Listing.txt", which was created on Apr. 24, 2017 and is 1.51 KB in size, are hereby incorporated by reference in their entireties.

BACKGROUND OF THE INVENTION

Lung conditions and particularly lung cancer present significant diagnostic challenges. In many asymptomatic patients, radiological screens such as computed tomography (CT) scanning are a first step in the diagnostic paradigm. Pulmonary nodules (PNs) or indeterminate nodules are located in the lung and are often discovered during screening of both high risk patients or incidentally. The number of PNs identified is expected to rise due to increased numbers of patients with access to health care, the rapid adoption of screening techniques and an aging population. It is estimated that over 3 million PNs are identified annually in the US. Although the majority of PNs are benign, some are malignant leading to additional interventions. For patients considered low risk for malignant nodules, current medical practice dictates scans every three to six months for at least two years to monitor for lung cancer. The time period between identification of a PN and diagnosis is a time of medical surveillance or "watchful waiting" and may induce stress on the patient and lead to significant risk and expense due to repeated imaging studies. If a biopsy is performed on a patient who is found to have a benign nodule, the costs and potential for harm to the patient increase unnecessarily. Major surgery is indicated in order to excise a specimen for tissue biopsy and diagnosis. All of these procedures are associated with risk to the patient including: illness, injury and death as well as high economic costs.

Frequently, PNs cannot be biopsied to determine if they are benign or malignant due to their size and/or location in the lung. However, PNs are connected to the circulatory system, and so if malignant, protein markers of cancer can enter the blood and provide a signal for determining if a PN is malignant or not.

Diagnostic methods that can replace or complement current diagnostic methods for patients presenting with PNs are needed to improve diagnostics, reduce costs and minimize invasive procedures and complications to patients. The present invention provides novel compositions, methods and kits for identifying protein markers to identify, diagnose, classify and monitor lung conditions, and particularly lung cancer. The present invention uses a blood-based multiplexed assay to distinguish benign pulmonary nodules from malignant pulmonary nodules to classify patients with or without lung cancer. The present invention may be used in patients who present with symptoms of lung cancer, but do not have pulmonary nodules.

SUMMARY OF THE INVENTION

The certain aspects present invention provides a method of determining the likelihood that a lung condition in a subject is not cancer by measuring an abundance of a panel of proteins in a sample obtained from the subject; calculating a probability of cancer score based on the protein measurements and ruling out cancer for the subject if the score is lower than a pre-determined score. When cancer is ruled out, the subject does not receive a treatment protocol and undergoes periodic monitoring. Periodic monitoring can include for example pulmonary function test (PFT), pulmonary imaging, a biopsy or any combination thereof. In some embodiments, the imaging is an x-ray, a chest computed tomography (CT) scan, or a positron emission tomography (PET) scan.

In certain aspects the present invention provides a method of determining the likelihood that a pulmonary nodule in a subject is not lung cancer including contacting a blood sample obtained from the subject with a proteolytic enzyme to produce peptide fragments from a panel of proteins present in the blood sample, wherein the panel comprises two proteins selected from BGH3, C163A, LG3BP, GELS, IBP3, LUM, MASP1, PEDF, and S10A6; combining the produced peptide fragments from the panel with labeled, synthetic peptide fragments which correspond to the produced peptide fragments from the panel; performing selected reaction monitoring mass spectrometry to measure the abundance of the peptide fragments; calculating a probability of lung cancer score based on the peptide fragment measurements; and ruling out lung cancer for the subject if the score in step is lower than a pre-determined score.

In some aspects, the panel includes LG3BP and C163A. When lung cancer is ruled out, the subject is monitored periodically. In certain aspects, the subject has low to moderate cancer risk.

In further aspects, the method further includes a physician's assessment of cancer risk. In certain aspects the subject is assigned a physician's assessment of cancer risk from between 0 to 1.

In some aspects, the cancer risk is determined by a cancer risk predictor $C_i(k)$ which is determined as $$Ci(k) = \begin{cases} 0 & \text{if } pCA(k) \le Ti \\ pCA(k), & \text{otherwise} \end{cases}$$

where the decision threshold $T_i$ is the median value of $\{Si(k)\}$ of patients with nodules no larger than 15 mm.

In other aspects, the pulmonary nodule has a diameter of less than or equal to 3 cm. In some aspects, the pulmonary nodule has a diameter of about 0.8 cm to 3.0 cm.

In some aspects, the panel comprises LG3BP and C163A and the reversal ratio is 0.07. In some aspects, the panel comprises BGH3 and C163A and the reversal ratio is 0.06. In some aspects, the panel comprises LG3BP and GELS and the reversal ratio is 0.05. In some aspects, the panel comprises LG3BP and IBP3 and the reversal ratio is 0.07. In some aspects, the panel comprises LUM and C163A and the reversal ratio is 0.06. In some aspects, the panel comprises MASP1 and C163A and the reversal ratio is 0.07. In some aspects, the panel comprises MASP1 and IBP3 and the reversal ratio is 0.06. In some aspects, the panel comprises PEDF and C163A and the reversal ratio is 0.07. In some aspects, the panel comprises S10A6 and C163A and the reversal ratio is 0.06. In some aspects, the panel comprises S10A6 and ENPL and the reversal ratio is 0.06. In some aspects, the panel comprises LUM and GELS and the reversal ratio is 0.02.

The present invention is directed to the Xpresys Lung version 2 (XL2) blood test for use in identifying lung nodules that are likely benign so those nodules can safely avoid risky and costly invasive procedures such as biopsy and surgery. Although the majority of lung nodules detected annually are benign (75%-85%), 62% undergo an unnecessary biopsy and 35% undergo an unnecessary surgery, or both.

The key performance metric for XL2 is its negative predictive value (NPV) as XL2 is a cancer rule out test. The median NPV for XL2 is 98% (CI: 92%-100%) based on the prospective PANOPTIC study that spanned 33 sites and enrolled 685 subjects. The American College of Chest Physician's (ACCP) guidelines recommend a 95% NPV to observe a lung nodule over time.

Xpresys Lung version 2 (XL2) is superior to Xpresys Lung version 1 (XL1) in several ways, most notably:

XL2 was developed and validated on two large prospective studies; XL1 was developed and validated on two moderate-size retrospective studies.
  XL2 utilizes a subset of the XL1 protein biomarkers most accurate in identifying benign lung nodules.
  XL2 integrates protein biomarkers with five clinical factors previously validated (and endorsed by the ACCP Guidelines) as having utility for evaluating the cancer/benign status of a lung nodule.
  XL2 has statistically superior performance to PET. Specifically, in the PANOPTIC study, where XL2 and PET can be directly compared on the same subjects, the NPV of XL2 is 98% (CI: 92%-100%) whereas the NPV of PET is 79% (CI: 66%-88%). XL2 has statistically superior performance to the four most common clinical risk factor algorithms (Mayo, VA, Brock and Herder) where XL2 and the clinical risk factor algorithms are compared on the same subjects. XL2 has statistically superior performance to physicians where XL2 and physician cancer risk assessment are compared on the same subjects.

If XL2 were used in PANOPTIC then 36% of unnecessary invasive procedures (biopsies and/or surgeries) could have been avoided. XL2 has the potential to avoid over 36,000 surgeries, 1,600 hospitalizations, and almost 750 deaths per year. In addition, XL2 will add another safety factor to current practice. If XL2 were used in PANOPTIC then only 3% of malignant nodules would have been erroneously routed to CT surveillance. In comparison, 45% of patients with malignant lung nodules in the PANOPTIC trial intended use population were erroneously routed to CT surveillance (i.e. current practice).

In certain aspects the present invention also provides a method of determining the likelihood that a pulmonary nodule in a subject is lung cancer, comprising: contacting a blood sample obtained from the subject with a proteolytic enzyme to produce peptide fragments from a panel of proteins present in the blood sample, wherein the panel comprises two proteins selected from BGH3, C163A, LG3BP, GELS, IBP3, LUM, MASP1, PEDF, and S10A6; combining the produced peptide fragments from the panel with labeled, synthetic peptide fragments which correspond to the produced peptide fragments from the panel; performing selected reaction monitoring mass spectrometry to measure the abundance of the peptide fragments; calculating a probability of lung cancer score based on the peptide fragment measurements; and ruling in lung cancer for the subject if the score is equal to or higher than a predetermined score.

In some aspects, the panel includes LG3BP and C163A. When lung cancer is ruled in, the subject is monitored periodically. In certain aspects, the subject has low to moderate cancer risk.

In further aspects, the method further includes a physician's assessment of cancer risk. In certain aspects, the subject is assigned a physician's assessment of cancer risk from between 0 to 1.

In some aspects, the cancer risk is determined by a cancer risk predictor $C_i(k)$ which is determined as $$Ci(k) = \begin{cases} 0 & \text{if } pCA(k) \le Ti \\ pCA(k), & \text{otherwise} \end{cases}$$

where the decision threshold $T_i$ is the median value of $\{Si(k)\}$ of patients with nodules no larger than 15 mm.

Unless defined otherwise, all technical and scientific terms used herein have the same meaning as commonly understood by one of ordinary skill in the art to which this invention belongs. All patents and publications cited in this specification are incorporated by reference.

BRIEF DESCRIPTION OF THE DRAWINGS

FIG. 1A depicts bar graphs of pCA with all samples (n=422; 263 benign, 159 cancer); the cancer prevalence is 38%. KOL guidance may be to focus rule out test on low-to-moderate risk subjects (pCA<=50%). FIG. 1B depicts a bar graph with pCA with all samples at stage 1a (n=340; 224 benign, 116 cancer); the cancer prevalence is 34%.

DETAILED DESCRIPTION OF THE INVENTION

Figure 1A:
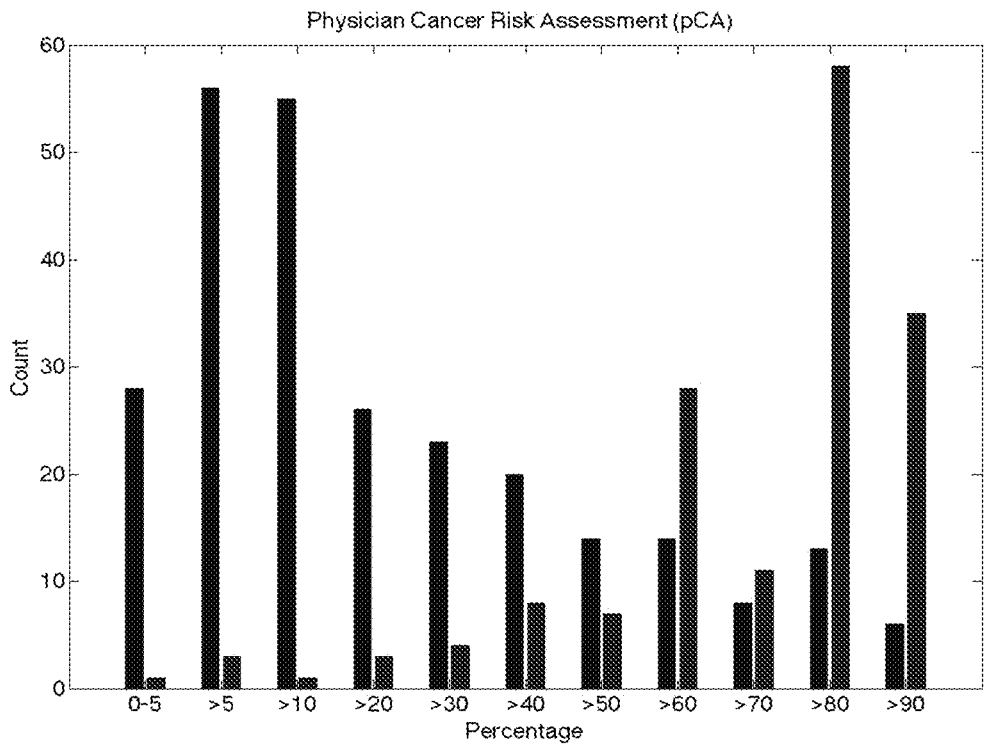
FIGS. 1A and 1B are a series of graphs that depict Physician Cancer Risk Assessment (pCA) of samples obtained from the prospective PANOPTIC study.
Figure 1A:
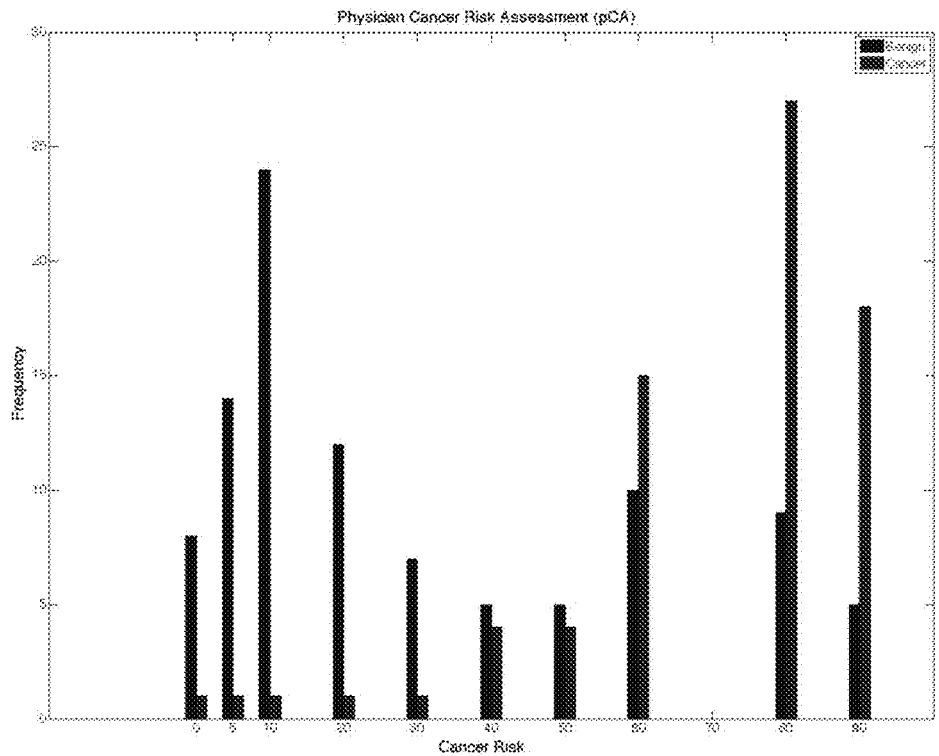

The disclosed invention derives from the surprising discovery, that in patients presenting with pulmonary nodule(s), protein markers in the blood exist that specifically identify and classify lung cancer. Accordingly the invention provides unique advantages to the patient associated with early detection of lung cancer in a patient, including increased life span, decreased morbidity and mortality, decreased exposure to radiation during screening and repeat screenings and a minimally invasive diagnostic model. Importantly, the methods of the invention allow for a patient to avoid invasive procedures.

The routine clinical use of chest computed tomography (CT) scans identifies millions of pulmonary nodules annually, of which only a small minority are malignant but contribute to the dismal 15% five-year survival rate for patients diagnosed with non-small cell lung cancer (NSCLC). The early diagnosis of lung cancer in patients with pulmonary nodules is a top priority, as decision-making based on clinical presentation, in conjunction with current non-invasive diagnostic options such as chest CT and positron emission tomography (PET) scans, and other invasive alternatives, has not altered the clinical outcomes of patients with Stage I NSCLC. The subgroup of pulmonary nodules between 8 mm and 20 mm in size is increasingly recognized as being "intermediate" relative to the lower rate of malignancies below 8 mm and the higher rate of malignancies above 20 mm [9]. Invasive sampling of the lung nodule by biopsy using transthoracic needle aspiration or bronchoscopy may provide a cytopathologic diagnosis of NSCLC, but are also associated with both false-negative and non-diagnostic results. In summary, a key unmet clinical need for the management of pulmonary nodules is a non-invasive diagnostic test that discriminates between malignant and benign processes in patients with indeterminate pulmonary nodules (IPNs), especially between 8 mm and 20 mm in size.

The clinical decision to be more or less aggressive in treatment is based on risk factors, primarily nodule size, smoking history and age [9] in addition to imaging. As these are not conclusive, there is a great need for a molecular-based blood test that would be both non-invasive and provide complementary information to risk factors and imaging.

Accordingly, these and related embodiments will find uses in screening methods for lung conditions, and particularly lung cancer diagnostics. More importantly, the invention finds use in determining the clinical management of a patient. That is, the method of invention is useful in ruling in or ruling out a particular treatment protocol for an individual subject.

Cancer biology requires a molecular strategy to address the unmet medical need for an assessment of lung cancer risk. The field of diagnostic medicine has evolved with technology and assays that provide sensitive mechanisms for detection of changes in proteins. The methods described herein use a LC-SRM-MS technology for measuring the concentration of blood plasma proteins that are collectively changed in patients with a malignant PN. This protein signature is indicative of lung cancer. LC-SRM-MS is one method that provides for both quantification and identification of circulating proteins in plasma. Changes in protein expression levels, such as but not limited to signaling factors, growth factors, cleaved surface proteins and secreted proteins, can be detected using such a sensitive technology to assay cancer. Presented herein is a blood-based classification test to determine the likelihood that a patient presenting with a pulmonary nodule has a nodule that is benign or malignant. The present invention presents a classification algorithm that predicts the relative likelihood of the PN being benign or malignant.

More broadly, it is demonstrated that there are many variations on this invention that are also diagnostic tests for the likelihood that a PN is benign or malignant. These are variations on the panel of proteins, protein standards, measurement methodology and/or classification algorithm.

As disclosed herein, a two-protein panel assay was developed based on a large prospective study of subjects presenting with pulmonary nodules.

Table A provides exemplary pairings for two-protein panels of the disclosure.

TABLE A

| Combinations of two proteins for use in ruling out lung cancer. | | | | | | | | |
|---|---|---|---|---|---|---|---|---|
| | BGH3 | C163A | LG3BP | GELS | IBP3 | LUM | MASP1 | PEDF | S10A6 |
| BGH3 | | | | | | | | | |
| C163A | 1 | | | | | | | | |
| LG3BP | 2 | 9 | | | | | | | |
| GELS | 3 | 10 | 11 | | | | | | |
| IBP3 | 4 | 12 | 13 | 14 | | | | | |
| LUM | 5 | 15 | 16 | 17 | 18 | | | | |
| MASP1 | 6 | 19 | 20 | 21 | 22 | 23 | | | |
| PEDF | 7 | 24 | 25 | 26 | 27 | 28 | 29 | | |
| S10A6 | 8 | 30 | 31 | 32 | 33 | 34 | 35 | 36 | |

Numbers in Table A represent distinct compositions of the disclosure that comprise two proteins for use in a method of determining the likelihood that a pulmonary module in a subject is not lung cancer. For example, composition #1 comprises genes BGH3 and C163A whereas composition #10 comprises genes C163A and GELS.

Preferred panels for ruling out cancer in a subject are presented in Table 1. In various other embodiments, the panels according to the invention include measuring at least 1, 2, 3, 4, 5, 6, 7, 8, 9, 10, 11, 12, 13, 14, 15 or more of the proteins listed on Table 1.

Table B provides exemplary combinations for multi-protein panels of the disclosure comprising one or more of BGH3, C163A, LG3BP, GELS, IBP3, LUM, MASP1, PEDF and S10A6.

TABLE B

Combinations of at least one protein for use in ruling out lung cancer.

| Combination | | BGH3 | C163A | LG3BP | GELS | IBP3 | LUM | MASP1 | PEDF | S10A6 |
|---|---|---|---|---|---|---|---|---|---|---|
| | 1 | X | | | | | | | | |
| | 2 | | X | | | | | | | |
| | 3 | | | X | | | | | | |
| | 4 | | | | X | | | | | |
| | 5 | | | | | X | | | | |
| | 6 | | | | | | X | | | |
| | 7 | | | | | | | X | | |
| | 8 | | | | | | | | X | |
| | 9 | | | | | | | | | X |
| | 10 | X | X | | | | | | | |
| | 11 | X | | X | | | | | | |
| | 12 | X | | | X | | | | | |
| | 13 | X | | | | X | | | | |
| | 14 | X | | | | | X | | | |
| | 15 | X | | | | | | X | | |
| | 16 | X | | | | | | | X | |
| | 17 | X | | | | | | | | X |
| | 18 | | X | X | | | | | | |
| | 19 | | X | | X | | | | | |
| | 20 | | X | | | X | | | | |
| | 21 | | X | | | | X | | | |
| | 22 | | X | | | | | X | | |
| | 23 | | X | | | | | | X | |
| | 24 | | X | | | | | | | X |
| | 25 | | | X | X | | | | | |
| | 26 | | | X | | X | | | | |
| | 27 | | | X | | | X | | | |
| | 28 | | | X | | | | X | | |
| | 29 | | | X | | | | | X | |
| | 30 | | | X | | | | | | X |
| | 31 | | | | X | X | | | | |
| | 32 | | | | X | | X | | | |
| | 33 | | | | X | | | X | | |
| | 34 | | | | X | | | | X | |
| | 35 | | | | X | | | | | X |
| | 36 | | | | | X | X | | | |
| | 37 | | | | | X | | X | | |
| | 38 | | | | | X | | | X | |
| | 39 | | | | | X | | | | X |
| | 40 | | | | | | X | X | | |
| | 41 | | | | | | X | | X | |
| | 42 | | | | | | X | | | X |
| | 43 | | | | | | | X | X | |
| | 44 | | | | | | | X | | X |
| | 45 | | | | | | | | X | X |
| | 46 | X | X | X | | | | | | |
| | 47 | X | X | | X | | | | | |
| | 48 | X | X | | | X | | | | |
| | 49 | X | X | | | | X | | | |
| | 50 | X | X | | | | | X | | |
| | 51 | X | X | | | | | | X | |
| | 52 | X | X | | | | | | | X |
| | 53 | X | | X | X | | | | | |
| | 54 | X | | X | | X | | | | |
| | 55 | X | | X | | | X | | | |
| | 56 | X | | X | | | | X | | |
| | 57 | X | | X | | | | | X | |
| | 58 | X | | X | | | | | | X |
| | 59 | X | | | X | X | | | | |
| | 60 | X | | | X | | X | | | |
| | 61 | X | | | X | | | X | | |
| | 62 | X | | | X | | | | X | |
| | 63 | X | | | X | | | | | X |
| | 64 | X | | | | X | X | | | |
| | 65 | X | | | | X | | X | | |
| | 66 | X | | | | X | | | X | |
| | 67 | X | | | | | X | X | | |
| | 68 | X | | | | | X | | X | |
| | 69 | X | | | | | | X | X | |
| | 70 | X | | | | | | X | | X |
| | 71 | X | | | | | | | X | X |

TABLE B-continued

Combinations of at least one protein for use in ruling out lung cancer.

| | BGH3 | C163A | LG3BP | GELS | IBP3 | LUM | MASP1 | PEDF | S10A6 |
|---|---|---|---|---|---|---|---|---|---|
| 72 | | X | X | X | | | | | |
| 73 | | X | X | | X | | | | |
| 74 | | X | X | | | X | | | |
| 75 | | X | X | | | | X | | |
| 76 | | X | X | | | | | X | |
| 77 | | X | X | | | | | | X |
| 78 | | X | | X | X | | | | |
| 79 | | X | | X | | X | | | |
| 80 | | X | | X | | | X | | |
| 81 | | X | | X | | | | X | |
| 82 | | X | | X | | | | | X |
| 83 | | X | | | X | X | | | |
| 84 | | X | | | X | | X | | |
| 85 | | X | | | X | | | X | |
| 86 | | X | | | X | | | | X |
| 87 | | X | | | | X | X | | |
| 88 | | X | | | | X | | X | |
| 89 | | X | | | | X | | | X |
| 90 | | X | | | | | X | X | |
| 91 | | X | | | | | X | | X |
| 92 | | X | | | | | | X | X |
| 93 | | | X | X | X | | | | |
| 94 | | | X | X | | X | | | |
| 95 | | | X | X | | | X | | |
| 96 | | | X | X | | | | X | |
| 97 | | | X | X | | | | | X |
| 98 | | | X | | X | X | | | |
| 99 | | | X | | X | | X | | |
| 100 | | | X | | X | | | X | |
| 101 | | | X | | X | | | | X |
| 102 | | | X | | | X | X | | |
| 103 | | | X | | | X | | X | |
| 104 | | | X | | | X | | | X |
| 105 | | | X | | | | X | X | |
| 106 | | | X | | | | X | | X |
| 107 | | | X | | | | | X | X |
| 108 | | | | X | X | X | | | |
| 109 | | | | X | X | | X | | |
| 110 | | | | X | X | | | X | |
| 111 | | | | X | X | | | | X |
| 112 | | | | X | | X | X | | |
| 113 | | | | X | | X | | X | |
| 114 | | | | X | | X | | | X |
| 115 | | | | X | | | X | X | |
| 116 | | | | X | | | X | | X |
| 117 | | | | X | | | | X | X |
| 118 | | | | | X | X | X | | |
| 119 | | | | | X | X | | X | |
| 120 | | | | | X | X | | | X |
| 121 | | | | | X | | X | X | |
| 122 | | | | | X | | X | | X |
| 123 | | | | | X | | | X | X |
| 124 | | | | | | X | X | X | |
| 125 | | | | | | X | X | | X |
| 126 | | | | | | X | | X | X |
| 127 | | | | | | | X | X | X |
| 128 | X | X | X | X | | | | | |
| 129 | X | X | X | | X | | | | |
| 130 | X | X | X | | | X | | | |
| 131 | X | X | X | | | | X | | |
| 132 | X | X | X | | | | | X | |
| 133 | X | X | X | | | | | | X |
| 134 | X | | X | X | X | | | | |
| 135 | X | | X | X | | X | | | |
| 136 | X | | X | X | | | X | | |
| 137 | X | | X | X | | | | X | |
| 138 | X | | X | X | | | | | X |
| 139 | X | | | X | X | X | | | |
| 140 | X | | | X | X | | X | | |
| 141 | X | | | X | X | | | X | |
| 142 | X | | | X | X | | | | X |
| 143 | X | | | | X | X | X | | |
| 144 | X | | | | X | X | | X | |
| 145 | X | | | | X | X | | | X |

TABLE B-continued

Combinations of at least one protein for use in ruling out lung cancer.

| | BGH3 | C163A | LG3BP | GELS | IBP3 | LUM | MASP1 | PEDF | S10A6 |
|---|---|---|---|---|---|---|---|---|---|
| 146 | X | | | | | X | X | X | |
| 147 | X | | | | | X | X | | X |
| 148 | X | | | | | | X | X | X |
| 149 | X | | X | | X | X | | | |
| 150 | X | | X | | X | | X | | |
| 151 | X | | X | | X | | | X | |
| 152 | X | | X | | X | | | | X |
| 153 | X | | X | | | X | X | | |
| 154 | X | | X | | | X | | X | |
| 155 | X | | X | | | X | | | X |
| 156 | X | | X | | | | X | X | |
| 157 | X | | X | | | | X | | X |
| 158 | X | | X | | | | | X | X |
| 159 | X | | | X | | X | X | | |
| 160 | X | | | X | | X | | X | |
| 161 | X | | | X | | X | | | X |
| 162 | X | | | X | | | X | X | |
| 163 | X | | | X | | | X | | X |
| 164 | X | | | X | | | | X | X |
| 165 | X | | | | X | | X | X | |
| 166 | X | | | | X | | X | | X |
| 167 | X | | | | X | | | X | X |
| 168 | X | | | | | X | | X | X |
| 169 | | X | X | X | X | | | | |
| 170 | | X | X | X | | X | | | |
| 171 | | X | X | X | | | X | | |
| 172 | | X | X | X | | | | X | |
| 173 | | X | X | X | | | | | X |
| 174 | | X | X | | X | X | | | |
| 175 | | X | X | | X | | X | | |
| 176 | | X | X | | X | | | X | |
| 177 | | X | X | | X | | | | X |
| 178 | | X | X | | | X | X | | |
| 179 | | X | X | | | X | | X | |
| 180 | | X | X | | | X | | | X |
| 181 | | X | | | | X | X | X | |
| 182 | | X | | | | X | X | | X |
| 183 | | X | | | | | X | X | X |
| 184 | | X | | X | | X | X | | |
| 185 | | X | | X | | X | | X | |
| 186 | | X | | X | | X | | | X |
| 187 | | X | | X | | | X | X | |
| 188 | | X | | X | | | X | | X |
| 189 | | X | | X | | | | X | X |
| 190 | | X | | | X | | X | X | |
| 191 | | X | | | X | | X | | X |
| 192 | | X | | | X | | | X | X |
| 193 | | X | | | | X | | X | X |
| 194 | | | X | X | X | X | | | |
| 195 | | | X | X | X | | X | | |
| 196 | | | X | X | X | | | X | |
| 197 | | | X | X | X | | | | X |
| 198 | | | X | X | | X | X | | |
| 199 | | | X | X | | X | | X | |
| 200 | | | X | X | | X | | | X |
| 201 | | | X | | | X | X | X | |
| 202 | | | X | | | X | X | | X |
| 203 | | | X | | | | X | X | X |
| 204 | | | X | | X | | X | X | |
| 205 | | | X | | X | | X | | X |
| 206 | | | X | | X | | | X | X |
| 207 | | | X | | | X | | X | X |
| 208 | | | | X | X | X | X | | |
| 209 | | | | X | X | X | | X | |
| 210 | | | | X | X | | | | X |
| 211 | | | | X | | X | X | X | |
| 212 | | | | X | | X | X | | X |
| 213 | | | | X | | | X | X | X |
| 214 | | | | | X | X | X | X | |
| 215 | | | | | X | X | X | | X |
| 216 | | | | | X | | X | X | X |
| 217 | | | | | | X | X | X | X |
| 218 | X | X | X | X | X | | | | |
| 219 | X | X | X | X | | X | | | |

TABLE B-continued

Combinations of at least one protein for use in ruling out lung cancer.

| | Gene | | | | | | | | |
|---|---|---|---|---|---|---|---|---|---|
| | BGH3 | C163A | LG3BP | GELS | IBP3 | LUM | MASP1 | PEDF | S10A6 |
| 220 | X | X | X | X | | | X | | |
| 221 | X | X | X | X | | | | X | |
| 222 | X | X | X | X | | | | | X |
| 223 | X | | X | X | X | X | | | |
| 224 | X | | X | X | X | | X | | |
| 225 | X | | X | X | X | | | X | |
| 226 | X | | X | X | X | | | | X |
| 227 | X | | | X | X | X | X | | |
| 228 | X | | | X | X | X | | X | |
| 229 | X | | | X | X | | | | X |
| 230 | X | | | X | | X | X | X | |
| 231 | X | | | | X | X | X | | X |
| 232 | X | | | | | X | X | X | X |
| 233 | X | | X | | X | X | X | | |
| 234 | X | | X | | X | X | | X | |
| 235 | X | | X | | X | X | | | X |
| 236 | X | | X | | | X | X | X | |
| 237 | X | | X | | | X | X | | X |
| 238 | X | | X | | | | X | X | X |
| 239 | X | | | X | | X | X | X | |
| 240 | X | | | X | | X | X | | X |
| 241 | X | | | | X | | X | X | X |
| 242 | | X | X | X | X | X | | | |
| 243 | | X | X | X | X | | X | | |
| 244 | | X | X | X | X | | | X | |
| 245 | | X | X | X | X | | | | X |
| 246 | | X | | X | X | X | X | | |
| 247 | | X | | X | X | X | | X | |
| 248 | | X | | X | X | X | | | X |
| 249 | | X | | | X | X | X | X | |
| 250 | | X | | X | | X | X | | X |
| 251 | | X | | | | X | X | X | X |
| 252 | | X | | X | | X | X | X | |
| 253 | | X | | X | | | X | X | X |
| 254 | | X | | | X | | X | X | X |
| 255 | | | X | X | X | X | X | | |
| 256 | | | X | X | X | X | | X | |
| 257 | | | X | X | X | X | | | X |
| 258 | | | X | X | | X | X | X | |
| 259 | | | X | X | | X | X | | X |
| 260 | | | X | | | X | X | X | X |
| 261 | | | X | | X | | X | X | X |
| 262 | | | X | | | X | X | X | X |
| 263 | | | | X | X | X | X | X | |
| 264 | | | | X | X | X | X | | X |
| 265 | | | | X | | X | X | X | X |
| 266 | | | | | X | X | X | X | X |
| 267 | X | X | X | X | X | X | | | |
| 268 | X | X | X | X | X | | X | | |
| 269 | X | X | X | X | X | | | X | |
| 270 | X | X | X | X | X | | | | X |
| 271 | X | | X | X | X | X | X | | |
| 272 | X | | X | X | X | X | | X | |
| 273 | X | | X | X | X | X | | | X |
| 274 | X | | | X | X | X | X | X | |
| 275 | X | | | X | X | X | X | | X |
| 276 | X | | X | | X | X | X | X | |
| 277 | X | | X | | | X | X | X | X |
| 278 | X | | | X | | X | X | X | X |
| 279 | | X | X | X | X | X | X | | |
| 280 | | X | X | X | X | X | | X | |
| 281 | | X | X | X | X | X | | | X |
| 282 | | X | | X | X | X | X | X | |
| 283 | | X | | X | X | X | X | | X |
| 284 | | X | | | X | X | X | X | X |
| 285 | | X | | X | | X | X | X | X |
| 286 | | | X | X | X | X | X | X | |
| 287 | | | X | X | X | X | X | | X |
| 288 | | | X | | X | X | X | X | X |
| 289 | | | | X | X | X | X | X | X |
| 290 | X | X | X | X | X | X | X | | |
| 291 | X | X | X | X | X | X | | X | |
| 292 | X | X | X | X | X | X | | | X |
| 293 | X | | X | X | X | X | X | X | |

TABLE B-continued

Combinations of at least one protein for use in ruling out lung cancer.

| | BGH3 | C163A | LG3BP | GELS | IBP3 | LUM | MASP1 | PEDF | S10A6 |
|---|---|---|---|---|---|---|---|---|---|
| 294 | X | | X | X | X | X | X | | X |
| 295 | | X | X | X | X | X | X | X | |
| 296 | | X | X | | X | X | X | | X |
| 297 | | X | | X | X | X | X | X | X |
| 298 | | | X | X | X | X | X | X | X |
| 299 | X | X | X | X | X | X | X | X | |
| 300 | | X | X | X | X | X | X | | X |
| 301 | X | | X | X | X | X | X | X | X |
| 302 | X | X | | X | X | X | X | X | X |
| 303 | X | X | X | | X | X | X | X | X |
| 304 | X | X | X | X | | X | X | X | X |
| 305 | X | X | X | X | X | | X | X | X |
| 306 | X | X | X | X | X | X | | X | X |
| 307 | X | X | X | X | X | X | X | | X |
| 308 | X | X | X | X | X | X | X | X | |
| 309 | X | X | X | X | X | X | X | X | X |

Numbers in Table B represent distinct compositions of the disclosure that comprise at least one protein selected from the group comprising BGH3, C163A, LG3BP, GELS, IBP3, LUM, MASP1, PEDF and S10A6, for use in a method of determining the likelihood that a pulmonary module in a subject is not lung cancer. For example, composition #1 comprises gene BGH3 whereas composition #309 comprises genes BGH3, C163A, LG3BP, GELS, IBP3, LUM, MASP1, PEDF and S10A6.

The term "pulmonary nodules" (PNs) refers to lung lesions that can be visualized by radiographic techniques. A pulmonary nodule is any nodules less than or equal to three centimeters in diameter. In one example a pulmonary nodule has a diameter of about 0.8 cm to 2 cm.

The term "masses" or "pulmonary masses" refers to lung nodules that are greater than three centimeters maximal diameter.

The term "blood biopsy" refers to a diagnostic study of the blood to determine whether a patient presenting with a nodule has a condition that may be classified as either benign or malignant.

The term "acceptance criteria" refers to the set of criteria to which an assay, test, diagnostic or product should conform to be considered acceptable for its intended use. As used herein, acceptance criteria are a list of tests, references to analytical procedures, and appropriate measures, which are defined for an assay or product that will be used in a diagnostic. For example, the acceptance criteria for the classifier refer to a set of predetermined ranges of coefficients.

The term "average maximal AUC" refers to the methodology of calculating performance. For the present invention, in the process of defining the set of proteins that should be in a panel by forward or backwards selection proteins are removed or added one at a time. A plot can be generated with performance (AUC or partial AUC score on the Y axis and proteins on the X axis) the point which maximizes performance indicates the number and set of proteins the gives the best result.

The term "partial AUC factor or pAUC factor" is greater than expected by random prediction. At sensitivity=0.90 the pAUC factor is the trapezoidal area under the ROC curve from 0.9 to 1.0 Specificity/(0.1*0.1/2).

The term "incremental information" refers to information that may be used with other diagnostic information to enhance diagnostic accuracy. Incremental information is independent of clinical factors such as including nodule size, age, or gender.

The term "score" or "scoring" refers to the refers to calculating a probability likelihood for a sample. For the present invention, values closer to 1.0 are used to represent the likelihood that a sample is cancer, values closer to 0.0 represent the likelihood that a sample is benign.

The term "robust" refers to a test or procedure that is not seriously disturbed by violations of the assumptions on which it is based. For the present invention, a robust test is a test wherein the proteins or transitions of the mass spectrometry chromatograms have been manually reviewed and are "generally" free of interfering signals The term "coefficients" refers to the weight assigned to each protein used to in the logistic regression equation to score a sample.

In certain embodiments of the invention, it is contemplated that in terms of the logistic regression model of MC CV, the model coefficient and the coefficient of variation (CV) of each protein's model coefficient may increase or decrease, dependent upon the method (or model) of measurement of the protein classifier. For each of the listed proteins in the panels, there is about, at least, at least about, or at most about a 2-, 3-, 4-, 5-, 6-, 7-, 8-, 9-, or 10-, -fold or any range derivable therein for each of the coefficient and CV. Alternatively, it is contemplated that quantitative embodiments of the invention may be discussed in terms of as about, at least, at least about, or at most about 10, 20, 30, 40, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% or more, or any range derivable therein.

The term "best team players" refers to the proteins that rank the best in the random panel selection algorithm, i.e., perform well on panels. When combined into a classifier these proteins can segregate cancer from benign samples. "Best team player" proteins is synonymous with "cooperative proteins". The term "cooperative proteins" refers proteins that appear more frequently on high performing panels of proteins than expected by chance. This gives rise to a protein's cooperative score which measures how (in)frequently it appears on high performing panels. For example, a protein with a cooperative score of 1.5 appears on high performing panels 1.5× more than would be expected by chance alone.

The term "classifying" as used herein with regard to a lung condition refers to the act of compiling and analyzing expression data for using statistical techniques to provide a classification to aid in diagnosis of a lung condition, particularly lung cancer.

The term "classifier" as used herein refers to an algorithm that discriminates between disease states with a predetermined level of statistical significance. A two-class classifier is an algorithm that uses data points from measurements from a sample and classifies the data into one of two groups. In certain embodiments, the data used in the classifier is the relative expression of proteins in a biological sample. Protein expression levels in a subject can be compared to levels in patients previously diagnosed as disease free or with a specified condition.

The "classifier" maximizes the probability of distinguishing a randomly selected cancer sample from a randomly selected benign sample, i.e., the AUC of ROC curve.

In addition to the classifier's constituent proteins with differential expression, it may also include proteins with minimal or no biologic variation to enable assessment of variability, or the lack thereof, within or between clinical specimens; these proteins may be termed endogenous proteins and serve as internal controls for the other classifier proteins.

The term "normalization" or "normalizer" as used herein refers to the expression of a differential value in terms of a standard value to adjust for effects which arise from technical variation due to sample handling, sample preparation and mass spectrometry measurement rather than biological variation of protein concentration in a sample. For example, when measuring the expression of a differentially expressed protein, the absolute value for the expression of the protein can be expressed in terms of an absolute value for the expression of a standard protein that is substantially constant in expression. This prevents the technical variation of sample preparation and mass spectrometry measurement from impeding the measurement of protein concentration levels in the sample.

The term "condition" as used herein refers generally to a disease, event, or change in health status.

The term "treatment protocol" as used herein including further diagnostic testing typically performed to determine whether a pulmonary nodule is benign or malignant. Treatment protocols include diagnostic tests typically used to diagnose pulmonary nodules or masses such as for example, CT scan, positron emission tomography (PET) scan, bronchoscopy or tissue biopsy. Treatment protocol as used herein is also meant to include therapeutic treatments typically used to treat malignant pulmonary nodules and/or lung cancer such as for example, chemotherapy, radiation or surgery.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore the term diagnosis includes: a. prediction (determining if a patient will likely develop a hyperproliferative disease) b. prognosis (predicting whether a patient will likely have a better or worse outcome at a pre-selected time in the future) c. therapy selection d. therapeutic drug monitoring e. relapse monitoring.

The American Lung Cancer Society provides the following lung cancer staging definitions. In stage T0, there is no evidence of primary tumor. In stage Tis, there is carcinoma in situ. Stage T1 denotes tumors of 3 cm or less. Stage T1a denotes tumors having 2 cm or less. Stage T1b denotes a tumor having a dimension of more than 2 cm but less than 3 cm. Stage T2 denotes tumors of having dimensions of more than 3 cm but 7 cm or less. Stage T2a denotes tumors having dimensions of more than 3 cm but 5 cm or less. Stage T2b denotes tumors having more than 5 cm in dimension but being 7 cm or less. Stage T3 denotes tumors that are more than 7 cm or those tumors that invades the chest wall, phrenic nerve, diaphragm, parietal pleura, parietal pericardium or mediastinal pleura; or a tumor in the main bronchus that is less than 2 cm. Stage T4 denotes tumors that invades any of: heart, esophagus, mediastinum, trachea, recurrent laryngeal nerve, carina, vertebral body, or a separate tumor nodule in a different ipsilateral lobe.

In some embodiments, for example, classification of a biological sample as being derived from a subject with a lung condition may refer to the results and related reports generated by a laboratory, while diagnosis may refer to the act of a medical professional in using the classification to identify or verify the lung condition.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

As used herein, "lung cancer" preferably refers to cancers of the lung, but may include any disease or other disorder of the respiratory system of a human or other mammal. Respiratory neoplastic disorders include, for example small cell carcinoma or small cell lung cancer (SCLC), non-small cell carcinoma or non-small cell lung cancer (NSCLC), squamous cell carcinoma, adenocarcinoma, broncho-alveolar carcinoma, mixed pulmonary carcinoma, malignant pleural mesothelioma, undifferentiated large cell carcinoma, giant cell carcinoma, synchronous tumors, large cell neuroendocrine carcinoma, adenosquamous carcinoma, undifferentiated carcinoma; and small cell carcinoma, including oat cell cancer, mixed small cell/large cell carcinoma, and combined small cell carcinoma; as well as adenoid cystic carcinoma, hamartomas, mucoepidermoid tumors, typical carcinoid lung tumors, atypical carcinoid lung tumors, peripheral carcinoid lung tumors, central carcinoid lung tumors, pleural mesotheliomas, and undifferentiated pulmonary carcinoma and cancers that originate outside the lungs such as secondary cancers that have metastasized to the lungs from other parts of the body. Lung cancers may be of any stage or grade. Preferably the term may be used to refer collectively to any dysplasia, hyperplasia, neoplasia, or metastasis in which the protein biomarkers expressed above normal levels as may be determined, for example, by comparison to adjacent healthy tissue.

Examples of non-cancerous lung condition include chronic obstructive pulmonary disease (COPD), benign tumors or masses of cells (e.g., hamartoma, fibroma, neurofibroma), granuloma, sarcoidosis, and infections caused by bacterial (e.g., tuberculosis) or fungal (e.g. histoplasmosis) pathogens. In certain embodiments, a lung condition may be associated with the appearance of radiographic PNs.

As used herein, "lung tissue", and "lung cancer" refer to tissue or cancer, respectively, of the lungs themselves, as well as the tissue adjacent to and/or within the strata underlying the lungs and supporting structures such as the pleura, intercostal muscles, ribs, and other elements of the respiratory system. The respiratory system itself is taken in this context as representing nasal cavity, sinuses, pharynx, larynx, trachea, bronchi, lungs, lung lobes, aveoli, aveolar ducts, aveolar sacs, aveolar capillaries, bronchioles, respiratory bronchioles, visceral pleura, parietal pleura, pleural cavity, diaphragm, epiglottis, adenoids, tonsils, mouth and tongue, and the like. The tissue or cancer may be from a mammal and is preferably from a human, although monkeys, apes, cats, dogs, cows, horses and rabbits are within the scope of the present invention. The term "lung condition" as used herein refers to a disease, event, or change in health status relating to the lung, including for example lung cancer and various non-cancerous conditions.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarker proteins. Examples of biological samples include tissue, organs, or bodily fluids such as whole blood, plasma, serum, tissue, lavage or any other specimen used for detection of disease.

The term "subject" as used herein refers to a mammal, preferably a human.

The term "biomarker protein" as used herein refers to a polypeptide in a biological sample from a subject with a lung condition versus a biological sample from a control subject. A biomarker protein includes not only the polypeptide itself, but also minor variations thereof, including for example one or more amino acid substitutions or modifications such as glycosylation or phosphorylation.

The term "biomarker protein panel" as used herein refers to a plurality of biomarker proteins. In certain embodiments, the expression levels of the proteins in the panels can be correlated with the existence of a lung condition in a subject. In certain embodiments, biomarker protein panels comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 proteins. In certain embodiments, the biomarker proteins panels comprise from 100-125 proteins, 125-150 proteins, 150-200 proteins or more.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

The term "ruling out" as used herein is meant that the subject is selected not to receive a treatment protocol.

The term "ruling-in" as used herein is meant that the subject is selected to receive a treatment protocol.

Biomarker levels may change due to treatment of the disease. The changes in biomarker levels may be measured by the present invention. Changes in biomarker levels may be used to monitor the progression of disease or therapy.

"Altered", "changed" or "significantly different" refer to a detectable change or difference from a reasonably comparable state, profile, measurement, or the like. One skilled in the art should be able to determine a reasonable measurable change. Such changes may be all or none. They may be incremental and need not be linear. They may be by orders of magnitude. A change may be an increase or decrease by 1%, 5%, 10%, 20%, 30%, 40%, 50%, 60%, 70%, 80%, 90%, 95%, 99%, 100%, or more, or any value in between 0% and 100%. Alternatively the change may be 1-fold, 1.5-fold 2-fold, 3-fold, 4-fold, 5-fold or more, or any values in between 1-fold and five-fold. The change may be statistically significant with a p value of 0.1, 0.05, 0.001, or 0.0001.

Using the methods of the current invention, a clinical assessment of a patient is first performed. If there exists is a higher likelihood for cancer, the clinician may rule in the disease which will require the pursuit of diagnostic testing options yielding data which increase and/or substantiate the likelihood of the diagnosis. "Rule in" of a disease requires a test with a high specificity.

"FN" is false negative, which for a disease state test means classifying a disease subject incorrectly as non-disease or normal.

"FP" is false positive, which for a disease state test means classifying a normal subject incorrectly as having disease.

The term "rule in" refers to a diagnostic test with high specificity that coupled with a clinical assessment indicates a higher likelihood for cancer. If the clinical assessment is a lower likelihood for cancer, the clinician may adopt a stance to rule out the disease, which will require diagnostic tests which yield data that decrease the likelihood of the diagnosis. "Rule out" requires a test with a high sensitivity.

The term "rule out" refers to a diagnostic test with high sensitivity that coupled with a clinical assessment indicates a lower likelihood for cancer.

The term "sensitivity of a test" refers to the probability that a patient with the disease will have a positive test result. This is derived from the number of patients with the disease who have a positive test result (true positive) divided by the total number of patients with the disease, including those with true positive results and those patients with the disease who have a negative result, i.e. false negative.

The term "specificity of a test" refers to the probability that a patient without the disease will have a negative test result. This is derived from the number of patients without the disease who have a negative test result (true negative) divided by all patients without the disease, including those with a true negative result and those patients without the disease who have a positive test result, e.g. false positive. While the sensitivity, specificity, true or false positive rate, and true or false negative rate of a test provide an indication of a test's performance, e.g. relative to other tests, to make a clinical decision for an individual patient based on the test's result, the clinician requires performance parameters of the test with respect to a given population.

The term "positive predictive value" (PPV) refers to the probability that a positive result correctly identifies a patient who has the disease, which is the number of true positives divided by the sum of true positives and false positives.

The term "negative predictive value" or "NPV" is calculated by TN/(TN+FN) or the true negative fraction of all negative test results. It also is inherently impacted by the prevalence of the disease and pre-test probability of the population intended to be tested.

The term "disease prevalence" refers to the number of all new and old cases of a disease or occurrences of an event during a particular period. Prevalence is expressed as a ratio in which the number of events is the numerator and the population at risk is the denominator.

The term disease incidence refers to a measure of the risk of developing some new condition within a specified period of time; the number of new cases during some time period, it is better expressed as a proportion or a rate with a denominator.

Lung cancer risk according to the "National Lung Screening Trial" is classified by age and smoking history. High risk—age≥55 and ≥30 pack-years smoking history; Moderate risk—age≥50 and ≥20 pack-years smoking history; Low risk—<age 50 or <20 pack-years smoking history.

The term "negative predictive value" (NPV) refers to the probability that a negative test correctly identifies a patient without the disease, which is the number of true negatives divided by the sum of true negatives and false negatives. A positive result from a test with a sufficient PPV can be used to rule in the disease for a patient, while a negative result from a test with a sufficient NPV can be used to rule out the disease, if the disease prevalence for the given population, of which the patient can be considered a part, is known.

The clinician must decide on using a diagnostic test based on its intrinsic performance parameters, including sensitivity and specificity, and on its extrinsic performance parameters, such as positive predictive value and negative predictive value, which depend upon the disease's prevalence in a given population.

Additional parameters which may influence clinical assessment of disease likelihood include the prior frequency and closeness of a patient to a known agent, e.g. exposure risk, that directly or indirectly is associated with disease causation, e.g. second hand smoke, radiation, etc., and also the radiographic appearance or characterization of the pulmonary nodule exclusive of size. A nodule's description may include solid, semi-solid or ground glass which characterizes it based on the spectrum of relative gray scale density employed by the CT scan technology.

"Mass spectrometry" refers to a method comprising employing an ionization source to generate gas phase ions from an analyte presented on a sample presenting surface of a probe and detecting the gas phase ions with a mass spectrometer.

The technology liquid chromatography selected reaction monitoring mass spectrometry (LC-SRM-MS) was used to assay the expression levels of select protein panels in which the proteins were found in the blood. Candidate proteins are listed in Table 1.

TABLE 1

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| 1433B_HUMAN | 14-3-3 protein beta/alpha | YWHAB | Secreted, EPI | LungCancers | Cytoplasm. Melanosome. Note = Identified by mass spectrometry in melanosome fractions from stage I to stage IV. | Literature, Detection |
| 1433E_HUMAN | 14-3-3 protein epsilon | YWHAE | ENDO | LungCancers, Benign-Nodules | Cytoplasm (By similarity). Melanosome. Note = Identified by mass spectrometry in melanosome fractions from stage I to stage IV. | Literature, Detection |
| 1433S_HUMAN | 14-3-3 protein sigma | SFN | Secreted, EPI | LungCancers | Cytoplasm. Nucleus (By similarity). Secreted. Note = May be secreted by a non-classical secretory pathway. | UniProt, Literature, Detection |
| 1433T_HUMAN | 14-3-3 protein theta | YWHAQ | EPI | LungCancers, Benign-Nodules | Cytoplasm. Note = In neurons, axonally transported to the nerve terminals. | Detection |
| 1433Z_HUMAN | 14-3-3 protein zeta/delta | YWHAZ | EPI | LungCancers, Benign-Nodules | Cytoplasm. Melanosome. Note = Located to stage I to stage IV melanosomes. | Detection |
| 6PGD_HUMAN | 6-phosphogluconate dehydrogenase, decarboxylating | PGD | EPI, ENDO | | Cytoplasm (By similarity). | Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| A1AG1_HUMAN | Alpha-1-acid glycoprotein 1 | ORM1 | EPI | Symptoms | Secreted. | UniProt, Literature, Detection, Prediction |
| ABCD1_HUMAN | ATP-binding cassette sub-family D member 1 | ABCD1 | ENDO | | Peroxisome membrane; Multi-pass membrane protein. | Detection, Prediction |
| ADA12_HUMAN | Disintegrin and metalloproteinase domain-containing protein 12 | ADAM12 | | LungCancers, Benign-Nodules, Symptoms | Isoform 1: Cell membrane; Single-pass type I membrane protein. \|Isoform 2: Secreted. \|Isoform 3: Secreted (Potential). \|Isoform 4: Secreted (Potential). | UniProt, Detection, Prediction |
| ADML_HUMAN | ADM | ADM | | LungCancers, Benign-Nodules, Symptoms | Secreted. | UniProt, Literature, Detection, Prediction |
| AGR2_HUMAN | Anterior gradient protein 2 homolog | AGR2 | EPI | LungCancers | Secreted. Endoplasmic reticulum (By similarity). | UniProt, Prediction |
| AIFM1_HUMAN | Apoptosis-inducing factor 1, mitochondrial | AIFM1 | EPI, ENDO | LungCancers | Mitochondrion inter-membrane space. Nucleus. Note = Translocated to the nucleus upon induction of apoptosis. | Detection, Prediction |
| ALDOA_HUMAN | Fructose-bisphosphate aldolase A | ALDOA | Secreted, EPI | LungCancers, Symptoms | | Literature, Detection |
| AMPN_HUMAN | Aminopeptidase N | ANPEP | EPI, ENDO | LungCancers, Benign-Nodules, Symptoms | Cell membrane; Single-pass type II membrane protein. Cytoplasm, cytosol (Potential). Note = A soluble form has also been detected. | UniProt, Detection |
| ANGP1_HUMAN | Angiopoietin-1 | ANGPT1 | | LungCancers, Benign-Nodules | Secreted. | UniProt, Literature, Prediction |
| ANGP2_HUMAN | Angiopoietin-2 | ANGPT2 | | LungCancers, Benign-Nodules | Secreted. | UniProt, Literature, Prediction |
| APOA1_HUMAN | Apolipoprotein A-I | APOA1 | | LungCancers, Benign-Nodules, Symptoms | Secreted. | UniProt, Literature, Detection, Prediction |
| APOE_HUMAN | Apolipoprotein E | APOE | EPI, ENDO | LungCancers, Benign-Nodules, Symptoms | Secreted. | UniProt, Literature, Detection, Prediction |
| ASM3B_HUMAN | Acid sphingomyelinase-like phosphodiesterase 3b | SMPDL3B | EPI, ENDO | | Secreted (By similarity). | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| AT2A2_HUMAN | Sarcoplasmic/ endoplasmic reticulum calcium ATPase 2 | ATP2A2 | EPI, ENDO | LungCancers, Benign-Nodules | Endoplasmic reticulum membrane; Multi-pass membrane protein. Sarcoplasmic reticulum membrane; Multi-pass membrane protein. | Detection |
| ATS1_HUMAN | A disintegrin and metallo-proteinase with thrombospondin motifs 1 | ADAMTS1 | | LungCancers, Benign-Nodules, Symptoms | Secreted, extracellular space, extra-cellular matrix (By similarity). | UniProt, Literature, Prediction |
| ATS12_HUMAN | A disintegrin and metallo-proteinase with thrombospondin motifs 12 | ADAMTS12 | | LungCancers | Secreted, extracellular space, extra-cellular matrix (By similarity). | UniProt, Detection, Prediction |
| ATS19_HUMAN | A disintegrin and metallo-proteinase with thrombospondin motifs 19 | ADAMTS19 | | LungCancers | Secreted, extracellular space, extra-cellular matrix (By similarity). | UniProt, Prediction |
| BAGE1_HUMAN | B melanoma antigen 1 | BAGE | | LungCancers | Secreted (Potential). | UniProt, Prediction |
| BAGE2_HUMAN | B melanoma antigen 2 | BAGE2 | | LungCancers | Secreted (Potential). | UniProt, Prediction |
| BAGE3_HUMAN | B melanoma antigen 3 | BAGE3 | | LungCancers | Secreted (Potential). | UniProt, Prediction |
| BAGE4_HUMAN | B melanoma antigen 4 | BAGE4 | | LungCancers | Secreted (Potential). | UniProt, Prediction |
| BAGE5_HUMAN | B melanoma antigen 5 | BAGE5 | | LungCancers | Secreted (Potential). | UniProt, Prediction |
| BASP1_HUMAN | Brain acid soluble protein 1 | BASP1 | Secreted, EPI | | Cell membrane; Lipid-anchor. Cell projection, growth cone. Note = Associated with the membranes of growth cones that form the tips of elongating axons. | Detection |
| BAX_HUMAN | Apoptosis regulator BAX | BAX | EPI | LungCancers, Benign-Nodules | Isoform Alpha: Mitochondrion membrane; Single-pass membrane protein. Cytoplasm. Note = Colocalizes with 14-3-3 proteins in the cytoplasm. Under stress conditions, redistributes to the mitochondrion membrane through the release from | UniProt, Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | JNK-phosphorylated 14-3-3 proteins. \|Isoform Beta: Cytoplasm. \|Isoform Gamma: Cytoplasm. \|Isoform Delta: Cytoplasm (Potential). | |
| BDNF_HUMAN | Brain-derived neurotrophic factor | BDNF | | Benign-Nodules, Symptoms | Secreted. | UniProt, Literature, Prediction |
| BGH3_HUMAN | Transforming growth factor-beta-induced protein igh3 | TGFBI | | LungCancers, Benign-Nodules | Secreted, extracellular space, extra-cellular matrix. Note = May be associated both with microfibrils and with the cell surface. | UniProt, Detection |
| BMP2_HUMAN | Bone morphogenetic protein 2 | BMP2 | | LungCancers, Benign-Nodules, Symptoms | Secreted. | UniProt, Literature |
| BST1_HUMAN | ADP-ribosyl cyclase 2 | BST1 | EPI | Symptoms | Cell membrane; Lipid-anchor, GPI-anchor. | Detection, Prediction |
| C163A_HUMAN | Scavenger receptor cysteine-rich type 1 protein M130 | CD163 | EPI | Symptoms | Soluble CD163: Secreted. \|Cell membrane; Single-pass type I membrane protein. Note = Isoform 1 and isoform 2 show a lower surface expression when expressed in cells. | UniProt, Detection |
| C4BPA_HUMAN | C4b-binding protein alpha chain | C4BPA | | LungCancers, Symptoms | Secreted. | UniProt, Detection, Prediction |
| CAH9_HUMAN | Carbonic anhydrase 9 | CA9 | | LungCancers, Benign-Nodules, Symptoms | Nucleus. Nucleus, nucleolus. Cell membrane; Single-pass type I membrane protein. Cell projection, microvillus membrane; Single-pass type I membrane protein. Note = Found on the surface micro-villi and in the nucleus, | UniProt |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CALR_HUMAN | Calreticulin | CALR | EPI | Symptoms | particularly in nucleolus. Endoplasmic reticulum lumen. Cytoplasm, cytosol. Secreted, extracellular space, extracellular matrix. Cell surface. Note = Also found in cell surface (T cells), cytosol and extracellular matrix. Associated with the lytic granules in the cytolytic T-lymphocytes. | UniProt, Literature, Detection, Prediction |
| CALU_HUMAN | Calumenin | CALU | EPI | Symptoms | Endoplasmic reticulum lumen. Secreted. Melanosome. Sarcoplasmic reticulum lumen (By similarity). Note = Identified by mass spectrometry in melanosome fractions from stage I to stage IV. | UniProt, Detection, Prediction |
| CALX_HUMAN | Calnexin | CANX | Secreted, EPI, ENDO | Benign-Nodules | Endoplasmic reticulum membrane; Single-pass type I membrane protein. Melanosome. Note = Identified by mass spectrometry in melanosome fractions from stage I to stage IV. | UniProt, Literature, Detection |
| CAP7_HUMAN | Azurocidin | AZU1 | EPI | Symptoms | Cytoplasmic granule. Note = Cytoplasmic granules of neutrophils. | Prediction |
| CATB_HUMAN | Cathepsin B | CTSB | Secreted | LungCancers | Lysosome. Melanosome. Note = Identified by mass spectrometry in melanosome fractions from stage I to stage IV. | Literature, Detection, Prediction |
| CATG_HUMAN | Cathepsin G | CTSG | Secreted, ENDO | Benign-Nodules | Cell surface. | Detection, Prediction |
| CBPB2_HUMAN | Carboxypeptidase B2 | CPB2 | | LungCancers, Benign-Nodules, Symptoms | Secreted. | UniProt, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CCL22_HUMAN | C-C motif chemokine 22 | CCL22 | | LungCancers, Benign-Nodules | Secreted. | UniProt, Prediction |
| CD14_HUMAN | Monocyte differentiation antigen CD14 | CD14 | EPI | LungCancers, Benign-Nodules, Symptoms | Cell membrane; Lipid-anchor, GPI-anchor. | Literature, Detection, Prediction |
| CD24_HUMAN | Signal transducer CD24 | CD24 | | LungCancers, Benign-Nodules | Cell membrane; Lipid-anchor, GPI-anchor. | Literature |
| CD2A2_HUMAN | Cyclin-dependent kinase inhibitor 2A, isoform 4 | CDKN2A | | LungCancers, Benign-Nodules | Cytoplasm. Nucleus. \|Nucleus, nucleolus (By similarity). | Literature, Prediction |
| CD38_HUMAN | ADP-ribosyl cyclase 1 | CD38 | EPI, ENDO | Symptoms | Membrane; Single-pass type II membrane protein. | UniProt, Literature |
| CD40L_HUMAN | CD40 ligand | CD40LG | | LungCancers, Benign-Nodules, Symptoms | Cell membrane; Single-pass type II membrane protein. \|CD40 ligand, soluble form: Secreted. | UniProt, Literature |
| CD44_HUMAN | CD44 antigen | CD44 | EPI | LungCancers, Benign-Nodules, Symptoms | Membrane; Single-pass type I membrane protein. | UniProt, Literature, Detection, Prediction |
| CD59_HUMAN | CD59 glycoprotein | CD59 | | LungCancers, Benign-Nodules, Symptoms | Cell membrane; Lipid-anchor, GPI-anchor. Secreted. Note = Soluble form found in a number of tissues. | UniProt, Literature, Detection, Prediction |
| CD97_HUMAN | CD97 antigen | CD97 | EPI, ENDO | Symptoms | Cell membrane; Multi-pass membrane protein. \|CD97 antigen sub-unit alpha: Secreted, extracellular space. | UniProt |
| CDCP1_HUMAN | CUB domain-containing protein 1 | CDCP1 | | LungCancers | Isoform 1: Cell membrane; Single-pass membrane protein (Potential). Note = Shedding may also lead to a soluble peptide. \|Isoform 3: Secreted. | UniProt, Prediction |
| CDK4_HUMAN | Cell division protein kinase 4 | CDK4 | | LungCancers, Symptoms | | Literature |
| CEAM5_HUMAN | Carcinoembryonic antigen-related cell adhesion molecule 5 | CEA-CAM5 | EPI | LungCancers, Benign-Nodules, Symptoms | Cell membrane; Lipid-anchor, GPI-anchor. | Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CEAM8_HUMAN | Carcinoembryonic antigen-related cell adhesion molecule 8 | CEA-CAM8 | EPI | LungCancers | Cell membrane; Lipid-anchor, GPI-anchor. | Detection, Prediction |
| CERU_HUMAN | Ceruloplasmin | CP | EPI | LungCancers, Symptoms | Secreted. | UniProt, Literature, Detection, Prediction |
| CH10_HUMAN | 10 kDa heat shock protein, mitochondrial | HSPE1 | ENDO | LungCancers | Mitochondrion matrix. | Literature, Detection, Prediction |
| CH60_HUMAN | 60 kDa heat shock protein, mitochondrial | HSPD1 | Secreted, EPI, ENDO | LungCancers, Symptoms | Mitochondrion matrix. | Literature, Detection |
| CKAP4_HUMAN | Cytoskeleton-associated protein 4 | CKAP4 | EPI, ENDO | LungCancers | Endoplasmic reticulum-Golgi intermediate compartment membrane; Single-pass membrane protein (Potential). | UniProt |
| CL041_HUMAN | Uncharacterized protein C12orf41 | C12orf41 | ENDO | | | Prediction |
| CLCA1_HUMAN | Calcium-activated chloride channel regulator 1 | CLCA1 | | LungCancers, Benign-Nodules | Secreted, extracellular space. Cell membrane; Peripheral membrane protein; Extracellular side. Note = Protein that remains attached to the plasma membrane appeared to be predominantly localized to microvilli. | UniProt, Prediction |
| CLIC1_HUMAN | Chloride intracellular channel protein 1 | CLIC1 | EPI | | Nucleus. Nucleus membrane; Single-pass membrane protein (Probable). Cytoplasm. Cell membrane; Single-pass membrane protein (Probable). Note = Mostly in the nucleus including in the nuclear membrane. Small amount in the cytoplasm and the plasma membrane. Exists both as soluble cytoplasmic | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | protein and as membrane protein with probably a single transmembrane domain. | |
| CLUS_HUMAN | Clusterin | CLU | EPI, ENDO | LungCancers, Benign-Nodules, Symptoms | Secreted. | UniProt, Literature, Detection, Prediction |
| CMGA_HUMAN | Chromogranin-A | CHGA | | LungCancers, Benign-Nodules | Secreted. Note = Neuro endocrine and endocrine secretory granules. | UniProt, Literature, Detection, Prediction |
| CNTN1_HUMAN | Contactin-1 | CNTN1 | | LungCancers | Isoform 1: Cell membrane; Lipid-anchor, GPI-anchor; Extracellular side.\|Isoform 2: Cell membrane; Lipid-anchor, GPI-anchor; Extracellular side. | Detection, Prediction |
| CO4A1_HUMAN | Collagen alpha-1(IV) chain | COL4A1 | | LungCancers | Secreted, extracellular space, extra-cellular matrix, basement membrane. | UniProt, Detection, Prediction |
| CO5A2_HUMAN | Collagen alpha-2(V) chain | COL5A2 | | LungCancers | Secreted, extracellular space, extra-cellular matrix (By similarity). | UniProt, Detection, Prediction |
| CO6A3_HUMAN | Collagen alpha-3(VI) chain | COL6A3 | Secreted | Symptoms | Secreted, extracellular space, extra-cellular matrix (By similarity). | UniProt, Detection, Prediction |
| CO-CA1_HUMAN | Collagen alpha-1(XII) chain | COL12A1 | ENDO | LungCancers, Symptoms | Secreted, extracellular space, extra-cellular matrix (By similarity). | UniProt, Prediction |
| COF1_HUMAN | Cofilin-1 | CFL1 | Secreted, EPI | LungCancers, Benign-Nodules | Nucleus matrix. Cytoplasm, cytoskeleton. Note = Almost completely in nucleus in cells exposed to heat shock or 10% di-methyl sulfoxide. | Detection, Prediction |
| COIA1_HUMAN | Collagen alpha-1(XVIII) chain | COL18A1 | | LungCancers, Benign-Nodules | Secreted, extracellular space, extra-cellular matrix (By similarity). | UniProt, Literature, Detection, Prediction |
| COX5A_HUMAN | Cytochrome c oxidase subunit 5A, mitochondrial | COX5A | Secreted, ENDO | | Mitochondrion inner membrane. | Prediction |
| CRP_HUMAN | C-reactive protein | CRP | | LungCancers, Benign-Nodules, Symptoms | Secreted. | UniProt, Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| CS051_HUMAN | UPF0470 protein C19orf51 | C19orf51 | ENDO | | | Prediction |
| CSF1_HUMAN | Macrophage colony-stimulating factor 1 | CSF1 | | LungCancers, Benign-Nodules | Cell membrane; Single-pass membrane protein (By similarity). \|Processed macrophage colony-stimulating factor 1: Secreted, extracellular space (By similarity). | UniProt, Literature, Detection |
| CSF2_HUMAN | Granulocyte-macrophage colony-stimulating factor | CSF2 | | LungCancers, Benign-Nodules | Secreted. | UniProt, Literature, Prediction |
| CT085_HUMAN | Uncharacterized protein C20orf85 | C20orf85 | | LungCancers, Benign-Nodules | | Prediction |
| CTGF_HUMAN | Connective tissue growth factor | CTGF | | LungCancers, Benign-Nodules | Secreted, extracellular space, extra-cellular matrix (By similarity). Secreted (By similarity). | UniProt, Literature, Detection, Prediction |
| CYR61_HUMAN | Protein CYR61 | CYR61 | | LungCancers, Benign-Nodules | Secreted. | UniProt, Prediction |
| CYTA_HUMAN | Cystatin-A | CSTA | | LungCancers | Cytoplasm. | Literature, Detection |
| CYTB_HUMAN | Cystatin-B | CSTB | Secreted | | Cytoplasm. Nucleus. | Literature, Detection |
| DDX17_HUMAN | Probable ATP-dependent RNA helicase DDX17 | DDX17 | ENDO | LungCancers, Benign-Nodules | Nucleus. | Detection, Prediction |
| DEFB1_HUMAN | Beta-defensin 1 | DEFB1 | | LungCancers, Benign-Nodules | Secreted. | UniProt, Prediction |
| DESP_HUMAN | Desmoplakin | DSP | EPI, ENDO | LungCancers | Cell junction, desmosome. Cytoplasm, cytoskeleton. Note = Inner most portion of the desmosomal plaque. | Detection |
| DFB4A_HUMAN | Beta-defensin 4A | DEFB4A | | LungCancers, Benign-Nodules | Secreted. | UniProt |
| DHI1L_HUMAN | Hydroxysteroid 11-beta-dehydrogenase 1-like protein | HSD11B1L | | LungCancers | Secreted (Potential). | UniProt, Prediction |
| DMBT1_HUMAN | Deleted in malignant brain tumors 1 protein | DMBT1 | | LungCancers, Benign-Nodules | Secreted (By similarity). Note = Some isoforms may be membrane-bound. Localized to the lumenal aspect of | UniProt, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | crypt cells in the small intestine. In the colon, seen in the lumenal aspect of surface epithelial cells. Formed in the ducts of von Ebner gland, and released into the fluid bathing the taste buds contained in the taste papillae (By similarity). | |
| DMKN_HUMAN | Dermokine | DMKN | | LungCancers | Secreted. | UniProt, Detection, Prediction |
| DPP4_HUMAN | Dipeptidyl peptidase 4 | DPP4 | EPI | LungCancers, Benign-Nodules, Symptoms | Dipeptidyl peptidase 4 soluble form: Secreted. |Cell membrane; Single-pass type II membrane protein. | UniProt, Detection |
| DSG2_HUMAN | Desmoglein-2 | DSG2 | ENDO | Symptoms | Cell membrane; Single-pass type I membrane protein. Cell junction, desmosome. | UniProt, Detection |
| DX39A_HUMAN | ATP-dependent RNA helicase DDX39A | DDX39A | EPI | | Nucleus (By similarity). | Prediction |
| DX39B_HUMAN | Spliceosome RNA helicase DDX39B | DDX39B | EPI | | Nucleus. Nucleus speckle. | Prediction |
| DYRK2_HUMAN | Dual specificity tyrosine-phosphorylation-regulated kinase 2 | DYRK2 | ENDO | LungCancers | Cytoplasm. Nucleus. Note = Translocates into the nucleus following DNA damage. | Literature |
| EDN2_HUMAN | Endothelin-2 | EDN2 | | LungCancers | Secreted. | UniProt, Prediction |
| EF1A1_HUMAN | Elongation factor 1-alpha 1 | EEF1A1 | Secreted, EPI | LungCancers, Benign-Nodules | Cytoplasm. | Detection |
| EF1D_HUMAN | Elongation factor 1-delta | EEF1D | Secreted, EPI | LungCancers | | Prediction |
| EF2_HUMAN | Elongation factor 2 | EEF2 | Secreted, EPI | | Cytoplasm. | Literature, Detection |
| EGF_HUMAN | Pro-epidermal growth factor | EGF | | LungCancers, Benign-Nodules, Symptoms | Membrane; Single-pass type I membrane protein. | UniProt, Literature |
| EGFL6_HUMAN | Epidermal growth factor-like protein 6 | EGFL6 | | LungCancers | Secreted, extracellular space, extra-cellular matrix, basement membrane (By similarity). | UniProt, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| ENOA_HUMAN | Alpha-enolase | ENO1 | Secreted, EPI, ENDO | LungCancers, Benign-Nodules, Symptoms | Cytoplasm. Cell membrane. Cytoplasm, myofibril, sarcomere, M-band. Note = Can translocate to the plasma membrane in either the homodimeric (alpha/ alpha) or heterodimeric (alpha/ gamma) form. ENO1 is localized to the M-band.\|Isoform MBP-1: Nucleus. | Literature, Detection, Prediction |
| ENOG_HUMAN | Gamma-enolase | ENO2 | EPI | LungCancers, Symptoms | Cytoplasm (By similarity). Cell membrane (By similarity). Note = Can translocate to the plasma membrane in either the homodimeric (alpha/ alpha) or heterodimeric (alpha/ gamma) form (By similarity). | Literature, Detection, Prediction |
| ENOX2_HUMAN | Ecto-NOX di-sulfide-thiol exchanger 2 | ENOX2 | | LungCancers | Cell membrane. Secreted, extracellular space. Note = Extracellular and plasma membrane-associated. | UniProt, Detection |
| ENPL_HUMAN | Endo-plasmin | HSP90B1 | Secreted, EPI, ENDO | LungCancers, Benign-Nodules, Symptoms | Endoplasmic reticulum lumen. Melanosome. Note = Identified by mass spectrometry in melanosome fractions from stage I to stage IV. | Literature, Detection, Prediction |
| EPHB6_HUMAN | Ephrin type-B receptor 6 | EPHB6 | | LungCancers | Membrane; Single-pass type I membrane protein. \|Isoform 3: Secreted (Probable). | UniProt, Literature |
| EPOR_HUMAN | Erythro-poietin receptor | EPOR | | LungCancers, Benign-Nodules, Symptoms | Cell membrane; Single-pass type I membrane protein. | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| ERBB3_HUMAN | Receptor tyrosine-protein kinase erbB-3 | ERBB3 | | LungCancers, Benign-Nodules | \|Isoform EPOR-S: Secreted. Note = Secreted and located to the cell surface. Isoform 1: Cell membrane; Single-pass type I membrane protein. \|Isoform 2: Secreted. | UniProt, Literature, Prediction |
| EREG_HUMAN | Proepiregulin | EREG | | LungCancers | Epiregulin: Secreted, extracellular space.\|Proepiregulin: Cell membrane; Single-pass type I membrane protein. | UniProt |
| ERO1A_HUMAN | ERO1-like protein alpha | ERO1L | Secreted, EPI, ENDO | Symptoms | Endoplasmic reticulum membrane; Peripheral membrane protein; Lumenal side. Note = The association with ERP44 is essential for its retention in the endoplasmic reticulum. | Prediction |
| ESM1_HUMAN | Endothelial cell-specific molecule 1 | ESM1 | | LungCancers, Benign-Nodules | Secreted. | UniProt, Prediction |
| EZRI_HUMAN | Ezrin | EZR | Secreted | LungCancers, Benign-Nodules | Apical cell membrane; Peripheral membrane protein; Cytoplasmic side. Cell projection. Cell projection, micro-villus membrane; Peripheral membrane protein; Cytoplasmic side. Cell projection, ruffle membrane; Peripheral membrane protein; Cytoplasmic side. Cytoplasm, cell cortex. Cytoplasm, cytoskeleton. Note = Localization to the apical membrane of parietal cells depends on the interaction with MPP5. Localizes | Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | to cell extensions and peripheral processes of astrocytes (By similarity). Microvillar peripheral membrane protein (cytoplasmic side). | |
| F10A1_HUMAN | Hsc70-interacting protein | ST13 | EPI | | Cytoplasm (By similarity). \|Cytoplasm (Probable). | Detection, Prediction |
| FAM3C_HUMAN | Protein FAM3C | FAM3C | EPI, ENDO | | Secreted (Potential). | UniProt, Detection |
| FAS_HUMAN | Fatty acid synthase | FASN | EPI | LungCancers, Benign-Nodules, Symptoms | Cytoplasm. Melanosome. Note = Identified by mass spectrometry in melanosome fractions from stage I to stage IV. | Literature, Detection |
| FCGR1_HUMAN | High affinity immunoglobulin gamma Fc receptor I | FCGR1A | EPI | LungCancers, Benign-Nodules, Symptoms | Cell membrane; Single-pass type I membrane protein. Note = Stabilized at the cell membrane through interaction with FCER1G. | UniProt |
| FGF10_HUMAN | Fibroblast growth factor 10 | FGF10 | | LungCancers | Secreted (Potential). | UniProt, Prediction |
| FGF2_HUMAN | Heparin-binding growth factor 2 | FGF2 | | LungCancers, Benign-Nodules, Symptoms | | Literature |
| FGF7_HUMAN | Keratinocyte growth factor | FGF7 | | LungCancers, Benign-Nodules | Secreted. | UniProt, Literature, Prediction |
| FGF9_HUMAN | Glia-activating factor | FGF9 | | LungCancers | Secreted. | UniProt, Literature, Prediction |
| FGFR2_HUMAN | Fibroblast growth factor receptor 2 | FGFR2 | | LungCancers, Benign-Nodules | Cell membrane; Single-pass type I membrane protein. \|Isoform 14: Secreted. \|Isoform 19: Secreted. | UniProt, Literature, Prediction |
| FGFR3_HUMAN | Fibroblast growth factor receptor 3 | FGFR3 | | LungCancers | Membrane; Single-pass type I membrane protein. | UniProt, Literature, Prediction |
| FGL2_HUMAN | Fibroleukin | FGL2 | | Benign-Nodules, Symptoms | Secreted. | UniProt, Detection, Prediction |
| FHIT_HUMAN | Bis(5'-adenosyl)-triphosphatase | FHIT | | LungCancers, Benign-Nodules, Symptoms | Cytoplasm. | Literature |
| FIBA_HUMAN | Fibrinogen alpha chain | FGA | | LungCancers, Benign-Nodules, Symptoms | Secreted. | UniProt, Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| FINC_HUMAN | Fibronectin | FN1 | Secreted, EPI, ENDO | LungCancers, Benign-Nodules, Symptoms | Secreted, extracellular space, extra-cellular matrix. | UniProt, Literature, Detection, Prediction |
| FKB11_HUMAN | Peptidyl-prolyl cis-trans isomerase FKBP11 | FKBP11 | EPI, ENDO | | Membrane; Single-pass membrane protein (Potential). | UniProt, Prediction |
| FOLH1_HUMAN | Glutamate carboxy-peptidase 2 | FOLH1 | ENDO | LungCancers, Symptoms | Cell membrane; Single-pass type II membrane protein. IIsoform PSMA': Cytoplasm. | UniProt, Literature |
| FOLR1_HUMAN | Folate receptor alpha | FOLR1 | | LungCancers | Cell membrane; Lipid-anchor, GPI-anchor. Secreted (Probable). | UniProt |
| FOXA2_HUMAN | Hepatocyte nuclear factor 3-beta | FOXA2 | | LungCancers | Nucleus. | Detection, Prediction |
| FP100_HUMAN | Fanconi anemia-associated protein of 100 kDa | C17orf70 | ENDO | Symptoms | Nucleus. | Prediction |
| FRIH_HUMAN | Ferritin heavy chain | FTH1 | EPI | LungCancers, Benign-Nodules | | Literature, Detection, Prediction |
| FRIL_HUMAN | Ferritin light chain | FTL | Secreted, EPI, ENDO | Benign-Nodules, Symptoms | | Literature, Detection |
| G3P_HUMAN | Glyceraldehyde-3-phosphate dehydrogenase | GAPDH | Secreted, EPI, ENDO | LungCancers, Benign-Nodules, Symptoms | Cytoplasm. Cytoplasm, perinuclear region. Membrane. Note = Postnuclear and Perinuclear regions. | Detection |
| G6PD_HUMAN | Glucose-6-phosphate 1-dehydrogenase | G6PD | Secreted, EPI | LungCancers, Symptoms | | Literature, Detection |
| G6PI_HUMAN | Glucose-6-phosphate isomerase | GPI | Secreted, EPI | Symptoms | Cytoplasm. Secreted. | UniProt, Literature, Detection |
| GA2L1_HUMAN | GAS2-like protein 1 | GAS2L1 | ENDO | | Cytoplasm, cytoskeleton (Probable). | Prediction |
| GALT2_HUMAN | Polypeptide N-acetylgalactosaminyl-transferase 2 | GALNT2 | EPI, ENDO | | Golgi apparatus, Golgi stack membrane; Single-pass type II membrane protein. Secreted. Note = Resides preferentially in the trans and medial parts of the Golgi stack. A secreted | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | form also exists. | |
| GAS6_HUMAN | Growth arrest-specific protein 6 | GAS6 | | LungCancers | Secreted. | UniProt, Detection, Prediction |
| GDIR2_HUMAN | Rho GDP-dissociation inhibitor 2 | ARHGDIB | EPI | | Cytoplasm. | Detection |
| GELS_HUMAN | Gelsolin | GSN | | LungCancers, BenignNodules | Isoform 2: Cytoplasm, cytoskeleton. \|Isoform 1: Secreted. | UniProt, Literature, Detection, Prediction |
| GGH_HUMAN | Gamma-glutamyl hydrolase | GGH | | LungCancers | Secreted, extracellular space. Lysosome. Melanosome. Note = While its intracellular location is primarily the lysosome, most of the enzyme activity is secreted. Identified by mass spectrometry in melanosome fractions from stage I to stage IV. | UniProt, Detection, Prediction |
| GPC3_HUMAN | Glypican-3 | GPC3 | | LungCancers, Symptoms | Cell membrane; Lipid-anchor, GPI-anchor; Extracellular side (By similarity). \|Secreted glypican-3: Secreted, extracellular space (By similarity). | UniProt, Literature, Prediction |
| GRAN_HUMAN | Grancalcin | GCA | EPI | | Cytoplasm. Cytoplasmic granule membrane; Peripheral membrane protein; Cytoplasmic side. Note = Primarily cytosolic in the absence of calcium or magnesium ions. Relocates to granules and other membranes in response to elevated calcium and magnesium levels. | Prediction |
| GREB1_HUMAN | Protein GREB1 | GREB1 | ENDO | | Membrane; Single-pass membrane protein (Potential). | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| GREM1_HUMAN | Gremlin-1 | GREM1 | | LungCancers, Benign-Nodules | Secreted (Probable). | UniProt, Prediction |
| GRP_HUMAN | Gastrin-releasing peptide | GRP | | LungCancers, Symptoms | Secreted. | UniProt, Prediction |
| GRP78_HUMAN | 78 kDa glucose-regulated protein | HSPA5 | Secreted, EPI, ENDO | LungCancers, Benign-Nodules | Endoplasmic reticulum lumen. Melanosome. Note = Identified by mass spectrometry in melanosome fractions from stage I to stage IV. | Detection, Prediction |
| GSLG1_HUMAN | Golgi apparatus protein 1 | GLG1 | EPI, ENDO | Benign-Nodules | Golgi apparatus membrane; Single-pass type I membrane protein. | UniProt |
| GSTP1_HUMAN | Glutathione S-transferase P | GSTP1 | Secreted | LungCancers, Benign-Nodules, Symptoms | | Literature, Detection, Prediction |
| GTR1_HUMAN | Solute carrier family 2, facilitated glucose transporter member 1 | SLC2A1 | EPI, ENDO | LungCancers, Benign-Nodules, Symptoms | Cell membrane; Multi-pass membrane protein (By similarity). Melanosome. Note = Localizes primarily at the cell surface (By similarity). Identified by mass spectrometry in melanosome fractions from stage I to stage IV. | Literature |
| GTR3_HUMAN | Solute carrier family 2, facilitated glucose transporter member 3 | SLC2A3 | EPI | | Membrane; Multi-pass membrane protein. | Detection |
| H2A1_HUMAN | Histone H2A type 1 | HIST1H2AG | Secreted | | Nucleus. | Detection, Prediction |
| H2A1B_HUMAN | Histone H2A type 1-B/E | HIST1H2AB | Secreted | | Nucleus. | Detection, Prediction |
| H2A1C_HUMAN | Histone H2A type 1-C | HIST1H2AC | Secreted | | Nucleus. | Literature, Detection, Prediction |
| H2A1D_HUMAN | Histone H2A type 1-D | HIST1H2AD | Secreted | | Nucleus. | Detection, Prediction |
| HG2A_HUMAN | HLA class II histo-compatibility antigen gamma chain | CD74 | | LungCancers, Benign-Nodules, Symptoms | Membrane; Single-pass type II membrane protein (Potential). | UniProt, Literature |
| HGF_HUMAN | Hepatocyte growth factor | HGF | | LungCancers, Benign-Nodules, Symptoms | | Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| HMGA1_HUMAN | High mobility group protein HMG-I/HMG-Y | HMGA1 | | LungCancers, Benign-Nodules, Symptoms | Nucleus. | Literature |
| HPRT_HUMAN | Hypoxanthine-guanine phosphoribosyltransferase | HPRT1 | EPI | | Cytoplasm. | Detection, Prediction |
| HPSE_HUMAN | Heparanase | HPSE | | LungCancers, Benign-Nodules, Symptoms | Lysosome membrane; Peripheral membrane protein. Secreted. Note = Secreted, internalised and transferred to late endosomes/lysosomes as a proheparanase. In lysosomes, it is processed into the active form, the heparanase. The uptake or internalisation of proheparanase is mediated by HSPGs. Heparin appears to be a competitor and retain proheparanase in the extracellular medium. | UniProt, Prediction |
| HPT_HUMAN | Haptoglobin | HP | | LungCancers, Benign-Nodules, Symptoms | Secreted. | UniProt, Literature, Detection, Prediction |
| HS90A_HUMAN | Heat shock protein HSP 90-alpha | HSP90AA1 | Secreted, EPI | LungCancers, Symptoms | Cytoplasm. Melanosome. Note = Identified by mass spectrometry in melanosome fractions from stage I to stage IV. | Literature, Detection |
| HS90B_HUMAN | Heat shock protein HSP 90-beta | HSP90AB1 | Secreted, EPI | LungCancers | Cytoplasm. Melanosome. Note = Identified by mass spectrometry in melanosome fractions from stage I to stage IV. | Literature, Detection |
| HSPB1_HUMAN | Heat shock protein beta-1 | HSPB1 | Secreted, EPI | LungCancers, Benign-Nodules | Cytoplasm. Nucleus. Cytoplasm, cytoskeleton, spindle. Note = Cytoplasmic in interphase cells. Colocalizes with mitotic spindles in mitotic cells. | Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| HTRA1_HUMAN | Serine protease HTRA1 | HTRA1 | | LungCancers | Translocates to the nucleus during heat shock. Secreted. | UniProt, Prediction |
| HXK1_HUMAN | Hexokinase-1 | HK1 | ENDO | Symptoms | Mitochondrion outer membrane. Note = Its hydrophobic N-terminal sequence may be involved in membrane binding. | Literature, Detection |
| HYAL2_HUMAN | Hyaluronidase-2 | HYAL2 | | LungCancers | Cell membrane; Lipid-anchor, GPI-anchor. | Prediction |
| HYOU1_HUMAN | Hypoxia up-regulated protein 1 | HYOU1 | EPI, ENDO | Symptoms | Endoplasmic reticulum lumen. | Detection |
| IBP2_HUMAN | Insulin-like growth factor-binding protein 2 | IGFBP2 | | LungCancers | Secreted. | UniProt, Literature, Detection, Prediction |
| IBP3_HUMAN | Insulin-like growth factor-binding protein 3 | IGFBP3 | | LungCancers, Benign-Nodules, Symptoms | Secreted. | UniProt, Literature, Detection, Prediction |
| ICAM1_HUMAN | Intercellular adhesion molecule 1 | ICAM1 | | LungCancers, Benign-Nodules, Symptoms | Membrane; Single-pass type I membrane protein. | UniProt, Literature, Detection |
| ICAM3_HUMAN | Intercellular adhesion molecule 3 | ICAM3 | EPI, ENDO | LungCancers, Benign-Nodules, Symptoms | Membrane; Single-pass type I membrane protein. | UniProt, Detection |
| IDHP_HUMAN | Isocitrate dehydrogenase [NADP], mitochondrial | IDH2 | Secreted, ENDO | | Mitochondrion. | Prediction |
| IF4A1_HUMAN | Eukaryotic initiation factor 4A-I | EIF4A1 | Secreted, EPI, ENDO | | | Detection, Prediction |
| IGF1_HUMAN | Insulin-like growth factor I | IGF1 | | LungCancers, Benign-Nodules, Symptoms | Secreted. |Secreted. | UniProt, Literature, Detection, Prediction |
| IKIP_HUMAN | Inhibitor of nuclear factor kappa-B kinase-interacting protein | IKIP | ENDO | Symptoms | Endoplasmic reticulum membrane; Single-pass membrane protein. Note = Isoform 4 deletion of the hydrophobic, or transmembrane region between AA 45-63 results in uniform distribution troughout | UniProt, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | the cell, suggesting that this region is responsible for endoplasmic reticulum localization. | |
| IL18_HUMAN | Interleukin-18 | IL18 | | LungCancers, Benign-Nodules, Symptoms | Secreted. | UniProt, Literature, Prediction |
| IL19_HUMAN | Interleukin-19 | IL19 | | LungCancers | Secreted. | UniProt, Detection, Prediction |
| IL22_HUMAN | Interleukin-22 | IL22 | | LungCancers, Benign-Nodules | Secreted. | UniProt, Prediction |
| IL32_HUMAN | Interleukin-32 | IL32 | | LungCancers, Benign-Nodules | Secreted. | UniProt, Prediction |
| IL7_HUMAN | Interleukin-7 | IL7 | | LungCancers, Benign-Nodules | Secreted. | UniProt, Literature, Prediction |
| IL8_HUMAN | Interleukin-8 | IL8 | | LungCancers, Benign-Nodules, Symptoms | Secreted. | UniProt, Literature |
| ILEU_HUMAN | Leukocyte elastase inhibitor | SERPINB1 | Secreted, EPI | | Cytoplasm (By similarity). | Detection, Prediction |
| ILK_HUMAN | Integrin-linked protein kinase | ILK | Secreted | LungCancers, Benign-Nodules, Symptoms | Cell junction, focal adhesion. Cell membrane; Peripheral membrane protein; Cytoplasmic side. | Literature, Detection |
| INHBA_HUMAN | Inhibin beta A chain | INHBA | | LungCancers, Benign-Nodules | Secreted. | UniProt, Literature, Prediction |
| ISLR_HUMAN | Immunoglobulin superfamily containing leucine-rich repeat protein | ISLR | | LungCancers | Secreted (Potential). | UniProt, Detection, Prediction |
| ITA5_HUMAN | Integrin alpha-5 | ITGA5 | EPI | LungCancers, Benign-Nodules, Symptoms | Membrane; Single-pass type I membrane protein. | UniProt, Literature, Detection |
| ITAM_HUMAN | Integrin alpha-M | ITGAM | EPI, ENDO | LungCancers, Benign-Nodules, Symptoms | Membrane; Single-pass type I membrane protein. | UniProt, Literature |
| K0090_HUMAN | Uncharacterized protein KIAA0090 | KIAA0090 | EPI | Symptoms | Membrane; Single-pass type I membrane protein (Potential). | UniProt, Prediction |
| K1C18_HUMAN | Keratin, type I cytoskeletal 18 | KRT18 | Secreted | LungCancers, Benign-Nodules | Cytoplasm, perinuclear region. | Literature, Detection, Prediction |
| K1C19_HUMAN | Keratin, type I cytoskeletal 19 | KRT19 | | LungCancers, Benign-Nodules | | Literature, Detection, Prediction |
| K2C8_HUMAN | Keratin, type II cytoskeletal 8 | KRT8 | EPI | LungCancers | Cytoplasm. | Literature, Detection |
| KIT_HUMAN | Mast/stem cell growth | KIT | | LungCancers | Membrane; Single-pass type I membrane | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | factor receptor | | | | protein. | |
| KITH_HUMAN | Thymidine kinase, cytosolic | TK1 | | LungCancers | Cytoplasm. | Literature, Prediction |
| KLK11_HUMAN | Kallikrein-11 | KLK11 | | LungCancers | Secreted. | UniProt, Literature, Prediction |
| KLK13_HUMAN | Kallikrein-13 | KLK13 | | LungCancers | Secreted (Probable). | UniProt, Literature, Detection, Prediction |
| KLK14_HUMAN | Kallikrein-14 | KLK14 | | LungCancers, Symptoms | Secreted, extracellular space. | UniProt, Literature, Prediction |
| KLK6_HUMAN | Kallikrein-6 | KLK6 | | LungCancers, Benign-Nodules, Symptoms | Secreted. Nucleus, nucleolus. Cytoplasm. Mitochondrion. Microsome. Note = In brain, detected in the nucleus of glial cells and in the nucleus and cytoplasm of neurons. Detected in the mitochondrial and microsomal fractions of HEK-293 cells and released into the cytoplasm following cell stress. | UniProt, Literature, Detection, Prediction |
| KNG1_HUMAN | Kininogen-1 | KNG1 | | LungCancers, Benign-Nodules, Symptoms | Secreted, extracellular space. | UniProt, Detection, Prediction |
| KPYM_HUMAN | Pyruvate kinase isozymes M1/M2 | PKM2 | Secreted, EPI | LungCancers, Symptoms | Cytoplasm. Nucleus. Note = Translocates to the nucleus in response to different apoptotic stimuli. Nuclear translocation is sufficient to induce cell death that is caspase independent, isoform-specific and independent of its enzymatic activity. | Literature, Detection |
| KRT35_HUMAN | Keratin, type I cuticular Ha5 | KRT35 | ENDO | | | Detection, Prediction |
| LAMB2_HUMAN | Laminin subunit beta-2 | LAMB2 | ENDO | LungCancers, Symptoms | Secreted, extracellular space, extra-cellular matrix, basement membrane. Note = S-laminin is | UniProt, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | concentrated in the synaptic cleft of the neuromuscular junction. | |
| LDHA_HUMAN | L-lactate dehydrogenase A chain | LDHA | Secreted, EPI, ENDO | LungCancers | Cytoplasm. | Literature, Detection, Prediction |
| LDHB_HUMAN | L-lactate dehydrogenase B chain | LDHB | EPI | LungCancers | Cytoplasm. | Detection, Prediction |
| LEG1_HUMAN | Galectin-1 | LGALS1 | Secreted | LungCancers | Secreted, extracellular space, extracellular matrix. | UniProt, Detection |
| LEG3_HUMAN | Galectin-3 | LGALS3 | | LungCancers, BenignNodules | Nucleus. Note = Cytoplasmic in adenomas and carcinomas. May be secreted by a non-classical secretory pathway and associate with the cell surface. | Literature, Detection, Prediction |
| LEG9_HUMAN | Galectin-9 | LGALS9 | ENDO | Symptoms | Cytoplasm (By similarity). Secreted (By similarity). Note = May also be secreted by a non-classical secretory pathway (By similarity). | UniProt |
| LG3BP_HUMAN | Galectin-3-binding protein | LGALS3BP | Secreted | LungCancers, BenignNodules, Symptoms | Secreted. Secreted, extracellular space, extracellular matrix. | UniProt, Literature, Detection, Prediction |
| LPLC3_HUMAN | Long palate, lung and nasal epithelium carcinoma-associated protein 3 | C20orf185 | | LungCancers | Secreted (By similarity). Cytoplasm. Note = According to PubMed: 12837268 it is cytoplasmic. | UniProt, Prediction |
| LPLC4_HUMAN | Long palate, lung and nasal epithelium carcinoma-associated protein 4 | C20orf186 | | LungCancers | Secreted (By similarity). Cytoplasm. | UniProt, Prediction |
| LPPRC_HUMAN | Leucine-rich PPR motif-containing protein, mitochondrial | LRPPRC | Secreted, ENDO | LungCancers, Symptoms | Mitochondrion. Nucleus, nucleoplasm. Nucleus inner membrane. Nucleus outer membrane. Note = Seems to be predominantly mitochondrial. | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| LRP1_HUMAN | Prolow-density lipoprotein receptor-related protein 1 | LRP1 | EPI | LungCancers, Symptoms | Low-density lipoprotein receptor-related protein 1 85 kDa subunit: Cell membrane; Single-pass type I membrane protein. Membrane, coated pit.\|Low-density lipo-protein receptor-related protein 1 515 kDa subunit: Cell membrane; Peripheral membrane protein; Extracellular side. Membrane, coated pit.\|Low-density lipo-protein receptor-related protein 1 intra-cellular domain: Cytoplasm. Nucleus. Note = After cleavage, the intracellular domain (LRPICD) is detected both in the cytoplasm and in the nucleus. | UniProt, Detection |
| LUM_HUMAN | Lumican | LUM | Secreted, EPI | LungCancers, Benign-Nodules, Symptoms | Secreted, extracellular space, extra-cellular matrix (By similarity). | UniProt, Detection, Prediction |
| LY6K_HUMAN | Lymphocyte antigen 6K | LY6K | | LungCancers, Symptoms | Secreted. Cytoplasm. Cell membrane; Lipid-anchor, GPI-anchor (Potential). | UniProt, Prediction |
| LYAM2_HUMAN | E-selectin | SELE | | LungCancers, Benign-Nodules, Symptoms | Membrane; Single-pass type I membrane protein. | UniProt, Literature, Detection |
| LYAM3_HUMAN | P-selectin | SELP | | LungCancers, Benign-Nodules, Symptoms | Membrane; Single-pass type I membrane protein. | UniProt, Literature, Detection |
| LYOX_HUMAN | Protein-lysine 6-oxidase | LOX | | LungCancers, Benign-Nodules | Secreted, extracellular space. | UniProt, Detection, Prediction |
| LYPD3_HUMAN | Ly6/PLAUR domain-containing protein 3 | LYPD3 | | LungCancers | Cell membrane; Lipid-anchor, GPI-anchor. | Detection, Prediction |
| MAGA4_HUMAN | Melanoma-associated antigen 4 | MAGEA4 | | LungCancers | | Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| MASP1_HUMAN | Mannan-binding lectin serine protease 1 | MASP1 | | LungCancers, Symptoms | Secreted. | UniProt, Detection, Prediction |
| MDHC_HUMAN | Malate dehydrogenase, cytoplasmic | MDH1 | Secreted | | Cytoplasm. | Literature, Detection, Prediction |
| MDHM_HUMAN | Malate dehydrogenase, mitochondrial | MDH2 | ENDO | LungCancers | Mitochondrion matrix. | Detection, Prediction |
| MIF_HUMAN | Macrophage migration inhibitory factor | MIF | Secreted | LungCancers, Benign-Nodules, Symptoms | Secreted. Cytoplasm. Note = Does not have a cleavable signal sequence and is secreted via a specialized, non-classical pathway. Secreted by macrophages upon stimulation by bacterial lipopolysaccharide (LPS), or by *M. tuberculosis* antigens. | UniProt, Literature, Prediction |
| MLH1_HUMAN | DNA mismatch repair protein Mlh1 | MLH1 | ENDO | LungCancers, Benign-Nodules, Symptoms | Nucleus. | Literature |
| MMP1_HUMAN | Interstitial collagenase | MMP1 | | LungCancers, Benign-Nodules, Symptoms | Secreted, extracellular space, extra-cellular matrix (Probable). | UniProt, Literature, Prediction |
| MMP11_HUMAN | Stromelysin-3 | MMP11 | | LungCancers, Symptoms | Secreted, extracellular space, extra-cellular matrix (Probable). | UniProt, Literature, Prediction |
| MMP12_HUMAN | Macrophage metalloelastase | MMP12 | | LungCancers, Benign-Nodules, Symptoms | Secreted, extracellular space, extra-cellular matrix (Probable). | UniProt, Literature, Prediction |
| MMP14_HUMAN | Matrix metallo-proteinase-14 | MMP14 | ENDO | LungCancers, Benign-Nodules, Symptoms | Membrane; Single-pass type I membrane protein (Potential). Melanosome. Note = Identified by mass spectrometry in melanosome fractions from stage I to stage IV. | UniProt, Literature, Detection |
| MMP2_HUMAN | 72 kDa type IV collagenase | MMP2 | | LungCancers, Benign-Nodules, Symptoms | Secreted, extracellular space, extra-cellular matrix (Probable). | UniProt, Literature, Detection, Prediction |
| MMP26_HUMAN | Matrix metallo-proteinase-26 | MMP26 | | LungCancers | Secreted, extracellular space, extra-cellular matrix. | UniProt, Prediction |
| MMP7_HUMAN | Matrilysin | MMP7 | | LungCancers, Benign- | Secreted, extracellular | UniProt, Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | Nodules, Symptoms | space, extra-cellular matrix (Probable). | |
| MMP9_HUMAN | Matrix metallo-proteinase-9 | MMP9 | | LungCancers, Benign-Nodules, Symptoms | Secreted, extracellular space, extra-cellular matrix (Probable). | UniProt, Literature, Detection, Prediction |
| MOGS_HUMAN | Mannosyl-oligosaccharide glucosidase | MOGS | ENDO | | Endoplasmic reticulum membrane; Single-pass type II membrane protein. | UniProt, Prediction |
| MPRI_HUMAN | Cation-independent mannose-6-phosphate receptor | IGF2R | EPI, ENDO | LungCancers, Symptoms | Lysosome membrane; Single-pass type I membrane protein. | UniProt, Literature, Detection |
| MRP3_HUMAN | Canalicular multi-specific organic anion transporter 2 | ABCC3 | EPI | LungCancers | Membrane; Multi-pass membrane protein. | Literature, Detection |
| MUC1_HUMAN | Mucin-1 | MUC1 | EPI | LungCancers, Benign-Nodules, Symptoms | Apical cell membrane; Single-pass type I membrane protein. Note = Exclusively located in the apical domain of the plasma membrane of highly polarized epithelial cells. After endocytosis, internalized and recycled to the cell membrane. Located to microvilli and to the tips of long filopodial protusions. |Isoform 5: Secreted. |Isoform 7: Secreted. |Isoform 9: Secreted. |Mucin-1 subunit beta: Cell membrane. Cytoplasm. Nucleus. Note = On EGF and PDGFRB stimulation, transported to the nucleus through interaction with CTNNB1, a | UniProt, Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| MUC16_HUMAN | Mucin-16 | MUC16 | | LungCancers | process which is stimulated by phosphorylation. On HRG stimulation, colocalizes with JUP/gamma-catenin at the nucleus. Cell membrane; Single-pass type I membrane protein. Secreted, extracellular space. Note = May be liberated into the extracellular space following the phosphorylation of the intracellular C-terminus which induces the proteolytic cleavage and liberation of the extracellular domain. | UniProt, Detection |
| MUC4_HUMAN | Mucin-4 | MUC4 | | LungCancers, Benign-Nodules | Membrane; Single-pass membrane protein (Potential). Secreted. Note = Isoforms lacking the Cys-rich region, EGF-like domains and transmembrane region are secreted. Secretion occurs by splicing or proteolytic processing. \|Mucin-4 beta chain: Cell membrane; Single-pass membrane protein. \|Mucin-4 alpha chain: Secreted. \|Isoform 3: Cell membrane; Single-pass membrane protein. \|Isoform 15: Secreted. | UniProt |

TABLE 1-continued

| UniProt Protein | Protein Name | Gene Symbol | Sources of Tissue Biomarkers | Biomarkers in Literature | Subcellular Location (UniProt) | Evidence for Presence in Blood |
| --- | --- | --- | --- | --- | --- | --- |
| MUC5B_HUMAN | Mucin-5B | MUC5B | | LungCancers, Benign-Nodules | Secreted. | UniProt, Detection, Prediction |
| MUCL1_HUMAN | Mucin-like protein 1 | MUCL1 | | LungCancers | Secreted (Probable). Membrane (Probable). | UniProt, Prediction |
| NAMPT_HUMAN | Nicotinamide phosphoribosyltransferase | NAMPT | EPI | LungCancers, Benign-Nodules, Symptoms | Cytoplasm (By similarity). | Literature, Detection |
| NAPSA_HUMAN | Napsin-A | NAPSA | Secreted | LungCancers | | Prediction |
| NCF4_HUMAN | Neutrophil cytosol factor 4 | NCF4 | ENDO | | Cytoplasm. | Prediction |
| NDKA_HUMAN | Nucleoside di-phosphate kinase A | NME1 | Secreted | LungCancers, Benign-Nodules, Symptoms | Cytoplasm. Nucleus. Note = Cell-cycle dependent nuclear localization which can be induced by interaction with Epstein-barr viral proteins or by degradation of the SET complex by GzmA. | Literature, Detection |
| NDKB_HUMAN | Nucleoside di-phosphate kinase B | NME2 | Secreted, EPI | Benign-Nodules | Cytoplasm. Nucleus. Note = Isoform 2 is mainly cytoplasmic and isoform 1 and isoform 2 are excluded from the nucleolus. | Literature, Detection |
| NDUS1_HUMAN | NADH-ubiquinone oxidoreductase 75 kDa subunit, mitochondrial | NDUFS1 | Secreted, ENDO | Symptoms | Mitochondrion inner membrane. | Prediction |
| NEBL_HUMAN | Nebulette | NEBL | ENDO | | | Prediction |
| NEK4_HUMAN | Serine/threonine-protein kinase Nek4 | NEK4 | ENDO | LungCancers | Nucleus (Probable). | Prediction |
| NET1_HUMAN | Netrin-1 | NTN1 | | LungCancers, Benign-Nodules | Secreted, extracellular space, extra-cellular matrix (By similarity). | UniProt, Literature, Prediction |
| NEU2_HUMAN | Vasopressin-neurophysin 2-copeptin | AVP | | LungCancers, Symptoms | Secreted. | UniProt, Prediction |
| NGAL_HUMAN | Neutrophil gelatinase-associated lipocalin | LCN2 | EPI | LungCancers, Benign-Nodules, Symptoms | Secreted. | UniProt, Detection, Prediction |
| NGLY1_HUMAN | Peptide-N(4)-(N-acetyl-beta-glucosaminyl)asparagine amidase | NGLY1 | ENDO | | Cytoplasm. | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| NHRF1_HUMAN | Na(+)/H(+) exchange regulatory cofactor NHE-RF1 | SLC9A3R1 | EPI | Benign-Nodules | Endomembrane system; Peripheral membrane protein. Cell projection, filopodium. Cell projection, ruffle. Cell projection, microvillus. Note = Colocalizes with actin in microvilli-rich apical regions of the syncytio-trophoblast. Found in microvilli, ruffling membrane and filopodia of HeLa cells. Present in lipid rafts of T-cells. | Detection |
| NIBAN_HUMAN | Protein Niban | FAM129A | EPI | | Cytoplasm. | Literature, Detection |
| NMU_HUMAN | Neuromedin-U | NMU | | LungCancers | Secreted. | UniProt, Prediction |
| NRP1_HUMAN | Neuropilin-1 | NRP1 | | LungCancers, Benign-Nodules, Symptoms | Cell membrane; Single-pass type I membrane protein. \|Isoform 2: Secreted. | UniProt, Literature, Detection, Prediction |
| ODAM_HUMAN | Odontogenic ameloblast-associated protein | ODAM | | LungCancers | Secreted (By similarity). | UniProt, Prediction |
| OSTP_HUMAN | Osteopontin | SPP1 | | LungCancers, Benign-Nodules, Symptoms | Secreted. | UniProt, Literature, Detection, Prediction |
| OVOS2_HUMAN | Ovostatin homolog 2 | OVOS2 | ENDO | | Secreted (By similarity). | UniProt, Prediction |
| P5CS_HUMAN | Delta-1-pyrroline-5-carboxylate synthase | ALDH18A1 | ENDO | | Mitochondrion inner membrane. | Prediction |
| PA2GX_HUMAN | Group 10 secretory phospholipase A2 | PLA2G10 | | Symptoms | Secreted. | UniProt |
| PAPP1_HUMAN | Pappalysin-1 | PAPPA | | LungCancers, Benign-Nodules, Symptoms | Secreted. | UniProt, Literature, Prediction |
| PBIP1_HUMAN | Pre-B-cell leukemia transcription factor-interacting protein 1 | PBXIP1 | EPI | | Cytoplasm, cytoskeleton. Nucleus. Note = Shuttles between the nucleus and the cytosol. Mainly localized in the cytoplasm, associated with microtubules. | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PCBP1_HUMAN | Poly(rC)-binding protein 1 | PCBP1 | EPI, ENDO | | Detected in small amounts in the nucleus. Nucleus. Cytoplasm. Note = Loosely bound in the nucleus. May shuttle between the nucleus and the cytoplasm. | Detection, Prediction |
| PCBP2_HUMAN | Poly(rC)-binding protein 2 | PCBP2 | EPI | | Nucleus. Cytoplasm. Note = Loosely bound in the nucleus. May shuttle between the nucleus and the cytoplasm. | Detection, Prediction |
| PCD15_HUMAN | Protocadherin-15 | PCDH15 | ENDO | | Cell membrane; Single-pass type I membrane protein (By similarity). |Isoform 3: Secreted. | UniProt, Detection |
| PCNA_HUMAN | Proliferating cell nuclear antigen | PCNA | EPI | LungCancers, Benign-Nodules, Symptoms | Nucleus. | Literature, Prediction |
| PCYOX_HUMAN | Prenylcysteine oxidase 1 | PCYOX1 | Secreted | LungCancers, Symptoms | Lysosome. | Detection, Prediction |
| PDGFA_HUMAN | Platelet-derived growth factor subunit A | PDGFA | | LungCancers | Secreted. | UniProt, Literature, Prediction |
| PDGFB_HUMAN | Platelet-derived growth factor subunit B | PDGFB | | LungCancers, Benign-Nodules, Symptoms | Secreted. | UniProt, Literature, Detection, Prediction |
| PDGFD_HUMAN | Platelet-derived growth factor D | PDGFD | | LungCancers | Secreted. | UniProt, Prediction |
| PDIA3_HUMAN | Protein disulfide-isomerase A3 | PDIA3 | ENDO | LungCancers | Endoplasmic reticulum lumen (By similarity). Melanosome. Note = Identified by mass spectrometry in melanosome fractions from stage I to stage IV. | Detection, Prediction |
| PDIA4_HUMAN | Protein disulfide-isomerase A4 | PDIA4 | Secreted, EPI, ENDO | | Endoplasmic reticulum lumen. Melanosome. Note = Identified by mass spectrometry in melanosome fractions from stage I to stage IV. | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PDIA6_HUMAN | Protein disulfide-isomerase A6 | PDIA6 | Secreted, EPI, ENDO | | Endoplasmic reticulum lumen (By similarity). Melanosome. Note = Identified by mass spectrometry in melanosome fractions from stage I to stage IV. | Detection, Prediction |
| PECA1_HUMAN | Platelet endothelial cell adhesion molecule | PECAM1 | | LungCancers, Benign-Nodules, Symptoms | Membrane; Single-pass type I membrane protein. | UniProt, Literature, Detection |
| PEDF_HUMAN | Pigment epithelium-derived factor | SERPINF1 | | LungCancers, Symptoms | Secreted. Melanosome. Note = Enriched in stage I melanosomes. | UniProt, Literature, Detection, Prediction |
| PERM_HUMAN | Myeloperoxidase | MPO | Secreted, EPI, ENDO | LungCancers, Benign-Nodules, Symptoms | Lysosome. | Literature, Detection, Prediction |
| PERP1_HUMAN | Plasma cell-induced resident endoplasmic reticulum protein | PACAP | EPI, ENDO | | Secreted (Potential). Cytoplasm. Note = In (PubMed: 11350957) diffuse granular localization in the cytoplasm surrounding the nucleus. | UniProt, Detection, Prediction |
| PGAM1_HUMAN | Phosphoglycerate mutase 1 | PGAM1 | Secreted, EPI | LungCancers, Symptoms | | Detection |
| PLAC1_HUMAN | Placenta-specific protein 1 | PLAC1 | | LungCancers | Secreted (Probable). | UniProt, Prediction |
| PLACL_HUMAN | Placenta-specific 1-like protein | PLAC1L | | LungCancers | Secreted (Potential). | UniProt, Prediction |
| PLIN2_HUMAN | Perilipin-2 | ADFP | ENDO | LungCancers | Membrane; Peripheral membrane protein. | Prediction |
| PLIN3_HUMAN | Perilipin-3 | M6PRBP1 | EPI | | Cytoplasm. Endosome membrane; Peripheral membrane protein; Cytoplasmic side (Potential). Lipid droplet (Potential). Note = Membrane associated on endosomes. Detected in the envelope and the core of lipid bodies and in lipid sails. | Detection, Prediction |
| PLOD1_HUMAN | Procollagen-lysine,2-oxoglutarate 5-dioxygenase 1 | PLOD1 | EPI, ENDO | | Rough endoplasmic reticulum membrane; Peripheral membrane protein; | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| PLOD2_HUMAN | Procollagen-lysine,2-oxoglutarate 5-dioxygenase 2 | PLOD2 | ENDO | Benign-Nodules, Symptoms | Lumenal side. Rough endoplasmic reticulum membrane; Peripheral membrane protein; Lumenal side. | Prediction |
| PLSL_HUMAN | Plastin-2 | LCP1 | Secreted, EPI | LungCancers | Cytoplasm, cytoskeleton. Cell junction. Cell projection. Cell projection, ruffle membrane; Peripheral membrane protein; Cytoplasmic side (By similarity). Note = Relocalizes to the immunological synapse between peripheral blood T lymphocytes and anti-body-presenting cells in response to costimulation through TCR/CD3 and CD2 or CD28. Associated with the actin cytoskeleton at membrane ruffles (By similarity). Relocalizes to actin-rich cell projections upon serine phosphorylation. | Detection, Prediction |
| PLUNC_HUMAN | Protein Plunc | PLUNC | | LungCancers, Benign-Nodules | Secreted (By similarity). Note = Found in the nasal mucus (By similarity). Apical side of airway epithelial cells. Detected in nasal mucus (By similarity). | UniProt, Prediction |
| PLXB3_HUMAN | Plexin-B3 | PLXNB3 | ENDO | | Membrane; Single-pass type I membrane protein. | UniProt, Detection, Prediction |
| PLXC1_HUMAN | Plexin-C1 | PLXNC1 | EPI | | Membrane; Single-pass type I membrane protein (Potential). | UniProt, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| POSTN_HUMAN | Periostin | POSTN | Secreted, ENDO | LungCancers, Benign-Nodules, Symptoms | Secreted, extracellular space, extra-cellular matrix. | UniProt, Literature, Detection, Prediction |
| PPAL_HUMAN | Lysosomal acid phosphatase | ACP2 | EPI | Symptoms | Lysosome membrane; Single-pass membrane protein; Lumenal side. Lysosome lumen. Note = The soluble form arises by proteolytic processing of the membrane-bound form. | UniProt, Prediction |
| PPBT_HUMAN | Alkaline phosphatase, tissue-nonspecific isozyme | ALPL | EPI | LungCancers, Benign-Nodules, Symptoms | Cell membrane; Lipid-anchor, GPI-anchor. | Literature, Detection, Prediction |
| PPIB_HUMAN | Peptidyl-prolyl cis-trans isomerase B | PPIB | Secreted, EPI, ENDO | | Endoplasmic reticulum lumen. Melanosome. Note = Identified by mass spectrometry in melanosome fractions from stage I to stage IV. | Detection, Prediction |
| PRDX1_HUMAN | Peroxiredoxin-1 | PRDX1 | EPI | LungCancers | Cytoplasm. Melanosome. Note = Identified by mass spectrometry in melanosome fractions from stage I to stage IV. | Detection, Prediction |
| PRDX4_HUMAN | Peroxiredoxin-4 | PRDX4 | Secreted, EPI, ENDO | | Cytoplasm. | Literature, Detection, Prediction |
| PROF1_HUMAN | Profilin-1 | PFN1 | Secreted, EPI | LungCancers | Cytoplasm, cytoskeleton. | Detection |
| PRP31_HUMAN | U4/U6 small nuclear ribo-nucleo-protein Prp31 | PRPF31 | ENDO | | Nucleus speckle. Nucleus, Cajal body. Note = Predominantly found in speckles and in Cajal bodies. | Prediction |
| PRS6A_HUMAN | 26S protease regulatory subunit 6A | PSMC3 | EPI | Benign-Nodules | Cytoplasm (Potential). Nucleus (Potential). | Detection |
| PSCA_HUMAN | Prostate stem cell antigen | PSCA | | LungCancers | Cell membrane; Lipid-anchor, GPI-anchor. | Literature, Prediction |
| PTGIS_HUMAN | Prostacyclin synthase | PTGIS | EPI | LungCancers, Benign-Nodules | Endoplasmic reticulum membrane; Single-pass membrane protein. | UniProt, Detection, Prediction |
| PTPA_HUMAN | Serine/threonine- | PPP2R4 | ENDO | Symptoms | | Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | protein phosphatase 2A activator | | | | | |
| PTPRC_HUMAN | Receptor-type tyrosine-protein phosphatase C | PTPRC | Secreted, EPI, ENDO | LungCancers | Membrane; Single-pass type I membrane protein. | UniProt, Detection, Prediction |
| PTPRJ_HUMAN | Receptor-type tyrosine-protein phosphatase eta | PTPRJ | EPI | LungCancers, Symptoms | Membrane; Single-pass type I membrane protein. | UniProt, Detection, Prediction |
| PVR_HUMAN | Poliovirus receptor | PVR | | Symptoms | Isoform Alpha: Cell membrane; Single-pass type I membrane protein. \|Isoform Delta: Cell membrane; Single-pass type I membrane protein. \|Isoform Beta: Secreted. \|Isoform Gamma: Secreted. | UniProt, Detection, Prediction |
| RAB32_HUMAN | Ras-related protein Rab-32 | RAB32 | EPI | | Mitochondrion. | Prediction |
| RAGE_HUMAN | Advanced glycosylation end product-specific receptor | AGER | Secreted | LungCancers, Benign-Nodules | Isoform 1: Cell membrane; Single-pass type I membrane protein. \|Isoform 2: Secreted. | UniProt, Literature |
| RAN_HUMAN | GTP-binding nuclear protein Ran | RAN | Secreted, EPI | LungCancers, Benign-Nodules | Nucleus. Cytoplasm. Melanosome. Note = Becomes dispersed throughout the cytoplasm during mitosis. Identified by mass spectrometry in melanosome fractions from stage I to stage IV. | Detection, Prediction |
| RAP2B_HUMAN | Ras-related protein Rap-2b | RAP2B | EPI | | Cell membrane; Lipid-anchor; Cytoplasmicside (Potential). | Prediction |
| RAP2C_HUMAN | Ras-related protein Rap-2c | RAP2C | EPI | | Cell membrane; Lipid-anchor; Cytoplasmic side (Potential). | Prediction |
| RCN3_HUMAN | Reticulocalbin-3 | RCN3 | EPI | Symptoms | Endoplasmic reticulum lumen (Potential). | Prediction |
| RL24_HUMAN | 60S ribosomal protein L24 | RPL24 | EPI | | | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| S10A1_HUMAN | Protein S100-A1 | S100A1 | | Symptoms | Cytoplasm. | Literature, Prediction |
| S10A6_HUMAN | Protein S100-A6 | S100A6 | Secreted | LungCancers | Nucleus envelope. Cytoplasm. | Literature, Detection, Prediction |
| S10A7_HUMAN | Protein S100-A7 | S100A7 | | LungCancers | Cytoplasm. Secreted. Note = Secreted by a non-classical secretory pathway. | UniProt, Literature, Detection, Prediction |
| SAA_HUMAN | Serum amyloid A protein | SAA1 | | Symptoms | Secreted. | UniProt, Literature, Detection, Prediction |
| SCF_HUMAN | Kit ligand | KITLG | | LungCancers, Symptoms | Isoform 1: Cell membrane; Single-pass type I membrane protein (By similarity). Secreted (By similarity). Note = Also exists as a secreted soluble form (isoform 1 only) (By similarity). \|Isoform 2: Cell membrane; Single-pass type I membrane protein (By similarity). Cytoplasm, cytoskeleton (By similarity). | UniProt, Literature |
| SDC1_HUMAN | Syndecan-1 | SDC1 | | LungCancers, Benign-Nodules, Symptoms | Membrane; Single-pass type I membrane protein. | UniProt, Literature, Detection |
| SEM3G_HUMAN | Semaphorin-3G | SEMA3G | | LungCancers | Secreted (By similarity). | UniProt, Prediction |
| SEPR_HUMAN | Seprase | FAP | ENDO | Symptoms | Cell membrane; Single-pass type II membrane protein. Cell projection, lamellipodium membrane; Single-pass type II membrane protein. Cell projection, invadopodium membrane; Single-pass type II membrane protein. Note = Found in cell surface lamel-lipodia, in-vadopodia | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | and on shed vesicles. | |
| SERPH_HUMAN | Serpin H1 | SERPINH1 | Secreted, EPI, ENDO | LungCancers, Benign-Nodules | Endoplasmic reticulum lumen. | Detection, Prediction |
| SFPA2_HUMAN | Pulmonary surfactant-associated protein A2 | SFTPA2 | Secreted | LungCancers, Benign-Nodules | Secreted, extracellular space, extra-cellular matrix. Secreted, extracellular space, surface film. | UniProt, Prediction |
| SFTA1_HUMAN | Pulmonary surfactant-associated protein A1 | SFTPA1 | Secreted | LungCancers, Benign-Nodules, Symptoms | Secreted, extracellular space, extra-cellular matrix. Secreted, extracellular space, surface film. | UniProt, Prediction |
| SG3A2_HUMAN | Secretoglobin family 3A member 2 | SCGB3A2 | | LungCancers, Benign-Nodules | Secreted. | UniProt, Prediction |
| SGPL1_HUMAN | Sphingosine-1-phosphate lyase 1 | SGPL1 | ENDO | | Endoplasmic reticulum membrane; Single-pass type III membrane protein. | UniProt, Prediction |
| SIAL_HUMAN | Bone sialoprotein 2 | IBSP | | LungCancers | Secreted. | UniProt, Literature, Prediction |
| SLPI_HUMAN | Antileukoproteinase | SLPI | | LungCancers, Benign-Nodules | Secreted. | UniProt, Literature, Detection, Prediction |
| SMD3_HUMAN | Small nuclear ribonucleoprotein Sm D3 | SNRPD3 | Secreted | Benign-Nodules | Nucleus. | Prediction |
| SMS_HUMAN | Somatostatin | SST | | LungCancers | Secreted. | UniProt, Literature, Prediction |
| SODM_HUMAN | Superoxide dismutase [Mn], mitochondrial | SOD2 | Secreted | LungCancers, Benign-Nodules, Symptoms | Mitochondrion matrix. | Literature, Detection, Prediction |
| SORL_HUMAN | Sortilin-related receptor | SORL1 | EPI | LungCancers, Symptoms | Membrane; Single-pass type I membrane protein (Potential). | UniProt, Detection |
| SPB3_HUMAN | Serpin B3 | SERPINB3 | | LungCancers, Benign-Nodules | Cytoplasm. Note = Seems to also be secreted in plasma by cancerous cells but at a low level. | Literature, Detection |
| SPB5_HUMAN | Serpin B5 | SERPINB5 | | LungCancers | Secreted, extracellular space. | UniProt, Detection |
| SPON2_HUMAN | Spondin-2 | SPON2 | | LungCancers, Benign-Nodules | Secreted, extracellular space, extra-cellular matrix (By similarity). | UniProt, Prediction |
| SPRC_HUMAN | SPARC | SPARC | | LungCancers, Benign-Nodules, Symptoms | Secreted, extracellular space, extra-cellular matrix, basement membrane. Note = In or | UniProt, Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | around the basement membrane. | |
| SRC_HUMAN | Proto-oncogene tyrosine-protein kinase Src | SRC | ENDO | LungCancers, Benign-Nodules, Symptoms | | Literature |
| SSRD_HUMAN | Translocon-associated protein subunit delta | SSR4 | Secreted, ENDO | | Endoplasmic reticulum membrane; Single-pass type I membrane protein. | UniProt, Prediction |
| STAT1_HUMAN | Signal transducer and activator of transcription 1-alpha/beta | STAT1 | EPI | LungCancers, Benign-Nodules | Cytoplasm. Nucleus. Note = Translocated into the nucleus in response to IFN-gamma-induced tyrosine phosphorylation and dimerization. | Detection |
| STAT3_HUMAN | Signal transducer and activator of transcription 3 | STAT3 | ENDO | LungCancers, Benign-Nodules, Symptoms | Cytoplasm. Nucleus. Note = Shuttles between the nucleus and the cytoplasm. Constitutive nuclear presence is independent of tyrosine phosphorylation. | Prediction |
| STC1_HUMAN | Stannio-calcin-1 | STC1 | | LungCancers, Symptoms | Secreted. | UniProt, Prediction |
| STT3A_HUMAN | Dolichyl-diphosphooligo-saccharide--protein glycosyl-transferase subunit STT3A | STT3A | EPI | Symptoms | Endoplasmic reticulum membrane; Multi-pass membrane protein. | Literature |
| TAGL_HUMAN | Transgelin | TAGLN | EPI | LungCancers | Cytoplasm (Probable). | Literature, Prediction |
| TARA_HUMAN | TRIO and F-actin-binding protein | TRIOBP | ENDO | | Nucleus. Cytoplasm, cytoskeleton. Note = Localized to F-actin in a periodic pattern. | Detection, Prediction |
| TBA1B_HUMAN | Tubulin alpha-1B chain | TUBA1B | EPI | LungCancers | | Detection |
| TBB2A_HUMAN | Tubulin beta-2A chain | TUBB2A | EPI | LungCancers, Benign-Nodules | | Detection, Prediction |
| TBB3_HUMAN | Tubulin beta-3 chain | TUBB3 | EPI | LungCancers, Benign-Nodules | | Detection |
| TBB5_HUMAN | Tubulin beta chain | TUBB | EPI | LungCancers, Benign-Nodules | | Detection |
| TCPA_HUMAN | T-complex protein 1 subunit alpha | TCP1 | EPI | | Cytoplasm. | Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| TCPD_HUMAN | T-complex protein 1 subunit delta | CCT4 | EPI | | Cytoplasm. Melanosome. Note = Identified by mass spectrometry in melanosome fractions from stage I to stage IV. | Detection, Prediction |
| TCPQ_HUMAN | T-complex protein 1 subunit theta | CCT8 | Secreted, EPI | | Cytoplasm. | Prediction |
| TCPZ_HUMAN | T-complex protein 1 subunit zeta | CCT6A | Secreted, EPI | | Cytoplasm. | Detection |
| TDRD3_HUMAN | Tudor domain-containing protein 3 | TDRD3 | ENDO | | Cytoplasm. Nucleus. Note = Predominantly cytoplasmic. Associated with actively translating polyribosomes and with mRNA stress granules. | Prediction |
| TENA_HUMAN | Tenascin | TNC | ENDO | LungCancers, BenignNodules, Symptoms | Secreted, extracellular space, extra-cellular matrix. | UniProt, Literature, Detection |
| TENX_HUMAN | Tenascin-X | TNXB | ENDO | LungCancers, Symptoms | Secreted, extracellular space, extra-cellular matrix. | UniProt, Detection, Prediction |
| TERA_HUMAN | Transitional endoplasmic reticulum ATPase | VCP | EPI | LungCancers, BenignNodules | Cytoplasm, cytosol. Nucleus. Note = Present in the neuronal hyaline inclusion bodies specifically found in motor neurons from amyotrophic lateral sclerosis patients. Present in the Lewy bodies specifically found in neurons from Parkinson disease patients. | Detection |
| TETN_HUMAN | Tetranectin | CLEC3B | | LungCancers | Secreted. | UniProt, Literature, Detection, Prediction |
| TF_HUMAN | Tissue factor | F3 | | LungCancers, BenignNodules, Symptoms | Membrane; Single-pass type I membrane protein. | UniProt, Literature |
| TFR1_HUMAN | Transferrin receptor protein 1 | TFRC | Secreted, EPI, ENDO | LungCancers, BenignNodules, Symptoms | Cell membrane; Single-pass type II membrane protein. Melanosome. Note = Identified | UniProt, Literature, Detection |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | by mass spectrometry in melanosome fractions from stage I to stage IV.\|Transferrin receptor protein 1, serum form: Secreted. | |
| TGFA_HUMAN | Protransforming growth factor alpha | TGFA | | LungCancers, Benign-Nodules | Transforming growth factor alpha: Secreted, extracellular space.\|Protransforming growth factor alpha: Cell membrane; Single-pass type I membrane protein. | UniProt, Literature |
| THAS_HUMAN | Thromboxane-A synthase | TBXAS1 | EPI, ENDO | LungCancers, Benign-Nodules, Symptoms | Membrane; Multi-pass membrane protein. | Prediction |
| THY1_HUMAN | Thy-1 membrane glycoprotein | THY1 | EPI | Symptoms | Cell membrane; Lipid-anchor, GPI-anchor (By similarity). | Detection, Prediction |
| TIMP1_HUMAN | Metallo-proteinase inhibitor 1 | TIMP1 | | LungCancers, Benign-Nodules, Symptoms | Secreted. | UniProt, Literature, Detection, Prediction |
| TIMP3_HUMAN | Metallo-proteinase inhibitor 3 | TIMP3 | | LungCancers, Benign-Nodules | Secreted, extracellular space, extra-cellular matrix. | UniProt, Literature, Prediction |
| TLL1_HUMAN | Tolloid-like protein 1 | TLL1 | ENDO | | Secreted (Probable). | UniProt, Prediction |
| TNF12_HUMAN | Tumor necrosis factor ligand super-family member 12 | TNFSF12 | | LungCancers, Benign-Nodules | Cell membrane; Single-pass type II membrane protein.\|Tumor necrosis factor ligand superfamily member 12, secreted form: Secreted. | UniProt |
| TNR6_HUMAN | Tumor necrosis factor receptor super-family member 6 | FAS | | LungCancers, Benign-Nodules, Symptoms | Isoform 1: Cell membrane; Single-pass type I membrane protein. \|Isoform 2: Secreted. \|Isoform 3: Secreted. \|Isoform 4: Secreted. \|Isoform 5: Secreted. \|Isoform 6: Secreted. | UniProt, Literature, Prediction |
| TPIS_HUMAN | Tri-osephosphate isomerase | TPI1 | Secreted, EPI | Symptoms | | Literature, Detection, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| TRFL_HUMAN | Lacto-transferrin | LTF | Secreted, EPI, ENDO | LungCancers, Benign-Nodules, Symptoms | Secreted. | UniProt, Literature, Detection, Prediction |
| TSP1_HUMAN | Thrombospondin-1 | THBS1 | | LungCancers, Benign-Nodules, Symptoms | | Literature, Detection, Prediction |
| TTHY_HUMAN | Transthyretin | TTR | | LungCancers, Benign-Nodules | Secreted. Cytoplasm. | UniProt, Literature, Detection, Prediction |
| TYPH_HUMAN | Thymidine phosphorylase | TYMP | EPI | LungCancers, Benign-Nodules, Symptoms | | Literature, Detection, Prediction |
| UGGG1_HUMAN | UDP-glucose:glyco protein glucosyl-transferase 1 | UGGT1 | Secreted, ENDO | | Endoplasmic reticulum lumen. Endoplasmic reticulum-Golgi intermediate compartment. | Detection, Prediction |
| UGGG2_HUMAN | UDP-glucose:glyco protein glucosyl-transferase 2 | UGGT2 | ENDO | | Endoplasmic reticulum lumen. Endoplasmic reticulum-Golgi intermediate compartment. | Prediction |
| UGPA_HUMAN | UTP--glucose-1-phosphate uridyl-yltransferase | UGP2 | EPI | Symptoms | Cytoplasm. | Detection |
| UPAR_HUMAN | Urokinase plasminogen activator surface receptor | PLAUR | | LungCancers, Benign-Nodules, Symptoms | Isoform 1: Cell membrane; Lipid-anchor, GPI-anchor. \|Isoform 2: Secreted (Probable). | UniProt, Literature, Prediction |
| UTER_HUMAN | Utero-globin | SCGB1A1 | | LungCancers, Benign-Nodules, Symptoms | Secreted. | UniProt, Literature, Detection, Prediction |
| VA0D1_HUMAN | V-type proton ATPase subunit d1 | ATP6V0D1 | EPI | | | Prediction |
| VAV3_HUMAN | Guanine nucleotide exchange factor VAV3 | VAV3 | ENDO | | | Prediction |
| VEGFA_HUMAN | Vascular endothelial growth factor A | VEGFA | | LungCancers, Benign-Nodules, Symptoms | Secreted. Note = VEGF 121 is acidic and freely secreted. VEGF165 is more basic, has heparin-binding properties and, although a signicant proportion remains cell-associated, most is freely secreted. VEGF189 is very basic, it | UniProt, Literature, Prediction |

TABLE 1-continued

| UniProt Protein | Protein Name | Gene Symbol | Sources of Tissue Biomarkers | Biomarkers in Literature | Subcellular Location (UniProt) | Evidence for Presence in Blood |
|---|---|---|---|---|---|---|
| | | | | | is cell-associated after secretion and is bound avidly by heparin and the extracellular matrix, although it may be released as a soluble form by heparin, heparinase or plasmin. | |
| VEGFC_HUMAN | Vascular endothelial growth factor C | VEGFC | | LungCancers, Benign-Nodules | Secreted. | UniProt, Literature, Prediction |
| VEGFD_HUMAN | Vascular endothelial growth factor D | FIGF | | LungCancers | Secreted. | UniProt, Literature, Prediction |
| VGFR1_HUMAN | Vascular endothelial growth factor receptor 1 | FLT1 | | LungCancers, Benign-Nodules, Symptoms | Isoform Flt1: Cell membrane; Single-pass type I membrane protein. \|Isoform sFlt1: Secreted. | UniProt, Literature, Detection, Prediction |
| VTNC_HUMAN | Vitronectin | VTN | ENDO | Symptoms | Secreted, extracellular space. | UniProt, Literature, Detection, Prediction |
| VWC2_HUMAN | Brorin | VWC2 | | LungCancers | Secreted, extracellular space, extracellular matrix, basement membrane (By similarity). | UniProt, Prediction |
| WNT3A_HUMAN | Protein Wnt-3a | WNT3A | | LungCancers, Symptoms | Secreted, extracellular space, extracellular matrix. | UniProt, Prediction |
| WT1_HUMAN | Wilms tumor protein | WT1 | | LungCancers, Benign-Nodules, Symptoms | Nucleus. Cytoplasm (By similarity). Note = Shuttles between nucleus and cytoplasm (By similarity). \|Isoform 1: Nucleus speckle. \|Isoform 4: Nucleus, nucleoplasm. | Literature, Prediction |
| ZA2G_HUMAN | Zinc-alpha-2-glycoprotein | AZGP1 | | LungCancers, Symptoms | Secreted. | UniProt, Literature, Detection, Prediction |
| ZG16B_HUMAN | Zymogen granule protein 16 homolog B | ZG16B | | LungCancers | Secreted (Potential). | UniProt, Prediction |

In an embodiment of the invention, panels comprising 2 proteins were validated for ruling out lung cancer in a subject. In some aspects, protein panels include 1, 2, 3, 4, 5, 6, 7, 8, 9, 10, 11, 12, 13, 14, 15, 16, 17, 18, 19, 20 or more proteins selected from Table 1. In some aspects, the pulmonary nodule is about between 1 mm to 80 mm. For example, the pulmonary nodule can be between 8 mm-30 mm.

Bioinformatic and biostatistical analyses were used first to identify individual proteins with statistically significant differential expression, and then using these proteins to derive one or more combinations of proteins or panels of proteins, which collectively demonstrated superior discriminatory performance compared to any individual protein. Bioinformatic and biostatistical methods are used to derive coefficients (C) for each individual protein in the panel that reflects its relative expression level, i.e. increased or decreased, and its weight or importance with respect to the panel's net discriminatory ability, relative to the other proteins. The quantitative discriminatory ability of the panel can be expressed as a mathematical algorithm with a term for each of its constituent proteins being the product of its coefficient and the protein's plasma expression level (P) (as measured by LC-SRM-MS), e.g. C×P, with an algorithm consisting of n proteins described as: C1×P1+C2×P2+C3×P3+ . . . +Cn×Pn. An algorithm that discriminates between disease states with a predetermined level of statistical significance may be refers to a "disease classifier". In addition to the classifier's constituent proteins with differential expression, it may also include proteins with minimal or no biologic variation to enable assessment of variability, or the lack thereof, within or between clinical specimens; these proteins may be termed typical native proteins and serve as internal controls for the other classifier proteins.

In certain embodiments, peptide expression levels are measured by MS. MS analyzes the mass spectrum produced by an ion after its production by the vaporization of its parent protein and its separation from other ions based on its mass-to-charge ratio. The most common modes of acquiring MS data are 1) full scan acquisition resulting in the typical total ion current plot (TIC), 2) selected ion monitoring (SIM), and 3) selected reaction monitoring (SRM).

In certain embodiments of the methods provided herein, biomarker protein expression levels are measured by LC-SRM-MS. LC-SRM-MS is a highly selective method of tandem mass spectrometry which has the potential to effectively filter out all molecules and contaminants except the desired analyte(s). This is particularly beneficial if the analysis sample is a complex mixture which may comprise several isobaric species within a defined analytical window. LC-SRM-MS methods may utilize a triple quadrupole mass spectrometer which, as is known in the art, includes three quadrupole rod sets. A first stage of mass selection is performed in the first quadrupole rod set, and the selectively transmitted ions are fragmented in the second quadrupole rod set. The resultant transition (product) ions are conveyed to the third quadrupole rod set, which performs a second stage of mass selection. The product ions transmitted through the third quadrupole rod set are measured by a detector, which generates a signal representative of the numbers of selectively transmitted product ions. The RF and DC potentials applied to the first and third quadrupoles are tuned to select (respectively) precursor and product ions that have m/z values lying within narrow specified ranges. By specifying the appropriate transitions (m/z values of precursor and product ions), a peptide corresponding to a targeted protein may be measured with high degrees of sensitivity and selectivity. Signal-to-noise ratio is superior to conventional tandem mass spectrometry (MS/MS) experiments, which select one mass window in the first quadrupole and then measure all generated transitions in the ion detector. LC-SRM-MS.

In certain embodiments, an SRM-MS assay for use in diagnosing or monitoring lung cancer as disclosed herein may utilize one or more peptides and/or peptide transitions derived from the proteins set forth in Table 1. In certain embodiments, the assay may utilize peptides and/or peptide transitions from 100 or more, 150 or more, 200 or more, 250 or more, 300 or more, 345 or more, or 371 or more biomarker proteins. In certain embodiments, two or more peptides may be utilized per biomarker proteins, and in certain of these embodiments three or more of four or more peptides may be utilized. Similarly, in certain embodiments two or more transitions may be utilized per peptide, and in certain of these embodiments three or more; four or more; or five or more transitions may be utilized per peptide. In one embodiment, an LC-SRM-MS assay for use in diagnosing lung cancer may measure the intensity of five transitions that correspond to selected peptides associated with each biomarker protein. The achievable limit of quantification (LOQ) may be estimated for each peptide according to the observed signal intensities during this analysis.

The expression level of a biomarker protein can be measured using any suitable method known in the art, including but not limited to mass spectrometry (MS), reverse transcriptase-polymerase chain reaction (RT-PCR), microarray, serial analysis of gene expression (SAGE), gene expression analysis by massively parallel signature sequencing (MPSS), immunoassays (e.g., ELISA, and other antibody based methods of detection), immunohistochemistry (IHC), transcriptomics, and proteomics.

To evaluate the diagnostic performance of a particular set of peptide transitions, a ROC curve is generated for each significant transition.

Figure 9:
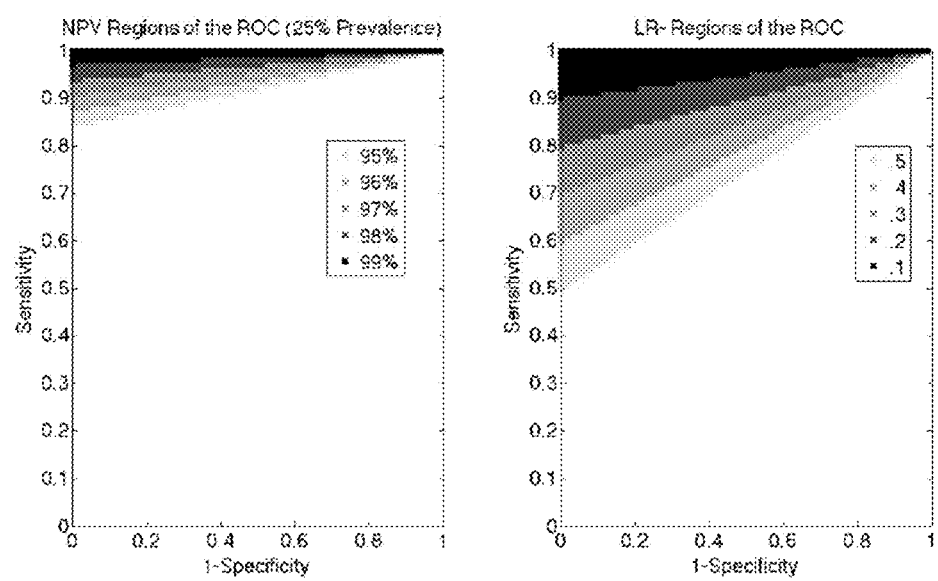
FIG. 9 is a pair of Receiver Operating Characteristic (ROC) plots depicting the negative predictive value (NPV) (left panel) and negative likelihood ratio (NLR) (right panel) regions relevant to XL2 performance.

An "ROC curve" (Receiver Operating Characteristic) as used herein refers to a plot of the true positive rate (sensitivity) against the false positive rate (specificity) for a binary classifier system as its discrimination threshold is varied. A ROC curve can be represented equivalently by plotting the fraction of true positives out of the positives (TPR=true positive rate) versus the fraction of false positives out of the negatives (FPR=false positive rate). Each point on the ROC curve represents a sensitivity/specificity pair corresponding to a particular decision threshold. FIGS. 7 and 9 provide a graphical representation of the functional relationship between the distribution of biomarker or biomarker panel sensitivity and specificity values in a cohort of diseased subjects and in a cohort of non-diseased subjects.

AUC represents the area under the ROC curve. The AUC is an overall indication of the diagnostic accuracy of 1) a biomarker or a panel of biomarkers and 2) a ROC curve. AUC is determined by the "trapezoidal rule." For a given curve, the data points are connected by straight line segments, perpendiculars are erected from the abscissa to each data point, and the sum of the areas of the triangles and trapezoids so constructed is computed. In certain embodiments of the methods provided herein, a biomarker protein has an AUC in the range of about 0.75 to 1.0. In certain of these embodiments, the AUC is in the range of about 0.8 to 0.8, 0.9 to 0.95, or 0.95 to 1.0.

The term "reversal" as used herein refers to a ratio of two proteins in a two-protein classifier.

The term "physician cancer assessment" (pCA) encompasses various estimates that physician's employ to estimate the probability of a nodule being cancer in a subject. For example, pCA can be based on the physician's clinical training and experience, including taking into account the appearance and size of the nodule from CAT scan (CT), a patient's age and smoking history. In some instances, pCA involves the use of equations that using the same factors described above (i.e. appearance and size of nodule, patient's age and smoking history). For example, the National Cancer Institute provides tools for physicians to assess cancer risk. While these tools are not developed specifically for lung cancer, some variables present in these assessments are relevant, including, but not limited to, the patient's medical history or family history of cancer, genetic predisposition to cancer, age, race, and lifestyle choices (exposure to carcinogens through smoking or exposure to radiation, diet, health of immune system, access to preventative care and health screenings, etc.).

The methods provided herein are minimally invasive and pose little or no risk of adverse effects. As such, they may be used to diagnose, monitor and provide clinical management of subjects who do not exhibit any symptoms of a lung condition and subjects classified as low risk for developing a lung condition. For example, the methods disclosed herein may be used to diagnose lung cancer in a subject who does not present with a PN and/or has not presented with a PN in the past, but who nonetheless deemed at risk of developing a PN and/or a lung condition. Similarly, the methods disclosed herein may be used as a strictly precautionary measure to diagnose healthy subjects who are classified as low risk for developing a lung condition.

The present invention provides a method of determining the likelihood that a lung condition in a subject is cancer by measuring an abundance of a panel of proteins in a sample obtained from the subject; calculating a probability of cancer score based on the protein measurements and ruling out cancer for the subject if the score) is lower than a pre-determined score, wherein when cancer is ruled out the subject does not receive a treatment protocol. Treatment protocols include for example pulmonary function test (PFT), pulmonary imaging, a biopsy, a surgery, a chemotherapy, a radiotherapy, or any combination thereof. In some embodiments, the imaging is an x-ray, a chest computed tomography (CT) scan, or a positron emission tomography (PET) scan.

In another aspect the invention further provides a method of determining the likelihood of the presence of a lung condition in a subject by measuring an abundance of panel of proteins in a sample obtained from the subject, calculating a probability of cancer score based on the protein measurements and concluding the presence of said lung condition if the score is equal or greater than a pre-determined score. The lung condition is lung cancer such as for example, non-small cell lung cancer (NSCLC). The subject at risk of developing lung cancer In some aspects, the panel includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, or 36 proteins selected from BGH3, C163A, LG3BP, GELS, IBP3, LUM, MASP1, PEDF, S10A6, TSP1, COIA1, ISLR, TETN, FRIL, GRP78, ALDOA, LRP1, FIBA, PRDX1, GSLG1, KIT, CD14, EF1A1, TENX, AIFM1, GGH, IBP3, ENPL, ERO1A, 6PGD, ICAM1, PTPA, NCF4, SEM3G, 1433T, RAP2B, MMP9, FOLH1, GSTP1, EF2, RAN, SODM, DSG2, FRIL, TSP1, LRP1, PRDX1, TETN, TBB3, COIA1, GGH, A1AG1, AIFM1, AMPN, CRP, GSLG1, IBP3, KIT, NRP1, 6PGD, CH10, CLIC1, COF1, CSF1, CYTB, DMKN, DSG2, EREG, ERO1A, FOLH1, ILEU, K1C19, LYOX, MMPI, NCF4, PDIA3, PTGIS, PTPA, RAN, SCF, SEM3G, TBA1B, TCPA, TERA, TIMP1, TNF12, and UGPA.

The subject has or is suspected of having a pulmonary nodule. The pulmonary nodule has a diameter of less than or equal to 3 cm. In one embodiment, the pulmonary nodule has a diameter of about 0.8 cm to 2.0 cm. The subject may have stage IA lung cancer (i.e., the tumor is smaller than 3 cm).

A cancer risk predictor $C_i$ (k) of a molecular risk reversal R is determined as as follows $$Ci(k) = \begin{cases} 0 & \text{if } pCA(k) \leq Ti \\ pCA(k), & \text{otherwise} \end{cases}$$

where the decision threshold $T_i$ for the reversal $R_i$ is defined in Table X and was the median value of $\{S_i(k)\}$ of patients with nodules no larger than 15 mm.

The biological sample such as for example tissue, blood, plasma, serum, whole blood, urine, saliva, genital secretion, cerebrospinal fluid, sweat and excreta.

In one aspect, the determining the likelihood of cancer is determined by the sensitivity, specificity, negative predictive value or positive predictive value associated with the score. The score determined has a negative predictive value (NPV) is at least about 60%, at least 70% or at least 80%.

The measuring step is performed by selected reaction monitoring mass spectrometry, using a compound that specifically binds the protein being detected or a peptide transition. In one embodiment, the compound that specifically binds to the protein being measured is an antibody or an aptamer.

In specific embodiments, the diagnostic methods disclosed herein are used to rule out a treatment protocol for a subject, measuring the abundance of a panel of proteins in a sample obtained from the subject, calculating a probability of cancer score based on the protein measurements and ruling out the treatment protocol for the subject if the score determined in the sample is lower than a pre-determined score. In some embodiments the panel contains at least 2 proteins selected ALDOA, FRIL, LG3BP, IBP3, LRP1, ISLR, TSP1, COIA1, GRP78, TETN, PRDX1 and CD14.

In some embodiments, if cancer is ruled out, there is a period of watchful waiting. Watchful waiting can include periodic follow examination to assess whether the pulmonary nodule has changed characteristics. The follow up examination can include for example a blood assay, an x-ray, a pulmonary function test, or a CT scan.

In certain embodiments, the diagnostic methods disclosed herein can be used in combination with other clinical assessment methods, including for example various radiographic and/or invasive methods. Similarly, in certain embodiments, the diagnostic methods disclosed herein can be used to identify candidates for other clinical assessment methods, or to assess the likelihood that a subject will benefit from other clinical assessment methods.

The high abundance of certain proteins in a biological sample such as plasma or serum can hinder the ability to assay a protein of interest, particularly where the protein of interest is expressed at relatively low concentrations. Several methods are available to circumvent this issue, including enrichment, separation, and depletion. Enrichment uses an affinity agent to extract proteins from the sample by class, e.g., removal of glycosylated proteins by glycocapture. Separation uses methods such as gel electrophoresis or isoelectric focusing to divide the sample into multiple fractions that largely do not overlap in protein content. Depletion typically uses affinity columns to remove the most abundant proteins in blood, such as albumin, by utilizing advanced technologies such as IgY14/Supermix (Sigma St. Louis, Mo.) that enable the removal of the majority of the most abundant proteins.

In certain embodiments of the methods provided herein, a biological sample may be subjected to enrichment, separation, and/or depletion prior to assaying biomarker or putative biomarker protein expression levels. In certain of these embodiments, blood proteins may be initially processed by a glycocapture method, which enriches for glycosylated proteins, allowing quantification assays to detect proteins in the high pg/ml to low ng/ml concentration range. Exemplary methods of glycocapture are well known in the art (see, e.g., U.S. Pat. No. 7,183,188; U.S. Patent Appl. Publ. No. 2007/0099251; U.S. Patent Appl. Publ. No. 2007/0202539; U.S. Patent Appl. Publ. No. 2007/0269895; and U.S. Patent Appl. Publ. No. 2010/0279382). In other embodiments, blood proteins may be initially processed by a protein depletion method, which allows for detection of commonly obscured biomarkers in samples by removing abundant proteins. In one such embodiment, the protein depletion method is a Supermix (Sigma) depletion method.

In certain embodiments, a biomarker protein panel comprises two to 100 biomarker proteins. In certain of these embodiments, the panel comprises 2 to 5, 6 to 10, 11 to 15, 16 to 20, 21-25, 5 to 25, 26 to 30, 31 to 40, 41 to 50, 25 to 50, 51 to 75, 76 to 100, biomarker proteins. In certain embodiments, a biomarker protein panel comprises one or more subpanels of biomarker proteins that each comprise at least two biomarker proteins. For example, biomarker protein panel may comprise a first subpanel made up of biomarker proteins that are overexpressed in a particular lung condition and a second subpanel made up of biomarker proteins that are under-expressed in a particular lung condition.

In certain embodiments of the methods, compositions, and kits provided herein, a biomarker protein may be a protein that exhibits differential expression in conjunction with lung cancer. For example, in certain embodiments a biomarker protein may be one of the proteins associated with lung cancer set forth in Table 1.

In other embodiments, the diagnosis methods disclosed herein may be used to distinguish between two different lung conditions. For example, the methods may be used to classify a lung condition as malignant lung cancer versus benign lung cancer, NSCLC versus SCLC, or lung cancer versus non-cancer condition (e.g., inflammatory condition).

In certain embodiments, kits are provided for diagnosing a lung condition in a subject. These kits are used to detect expression levels of one or more biomarker proteins. Optionally, a kit may comprise instructions for use in the form of a label or a separate insert. The kits can contain reagents that specifically bind to proteins in the panels described, herein. These reagents can include antibodies. The kits can also contain reagents that specifically bind to mRNA expressing proteins in the panels described, herein. These reagents can include nucleotide probes. The kits can also include reagents for the detection of reagents that specifically bind to the proteins in the panels described herein. These reagents can include fluorophores.

Xpresys Lung

1. Introduction 1.1 Background

Xpresys Lung has been in development by Integrated Diagnostics, Inc. (InDi) over the past seven years. The company was founded by scientists with backgrounds in Systems Biology, Computer Science, Chemistry, and Molecular Biology. Lee Hood, MD, PhD is a co-founder and Board member with multiple achievements and awards. The leadership team and investors are experienced and highly credentialed (see InDiDx.com).

1.2 Xpresys Lung Introductory Summary

Xpresys Lung has been developed to differentiate benign from malignant lung nodules. Xpresys Lung is a blood test for proteins that combines expertise in proteomics and computer science using large data sets. Mass spectrometry has been employed as a technology for molecular diagnostics for decades and recent advances in instrumentation allows measurement of hundreds of proteins at a time [X.-J. Li, C. Hayward, P.-Y. Fong, M. Dominguez, S. W. Hunsucker, L. W. Lee, M. McLean, S. Law, H. Butler, M. Schirm, O. Gingras, J. Lamontagne, R. Allard, D. Chelsky, N. D. Price, S. Lam, P. P. Massion, H. Pass, W. N. Rom, A. Vachani, K. C. Fang, L. Hood and P. Kearney, "A Blood-Based Proteomic Classifier for the Molecular Characterization of Pulmonary Nodules," *Science Translational Medicine*, vol. 5, no. 207, p. 207ra142, 2013] Cancers secrete and shed proteins that are different from normal cells and some of these proteins circulate in the blood. InDi started with 388 protein candidates and blood samples stored from both patients with benign and malignant lung nodules. The initial analyses discovered and validated a predictor for benign nodules using a combination of 11 proteins [A. Vachani, H. I. Pass, W. N. Rom, D. E. Medthun, E. S. Edell, M. Laviolette, X.-J. Li, P.-Y. Fong, S. W. Hunsucker, C. Hayward, P. J. Mazzone, D. K. Madtes, Y. E. Miller, M. G. Walker, J. Shi, P. Kearney, K. C. Fang and P. P. Massion, "Validation of a Multiprotein Plasma Classifier to Identify Benign Lung Nodules," *Journal of Thoracic Oncology*, vol. 10, no. 4, pp. 629-637, 2015]. Xpresys Lung version one (XL1) provided significant performance over clinical risk factors physicians use to differentiate benign from malignant lung nodules. InDi has now completed further work with protocol-collected blood samples to refine a second version of Xpresys Lung (XL2) which is a robust test for determining which nodules are benign.

This new version, XL2, improves on XL1 in four ways as described in Section 3.7. These are: 1) a refined intended use population; 2) the identification of 2 of the prior 11 proteins that are most accurate in identifying benign lung nodules; 3) the incorporation of five clinical risk factors; and 4) discovery and validation based on two large prospective studies where samples were collected using a uniform protocol rather than archival biobanks.

XL2 achieves high performance for identifying benign nodules. At a 98% negative predictive value (NPV), the sensitivity is 97% (Table H, Section 3.6). This improved test performs significantly better than PET (NPV of 79% (CI: 66%-88%)(Section 3.3.3.3.). XL2 also performs significantly better than four clinical risk predictors (Mayo, VA, Brock and Herder) (Section 3.3.3.2.). XL2 will provide physicians the best available evidence to determine which nodules are benign.

XL2 will be positioned before PET, bronchoscopy, needle biopsy, and surgery (Section 2.4.2). The confidence from the high NPV values with XL2 will guide more patients with benign nodules into CT surveillance. That will achieve the goal of Xpresys Lung: avoid unnecessary further evaluation of benign nodules, especially invasive procedures.

The projected clinical utility of XL2 is a 36% reduction of invasive procedures (Section 2.4.1). These reductions in invasive procedures will reduce surgeries, surgical mortality, and hospitalizations from biopsy complications (Section 2.4.3).

After the coverage determination, InDi intends to proceed with a prospective interventional trial. This trial will confirm XL2 produces results that have clinical utility in health care delivery settings. This trial is summarized in Section 4.

2. Clinical Aspects of Xpresys Lung and Lung Nodules 2.1 Xpresys Lung Intended Use and Description 2.1.1 Intended Use Xpresys Lung version 2 (XL2) is intended for the evaluation of 8-30 mm lung nodules in patients 40 years or older where the physician estimates a lower cancer risk (pretest probability of cancer is 0 to 50%). The goal for Xpresys Lung is to identify those nodules that are likely benign so those nodules can be safely observed by CT surveillance rather than undergo costly and risky invasive procedures such as biopsy and surgery.

2.1.2 Description of Xpresys Lung

XL2 is a risk predictor that integrates molecular (proteomic) measurements with clinical risk factors. Proteins associated with cancers or benign processes are measured. These proteins are secreted or shed from cells in the lung and measured in a blood plasma sample. The XL2 result will be reported as Likely Benign (90-98% negative predictive value) or Indeterminate (post-test cancer risk not significantly lower than the pre-test risk of cancer). For details see Section 3.6.

2.2 The Unmet Need for Lung Nodules is Significant and Growing 2.2.1 Lung Nodules 2.2.1.1 Definitions Lung nodules are rounded densities seen by x-ray imaging. X-ray imaging can be a chest radiograph (CXR) or computer-assisted tomography (CAT scan). Nodules are mostly surrounded by lung tissue and are also called coin lesions, solitary pulmonary nodules or lesions, or a "spot" on the lung. Rounded densities larger than 30 mm in diameter are lung masses, not nodules. The edges of the nodules can be described as smooth or irregular (stellate or spiculated), and irregular edges somewhat more indicative for cancer. Heavily calcified nodules with smooth edges are generally benign and solid nodules that have not shown growth over time are considered benign. With improved CT imaging subsolid nodules, ground-glass opacities or part-solid nodules, are now seen and have different guidelines. The focus of this application is 8-30 mm solid nodules and not subsolid nodules.

For a comprehensive review of nodules and their evaluation see the 2-part series by Patel, et al. [V. K. Patel, S. K. Naik, D. P. Naidich, W. D. Travis, J. A. Weingarten, R. Lazzaro, D. D. Gutterman, C. Wentowski, H. B. Grosu and S. Raoof, "A Practical Algorithmic Approach to the Diagnosis and Management of Solitary Pulmonary Nodules. Part 1: Radiologic Characteristics and Imaging Modalities," *Chest*, vol. 143, no. 3, pp. 825-339, 2013; V. K. Patel, S. K. Naik, D. P. Naidich, W. D. Travis, J. A. Weingarten, R. Lazzaro, D. D. Gutterman, C. Wentowski, H. B. Grosu and S. Raoof, "A Practical Algorithmic Approach to the Diagnosis and Management of Solitary Pulmonary Nodules. Part 2: Pretest Probabiity and Algorithm," *Chest*, vol. 143, no. 3, pp. 840-846, 2013].

2.2.1.2 Numbers of Nodules Detected Annually

The estimated number of new lung nodules detected annually in the US is 1.57 million [M. K. Gould, T. Tang, I.-L. A. Liu, J. Lee, C. Zheng, K. N. Danforth, A. E. Kosco, J. L. Di Fiore and D. E. Suh, "Recent Trends in the Identification of Incidental Pulmonary Nodules," *American Journal of Respiratory and Critical Care Medicine*, vol. 192, no. 10, pp. 1208-1214, 2015]. The number of new lung nodules has been increasing due to a combination of factors including CT scan technology improvements and more CT scans being done. The 1.57 million estimate is for nodules that are 4-30 mm diameter; the estimate for 8-30 mm nodules is 800,000 per year.

2.2.1.3 Incidental and Screen-Detected Nodules

The above estimate of 1.57 million nodules per year is only for incidentally found nodules and does not include another 1.5 million screen-detected nodules. Incidental means the imaging was done for reasons other than nodule detection. For example, imaging of the heart, upper abdomen, and even mammography includes lung tissue so a lung nodule is an incidental finding.

Lung cancer screening now has coverage in the United States. As of Apr. 26, 2016 there were 806 sites registered for screening. Initial estimates are that another 1.5 million nodules per year will be found once screening programs are in place. The National Lung Screening Trial (NSLT) had a screen positive rate of 24% and estimated there are 7 million persons in the United States that meet NSLT enrollment criteria [The National Lung Screening Trial Research Team, "Reduced Lung-Cancer Mortality with Low-Dose Computed Tomographic Screening," The New England Journal of Medicine, vol. 365, pp. 395-409, 2011].

2.2.1.4 Lung Nodule "Epidemic" and Health Care

Early detection of lung nodules is a great opportunity to reduce lung cancer mortality but it comes with significant risks. These risks are both for patients and health care delivery. For patients a major problem is the risk of unnecessary invasive procedures to find the minority of nodules that are cancer. XL2 addresses these avoidable procedures.

For health care delivery, the risks are both costs and overloading the health care system. The majority of patients with nodules will be over 65 years of age. In the NLST, over 57% of enrollees in the NSLT were over 65 years of age. Also the rates of nodule detection increased dramatically with age, at least until age 89. So Medicare enrollees are more likely to meet lung cancer screening criteria and have more nodules detected. If the nodules are ≥8 mm, then further testing is indicated, XL2 addresses these avoidable procedures.

2.2.1.5 Relevance to Medicare Population

Of the expected 3 million nodules per year found incidentally or by lung cancer screening, the majority will be Medicare age. Four recent studies underscore the importance of lung cancer evaluations to the Medicare population:

The mean age of 377 eligible patients in an 18 site retrospective chart review study was 65 [M. T. Tanner, J. Aggarwal, M. K. Gould, P. Kearney, G. Diette, A. Vachini, K. C. Fang and G. A. Silvestri, "Management of Pulmonary Nodules by Community Pulmonologists. A Multicenter Observational Study," *Chest*, vol. 148, no. 6, pp. 1405-1414, 2015]. All patients had nodules 8-20 mm in diameter.

A prospective study across 12 sites and 475 patients found 62.5% of patients were 65 years of age or older [A. Vachani, Z. Hammoud, S. Springmeyer, N. Cohen, D. Nguyen, C. Williamson, S. Starnes, S. Hunsucker, S. Law, X.-J. Li, A. Porter and P. Kearney, "Clinical Utility of a Plasma Protein Classifier for Indeterminate Lung Nodules," *Lung*, vol. 193, no. 6, pp. 1023-1027, 2015]. All patients had nodules 8-30 mm in diameter.

Over 50% of patients in a prospective study across 33 sites and 685 patients were 65 years of age or older (PANOPTIC Study). All patients had nodules 8-30 mm in diameter.

A recent study reported that between January 2009 and December 2011, 8,979 Medicare patients from a random sampling of 5% of Medicare claims, underwent lung cancer evaluations because of an abnormal chest CT scan [T. Lokhandwala, M. A. Bittoni, R. A. Dann, A. O. D'Souza, M. Johnson, R. J. Nagy, R. B. Lanman, R. E. Merritt and D. P. Carbone, "Costs of Diagnostic Assessment for Lung Cancer: A Medicare Claims Analysis," *Clinical Lung Cancer*, 2016].

2.2.2 Lung Nodule Evaluation: Current Practice and Need for Improvement

2.2.2.1 Guidelines

Groups have published guidelines for the evaluation of lung nodules [H. MacMahon, J. H. Austin, G. Gamsu, C. J. Herold, J. R. Jett, D. P. Naidich, E. F. Patz and S. J. Swensen, "Guidelines for Management of Small Pulmonary Nodules Detected on CT Scans: A Statement from the Fleischner Society," *Radiology*, vol. 237, no. 2, pp. 395-400, 2005; M. K. Gould, J. Donington, W. R. Lynch, P. J. Mazzone, D. E. Midthun, D. P. Naidich and R. S. Wiener, "Evaluation of Individuals With Pulmonary Nodules: When Is It Lung Cancer?: Diagnosis and Management of Lung Cancer, 3rd ed: American Cllege of Chest Physicians Evidence-Based Clinical Practice Guidelines," *Chest*, vol. 143, no. 5 suppl, pp. e93S-e120S, 2013; M. E. Callister, D. R. Baldwin, A. R. Akram, S. Barnard, P. Cane, J. Draffan, K. Franks, F. Gleeson, R. Graham, P. Malhotra, M. Prokop, K. Rodger, M. Subesinghe, D. Waller and I. Woolhouse, "British Thoracic Society Guidelines For the Investigation and Management of Pulmonary Nodules," *Thorax*, vol. 70, no. Suppl 2, pp. ii1-ii54, 2015]. A set of guidelines regarding lung cancer is published and updated by the American College of Chest Physicians (ACCP). The ACCP guidelines for lung nodules, updated in 2013, are the primary reference used by pulmonologists in the United States. It is important to focus on ACCP section 4.0 for ≥8 mm nodules, the intended use for Xpresys Lung.

2.2.2.2 General Approach to 8-30 mm "Indeterminant" Nodules

Nodules are found with imaging other than chest CT scans (Section 2.2.1.3). Thus a chest CT with high-resolution imaging of the nodule is often needed. The CT findings alone or prior images may indicate a nodule is benign. The details of imaging and differential diagnosis of nodules has been reviewed by Patel and colleagues. When CT imaging alone is not definitive, the nodule is described as "indeterminant".

CT imaging accuracy was studied using expert reviewers in a retrospective study of 344 nodules before any nodules were determined to be benign [J. W. Fletcher, S. M. Kymes, M. Gould, N. Alzraki, R. E. Coleman, V. J. Lowe, C. Marn, G. Segall, L. A. Thet and K. Lee, "A Comparison of the Diagnostic Accuracy of {18}F-FDG PET and CT in the Characterization of Solitary Pulmonary Nodules," *Journal of Nuclear Medicine*, vol. 49, pp. 179-185, 2008.]. CT results (after excluding 128 [27%] without a "reference standard" or an "inconclusive result") showed a sensitivity of 95.6% (95% CI, 91.3%-97.9%), and a specificity of 40.6% (95% CI, 33.0%-48.7%). The results with CT interpretation of indeterminate nodules with general radiologists will be expected to be inferior.

Most 8-30 mm nodules are indeterminant. The ACCP Guidelines state: "Although clinical and radiographic [CT scans] characteristics cannot reliably distinguish between benign and malignant nodules in most individuals, it is nevertheless important to estimate the clinical probability of malignancy before ordering imaging tests or biopsy procedures". The pretest probability of malignancy (pCA) is estimated by using clinical judgment or with a quantitative risk model (see Section 2.2.4). Establishing a pCA creates three groupings (excluding patients at high surgical risk), Low, Intermediate, and High probability. The exact numbers changed between guideline revisions but are similar, with <5% pCA being Low and >65% pCA being High. The general concept is that Low risk patients will be observed with further CT surveillance to watch for growth if a nodule is malignant.

Conversely, the guidelines suggest those patients in the High risk group go directly to surgery. The logic is that the probability of cancer is high enough that a negative biopsy will not change the care pathway.

The Intermediate risk group (5-65% pCA) are recommended to enter the diagnostic odyssey with PET scanning often the next step. A negative PET suggests a benign nodule, so the patient is followed with CT scans. A positive PET scan goes on to surgery or biopsy. This is the overall concept, but PET has sensitivity and specificity problems as discussed in Sections 2.2.6.

2.2.2.3 The Problems with Guidelines and Current Practice

The guidelines are conceptually good, but are based on mostly weak evidence and there is evidence that they are not followed.

The guidelines are based on weak evidence. The ACCP guidelines use the GRADE system and most recommendations regarding ≥8 mm nodules are 2C, a weak recommendation with low quality evidence. There are 3 recommendations that are level 1C, a strong recommendation with low quality evidence, which are: soliciting patient preference, going to further evaluation if there's evidence of malignant growth, and a preference for thoracoscopic rather than open biopsy.

There is abundant evidence that suggest the guidelines are not followed [D. R. Baldwin, "Development of Guidelines for the Management of Pulmonary Nodules: Toward Better Implementation," *Chest*, vol. 148, no. 6, pp. 1365-1367, 2015; R. S. Wiener, M. K. Gould, C. G. Slatore, B. G. Fincke, L. M. Schwartz and S. Woloshin, "Resource Use and Guideline Concordance in Evaluation of Pulmonary Nodules for Cancer: Too Much and Too Little Care," *JAMA Internal Medicine*, vol. 174, no. 6, pp. 871-880, 2014]. A retrospective cohort study of 15 Veterans hospitals and 300 patients found that only 45% of the patient care for nodules was in concordance with guidelines. A pulmonary community practice observational record review of 18 practices and 377 patients found a wide variation in management of nodules. The surgery for benign nodules rate was 35% and the rate of surgery was the same for Low, Intermediate and High risk patients. The risk categories were calculated by the study and despite a Low risk, 28% had biopsies and 17% had surgery. Furthermore, the rate of malignant nodules observed with CT surveillance was 24.5%, resulting in a risk of delayed diagnosis.

The rates of surgery for benign nodules range between 10% and 55% as summarized by Vachani, et al. in their publication of a survey from 196 pulmonologists that supports the potential of a non-invasive biomarker to strongly and independently affect management decisions [A. Vachani, N. T. Tanner, J. Aggarwal, C. Mathews, P. Kearney, K. C. Fang, G. Silvestri and G. B. Diette, "Factors That Influence Physician Decision Making for Indeterminate Pulmonary Nodules," *Annals of the American Thoracic Society*, vol. 11, no. 10, pp. 1586-1591, 2014]. High rates of surgery for benign nodules are problematic because of the morbidity and mortality associated with surgery. Surgical risk figures are dependent on the population and the procedures used. The surgical mortality estimate after lobectomy in a Medicare age patient is 2-3% (Section 2.4.3.2).

Therefore, there is a clear opportunity for improvement in current practice. The rates of avoidable surgery for benign nodules was 35% in community practices [7] and reported as high as 55%. The high rates for avoidable PET scans, biopsies, and surgeries are addressed in Sections 2.4.1.3, 2.4.3.1, and 2.4.3.2 respectively.

2.2.3 Physician Pretest Probability of Cancer (pCA), Lower Cancer Risk Group and the Unmet Need The guidelines recommend a determination of the pretest probability of malignancy (pCA) by clinical judgment or with a model such as the Mayo equation [S. J. Swensen, M. D. Silverstein, D. M. Ilstrup, C. D. Schleck and E. S. Edell, "The Probbility of Malignancy in Solitary Pulmonary Nodules. Application to Small Radiologically Indeterminate Nodules," *Archives of Internal Medicine*, vol. 157, no. 8, pp. 849-855, 1997; S. J. Swensen, M. D. Silverstein, E. S. Edell, V. F. Trastek, G. L. Aughenbaugh, D. M. Ilstrup and C. D. Schleck, "Solitary Pulmonary Nodules: Clinical Prediction Model Versus Physicians," *Mayo Clinic Proceedings*, vol. 74, no. 4, pp. 319-329, 1999]. Pulmonologists uniformly used their clinical judgment for assigning pCA [R. S. Wiener, C. G. Slatore, C. Gillespie and J. A. Clark, "Pulmonologists' Reported Use of Guidelines and Shared Decision-making in Evaluation of Pulmonary Nodules: A Qualitative Study," *Chest*, vol. 148, no. 6, pp. 1415-1421, 2015], and other physicians do not determine a pCA [S. E. Golden, R. S. Wiener, D. Sullivan, L. Ganzini and C. G. Slatore, "Primary Care Providers and a System Problem: A Qualitative Study of Clinicians Caring for Patients With Incidental Pulmonary Nodules," *Chest*, vol. 148, no. 6, pp. 1422-1429, 2015].

The PANOPTIC trial (Section 2.3) collected pCA results upon clinical presentation, after a CT scan, and before other testing. The physicians in the study used their clinical judgment 80% of the time and were significantly better than the two quantitative risk models used most often, the VA [M. K. Gould, L. Ananth and P. G. Barnett, "A Clinical Model to Estimate the Pretest Probability of Lung Cancer in Patients with Solitary Pulmonary Nodules," *Chest*, vol. 131, no. 2, pp. 383-388, 2007] and Mayo, (AUC 0.85 vs 0.75 (VA) p<0.001 and vs 0.78 (Mayo) p=0.011). This indicates that physician pCA is best for separation of patients with nodules into higher and lower cancer risk groups such as a pCA of 50% or less risk of cancer (the intended use group for XL2).

Figure 24:
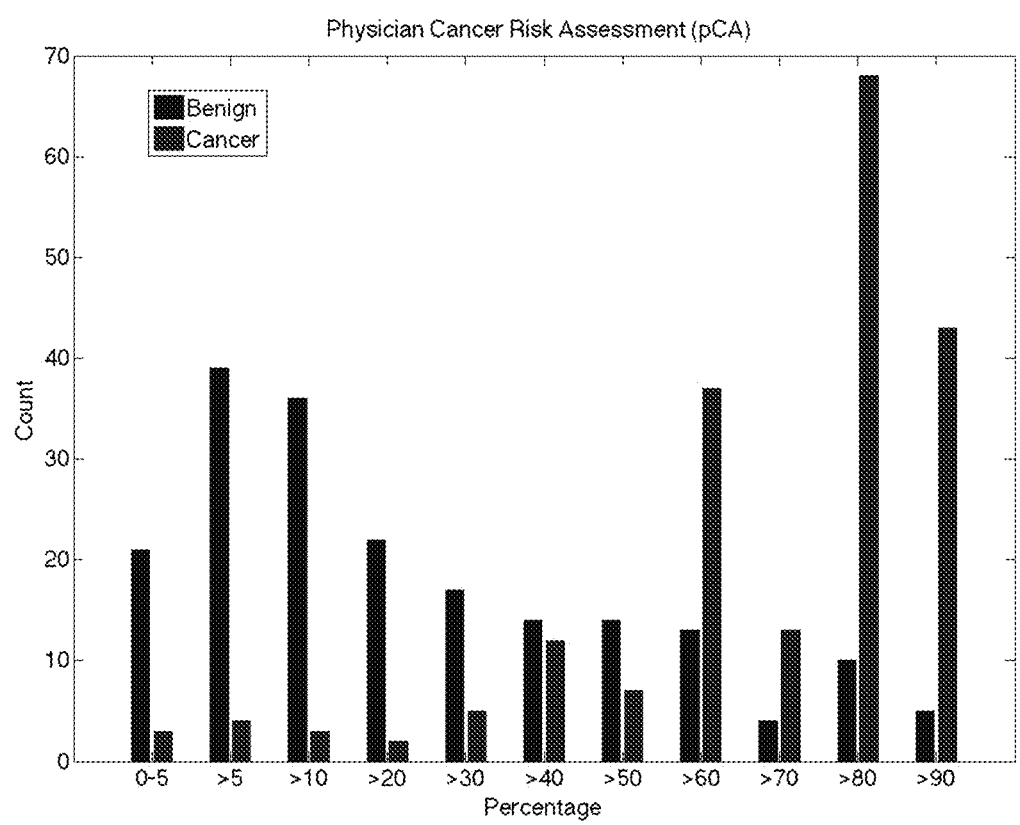
FIG. 24 is a graph showing PANOPTIC trial physician pretest probability (pCA) counts displayed by deciles (the first two columns are 5% increments). Shown are 196 cancer nodules and 196 benign nodules.

Further analyses of physician pCA data elucidates the need for XL2. As shown in FIG. 24, physicians are good at placing most cancerous nodules into pCA greater than 50% and most benign nodules into pCA of 50% or less. However, most benign nodules are not in the Low risk (0-5% pCA) category where CT surveillance is recommended. Most benign nodules are in the Intermediate risk category where further evaluation is recommended. These evaluations lead to many benign nodules undergoing risky and expensive procedures. In PANOPTIC, the 33 research sites were nearly all academic centers and integrated health networks yet the rates for surgery on benign nodules was 18% and biopsy of benign nodules was 30%. The comparable figures for community pulmonary practices (where most patients receive their care) are 35% of surgeries were performed on benign nodules and 62% of biopsies were performed on benign nodules.

Therefore, the unmet need is to provide the treating physician with a test for a Lower Risk nodule (pCA of 50% or less). This test should have a high Negative Predictive Value (NPV) result for a benign nodule. The post-test result then indicates the nodule is Low risk (0-5% pCA) and CT surveillance is recommended.

2.2.3.1 Physician pCA for Lower Risk Patients

As shown in FIG. 24, physicians were quite good establishing risk for all nodules (the entire risk population) with an AUC of 85%. However, they were not as good with lower risk (pCA 50% or less) patients (n=178 with 29 cancer and 149 benign nodules). In those lower risk patients, the physician AUC is 0.69 and is shown graphically in FIG. 28, Section 3.3.4.1.

Most of these benign nodules are within the Intermediate risk population where the guidelines recommend further evaluation. If the guidelines are followed, most of those 149 patients with benign nodules will undergo avoidable imaging and biopsy. This underscores the need for XL2 and is discussed further in Sections 2.4 and 3.4 on Clinical Utility.

2.2.4 Quantitative Cancer Risk Models

Figure 25:
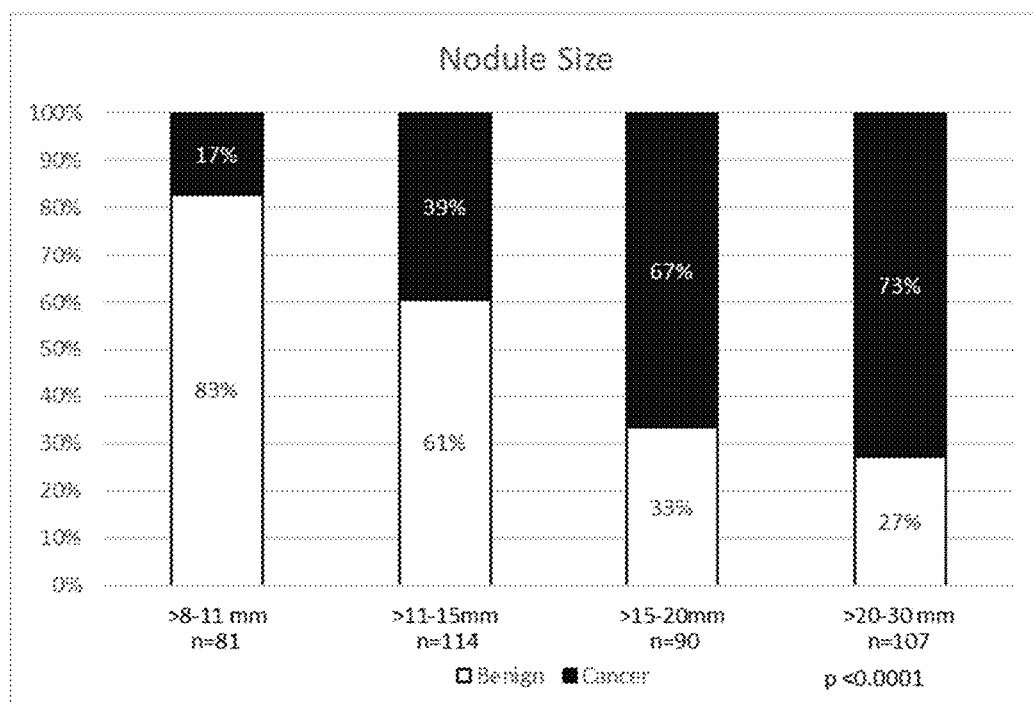
FIG. 25 is a graph showing lung nodules in the PANOPTIC trial separated by size with proportions of cancer and benign nodules. Shown are 392 nodules: 196 cancer nodules and 196 benign nodules.

The PANOPTIC results show that physicians are better than quantitative models at assigning pretest probability of cancer risk (pCA). The major factor for cancer risk in a pulmonary nodule is size. FIG. 25 shows the increasing prevalence of cancer associated with size. Other major factors are smoking history and age. Since CT screening is just being implemented in the United States, most risk models were developed for incidental nodules rather than screen detected nodules.

2.2.4.1 Incidental Nodule Models

The Mayo Clinic and a Veterans Administration (VA) Hospital group have developed prediction models that are based on similar but not identical factors. The prevalence of cancer in the VA model is considerably higher so it performs differently. These and other models have been summarized in the ACCP 2013 guidelines with support given to the Mayo model. The first sentence in Section 4.1 of the Guidelines reads: "Although clinical and radiographic characteristics cannot reliably distinguish between benign and malignant nodules in most individuals, it is nevertheless important to estimate the clinical probability of malignancy before ordering tests or biopsy procedures."

2.2.4.2 Screen-Detected Nodules

Using two Canadian lung cancer screening trials, McWilliams published a set of quantitative equations with AUC>0.90 [A. McWilliams, M. C. Tammemagi, J. R. Mayo, H. Roberts, G. Liu, K. Soghrati, K. Yasufuku, S. Martel, F. Laberge, M. Gingras, S. Atkar-Khattra, C. D. Berg, K. Evans, R. Finley, J. Yee, J. English, P. Nasute, J. Goffin, S. Puksa, L. Stewart, S. Tsai, M. R. Johnston, D. Manos, G. Nicholas, G. D. Goss, J. M. Seely, K. Amjadi, A. Tremblay, P. Burrowes, P. MacEachern, R. Bhatia, M.-S. Tsao and S. Lam, "Probability of Cancer in Pulmonary Nodules Detected on First Screening CT," *The New England Journal of Medicine*, vol. 369, no. 10, pp. 910-919, 2013]. The equations are available through Brock University. The combined data includes 2,961 patients, but only 144 (<5%) of the nodules were malignant. They included subsolid nodules, but 79% were solid. The mean nodule size was 4.1 mm and median was 3.4 mm consistent with a low proportion of cancers. Predictors of cancer in the model included older age, female sex, family history of lung cancer, emphysema, larger nodule size, location of the nodule in the upper lobe, part-solid nodule type, lower nodule count, and speculation.

The McWilliams paper recommends their equations be used for nodules from a baseline screening, low-dose CT scan (rather than incidentally found nodules).

2.2.5 Guidelines for Radiologists and CT Scan Nodule Reporting; Lung-RADS and Fleishner There are guidelines for radiologists regarding reporting lung nodules and the intervals for follow-up imaging. The guidelines for incidental nodules <8 mm come from the Fleishner Society. Fleishner guidelines were developed for incidentally found nodules.

Guidance from the American College of Radiology for lung cancer screening programs is Lung-RADS. Lung-RADS was developed to improve reporting and management recommendations to clinicians. One goal was to reduce the number of false positive reports needing further evaluation without increasing the false negatives. Based on the literature, they changed the size of nodules considered "positive" to 6 mm from 4 mm as used in the NLST. Another goal for Lung-RADS is a structured reporting system for lung cancer screening programs based on nodule size, CT imaging density, and whether the nodule was present at baseline, enlarging, or new at follow-up. Lung-RADS does not include other clinical factors that clinicians use such as smoking history, age, nodule location, or exposures (e.g. asbestos).

2.2.6 PET Scans

Positron Emission Tomography with contrast agents (PET) is useful in lung cancer staging, but PET has significant limitations for the diagnosis of lung nodules. These limitations are a lack of sensitivity, especially for smaller nodules, non-standardized reading and reporting, and false positive scans for inflammatory and infectious nodules.

2.2.6.1 PET sensitivity. Smaller nodules are difficult to image and PET was initially limited to nodules >10 mm. Small nodules and low-uptake of contrast in low-metabolic malignancies are major limits to sensitivity for PET imaging. The initial sensitivities reported from single-center experience with PET were estimated to be 95%. The estimate dropped to 87% when reviewed by the ACCP in 2007. Current estimates range from 72% to 94% and are reviewed in the 2013 ACCP Guidelines in section 4.2.3. A 2014 meta-analysis reports a pooled sensitivity of 89% (95% CI, 86%-91%) and high heterogeneity when areas of infectious lung disease are included [S. A. Deppen, J. D. Blume, C. D. Kensinger, A. M. Morgan, M. C. Aldrich, P. P. Massion, R. C. Walker, M. L. McPheeters, J. B. Putnam and E. L. Grogan, "Accuracy of FDG-PET to Diagnose Lung Cancer in Areas With Infectious Lung Disease. A Meta-analysis," *JAMA*, vol. 312, no. 12, pp. 1227-1236, 2014].

Early publications of PET about nodules were encouraging such that the 2007 ACCP guidelines gave PET an evidence Grade of 2A, but concerns about the quality of evidence and risk of bias decreased the recommendation to Grade 2C [V. S. Nair, V. Sundaram, M. K. Gould and M. Desai, "Utilization of [18F] FDG PET Imaging in the National Lung Screening Trial," *Chest*, 2016]. The review articles by Patel initially state that PET is "very accurate" but after a summary of more recent data they emphasize the shortcomings of PET, and add a limitation that PET is best suited for nodules with an "intermediate" pCA. A recent study using NLST data showed PET use for nodules was 11% of 14,195 patients, but there was still inappropriate PET use in 21% of cases which suggested overutilization with small nodules and concern about contributing to excess healthcare costs.

Recently PET has been combined with CT to improve resolution so the size limitation has been re-stated to 8-10 mm. The combination is anticipated to improve the results but with increased cost and much higher radiation exposure (Section 2.2.6.4)

2.2.6.2 The reporting of PET has variation and is often only reported subjectively. Since the isotope in the contrast agent degrades (~110 min half-life for fluorine-18), the dose administered to a patient depends on the proximity in time to when the isotope was created. So the degree of a positive or negative PET depends on comparison of uptake in a normal high metabolic area with the area in question. This comparison is often just reported subjectively but can be measured. A measured value, the Standard Uptake Value (SUV) is produced. A SUV value greater than 2.5 is considered positive. Some publications, such as Herder [G. J. Herder, H. van Tinteren, R. P. Golding, P. J. Kostense, E. F. Comans, E. F. Smit and O. S. Hoekstra, "Clinical Prediction Model to Characterize Pulmonary Nodules: Validation and Added Value of 18F-Fluorodeoxyglucose Positron Emission Tomography," *Chest*, vol. 128, no. 4, pp. 2490-2496, 2005] only reported subjective results on a four-point descriptive scale, without SUV values. Subsequent publications must guess at a similar scale using SUV values. For example, one of these publications (Al-Ameri) [A. Al-Ameri, P. Malhotra, H. Thygesen, P. K. Plant, S. Vaidyanathan, S. Karthik, A. Scarsbrook and M. E. Callister, "Risk of Malignancy in Pulmonary Nodules: A Validation Study of Four Prediction Models," *Lung Cancer*, vol. 89, no. 1, pp. 27-30, 2015] used a 3 division scale of SUV with good results. However, this paper did not report mean or median sizes of nodules nor numbers of nodules evaluated in their 139 patients with PET scans. Of the total of 244 patients, they report that 188 had a solitary nodule (presumably the remainder had multiple nodules), and the largest nodule was ≤10 mm in 103 patients and PET sensitivity was not addressed in the study which appears to have a lot of smaller nodules. Consequently, it is difficult to derive conclusions or compare to other studies where basic nodule characteristics (such as nodule size) are disclosed.

So these example publications, Herder and Al-Ameri, highlight the lack of standardization across sites and physicians in PET interpretation and reporting.

2.2.6.3 False positive scans for nodules are an additional problem. The Tanner chart review of community practices found a false positive PET scan rate of 39%. Also notable is that a PET scan was performed in 37% of patients and was associated with increased intensity of biopsy and surgery compared to surveillance (P<0.0001).

Deppen reported a meta-analysis which included endemic areas for infectious lung disease. Besides extreme heterogeneity regarding accuracy for diagnosis of lung nodules, the specificity in endemic regions was only 61% compared to 77% in nonendemic regions. They concluded their data did not support the use of FDP-PET to diagnose lung cancer in endemic regions. These endemic regions in the United States include the Mississippi, Ohio, and Missouri river valley regions along with the southwestern United States including the Central Valley of California.

2.2.6.4 PET is non-invasive but not risk free. The radiation dose from PET alone is significant at 14 mSv. When combined with CT, as is now usual, the dose increases to 24 mSv. For comparison, a low-dose CT for screening is 1.4 mSv.

2.3. InDi Clinical Research to Support Xpresys Lung

Integrated Diagnostics (InDi) has worked with leading physicians and scientists to produce peer-review publications and presentations in major journals and meetings. This research has been conceived, designed, and conducted with collaboration of major leaders in the fields of molecular diagnosis, lung cancer, and pulmonary nodules. These efforts will be summarized here with details of results in the appended publications. The results of XL2 and comparisons with existing evaluation tools are presented in Section 3.

2.3.1 Discovery, Verification, and Validation of XL1

The initial discovery for Xpresys Lung started with 388 candidate proteins and an assay was developed for 371 of them. The first samples were frozen plasma from 3 sites (n=143) and 36 cooperative proteins were identified for a classifier. Verification was with 13 proteins from 4 sites (n=104) and along with discovery work was published in Science Translational Medicine [1] in 2013. At this time, it was determined that this systems biology and proteomics approach was most suited for excluding malignancy in nodules between 8 and 30 mm in size. Validation for XL1 was done with 11 proteins, of which 5 were diagnostic and 6 were used for normalization, with new archival samples from 4 sites (n=141) and published in the Journal of Thoracic Oncology [2] in 2015.

2.3.2 Survey and Chart Review

InDi contracted with Boston Healthcare for a survey of pulmonary physicians to determine their practice patterns and potential acceptance of a biomarker for pulmonary nodules. The need and acceptance was confirmed and published in 2014.

Boston Healthcare also collected data for a comprehensive chart review of community pulmonary practices to understand practice patterns where most of pulmonary nodules are managed. Nodule management of 377 patients from 18 geographically diverse sites were assessed. The results have been presented at national meetings and published in 2015 [10]. Of particular note was finding that benign nodules had a 61% biopsy and 35% surgery rate.

2.3.3 Analytic Validation

Analytic validation has been performed and published in 2015 [X.-J. Li, L. W. Lee, C. Hayward, M.-Y. Brusniak, P.-Y. Fong, M. McLean, J. Mulligan, D. Spicer, K. C. Fang, S. W. Hunsucker and P. Kearney, "An Integrated Quantification Method to Increase the Precision, Rocustness, and Resolution of Protein Measurement in Human Plasma Samples," *Clinical Proteomics*, vol. 12, no. 3, 2015].

2.3.4 Clinical Utility and Discovery/Verification of XL2

Study 1013 is a prospective study started in 2012 and enrolled 475 patients from 12 sites. This study was unique since it included patients who were undergoing procedures to determine if a lung nodule is benign or cancerous. Therefore a tissue diagnosis was available and a potential change in the use of invasive procedures could be assessed if Xpresys Lung would have been used. The main finding was a 32% decrease if XL1 result was followed, but 24% of malignant nodules would have been routed to CT surveillance.

Study 1013 results were also used for the discovery of XL2 (Section 3.1).

2.3.5 PANOPTIC and XL2 Validation Study 1001

(PANOPTIC) was also started in 2012 and enrolled 685 patients from 33 sites. This study included all intended use nodules before any diagnostic testing had been initiated. The study is unique because physician pretest probability of cancer (pCA) was collected. Data was used to validate XL2 (Section 3.1) and present the performance and comparison data in this document.

2.4 Clinical Utility, Anticipated Clinical Use of XL2, and XL2 Impact on Invasive Procedures

2.4.1 Clinical Utility

XL2 is a robust test for determining which lower risk nodules are benign. The clinical need that XL2 addresses is to appropriately place more patients with benign nodules into CT surveillance. This will avoid unnecessary imaging and invasive procedures which is the primary clinical utility goal for XL2. Results from the PANOPTIC trial can be used to estimate the effect of XL2 at many Negative Predictive Values (NPV) (Table H, Section 3.6). Here we will use the 98% NPV values and discuss the clinical context. The 98% NPV is used as the majority of likely benign reports have a NPV of 98% (Table H, Section 3.6).

2.4.1.1 Clinical Utility at 98% NPV

At a NPV of 98%, the sensitivity of XL2 is 97%, with a specificity of 44% (Table D, Section 3.2). If XL2 was used in all lower risk nodules (n=178), the reduction of invasive procedures in PANOPTIC on benign nodules would be 36% (15 of 42) (Section 3.4).

The number of patients tested would be 178 patients, 69 (39%) would receive a "Likely Benign" test result with a 98% probability (NPV) of being benign. That very high NPV would likely lead to CT surveillance alone.

There were 29 malignant nodules in the lower risk group and 13 of 29 (45%) were routed to CT surveillance by the clinicians. The use of XL2 at the 98% NPV level, would route 1 patient (3%) to CT surveillance (Table G, Section 3.4).

2.4.1.2 Clinical Utility and PET Scans

At the 98% NPV level, 21 of 56 (36%) of PET scans that were obtained in patients with benign nodules would have been avoided with the use of XL2. In the same group there were 19 PET scans done on malignant nodules which were then incorrectly routed to CT surveillance. XL2 use would have reduced that to only 1 PET scan followed by CT surveillance.

2.4.2 Anticipated Clinical Use and Timing of XL2 Testing

Integrated Diagnostics (InDi) plans to promote XL2 to pulmonologists, both academic and community. The primary goal of XL2 is to reduce avoidable imaging and procedures on benign nodules in the intended use population. The test result document (Section 3.6) will report negative predictive values of 90-98% as both the actual value, and as "Likely Benign". The ordering physician can then decide with the patient what level of risk is appropriate. If a patient is adverse to procedures, a lower NPV result such as 95% may be chosen. Conversely, if a patient is very adverse to an observation period with a surveillance CT, then a 98% NPV result may be needed to decide for CT surveillance.

2.4.2.1 Timing of XL2 Testing

Xpresys Lung 2 will be used at one of several points in the evaluation of patients with nodules. Most often, XL2 will be used on lower risk indeterminate nodules (Section 2.2.2.2) after a CT scan and before any other imaging, such as PET. XL2 in PANOPTIC, showed favorable clinical utility if done before PET scanning (Section 2.4.1.2). This use would avoid both the expense of PET and the risk from high radiation (2.2.6.4).

XL2 can also be used in patients with contraindications to invasive procedures or surgery before deciding about CT surveillance or empiric treatments such as irradiation.

2.4.3 XL2 Impact on Invasive Procedures for Indeterminate Nodules

In this section InDi will estimate the effects of XL2 on invasive procedures and the morbidity and mortality associated with these procedures.

There are two types of invasive diagnostic procedures: biopsies and surgical resection.

2.4.3.1 Biopsies of Nodules

Biopsies can be obtained through a bronchoscope or a needle passed through the chest wall with CT image guidance. A community practice chart review found 38% of patients had a form of biopsy. Complications with biopsies or surgery are increased with age, smoking history, and other lung disease.

Biopsy through the bronchoscope has the lowest risk with a 2-4% risk of bleeding or pneumothorax. The disadvantage of this procedure is inaccurate sampling of the nodule. Correct sampling averages about 50%. The correct sampling rate may improve with modern navigation techniques that are being adopted. Bronchoscopic biopsy use for nodules is currently about 20% of nodules.

Needle biopsies are done in about 15% of patients with nodules with a 1% risk of bleeding, and a 15-19% risk of pneumothorax [R. S. Wiener, L. M. Schwartz, S. Woloshin and G. Welch, "Population-Based Risk for Complications After Transthoracic Needle Lung Biopsy of a Pulmonary Nodule: An Analysis of Discharge Records," *Annals of Internal Medicine*, vol. 155, no. 3, pp. 137-144, 2011]. About half (7%) of patients with a pneumothorax require chest tube placement with a significant period of hospitalization. Most needles biopsies are diagnostic but the risk of a non-diagnostic result with a malignant nodule is about 20%.

Biopsies (combined bronchoscopy and needle) are performed in about 25% of nodules (200,000) and the procedures are for benign nodules in 42-62% (104,000). Complications from biopsies result in hospitalization in 2-7% (range of bronchoscopy and needle biopsy complications, median 4.5%). That translates into 4,680 excess hospitalizations (104,000×0.045) per year that are potentially avoidable.

2.4.3.2 Surgery for Nodules

Eventually most malignant nodules go to surgery for resection and about 15-25% of patients have biopsy attempts before surgery (not included in XL2 Impact estimates). The overall surgery rate is about 34% (270,000 per year) for benign and malignant nodules in the nodule population. Complications include death (2% in CMS population [C. E. Iniguez, K. W. Armstrong, Z. Cooper, J. S. Weissman, C. T. Ducko, J. O. Wee, M. P. Martinez, R. Bueno, M. T. Jaklitsch and D. C. Wiener, "Thirty-Day Mortality After Lobectomy in Elderly Patients Eligible for Lung Cancer Screening," *The Annals of Thoracic Surgery*, vol. 101, no. 2, pp. 541-546, 2016]), prolonged lung air leak (3-5%), and pneumonia (1-8%).

Published rates for surgery for benign nodules range from 31-44% [The National Lung Screening Trial Research Team, "Results of Initial Low-Dose Computed Tomographic Screening for Lung Cancer," *The New England Journal of Medicine*, vol. 368, no. 21, pp. 1980-1991, 2013]. That translates into about 102,000 surgeries (270,000×0.38 [mid-range]) and 2,052 deaths (270,000×0.38×0.02) per year that are avoidable for patients that don't have lung cancer.

2.4.3.3 XL2 Impact Estimates

Using the figures for potential avoidable invasive procedures calculated above, and assuming XL2 has broad use after reimbursement. Add the clinical utility figure of a 36% reduction of invasive procedures (Sections 2.4.3 and 3.4), then XL2 has the potential to save over 36,000 surgeries, over 1,600 hospitalizations, and almost 750 deaths per year. The majority of these occurring in the CMS population of patients (Section 2.2.1.5).

3. Technical and Performance Summary of XL2

This section presents the following details of the XL2 test:
Development and Validation (Section 3.1):
XL2 was developed and validated on two large and generalizable prospective studies including the PANOPTIC study, which enrolled 685 subjects across 33 sites.
XL2 was developed and validated following the National Academy of Medicine's guidelines for rigorous test development.
XL2 development and validation achieves the highest level of evidence being both prospective and conducted on a large number of independent sites.

Performance (Section 3.2):
XL2 has a negative predictive value, sensitivity and specificity of 98% (CI: 92%-100%), 97% (CI: 82%-100%) and 44% (CI: 36%-52%).

Comparative Performance (Section 3.3):
XL2 compares favorably to current practice, PET and four clinical risk predictor models having statistically significant superior performance.

Potential Clinical Utility of XL2: Benefit and Harm (Section 3.4):
Two prospective studies allow calculation of the potential clinical utility of XL2.
In the PANOPTIC, if used XL2 would have eliminated 36% of invasive procedures on benign lung nodules.
Importantly, XL2 is also safer than current practice. If XL2 were used in PANOPTIC then only 3% of malignant lung nodules would have been erroneously routed away from invasive procedures. In comparison, the physicians erroneously routed 45% of malignant lung nodules away from invasive procedures.

This section closes with the formal specification of XL2 (Section 3.5), the reporting of XL2 results (Section 3.6), and also a description of the primary differences between XL1 and XL2 (Section 3.7).

3.1 Development and Validation of XL2

XL2 was developed on Study 1013 (NCT01752101) and then verified and validated on the PANOPTIC study (NCT01752114). Study 1013 and PANOPTIC are both prospective studies of lung nodules, designed and sponsored by Integrated Diagnostics, for the primary purpose of developing and validating Xpresys Lung. These studies are summarized in Table C.

TABLE C

Study 1013 and PANOPTIC showing development phases and numbers of sites and patients.

|  | Study 1013 | PANOPTIC |
| --- | --- | --- |
| Development Phase | Discovery | Verification & Validation |
| Number of Sites | 12 | 33 |
| Patients Enrolled | 475 | 685 |
| Intended Use Patients | 222 | 178 |

Development and validation of XL2 adhered to the best practices for test development as defined by the National Academy of Medicine (NAM) Guidelines for best practices in test development and validation [IOM (Institutes of Medicine), Evolution of Translational 'Omics: Lessons Learned and the Path Forward, Washington D.C.: The National Academies Press, 2012]. In particular, discovery and validation were both prospective and conducted on a large number of independent sites. Additionally, verification and validation were conducted under a strict blinding protocol and utilized a $3^{rd}$ party statistician. This is the highest level of clinical validation achievable by the NAM. Details of the early development of XL2 and discovery on Study 1013 [RD35, RDXX] are available for review. The validation protocol and results are also available for review [DES25, VAL25].

3.2 Performance of XL2 in the PANOPTIC Trial

3.2.1 Performance Measures and Results with XL2

The performance of XL2 is based on the 178 PANOPTIC subjects in the intended use population. The four standard performance measures for a diagnostic test are sensitivity, specificity, positive predictive value (PPV) and negative predictive value (NPV).

Sensitivity: The percentage of malignant lung nodules correctly predicted as malignant by XL2.

Specificity: The percentage of benign lung nodules correctly predicted as benign by XL2.

Negative Predictive Value (NPV): The percentage of lung nodules predicted to be benign by XL2 that are benign.

Positive Predictive Value (PPV): The percentage of lung nodules predicted to be malignant by XL2 that are malignant.

XL2 is designed to be a lung cancer rule out test, that is, it identifies lung nodules that are likely benign so that CT surveillance is used and invasive procedures can be avoided. Consequently, the accuracy at which it reports a lung nodule to be likely benign is of paramount clinical importance. This performance measure is the NPV.

What NPV will be best for deciding the pathway? It depends on patient preference and the physician's advice (Section 2.2.2.2). The ACCP guidelines recommend that a lung nodule can be observed with CT surveillance if the probability of cancer is under 5%. This is equivalent to NPV values over 95%. XL2 has been validated for NPV values of 90% and higher. Table D presents the performance of XL2 for NPV values of 90% to 98% along with 95% confidence intervals (CI). We note that the largest proportion of Likely Benign reports in the study have a NPV of 98%.

The 90% NPV value is the lowest to be considered "likely benign". This is because NPV values below 90% are not statistically different from the pre-test probability of a lung nodule being benign. Within the intended use population of PANOPTIC this value is 83.7%. This is below the 95% lower CI of all NPV values in Table D. A test result below 90% NPV does not have a post-test probability of a lung nodule being benign from its pre-test probability. In these cases, the result is considered "Indeterminate".

There are three landmarks on this ROC plot worth noting for the subsequent graphics.

Landmark #1 is the ROC curve itself for XL2. The further away from random, shown as the dashed diagonal line, this curve is, the better the overall performance of the diagnostic test. This is typically measured by the area under the curve (AUC).

Landmark #2 is the '95% NPV zone'. The NPV of a diagnostic test depends entirely on its sensitivity, specificity and disease prevalence. This dependency is captured by the following formula:

$$NPV = \frac{\text{specificity} * (1 - \text{prevalence})}{(1 - \text{sensitivity}) * \text{prevalence} + \text{specificity} * (1 - \text{prevalence})}$$

Figure 26:
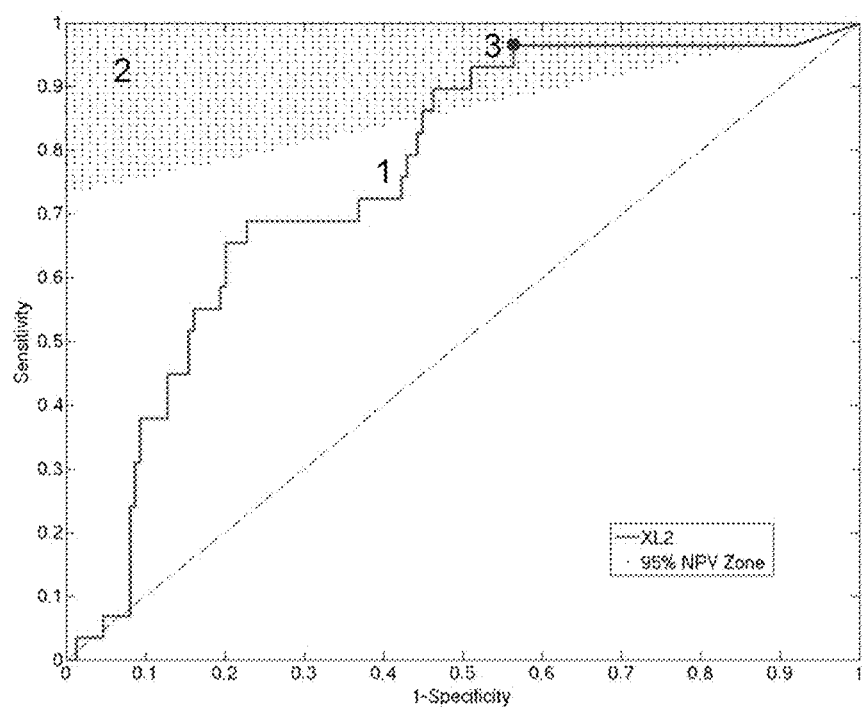
FIG. 26 is a graph showing the performance of XL2 on the PANOPTIC intended use group (n=178). The red curve is the Receiver Operator Characteristic (ROC) curve for XL2 (#1) which is 76% (95% CI 69%-82%) and significantly better than random (p-value 9.4E-5). The grey area (#2) represents all sensitivity and specificity pairs that yield a NPV of 95% and greater. The blue dot (#3) represents the sensitivity and specificity at which XL2 has a sensitivity of 97%, specificity of 44% and a NPV of 98%.

In the case of XL2, the cancer prevalence in the intended use population is 16.3%. The implication is that we can determine those sensitivity and specificity values that result in a clinically relevant NPV of at least 95%. These sensitivity and specificity values are depicted in FIG. 26 as the '95% NPV zone'. A robust diagnostic test for ruling out cancer in lung nodules should have sensitivity and specificity within this zone.

Another important aspect of the 95% NPV zone is that this is where XL2 will be compared to other cancer risk predictors (Section 3.3.3).

Landmark #3 is the point on the XL2 ROC curve where it reaches maximum NPV. At this point XL2 has sensitivity of 97%, specificity of 44% and NPV of 98%. The NPV is emphasized because this area of the graphic is most relevant for a rule-out test such as XL2.

3.3 Comparative Performance of XL2

3.3.1 Current Risk Predictor Selections for Comparison to XL2

This section compares the performance XL2 to six other cancer risk predictors for lung nodules. All comparisons are made using the same 178 PANOPTIC patients in the lower risk, intended use population. This allows for an 'apples-to-apples' comparison. These six predictors fall into three categories as follows.

Current Practice: Current practice for estimating the cancer risk of a lung nodule is the initial physician cancer risk assessment (pCA) based on physician clinical judgement [A. A. Balekian, G. A. Silvestri, S. M. Simkovich, P. J. Mestaz, G. D. Sanders, J. Daniel, J. Porcel and M. K. Gould, "Accuracy of Clinicians and Models for Estimating the Probability That a Pulmonary Nodule is Malignant," *Annals of the America Thoracic Society*, vol. 10, no. 6, pp. 629-635, 2013]. This also represents how cancer risk was estimated for over 80% of lung nodules evaluated in PANOPTIC and is also a practice recommended in the ACCP Guidelines (Section 2.2.4.1).

PET: PET is referenced in the ACCP Guidelines for use as a tool for assessing cancer risk. PET was used in 75/178=42% of intended use subjects in the PANOPTIC study.

Clinical Risk Predictors: Four clinical risk predictors have been discussed (Section 2.2.4) and here are assessed: Mayo, VA, Brock and Herder. Mayo and VA are referenced in the ACCP Guidelines, however, they were used by under 20% of physicians in the PANOPTIC study. The Brock and Herder models are included for completeness but were not utilized by physicians in the PANOPTIC study as discussed in Sections 2.2.4.2 and 2.2.6.2 respectively. We note that because the Herder model requires a PET to be performed,

TABLE D

Performance and Likely Benign Reports of XL2 on 178 patients from the PANOPTIC study at NPV values of 90% to 98% and below 90%. Test results with a NPV at or above 90% NPV are reported as "Likely Benign" whereas those below 90% NPV are reported as "Indeterminate".

| NPV (95% CI) | Sensitivity (95% CI) | Specificity (95% CI) | PPV (95% CI) | % of Reports |
|---|---|---|---|---|
| 98% (92%-100%) | 97% (82%-100%) | 44% (36%-52%) | 25% (17%-34%) | 39% |
| 97% (91%-100%) | 93% (77%-99%) | 49% (41%-57%) | 26% (18%-36%) | 5% |
| 96% (90%-99%) | 90% (73%-98%) | 54% (45%-62%) | 27% (19%-37%) | 4% |
| 95% (89%-99%) | 86% (68%-96%) | 55% (47%-63%) | 27% (18%-37%) | 2% |
| 94% (87%-98%) | 83% (64%-94%) | 56% (47%-64%) | 27% (18%-37%) | 1% |
| 93% (86%-98%) | 79% (60%-92%) | 57% (44%-65%) | 26% (18%-37%) | 2% |
| 92% (85%-97%) | 76% (56%-90%) | 58% (49%-66%) | 26% (17%-37%) | 1% |
| 91% (84%-96%) | 69% (49%-85%) | 64% (56%-72%) | 27% (18%-39%) | 6% |
| 90% (84%-95%) | 55% (36%-74%) | 83% (75%-88%) | 38% (24%-54%) | 18% |
| <90% | — | — | — | 22% |

3.2.2 Graphical Performance of XL2

The performance of a diagnostic test is often depicted graphically using a receiver operating characteristic (ROC) curve. FIG. 26 presents the ROC curve for XL2 alone on the 178 PANOPTIC subjects within the intended use population. This same graphical format will be used for multiple figures.

only 75/178=42% of the intended use subjects in the PANOPTIC study have a Herder result.

3.3.2 Comparison Methodology

In section 3.3.3, XL2 and six other cancer risk predictors are presented as ROC curves. This will give an overall impression of the performance of these risk predictors in terms of AUC and performance in the important '95% NPV zone'. However, no statistical claims are intended. Full statistical treatment is reserved for Section 3.3.4.

In Section 3.3.4, XL2 is compared 'apples-to-apples' to the six other cancer risk predictors in a strict statistical manner. Except in the case of PET, all of these comparisons are based on the following methodology:

Comparisons are made based on performance in the 95% NPV zone.

The McNemar statistical test is utilized [Q. McNemar, "Note On the Sampling Error of the Difference Between Correlated Proportions or Percentages," Psycometrika, vol. 12, no. 2, pp. 153-157, 1947]. The McNemar test is most appropriate when comparing predictors on the same set of samples and at a fixed sensitivity (or fixed specificity).

In the case of PET, a McNemar comparison is not possible due to PET's poor performance in the '95% NPV zone'. Instead, direct NPV performance comparisons are made.

3.3.3 Graphical Comparison of XL2 to All Other Risk Predictors

Before proceeding to a formal statistical comparison of XL2 to the other risk predictors, we begin with an overall picture of the performance of six risk predictors relative to XL2. For this purpose, we visualize performance using a ROC plot (FIG. 27) and measuring the entire AUC. We do not make statistical comparisons based on the entire AUC as this is not the relevant metric for a rule-out test (despite XL2 having the highest AUC). Section 3.3.4 makes use of formal statistical comparisons.

Figure 27:
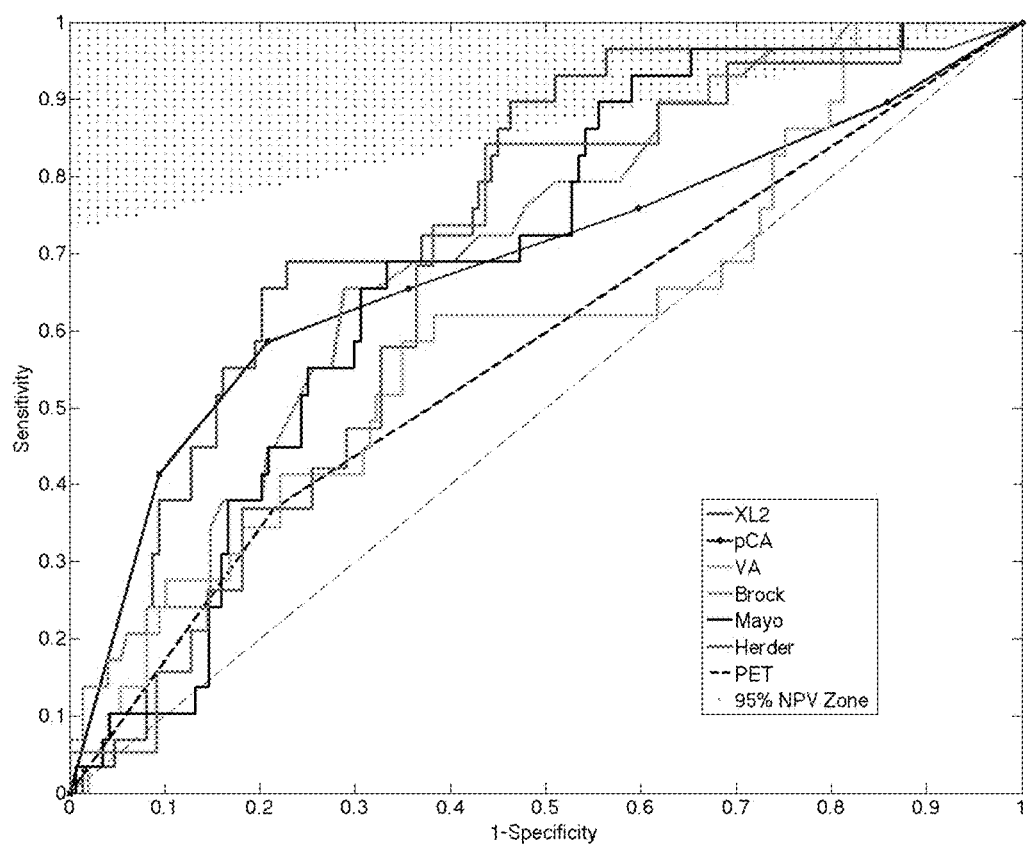
FIG. 27 is a graph showing the comparison of XL2 to Six Cancer Risk Predictors.

FIG. 27 presents XL2 and six other risk predictors in a single ROC plot. The AUCs for all of the predictors in FIG. 27 are presented in Table E. We make three immediate remarks on this head-to-head comparison in this intended use population with a cancer risk of 50% or less:

XL2 has superior performance overall (highest AUC), but more importantly, the best performance in the '95% NPV Zone'.

Current practice (pCA) performs very poorly overall (AUC=69%) but particularly poorly within '95% NPV zone'.

PET has the worst performance both overall (AUC=58%) and also within the '95% NPV zone'.

Although the most important factor is the superior performance of XL2 in the 95% NPV zone, it is notable that even outside the 95% NPV zone, the performance of XL2 continues to be superior, or equivalent, to all other cancer risk predictors, PET and pCA.

TABLE E

Overall AUC and 95% CI of the Cancer Risk Predictors

| Cancer Risk Predictor | AUC | 95% CI |
|---|---|---|
| XL2 | 76% | 69%-82% |
| pCA | 69% | 62%-76% |
| VA | 60% | 53%-67% |
| Brock | 71% | 63%-77% |
| Mayo | 69% | 62%-76% |
| Herder | 67% | 56%-78% |
| PET | 58% | 46%-69% |

3.3.4 Statistical Comparisons

In this section XL2 is compared, in a formal statistical sense, to current practice (pCA), four clinical risk predictors, and then PET.

3.3.4.1 Comparison of XL2 to Current Practice (pCA)

Figure 28:
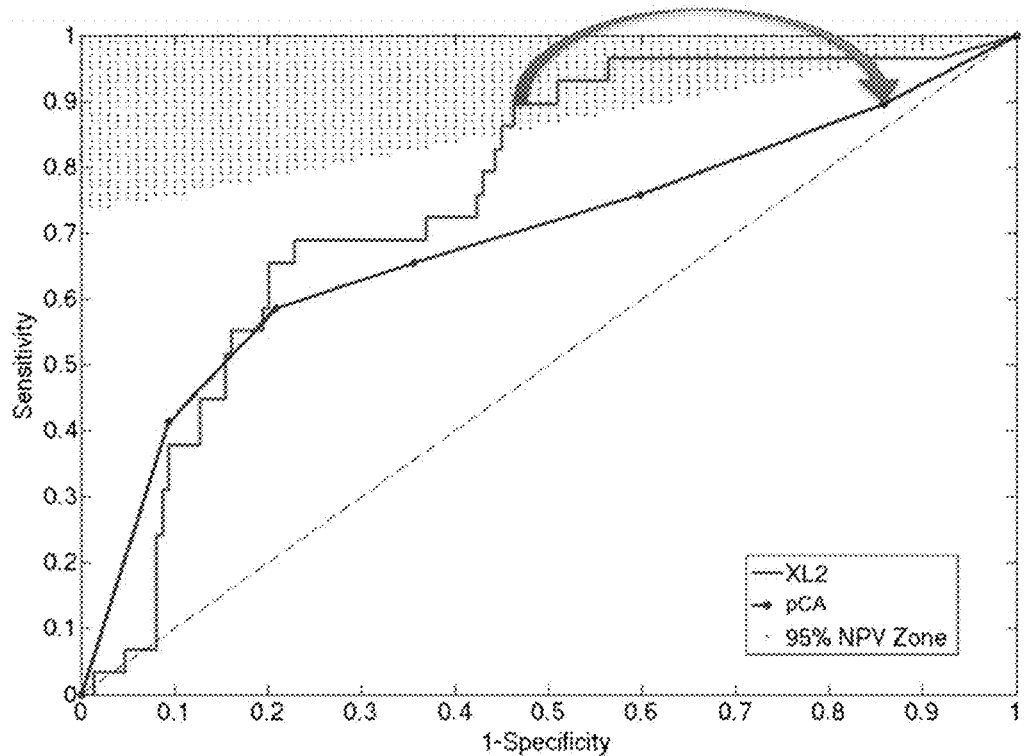
FIG. 28 is a graph showing the comparison of XL2 to pCA in the intended use group. Comparison of XL2 to pCA is made at 90% sensitivity, the highest sensitivity achieved by pCA. The blue arching arrow depicts the two points on the respective ROC curves being compared.

XL2 is compared to current practice, physician clinical judgment for the pretest probability of cancer (pCA) in the lower risk group (pCA 50% or less). As shown in FIG. 28, pCA never reaches the desired 95% NPV level. Since the highest sensitivity attained by pCA is 90%, this level is used to compare the performance of XL2 to pCA.

Using the McNemar test (Section 3.3.2), at the same sensitivity of 90%, XL2 has significantly greater specificity with p-value of 2.12E-11.

3.3.4.2 Comparison of XL2 to Clinical Risk Predictors

Figure 29:
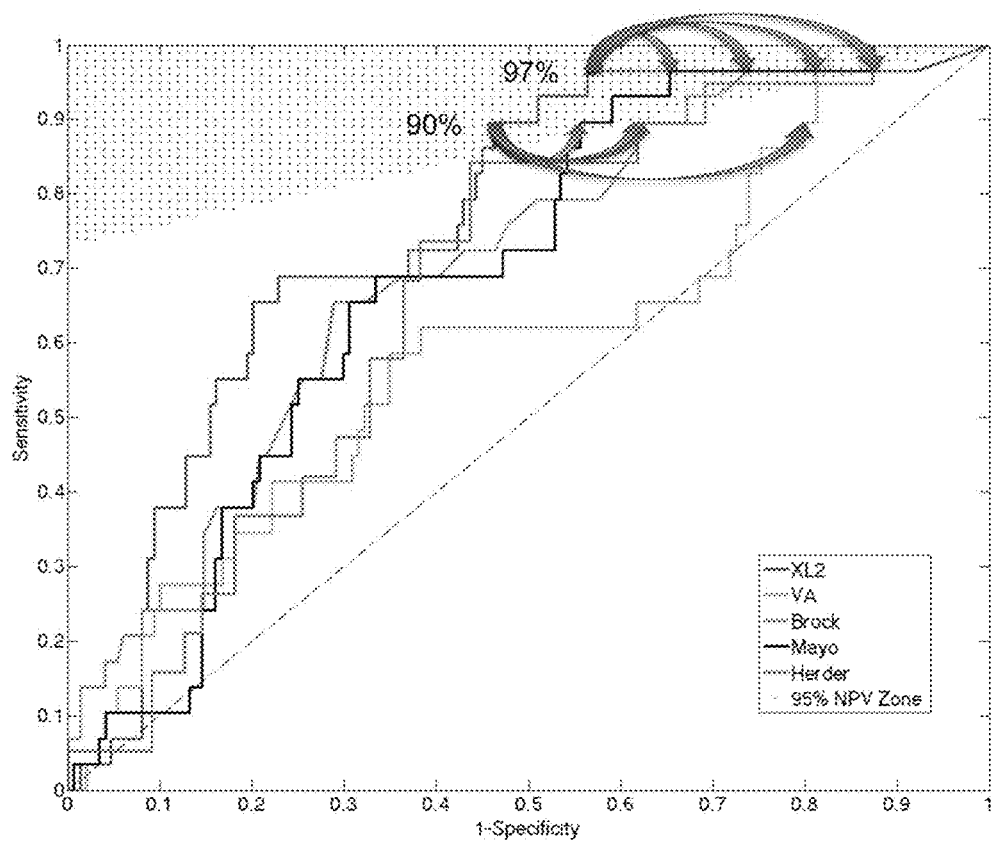
FIG. 29 is a graph showing the comparison of XL2 to four clinical risk predictors. Comparison is made at 90% and also at 97% sensitivity. The blue arrows depict the respective points on the four clinical risk predictor curves being compared to XL2.

We compare XL2 to four clinical risk predictors (Mayo, VA, Brock and Herder). See FIG. 29. The comparison is made at sensitivities of 90% and 97% which XL2, and all four clinical risk predictors, attain. We include these two sensitivities for a robust comparison.

Using the McNemar test (Section 3.3.2), at sensitivities of 90% and 97%, XL2 has significantly greater specificity than the four clinical risk predictors with p-values reported in Table F. We note that comparisons between XL2 and all models except Herder are made on all 178 PANOPTIC patients. For Herder (which requires a PET to be performed) only 75 patients could be compared. This lower sample number resulted in higher (but still significant) p-values.

TABLE F

Comparison of XL2 to Clinical Risk Predictors for incidental (Mayo & VA) and screen-detected (Brock) nodules. Herder combines clinical factors with PET.

| Comparison | 90% Sensitivity p-value | 97% Sensitivity p-value |
|---|---|---|
| XL2 vs. Mayo | 0.0009 | 0.0009 |
| XL2 vs. VA | 1.562e-11 | 2.71E-7 |
| XL2 vs. Brock | 0.0021 | 0.0051 |
| XL2 vs. Herder | 0.0455 | 0.0233 |

3.3.4.3 Comparison of XL2 to PET

Figure 30:
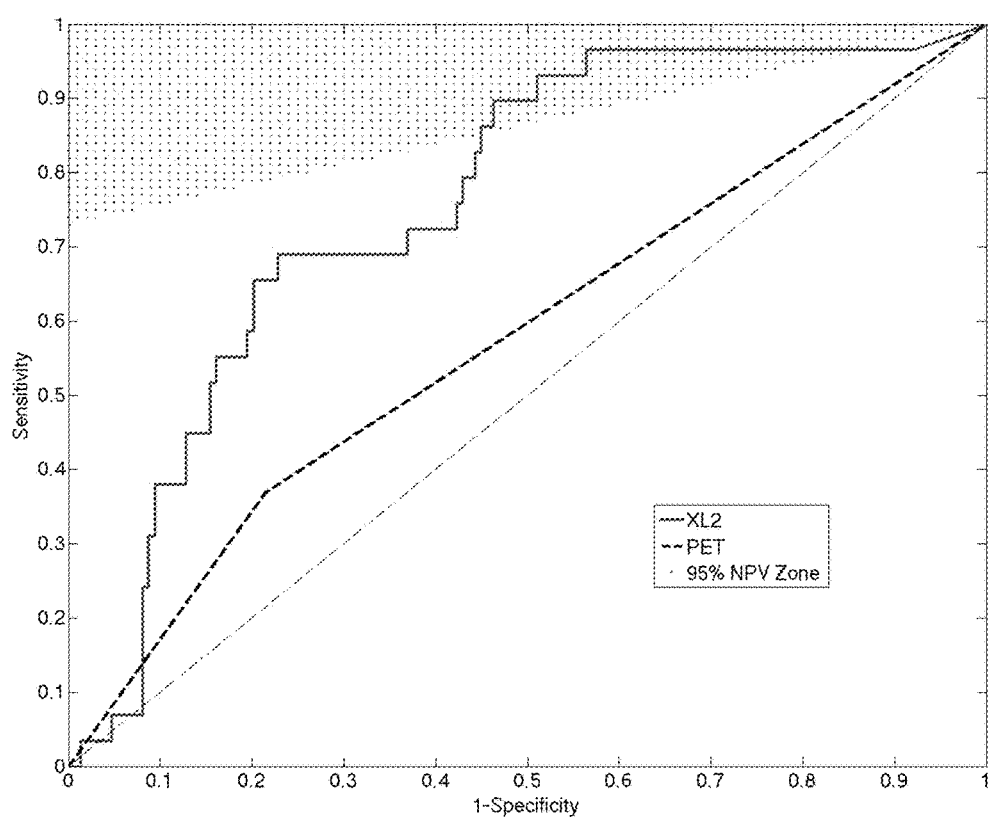
FIG. 30 is a graph showing the AUC comparisons of XL2 and PET with 75 patients in the intended use group that had a PET scan.

Of the 178 PANOPTIC patients within the intended use of XL2, 75 had a diagnostic PET performed. The comparison in FIG. 30 is based on these 75 patients.

Because PET never reaches the 95% NPV zone or a sufficiently high sensitivity, the McNemar test cannot be applied. Instead, we compare the NPV of PET directly to the NPV of XL2.

The highest NPV for PET is 79% (95% CI:66%-88%) so this is compared to when XL2 reaches a NPV of 95% (95% CI:89%-99%). These two CI do not overlap, and so, XL2 has significantly better NPV as compared to PET.

3.4 Potential Clinical Utility of XL2: Benefit and Harm

PANOPTIC was a non-interventional study, however, the potential clinical utility of XL2 can be estimated from PANOPTIC by answering the following question:

"If XL2 were used in PANOPTIC to identify lung nodules likely to be benign, how many benign (benefit) and malignant (harm) nodules would have been routed away from invasive procedures into CT surveillance?"

At NPV=98% (see Table G), XL2 has the following potential clinical utility in PANOPTIC:

$15/42$=36% of benign nodules would have been saved from unnecessary invasive procedures (benefit).

$1/29$=3% of malignant nodules would have been erroneously routed to CT surveillance (harm).

At NPV=95% (see Table G), XL2 has the following potential clinical utility in PANOPTIC:
- 20/42=48% of benign nodules would have been saved from unnecessary invasive procedures (benefit).
- 2/29=7% of malignant nodules would have been erroneously routed to CT surveillance (harm).

TABLE G

Potential Clinical Utility of XL2

| NPV | Reduction in Invasive Procedures on Benign Nodules (95% CI) | Malignant Nodules Sent to CT Surveillance (95% CI) |
|---|---|---|
| 98% | 15/42 = 36% (22%-52%) | 1/29 = 3% (0%-18%) |
| 97% | 17/42 = 40% (26%-57%) | 2/29 = 7% (1%-23%) |
| 96% | 19/42 = 45% (30%-61%) | 2/29 = 7% (1%-23%) |
| 95% | 20/42 = 48% (32%-64%) | 2/29 = 7% (1%-23%) |
| 94% | 20/42 = 48% (32%-64%) | 2/29 = 7% (1%-23%) |
| 93% | 22/42 = 52% (36%-68%) | 3/29 = 10% (2%-27%) |
| 92% | 22/42 = 52% (36%-68%) | 4/29 = 14% (4%-32%) |
| 91% | 25/42 = 60% (43%-74%) | 4/29 = 14% (4%-32%) |
| 90% | 32/42 = 76% (61%-88%) | 7/29 = 24% (10%-44%) |

How safe is XL2? We observe that in the intended use population in PANOPTIC, 13/29=45% of malignant nodules were routed to CT surveillance (then having a risk of delayed diagnosis). Comparing this to the estimates shown in Table G illustrates that XL2 will provide a safe test for both reducing unnecessary invasive procedures while simultaneously sending fewer malignant nodules to CT surveillance.

3.5 Technical Definition of XL2

XL2 integrates the relative abundance of two plasma proteins (LG3BP and C163A) with five clinical risk factors (age, smoking status, nodule diameter, nodule spiculation status and nodule location). Functional details on these proteins can be found in [1]. XL2 provides a numerical value, $XL\_2(k)$, for a subject k, as defined below:

$$XL\_2(k) = \begin{cases} \max(0, p(k) - 0.5), & \log_2\left(\frac{LG3BP}{C163A}\right) \le .38 \\ p(k), & \log_2\left(\frac{LG3BP}{C163A}\right) > .38 \end{cases}$$

$$p(k) = \frac{e^X}{1+e^X}$$

$$X = -6.8272 + 0.0391*Age + 0.7917*Smoker + 0.1274*Diameter + 1.0407*Spiculation + 0.7838*Location$$

where Age is the age of the subject in years, Smoker is 1 if the subject is a former or current smoker (otherwise 0), Diameter is the size of the lung nodule in mm, Spiculation is 1 if the lung nodule is spiculated (otherwise 0) and Location is 1 if the lung nodule is located in an upper lung lobe (otherwise 0). The linear function X that integrates the clinical risk factors is a simplification of the Mayo clinical risk predictor that eliminates the cancer risk history factor.

$XL\_2(\;)$ ranges between 0 and 1. The closer $XL\_2(k)$ is to 0, the more likely subject k has a very high NPV which is calculated using PANOPTIC data.

The ranges of the $XL\_2(\;)$ function for the NPV values of 90% to 98% are shown in Table H, along with the other key performance indicators.

3.6 Reporting XL2 results

XL2 results will be reported as Likely Benign or Indeterminate, with the NPV value and confidence intervals shown in the Likely Benign reports.

The separation of likely benign and indeterminate is based on the cancer prevalence of the study population and statistical comparisons. The cancer prevalence in the intended use population in the PANOPTIC study was 16.3% which corresponds to a benign prevalence of 83.7%. In other words, the pre-test probability of a lung nodule being benign is 83.7% before any clinical judgment or testing. XL2 reports "Likely Benign" when the post-test probability of being benign (i.e. the NPV) is 90% or higher as shown in Table H.

Note that when the "k" value exceeds 0.354, the lower confidence interval of an NPV of less than 90% will overlap with the prevalence of 83.7% for the population. Therefore, this will be when the test report changes from Likely Benign to Indeterminant.

TABLE H

XL2 Performance, Test Report, and Percentage of Reports at multiple negative predictive values for Likely Benign results (n = 178 patients)

| $XL\_2(k)$ Value | NPV (95% CI) | Sensitivity (95% CI) | Specificity (95% CI) | PPV (95% CI) | Test Report | Percentage of Tests Reported |
|---|---|---|---|---|---|---|
| 0 to 0.131 | 98% (92%-100%) | 97% (82%-100%) | 44% (36%-52%) | 25% (17%-34%) | Likely Benign | 39% |
| >0.131 to 0.1613 | 97% (91%-100%) | 93% (77%-99%) | 49% (41%-57%) | 26% (18%-36%) | Likely Benign | 5% |
| >0.1613 to 0.172 | 96% (90%-99%) | 90% (73%-98%) | 54% (45%-62%) | 27% (19%-37%) | Likely Benign | 4% |
| >0.172 to 0.176 | 95% (89%-99%) | 86% (68%-96%) | 55% (47%-63%) | 27% (18%-37%) | Likely Benign | 2% |
| >0.176 to 0.1785 | 94% (87%-98%) | 83% (64%-94%) | 56% (47%-64%) | 27% (18%-37%) | Likely Benign | 1% |
| >0.1785 to 0.193 | 93% (86%-98%) | 79% (60%-92%) | 57% (44%-65%) | 26% (18%-37%) | Likely Benign | 2% |
| >0.193 to 0.195 | 92% (85%-97%) | 76% (56%-90%) | 58% (49%-66%) | 26% (17%-37%) | Likely Benign | 1% |
| >0.195 to 0.2306 | 91% (84%-96%) | 69% (49%-85%) | 64% (56%-72%) | 27% (18%-39%) | Likely Benign | 6% |

TABLE H-continued

XL2 Performance, Test Report, and Percentage of Reports at multiple negative predictive values for Likely Benign results (n = 178 patients)

| XL_2(k) Value | NPV (95% CI) | Sensitivity (95% CI) | Specificity (95% CI) | PPV (95% CI) | Test Report | Percentage of Tests Reported |
|---|---|---|---|---|---|---|
| >0.2306 to 0.354 | 90% (84%-95%) | 55% (36%-74%) | 83% (75%-88%) | 38% (24%-54%) | Likely Benign | 18% |
| >0.354 | — | — | — | — | Indeterminate | 22% |

3.7 Primary Differences of Xpresys Lung 1 (XL1) and Xpresys Lung 2 (XL2)

XL2 is a second generation version of XL1 that has four significant improvements over XL1:

3.7.1. Intended Use Population

The intended use population of XL2 are patients with a lower cancer risk (50% or less pre-test probability), whereas the intended use population of XL1 included all patient risk groups (0%-100%). Under guidance from KOL leaders and commercial experience with XL1, it became clear that physicians needed a test to differentiate benign from malignant nodules. And that need is greatest in patients with lower risk rather than higher risk (Section 2.2.3). This focusing of the intended use population has led to performance improvements.

3.7.2. Reduction in Molecular Factors

Discovery work on Study 1013 identified two proteins (LG3BP and C163A) that were more accurate than the five diagnostic proteins of XL1 at identifying benign nodules for patients with a lower cancer risk. The likely reason for this is that protein expression differs between lower and higher risk nodules [RDXX].

3.7.3. Addition of Clinical Risk Factors

XL1 is purely a molecular test whereas XL2 incorporates molecular markers with known clinical risk factors (Section 3.5). This not only enhances the performance of XL2 over XL1, but is appealing to physicians as these are the clinical risk factors they currently use to assess cancer risk. That is, XL2 is not attempting to replace the current practice of using clinical risk factors but augments current practice with molecular factors (Section 3.3.3.1).

3.7.4. Quality of Clinical Evidence

XL1 was developed and validated on five archival biobanks. In contrast, XL2 was developed and validated in two prospective studies with samples collected using a uniform protocol. The first, 'Study 1013' spanned 12 sites and enrolled 475 subjects. The second, 'PANOPTIC' spanned 33 sites and enrolled 685 subjects. Consequently, XL2 is more generalizable to clinical practice. Furthermore, PANOPTIC collected physician probabilities of cancer risk and clinical factors to allow XL2 to be directly compared to current practice in lung nodule evaluation.

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

EXAMPLES

Example 1

Summary of Diagnostic Rule Out Studies Performed

Studies Performed

The evidence for diagnostic assays that are able to rule-out whether a subject has cancer is based on three major clinical validation and utility studies. These studies built upon the initial scientific and clinical findings published in Science Translational Medicine in late 2013 (Li, X. et al. Sci Transl Med. 2013 Oct. 16; 5(207):207ra142). The first major clinical validation study was a Retrospective Validation Study (Vachani, A. et al. J Thorac Oncol. 2015 April; 10(4):629-37) using 141 clinical specimens from patients falling into Xpresys Lung's clinical intended use. Four clinical sites utilizing multiple collection protocols were included in the study.

The second clinical study, Study 1013, was a prospectively collected, single protocol study of Clinical Utility. This large study included 353 clinical specimens collected from 12 sites. The study design focused upon higher cancer risk patients to determine whether diagnostic errors leading to unnecessary invasive diagnostic procedure including benign surgery could be identified and re-routed to standard of care CT follow-up to prove benignity (Vachani, A. et al. Lung. 2015 December; 193(6):1023-7.).

The third study, Study 1001, is ongoing and serves as both a second clinical utility study as well as a confirmatory clinical validation in the standard of care nodule work-up setting. This study is referred to herein as PANOPTIC. We are able to report interim analysis of this study as over 200 patients have completed the full 2-year follow-up and the remaining 400 patients are at least 1-year into the study. Study 1001 represents 604 clinical specimens from patients presenting within the XL intended use. Thirty-two sites in North America are participating and all nodule work-up data are included in the trial design including PET scan data (Presentation: ATS Podium Abstract; May 2016; manuscript in progress).

Study 1001 has the following significant advantages over the other two studies:
1. The performance of the rule-out diagnostic assay is most generalizable from Study 1001 as the sample collection is standardized, the study size and number of sites is large and the study is all-comers across all cancer risk groups (low, medium and high).
2. The rule-out diagnostic assay can be compared to all three clinical nodule risk management models ('VA', 'Mayo' and 'Brock') as data was collected in Study 1001 to allow for the calculation of these models.

3. The rule out diagnostic assay can be directly compared in terms of AUC as well as likelihood ratios vs. PET.

The objectives of PANOPTIC are: to confirm performance of XL1 (an 11 protein based rule-out assay (see U.S. Pat. Nos. 9,201,044 and 9,304,137); determine performance of XL2 which is a refinement of XL1 that is suitable for transfer to an antibody platform; and to determine that XL1 (and XL2) has incremental and synergistic benefit over Physician Assessment alone.

The PANOPTIC study allows for the initial physician's assessment of cancer risk to be captured. This allows for the exploration of how physicians assess risk, select follow on procedures based on risk assessment and how XL performs for different risk stratifications.

The following observations can be made for physician's assessment of clinical risk (pCA). Physicians effectively identify cancer subjects; in contrast the distribution of benign subjects remains uniform across the cancer risk axis. Commercial and clinical opportunities include that the XL assays will be able to rule out benign invasive procedures. At 60% pCA and above, cancers rise dramatically.

For high risk (60% and higher) it may not be recommended that a rule out test be used to direct a subject to CT Surveillance. Consequently, XL2 may have best performance for low and moderate risk subjects. The best reversals for low and moderate risk subjects (using nodule size as a proxy for risk) were identified in Study 1013 and validated in the interim analysis of Study 1001.

For a rule out test, the figures of merit are as follows: 1-Screen Positive Rate=Likely Benign Rate. This is the diagnostic yield of the test. Tests that yield more rule outs are preferable.NPV or LR-: The negative predictive value or the negative likelihood ratio capture the confidence that a "likely benign" result is correct (see, for example, FIG. 9).

XL2 is not just the molecular classifier, but the integration of the molecular classifier with a risk predictor such as pCA, VA, Mayo or Brock. The form of the integration is as follows where s is a subject being tested and P is the risk predictor integrated with XL2.

---
If XL2(s) <= threshold then
　　Risk(s) = P(s) − 50%
Else
　　Risk(s) = P(s)
end
---

If XL2 indicates "Likely Benign," then the physician should reduce risk by 50%. We do not need to have P(s) to perform the test.

Figure 10:
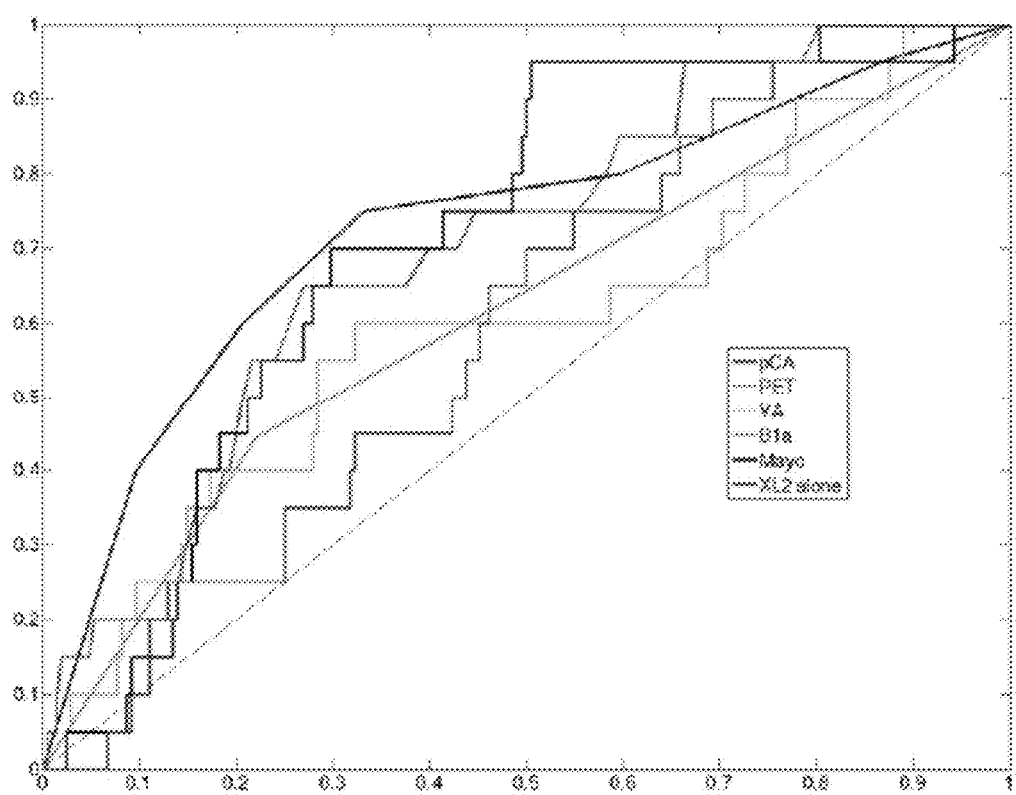
FIG. 10 is a graph depicting the performance of pCA, PET and various clinical models for low and moderate risk subjects (pCA<=50%). XL2 alone (panel of LG3BP and C163A).
Figure 11:
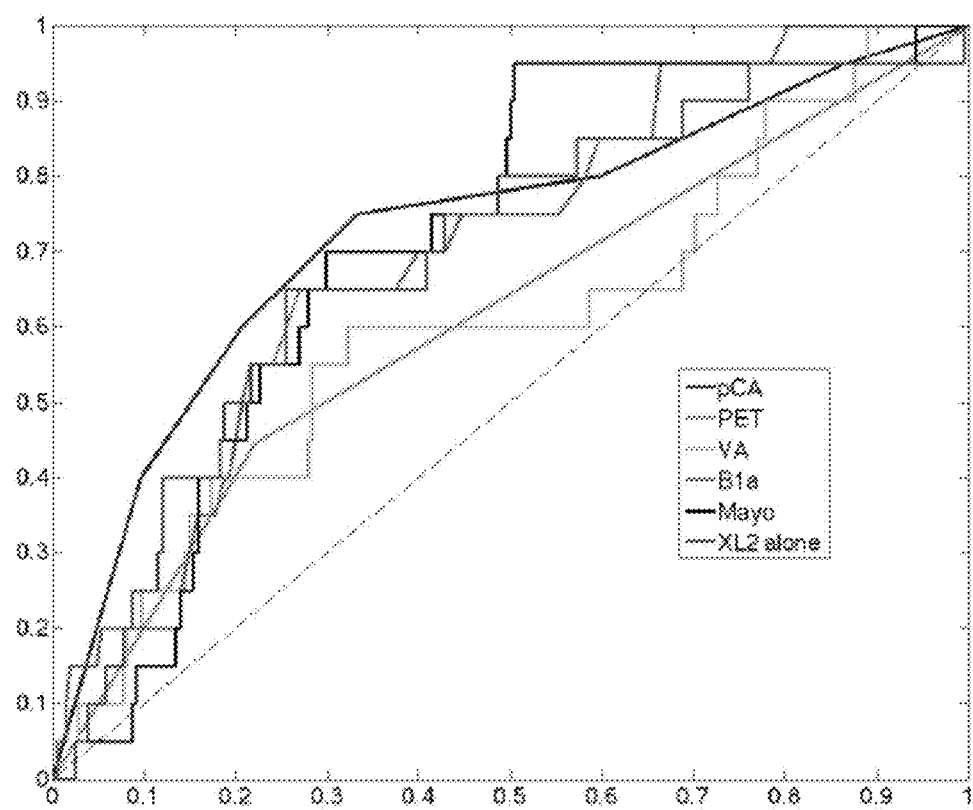
FIG. 11 is a graph depicting the performance of pCA, PET and various clinical models for low and moderate risk subjects (pCA<=50%). XL2 alone (panel of LUM and C163A).
Figure 12:
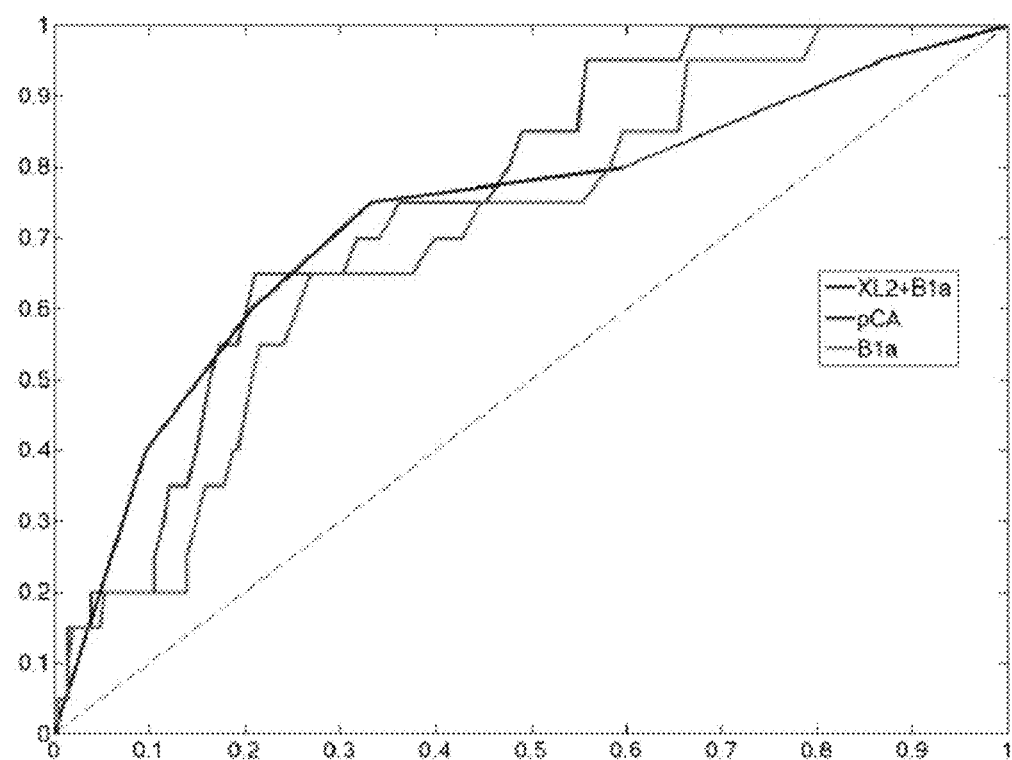
FIG. 12 is a graph depicting the performance of XL2 integrated with B1a. XL2+B1a outperforms both pCA and B1a in the critical region of performance (see FIG. 10).
Figure 13:
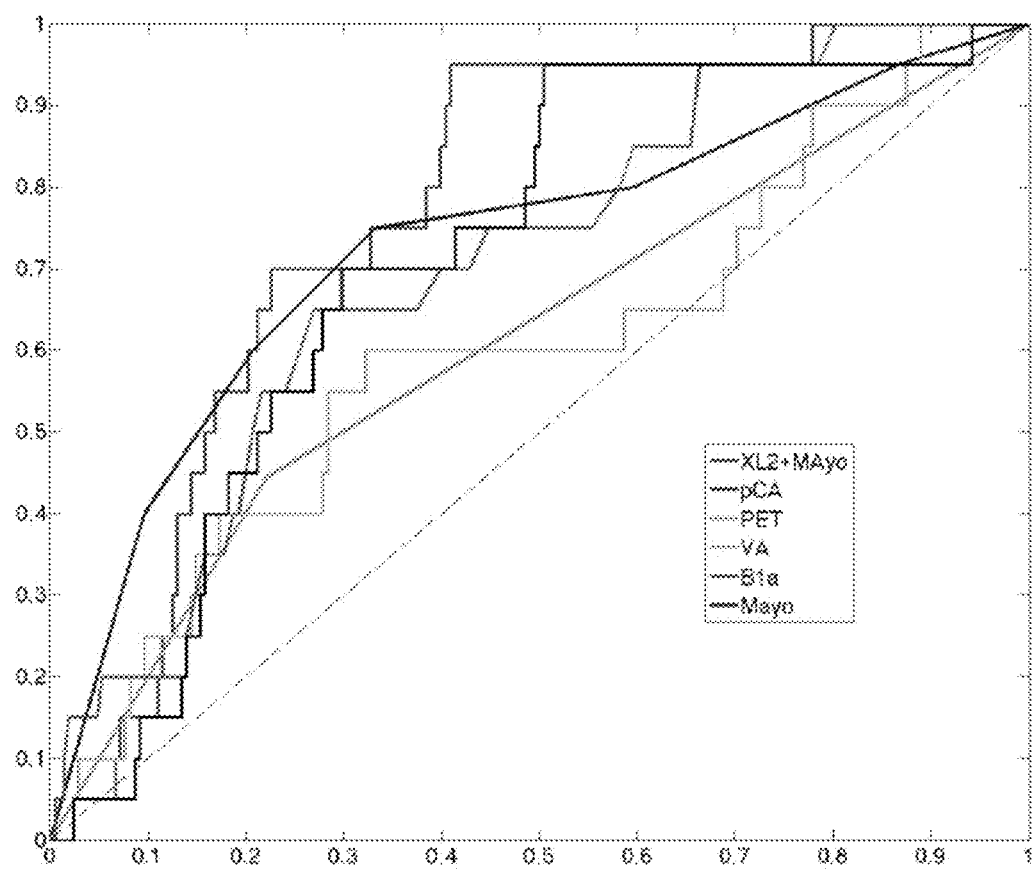
FIG. 13 is a graph depicting the performance of XL2 integrated with Mayo.
Figure 14:
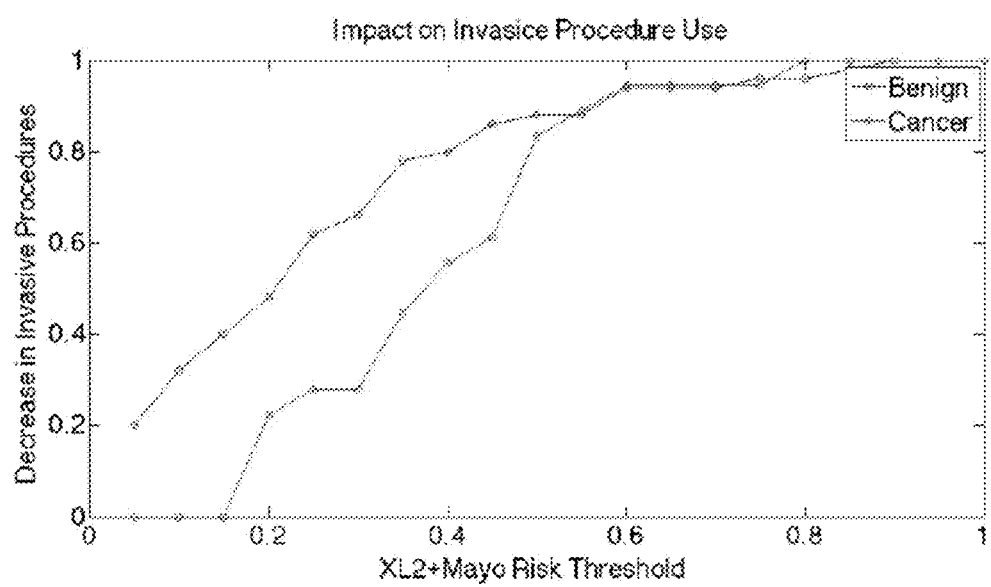
FIG. 14 is a graph depicting the impact of XL2 integrated with Mayo on Invasive Procedure Use. Up to a risk threshold of 0.15, none of the cancers (18) are erroneously routed to invasive procedures whereas 20 of the 50 benigns (40%) are rerouted back to CT Surveillance.
Figure 15:
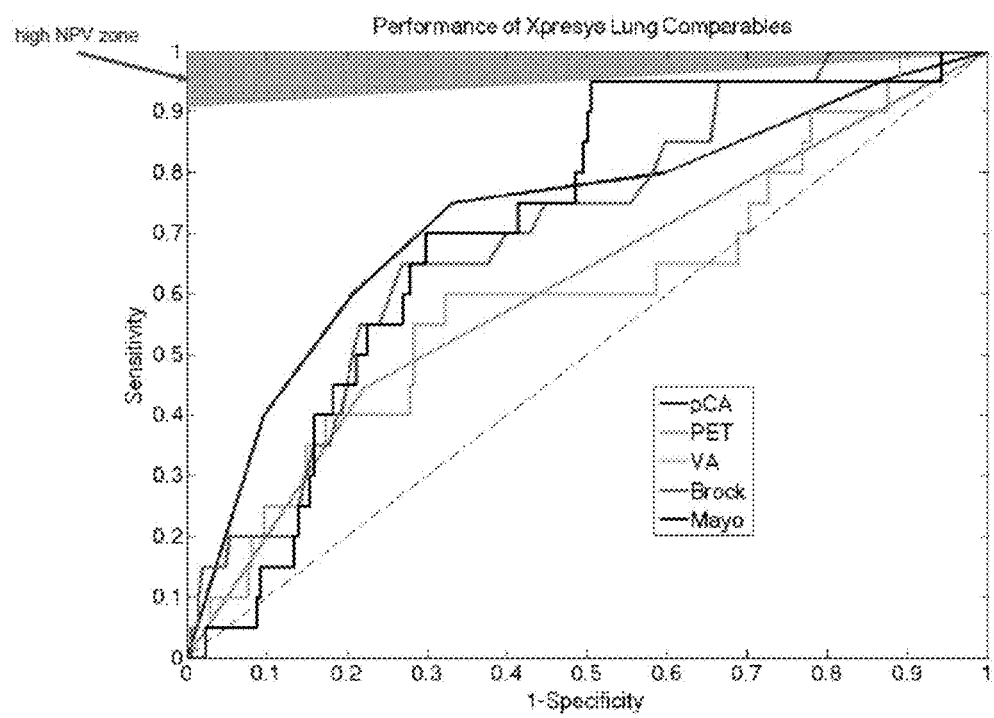
FIG. 15 is a graph depicting the sensitivity of alternative performance benchmarks as a function of the inverse specificity.
Figure 16:
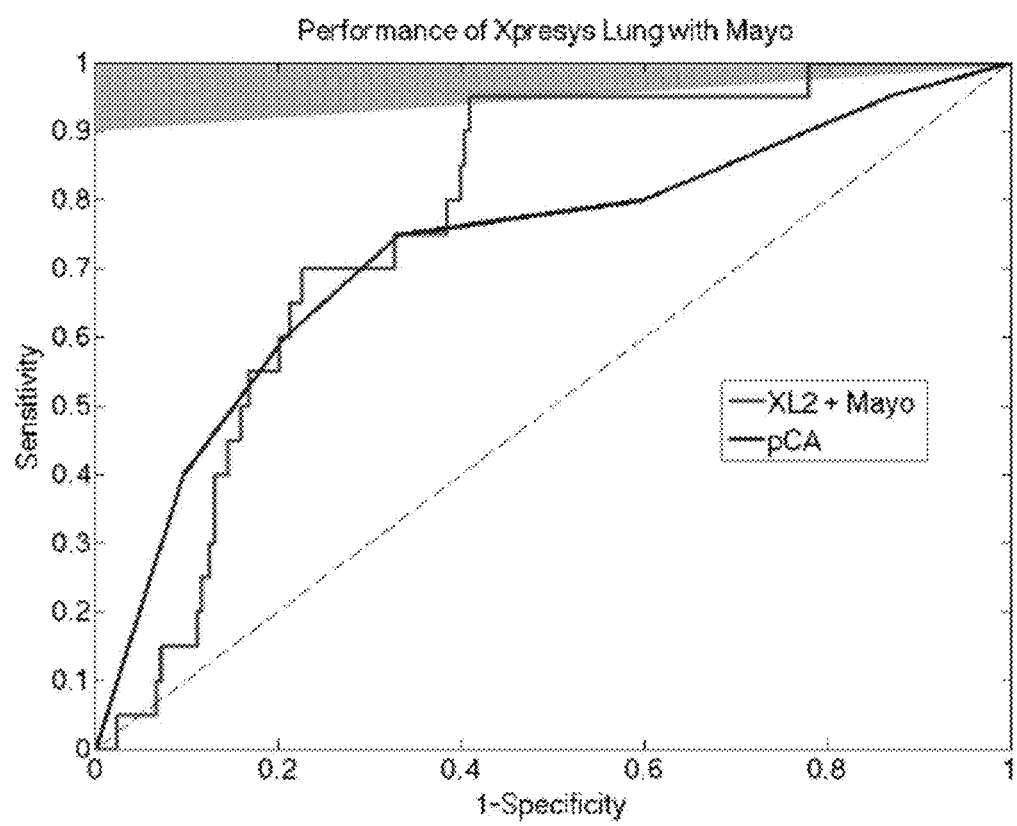
FIG. 16 is a graph depicting the sensitivity of pCA or XL2+Mayo as a function of the inverse specificity.
Figure 17:
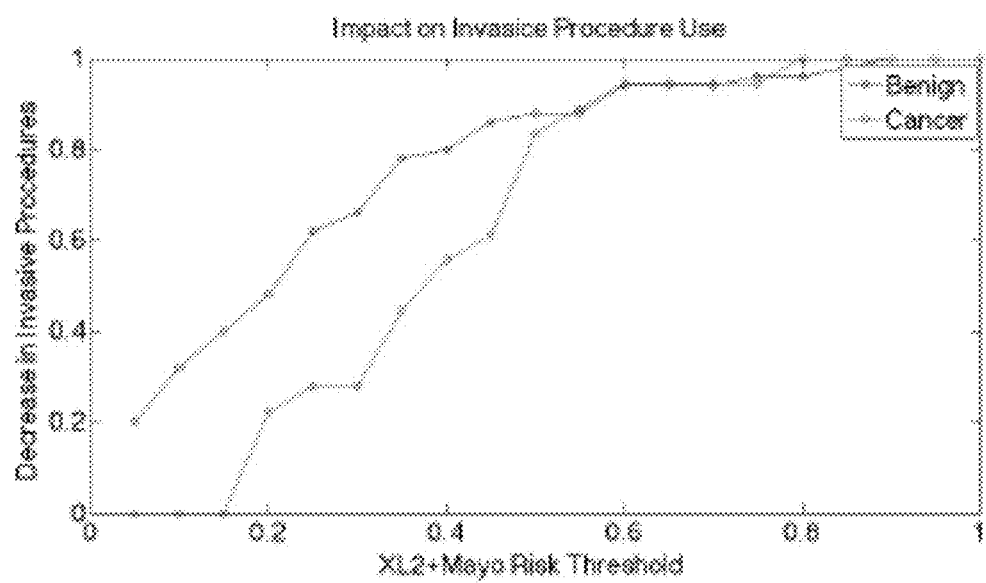
FIG. 17 is a graph depicting the decrease in invasive procedures as a function of the increased use of the XL2+Mayo Classifier.

To establish a baseline the performance of pCA, PET and various clinical models (VA, Mayo, Brock1a) for low and moderate risk subjects (pCA<=50%) was evaluated (see FIGS. 10-12). Note that Brock1b did not have sufficient subjects to generate a reliable ROC plot.

XL2 integrated with ANY risk predictor results in enhanced performance.

In FIGS. 10 and 11, the best performing predictor in the critical region is Mayo. Consequently, optimal performance from the integration of XL2 may occur with Mayo.

Two Protein Lung Cancer Assay for Ruling Out Lung Cancer.

Previously described lung cancer assays for ruling out lung cancer in a subject relied on an 11-protein assay. See U.S. Pat. Nos. 9,201,044 and 9,304,137, the contents of which are incorporated herein by reference in their entireties. Described herein is a 2-protein assay that has a greater diagnostic yield in comparison to the 11-protein assay referenced above. The 2-protein assay thus results in a reduction in invasive procedures for a subject having a benign lung nodule. The 2-protein assay described herein is also referred to as XL2. The 11-protein assay is also referred to as XL1.

XL2 was developed on a 353 subject/12 site prospective study and clinically validated on a subsequent 604 subject/33 site prospective study. The clinical validation study is referred to herein as PANOPTIC.

XL2 has various innovations over XL1 including:

XL2 was developed and validated on a large set of prospectively collected samples (~1000) from a large number of sites (~40) using a single sample collection protocol. In contrast, XL1 was developed and validated on a smaller set of archival samples from fewer set of sites.

XL2 is a refinement of the XL1. Specifically, XL1 consists of 5 diagnostic proteins and 6 normalization proteins. XL2 includes 1 of the 5 diagnostic proteins and 1 of the 6 normalization proteins. Accordingly, XL2 is a 2-protein based rule-out diagnostic assay.

XL2 was designed to integrate molecular markers with the physician's assessment of cancer risk (pCA). The validation of XL2 demonstrates that the integration of molecular markers and physician's assessment provides enhanced cancer risk assessment over each alone.

The intended use population of both the previously described 11-protein assay and the 2-protein assay described herein are individuals of at least 40 years of age having a pulmonary nodule between about 8 mm and 30 mm in size detected by radiology. Moreover, the intended use of XL2 is to identify likely benign lung nodules, of diameter 8 mm to 30 mm, with high probability. Although validated for all cancer risk groups, XL2 demonstrates optimal performance for low-to-moderate risk lung nodules.

The purpose of the study described herein was to validate one or more refinements to the 11-protein assay. Each refinement classifier, called a reversal herein, is based on a ratio of two proteins. The reversals validated are listed in Table 2 below.

TABLE 2

Reversals (two-protein classifiers)

| No. | Protein P1 | Transition for P1 | Protein P2 | Transition for P2 |
|---|---|---|---|---|
| 1 | LG3BP | VEIFYR_413.73_598.30 (SEQ ID NO.: 1) | C163A | INPASLDK_429.24_630.30 (SEQ ID NO.: 7) |
| 2 | MASP1 | TGVITSPDFPNPYPK_816.92_258.10 (SEQ ID NO.: 2) | C163A | INPASLDK_429.24_630.30 (SEQ ID NO.: 7) |

TABLE 2-continued

Reversals (two-protein classifiers)

| No. | Protein P1 | Transition for P1 | Protein P2 | Transition for P2 |
|---|---|---|---|---|
| 3 | PEDF | LQSLFDSPDFSK_692.34_593.30 (SEQ ID NO.: 3) | C163A | INPASLDK_429.24_630.30 (SEQ ID NO.: 7) |
| 4 | LG3BP | VEIFYR_413.73_598.30 (SEQ ID NO.: 1) | IBP3 | FLNVLSPR_473.28_685.40 (SEQ ID NO.: 8) |
| 5 | BGH3 | LTLLAPLNSVFK_658.40_804.50 (SEQ ID NO.: 4) | C163A | INPASLDK_429.24_630.30 (SEQ ID NO.: 7) |
| 6 | S10A6 | ELTIGSK_374.22_291.20 (SEQ ID NO.: 5) | C163A | INPASLDK_429.24_630.30 (SEQ ID NO.: 7) |
| 7 | LUM | SLEDLQLTHNK_433.23_499.30 (SEQ ID NO.: 6) | C163A | INPASLDK_429.24_630.30 (SEQ ID NO.: 7) |

The score $S_i(k)$ of a reversal $R_i$ on subject k is defined as $S_i(k) = \log_2[P1_i(k)/P2_i(k)]$, where $P1_i(k)$ and $P2_i(k)$ are the SIS-normalized abundance of protein P1 and P2, respectively, of the reversal $R_i$ in the plasma sample of subject k.

For each of the reversals listed in Table 2, the following parameters were tested sequentially.

Parameter 1: $pCA(k)+R_i$

In the PANOPTIC study, each subject k is assiged a cancer risk (0 to 1) by his/her phsyician. This is denoted as pCA(k). A cancer risk predictor $C_i(k)$ of a molecular risk reversal $R_i$ as follows $$C_i(k) = \begin{cases} 0 & \text{if } pCA(k) \leq 50\% \text{ and } S_i(k) \leq T_i \\ pCA(k), & \text{otherwise} \end{cases} \quad (1)$$

where the decision threshold $T_i$ for the reversal $R_i$ is defined in Table 3 and was the median value of $\{S_i(k)\}$ of patients with nodules no larger than 15 mm.

Parameter 1 of this study is that AUC of $\{C_i(k)\}$ of all subjects is significantly larger than 0.5.

TABLE 3

Decision threshold of reversals for Parameter 1

| No. | Protein P1 | Protein P2 | Threshold ($T_i$) |
|---|---|---|---|
| 1 | LG3BP | C163A | 1.2838 |
| 2 | MASP1 | C163A | −0.6518 |
| 3 | PEDF | C163A | 2.0114 |
| 4 | LG3BP | IBP3 | 0.0420 |
| 5 | BGH3 | C163A | 1.2933 |
| 6 | S10A6 | C163A | −0.3331 |
| 7 | LUM | C163A | 4.7819 |

Parameter 2: Ri with pCA(k)≤50%

Parameter 2 of this study is that AUC of $\{S_i(k)\}$ of subjects with pCA(k)≤50% is significantly larger than 0.5.

Parameter 3: $R_i$ with upper bounds on nodule size

Parameter 3 of this study is that AUC of $\{S_i(k)\}$ of subjects with nodule size no larger than a predefined bound B is significantly larger than 0.5. This parameter contains a series of sub-parameters, each corresponding to a specific value {B=15, 16, . . . , 30 mm}. A fixed sequence procedure (see A. Dmitrienko et al., "Key multiplicity Issues in Clinical Drug Development," *Stat Med,* 32 (2013), pages 1079-111; and A. Dmitrienko et al, "Multiple Testing Problems in Pharmaceutical Statistics, Chapman & Hall/Crc Biostatistics Series, pages xvi, 304p; the contents of each of which is incorporated herein by reference in their entireties) was used to test the subparameters sequentially as follows: The first subparameter with B=15 mm is tested. If it is validated, the next subclaim with B=16 mm is tested. If it is validated, the third subparameter is tested. During this sequence of testing, if the subparameter with B=N is not validated at a certain bound N, the testing procedure stops immediately and subsequent subparameters will not be tested at all. Parameter 3 is then validated with {B=15, 16, . . . , (N−1)mm}.

Parameter 4: $R_i$

Parameter 4 of this study is that the AUC of $\{Si(k)\}$ of all subjects is significantly larger than 0.5.

Example 2

Overview of the PANOPTIC Study

PANOPTIC is a prospective study with 683 patients enrolled across 33 sites. All eligible study participants met the intended use criteria described below.

The overall goal of this prospective, multi-center, and blinded observational study was to collect blood specimens and clinical data from subjects with newly diagnosed lung nodules nad divers demographic and geographic risk profiles for NSCLC. Subjects provided written informed consent prior to enrollment. A uniform protocol for blood specimen collection and handling was performed at the time of enrollment, in association with a surgical biopsy procedure, and at the Year 1 and Year 2 subject interviews in conjunction with clinical data capture on case report forms. Physician assessment of cancer risk was also collected. No therapies, procedures, or interventions were stipulated in the protocol for this observational study; however, the diagnostic standard of care (SOC) at each participating center will apply.

Subject Inclusion and Exclusion Criteria

Inclusion Criteria

Inclusion Criteria that must be met at the time of screening becore subject is enrolled in the study:

Age≥40 years

Smoking history: Never, Current, or Former

Subject undergoing evaluation for a lung nodule by a
  pulmonologist in a pulmonary or chest clinics and/or by
  a thoracic surgeon at the time of enrollment Baseline CT scan identifying lung nodule performed
  within 60 days of subject enrollment Maximal dimension of largest nodule identified by CT≥8 mm and ≤30 mm Subject willing to provide informed consent for the collection of blood specimens Exclusion Criteria Nodule work-up at the time of enrollment eligibility indicates any prior attempted or completed diagnostic biopsy procedure, such as transthoracic needle aspiration, bronchoscopic biopsy or surgery A prior CT scan is available that previously identifies the same 8 to 30 mm lung nodule under consideration for study inclusion on the most current CT scan, irrespective of the candidate nodule's radiographic characterization such as size density, or appearance Current diagnosis of any cancer Prior diagnosis of any cancer within 2 years of lung nodule detection, except for non-melanoma skin cancer Administration of blood products, e.g. packed red blood cells, fresh frozen plasma, platelets, within 30 days of subject enrollment Active participation in a therapeutic trial History of human immunodeficiency virus (HIV) or Hepatitis C Suitable Samples and Adjudication Rules Analysis should be constrained by the following:

Only samples from subjects whose initial CT scan was performed in November, 2013 or earlier can used in this study Only samples from patients that meet the inclusion/exclusion criteria described above can used in this study Each patient needs to have at least one other procedure other than the initial CT procedure, and has not dropped out of the study If a patient had surgery, there needs to be a final pathological diagnosis If a patient has a biopsy, there needs to be a final pathological diagnosis. The exception is the case in which a nodule has resolved after the biopsy was performed, and can be labeled as benign CT or PET (imaging) can only be used to make a presumptive benign diagnosis, but not a cancer diagnosis Blinding of Clinical Data To achieve the objective of performing a blinded study, the analysis team (comprised of members from the Bioinformatics and R&D teams) will not have access to the final clinical diagnosis, e.g. NSCLC or benign diagnoses, in the locked clinical database. The blinding procedure is overseen by program management.

Clinical Operations sends a list of eligible subjects to Program Management. The list includes subject ID (which also provides information about the site ID), sample ID, date of sample collection, subject age, subject gender, subject smoking status, number of pack years, and nodule size (as determined from the initial CT scan).

Program management creates new random numbers to replace each sample ID and site ID, then sends this list (not including the original sample ID's and site ID's) to the Bioinformatics team.

The Bioinformatics team then design experimental batch layouts of samples that, when possible, match benign and cancer samples based on site and storage age (based on date of blood collection) within batches and minimize any potential bias on benign or cancer status, nodule size, gender, subject age, smoking status, and number of pack years between batches.

Program Management receives the batch layouts, removes all subject clinical information, replaces the randomized sample and site numbers with the original ID numbers, randomizes the order of individual batches, and provides this list (only including subject ID and sample ID) to the Laboratory Personnel for analysis.

XL Lung Analysis

Protein levels were assayed in blood specimens using multiple reaction monitoring (MRM) mass spectrometry (MS) based on the procedures specified and described in U.S. Pat. Nos. 9,201,044 and 9,304,137, the contents of each of which are incorporated herein by reference in their entireties.

Sample Analysis

Each sample was analyzed using the LC-SRM-MS measurement methodology as follows:

1. Samples were depleted of high abundance proteins using the IGy14 and Supermix depletion columns from Sigma-Aldrich.

2. Samples were digested using trypsin into tryptic peptides.

3. Samples were analyzed by LC-SRM-MS using a 30 minute gradient on a Waters nanoacuity LC system followed by SRM-MS analysis of the 1550 transitions on a AB-Sciex 5500 triple quad device.

4. Raw transition ion counts were obtained and recorded for each of the 1550 transitions.

Matched samples were processed at each step either in parallel (steps 2 and 4) or back-to-back serially (steps 1 and 3). This minimizes analytical variation. Finally, steps 1 and 2 of the sample analysis are performed in batches of samples according to day of processing.

Preparation of IgY14-SuperMix Immunoaffinity Columns

Immunoaffinity columns were prepared in-house using a slurry containing a 2:1 ratio of IgY14 and SuperMix immunoaffinity resins, respectively (Sigma Aldrich). Briefly, a slurry (10 ml, 50%) of mixed immunoaffinity resins was added to a glass chromatography column (Tricorn, GE Healthcare) and the resin was allowed to settle under gravity flow, resulting in a 5 ml resin volume in the column. The column was capped and placed on an Agilent 1100 series HPLC system for further packing (20 minutes, 0.15M ammonium bicarbonate, 2 ml/min). The performance of each column used in the study was then assessed by replicate injections of aliquots of HPS sample. Column performance was assessed prior to beginning immunoaffinity separation of each batch of clinical samples.

IgY14-Sumermix Immunoaffinity Chromatography

Plasma samples (60 µl) were diluted (0.15M ammonium bicarbonate, 1:2 v/v, respectively) and filtered (0.2 µm AcroPrep 96-well filter plate, Pall Life Sciences) prior to immunoaffinity separation. Dilute plasma (90 µl) was separated on the IgY14-SuperMix column connected to an Agilent 1100 series HPLC system using a three buffers (loading/washing: 0.15M ammonium bicarbonate; stripping/elution: 0.1M glycine, pH 2.5; neutralization: 0.01M Tris-HCl, 0.15M NaCl, pH 7.4) with a load-wash-elute-neutralization-re-equilibration cycle (36 minutes total time). The unbound and bound fractions were monitored using a UV absorbance (280 nm) and were baseline resolved after separation. Only the unbound fraction containing the low abundance proteins was collected for downstream processing and analysis. Unbound fractions were lyophilized prior to enzymatic digestion.

Enzymatic Digestion of Low Abundance Proteins

Low abundance proteins were reconstituted under mild denaturing conditions (200 µl of 1:1 0.1M ammonium bicarbonate/trifluoroethanol v/v) and allowed to incubate (30 minutes, room temperature, orbital shaker). Samples were then diluted (800 µl of 0.1M ammonium bicarbonate) and digested with trypsin (Princeton Separations; 0.4 µg trypsin per sample, 37° C., 16 hours). Digested samples were lyophilized prior to solid-phase extraction.

Solid-Phase Extraction

Solid phase extraction was used to reduce salt and buffer contents in the samples prior to mass spectrometry. The lyophilized samples containing tryptic peptides were reconstituted (350 µl 0.01M ammonium bicarbonate) and allowed to incubate (15 minutes, room temperature, orbital shaker). A reducing agent was then added to the samples (30 µl 0.05M TCEP) and the samples were incubated (60 minutes, room temperature). Dilute acid and a low percentage of organic solvent (375 µl 90% water/10% acetonitrile/0.2% trifluoroacetic acid) were added to optimize the solid phase extraction of peptides. The extraction plate (Empore C18, 3M Bioanalytical Technologies) was conditioned according to manufacturer protocol. Samples were loaded onto the solid phase extraction plate, washed (500 µl 95% water/5% acetonitrile/0.1% trifluoroacetic acid) and eluted (200 µl 52% water/48% acetonitrile/0.1% trifluoroacetic acid) into a collection plate. The eluate was split into two equal aliquots and each aliquot was taken to dryness in a vacuum concentrator. One aliquot was used immediately for mass spectrometry, while the other was stored (−80° C.) and used as needed. Samples were reconstituted (12 µl 90% water/10% acetonitrile/0.2% formic acid) just prior to LC-SRM MS analysis.

Batch Processing Requirements

At the Laboratory Director's discretion, each of the batches may be run on a separate depletion column; or a depletion column may be used for other purposes privded there are no more than three batches per depletion column.

Data Analysis Plan

Classifiers

The reversals assayed in this study are listed in Table 2.

Validation of Classifiers

Each reversal will be tested against the four study claims sequentially. The one-sided 95% lower confidence bound (LCB) of AUC will be evaluated using the method described in DeLong et al. "Comparing the areas under two or more correlated receiver operating characteristic curves: a nonparametric approach," *Biometrics* 44 (1988), 837-45, the content of which is incorporated herein in its entirety.

Parameter 1

Evaluate the cancer risk predictors $\{C_i(k)\}$ using equation (1) for all subjects. Evaluate the AUC and its 95% LCB based on $\{C_i(k)\}$ and the disease status of all subjects. The parameter is validated if the 95% LCB of the AUC is no less than 0.5.

Parameter 2

Evaluate the AUC and its 95% LCB based on $\{Si(k)\}$ and the disease status of subjects with pCA(k)≤50%. The claim is validated if the 95% LCB of the AUC is no less than 0.5.

Parameter 3

A fixed sequence procedure (See Dimitrienko A. Dmitrienko et al., "Key multiplicity Issues in Clinical Drug Development," *Stat Med*, 32 (2013), pages 1079-111; and A. Dmitrienko et al., "Multiple Testing Problems in Pharmaceutical Statistics, Chapman & Hall/Crc Biostatistics Series, pages xvi, 304p; the contents of each of which is incorporated herein by reference in their entireties) was used to test the subparameters of this parameter. Basically, evaluate the AUC and its 95% LCB based on $\{S_i(k)\}$ and the disease status of subjects with nodule size no larger than B (15 mm). The subparameter is validated if the 95% LCB of the AUC is no less than 0.5. This procedure was repeated for other values of B (16, 17, . . . mm) until B=30 mm or a subparameter fails validation.

Parameter 4

Evaluate the AUC and its one-sided 95% LCB based on $\{Si(k)\}$ and the disease status of all subjects. The claim is validated if the 95% LCB of the AUC is no less than 0.5.

Analysis Overview

Bioinformatics will export Mass Spec data from Data Warehouse upon completion of experimental analysis of all samples.

For each sample, Bioinformatics will determine classifier score for each model to be tested Bioinformatics will send a spreadsheet containing the experimental Mass Spec data and the classifier scores for each sample to Program Management Program Management will time-stamp all relevant files Program Management will perform the data analysis as specified above Time-Stamping Documents Time Stamping Service Provider: DigiStamp, a time-stamp authority (TSA).

Software: The software creates a unique identifier, or fingerprint, for each file (a SHA-512 Hash). The software sends a file's fingerprint to DigiStamp's computer, which combines the file's fingerprint and current time to create a digital timestamp certificate that is returned and stored at a designated file location. The documents time-stamped before data analysis include PANOPTICS Study Clinical data profile, Experimental batch layout files, and experimental Mass Spec data.

Example 3

PANOPTIC Validation Report

Source Data

Subjects belonging to the original 220 subjects comprise the validation set. Of these five had a PET performed before the initial physician assessment, and so, were disqualified from the validation set. This results in a total of 169 subjects (98 benign, 71 cancer).

Validation Parameters

The validation parameters are described in Example 2. The results presented in this example follow the parameters presented in Example 2.

Considerations

Certain claims are made for those subjects with pCA<=50%. However, in the study collection, subjects are grouped into risk bins, in particular, 40%-50%, 50%-60%, etc. Consequently, pCA<50% is used to avoid inclusion of pCA risks of 51% to 60%.

PANOPTIC Results

The PANOPTIC results are presented in the tables below. The last two columns in each row is the AUC and one-sided Mann-Whitney significance test that has AUC>0.5.

TABLE 4

| LG3BP/C163A | | | |
|---|---|---|---|
| Parameter 1: | LG3BP/C163A | 0.87791 | 6.474e−18 |
| Parameter 2: | LG3BP/C163A | 0.70059 | 0.041215 |

TABLE 4-continued

| | | | | |
|---|---|---|---|---|
| \multicolumn{5}{c}{LG3BP/C163A} |
| Parameter 3: | LG3BP/C163A | Nodule Size: 15 | 0.63184 | 0.028399 |
| Parameter 3: | LG3BP/C163A | Nodule Size: 16 | 0.61783 | 0.029556 |
| Parameter 3: | LG3BP/C163A | Nodule Size: 17 | 0.60505 | 0.035917 |
| Parameter 3: | LG3BP/C163A | Nodule Size: 18 | 0.5941 | 0.045413 |
| Parameter 3: | LG3BP/C163A | Nodule Size: 19 | 0.60352 | 0.029089 |
| Parameter 3: | LG3BP/C163A | Nodule Size: 20 | 0.59985 | 0.029782 |
| Parameter 3: | LG3BP/C163A | Nodule Size: 21 | 0.60499 | 0.023339 |
| Parameter 3: | LG3BP/C163A | Nodule Size: 22 | 0.58333 | 0.04954 |
| Parameter 3: | LG3BP/C163A | Nodule Size: 23 | 0.5781 | 0.05642 |
| Parameter 3: | LG3BP/C163A | Nodule Size: 24 | 0.57759 | 0.05527 |
| Parameter 3: | LG3BP/C163A | Nodule Size: 25 | 0.58637 | 0.034599 |
| Parameter 3: | LG3BP/C163A | Nodule Size: 26 | 0.59313 | 0.023198 |
| Parameter 3: | LG3BP/C163A | Nodule Size: 27 | 0.58442 | 0.033643 |
| Parameter 3: | LG3BP/C163A | Nodule Size: 28 | 0.58354 | 0.034194 |
| Parameter 3: | LG3BP/C163A | Nodule Size: 29 | 0.5813 | 0.036829 |
| Parameter 3: | LG3BP/C163A | Nodule Size: 30 | 0.58408 | 0.031323 |
| Parameter 4: | LG3BP/C163A | | 0.58408 | 0.031323 |

Summary LG3BP/C163A: Claim 1, Claim 2, Claim 3 for nodule sizes 15 mm to 22 mm (inclusive) and Claim 4 are satisfied.

TABLE 5

| | | | | |
|---|---|---|---|---|
| \multicolumn{5}{c}{MASP1/C163A} |
| Parameter 1: | MASP1/C163A | | 0.88416 | 4.4301e−18 |
| Parameter 2: | MASP1/C163A | | 0.66732 | 0.073907 |
| Parameter 3: | MASP1/C163A | Nodule Size: 15 | 0.62438 | 0.036185 |
| Parameter 3: | MASP1/C163A | Nodule Size: 16 | 0.58737 | 0.080989 |
| Parameter 3: | MASP1/C163A | Nodule Size: 17 | 0.60396 | 0.037407 |
| Parameter 3: | MASP1/C163A | Nodule Size: 18 | 0.60674 | 0.027511 |
| Parameter 3: | MASP1/C163A | Nodule Size: 19 | 0.59444 | 0.04199 |
| Parameter 3: | MASP1/C163A | Nodule Size: 20 | 0.58165 | 0.06176 |
| Parameter 3: | MASP1/C163A | Nodule Size: 21 | 0.58078 | 0.06301 |
| Parameter 3: | MASP1/C163A | Nodule Size: 22 | 0.55919 | 0.12083 |
| Parameter 3: | MASP1/C163A | Nodule Size: 23 | 0.56181 | 0.10483 |
| Parameter 3: | MASP1/C163A | Nodule Size: 24 | 0.57234 | 0.068414 |
| Parameter 3: | MASP1/C163A | Nodule Size: 25 | 0.57215 | 0.064556 |
| Parameter 3: | MASP1/C163A | Nodule Size: 26 | 0.57627 | 0.051455 |
| Parameter 3: | MASP1/C163A | Nodule Size: 27 | 0.57463 | 0.052909 |
| Parameter 3: | MASP1/C163A | Nodule Size: 28 | 0.57247 | 0.056965 |
| Parameter 3: | MASP1/C163A | Nodule Size: 29 | 0.56819 | 0.066798 |
| Parameter 3: | MASP1/C163A | Nodule Size: 30 | 0.56051 | 0.09023 |
| Parameter 4: | MASP1/C163A | | 0.56051 | 0.09023 |

Summary MASP1/C163A: Claim 1 and Claim 3 for nodule size 15 mm are satisfied.

TABLE 6

| | | | | |
|---|---|---|---|---|
| \multicolumn{5}{c}{PEDF/C163A} |
| Parameter 1: | PEDF/C163A | | 0.87259 | 3.2344e−17 |
| Parameter 2: | PEDF/C163A | | 0.57534 | 0.25881 |
| Parameter 3: | PEDF/C163A | Nodule Size: 15 | 0.66418 | 0.0088174 |
| Parameter 3: | PEDF/C163A | Nodule Size: 16 | 0.63306 | 0.016511 |
| Parameter 3: | PEDF/C163A | Nodule Size: 17 | 0.62523 | 0.015913 |
| Parameter 3: | PEDF/C163A | Nodule Size: 18 | 0.61849 | 0.016582 |
| Parameter 3: | PEDF/C163A | Nodule Size: 19 | 0.61543 | 0.017316 |
| Parameter 3: | PEDF/C163A | Nodule Size: 20 | 0.6135 | 0.016101 |
| Parameter 3: | PEDF/C163A | Nodule Size: 21 | 0.61166 | 0.017184 |
| Parameter 3: | PEDF/C163A | Nodule Size: 22 | 0.59594 | 0.028772 |
| Parameter 3: | PEDF/C163A | Nodule Size: 23 | 0.5936 | 0.028672 |
| Parameter 3: | PEDF/C163A | Nodule Size: 24 | 0.59951 | 0.020315 |
| Parameter 3: | PEDF/C163A | Nodule Size: 25 | 0.60978 | 0.010438 |
| Parameter 3: | PEDF/C163A | Nodule Size: 26 | 0.60966 | 0.0094973 |
| Parameter 3: | PEDF/C163A | Nodule Size: 27 | 0.6051 | 0.011353 |
| Parameter 3: | PEDF/C163A | Nodule Size: 28 | 0.5993 | 0.015128 |
| Parameter 3: | PEDF/C163A | Nodule Size: 29 | 0.59308 | 0.02027 |
| Parameter 3: | PEDF/C163A | Nodule Size: 30 | 0.58709 | 0.026891 |
| Parameter 4: | PEDF/C163A | | 0.58709 | 0.026891 |

Summary PEDF/C163A: Claim 1, Claim 3 for nodule sizes 15 mm to 30 mm (inclusive) and Claim 4 are satisfied.

TABLE 7

| | | | | |
|---|---|---|---|---|
| \multicolumn{5}{c}{LG3BP/IBP3} |
| Parameter 1: | LG3BP/IBP3 | | 0.86325 | 5.034e−17 |
| Parameter 2: | LG3BP/IBP3 | | 0.52055 | 0.57429 |
| Parameter 3: | LG3BP/IBP3 | Nodule Size: 15 | 0.50995 | 0.55907 |
| Parameter 3: | LG3BP/IBP3 | Nodule Size: 16 | 0.51434 | 0.41041 |
| Parameter 3: | LG3BP/IBP3 | Nodule Size: 17 | 0.50342 | 0.4778 |
| Parameter 3: | LG3BP/IBP3 | Nodule Size: 18 | 0.50136 | 0.49135 |
| Parameter 3: | LG3BP/IBP3 | Nodule Size: 19 | 0.52411 | 0.33027 |
| Parameter 3: | LG3BP/IBP3 | Nodule Size: 20 | 0.53236 | 0.27129 |
| Parameter 3: | LG3BP/IBP3 | Nodule Size: 21 | 0.53533 | 0.25214 |
| Parameter 3: | LG3BP/IBP3 | Nodule Size: 22 | 0.52714 | 0.2961 |
| Parameter 3: | LG3BP/IBP3 | Nodule Size: 23 | 0.51923 | 0.34867 |
| Parameter 3: | LG3BP/IBP3 | Nodule Size: 24 | 0.51406 | 0.38686 |
| Parameter 3: | LG3BP/IBP3 | Nodule Size: 25 | 0.52983 | 0.26552 |
| Parameter 3: | LG3BP/IBP3 | Nodule Size: 26 | 0.53208 | 0.24669 |
| Parameter 3: | LG3BP/IBP3 | Nodule Size: 27 | 0.52317 | 0.30823 |
| Parameter 3: | LG3BP/IBP3 | Nodule Size: 28 | 0.52213 | 0.31502 |
| Parameter 3: | LG3BP/IBP3 | Nodule Size: 29 | 0.52577 | 0.28571 |
| Parameter 3: | LG3BP/IBP3 | Nodule Size: 30 | 0.53133 | 0.24423 |
| Parameter 4: | LG3BP/IBP3 | | 0.53133 | 0.24423 |

Summary LG3BP/IBP3: Claim 1 is satisfied.

TABLE 8

| | | | | |
|---|---|---|---|---|
| \multicolumn{5}{c}{BGH3/C163A} |
| Claim 1: | BGH3/C163A | | 0.87719 | 1.5657e−17 |
| Claim 2: | BGH3/C163A | | 0.55969 | 0.30474 |
| Claim 3: | BGH3/C163A | Nodule Size: 15 | 0.62687 | 0.033415 |
| Claim 3: | BGH3/C163A | Nodule Size: 16 | 0.60573 | 0.045205 |
| Claim 3: | BGH3/C163A | Nodule Size: 17 | 0.60793 | 0.032182 |
| Claim 3: | BGH3/C163A | Nodule Size: 18 | 0.60253 | 0.032678 |
| Claim 3: | BGH3/C163A | Nodule Size: 19 | 0.5899 | 0.049996 |
| Claim 3: | BGH3/C163A | Nodule Size: 20 | 0.57634 | 0.074952 |
| Claim 3: | BGH3/C163A | Nodule Size: 21 | 0.57782 | 0.070274 |
| Claim 3: | BGH3/C163A | Nodule Size: 22 | 0.5594 | 0.11998 |
| Claim 3: | BGH3/C163A | Nodule Size: 23 | 0.55671 | 0.12491 |
| Claim 3: | BGH3/C163A | Nodule Size: 24 | 0.56353 | 0.09572 |
| Claim 3: | BGH3/C163A | Nodule Size: 25 | 0.57527 | 0.05667 |
| Claim 3: | BGH3/C163A | Nodule Size: 26 | 0.58085 | 0.041904 |
| Claim 3: | BGH3/C163A | Nodule Size: 27 | 0.57696 | 0.047671 |
| Claim 3: | BGH3/C163A | Nodule Size: 28 | 0.57535 | 0.050122 |
| Claim 3: | BGH3/C163A | Nodule Size: 29 | 0.56701 | 0.070224 |
| Claim 3: | BGH3/C163A | Nodule Size: 30 | 0.56108 | 0.088175 |
| Claim 4: | BGH3/C163A | | 0.56108 | 0.088175 |

Summary BGH3/C163A: Claim 1 and Claim 3 for nodule sizes 15 mm to 19 mm (inclusive) are satisfied.

TABLE 9

| | | | | |
|---|---|---|---|---|
| \multicolumn{5}{c}{S10A6/C163A} |
| Parameter 1: | S10A6/C163A | | 0.88517 | 3.5019e−18 |
| Parameter 2: | S10A6/C163A | | 0.74951 | 0.015293 |
| Parameter 3: | S10A6/C163A | Nodule Size: 15 | 0.61692 | 0.045638 |
| Parameter 3: | S10A6/C163A | Nodule Size: 16 | 0.57258 | 0.12278 |
| Parameter 3: | S10A6/C163A | Nodule Size: 17 | 0.58054 | 0.083869 |
| Parameter 3: | S10A6/C163A | Nodule Size: 18 | 0.58326 | 0.067335 |
| Parameter 3: | S10A6/C163A | Nodule Size: 19 | 0.57119 | 0.096478 |
| Parameter 3: | S10A6/C163A | Nodule Size: 20 | 0.56244 | 0.11956 |
| Parameter 3: | S10A6/C163A | Nodule Size: 21 | 0.55682 | 0.14109 |
| Parameter 3: | S10A6/C163A | Nodule Size: 22 | 0.56688 | 0.092872 |
| Parameter 3: | S10A6/C163A | Nodule Size: 23 | 0.56024 | 0.11075 |
| Parameter 3: | S10A6/C163A | Nodule Size: 24 | 0.5744 | 0.062988 |
| Parameter 3: | S10A6/C163A | Nodule Size: 25 | 0.58082 | 0.044543 |
| Parameter 3: | S10A6/C163A | Nodule Size: 26 | 0.57643 | 0.051086 |
| Parameter 3: | S10A6/C163A | Nodule Size: 27 | 0.57525 | 0.05147 |
| Parameter 3: | S10A6/C163A | Nodule Size: 28 | 0.56822 | 0.068365 |
| Parameter 3: | S10A6/C163A | Nodule Size: 29 | 0.56848 | 0.065962 |

TABLE 9-continued

S10A6/C163A

| | | | | |
|---|---|---|---|---|
| Parameter 3: | S10A6/C163A | Nodule Size: 30 | 0.57287 | 0.053344 |
| Parameter 4: | S10A6/C163A | | 0.57287 | 0.053344 |

Summary S10A6/C163A: Claim 1, Claim 2 and Claim 3 for nodule sizes 15 mm are satisfied.

TABLE 10

LUM/C163A

| | | | | |
|---|---|---|---|---|
| Claim 1: | LUM/C163A | | 0.87978 | 7.175e-18 |
| Claim 2: | LUM/C163A | | 0.70254 | 0.039734 |
| Claim 3: | LUM/C163A | Nodule Size: 15 | 0.64988 | 0.015154 |
| Claim 3: | LUM/C163A | Nodule Size: 16 | 0.62903 | 0.019362 |
| Claim 3: | LUM/C163A | Nodule Size: 17 | 0.64216 | 0.0073979 |
| Claim 3: | LUM/C163A | Nodule Size: 18 | 0.62692 | 0.011249 |
| Claim 3: | LUM/C163A | Nodule Size: 19 | 0.61486 | 0.017766 |
| Claim 3: | LUM/C163A | Nodule Size: 20 | 0.61173 | 0.017495 |
| Claim 3: | LUM/C163A | Nodule Size: 21 | 0.61141 | 0.017384 |
| Claim 3: | LUM/C163A | Nodule Size: 22 | 0.60876 | 0.01565 |
| Claim 3: | LUM/C163A | Nodule Size: 23 | 0.59753 | 0.023826 |
| Claim 3: | LUM/C163A | Nodule Size: 24 | 0.61151 | 0.010887 |
| Claim 3: | LUM/C163A | Nodule Size: 25 | 0.62001 | 0.0057733 |
| Claim 3: | LUM/C163A | Nodule Size: 26 | 0.61964 | 0.0052434 |
| Claim 3: | LUM/C163A | Nodule Size: 27 | 0.61676 | 0.0056818 |
| Claim 3: | LUM/C163A | Nodule Size: 28 | 0.61264 | 0.0069845 |
| Claim 3: | LUM/C163A | Nodule Size: 29 | 0.61532 | 0.005575 |
| Claim 3: | LUM/C163A | Nodule Size: 30 | 0.60391 | 0.010689 |
| Claim 4: | LUM/C163A | | 0.60391 | 0.010689 |

Summary LUM/C163A: Claim 1, Claim 2, Claim 3 for nodule sizes 15 mm to 30 mm (inclusive) and Claim 4 are satisfied.

XL2 Performance in PANOPTIC Study

Physician Cancer Risk Assessment (pCA)

A unique and valuable feature of PANOPTIC is that the physician's initial assessment of cancer risk for a lung nodule is captured.

This allows for the exploration of how physicians assess risk, select follow on procedures based on risk assessment and how XL performs for different risk stratifications.

Figure 1B:
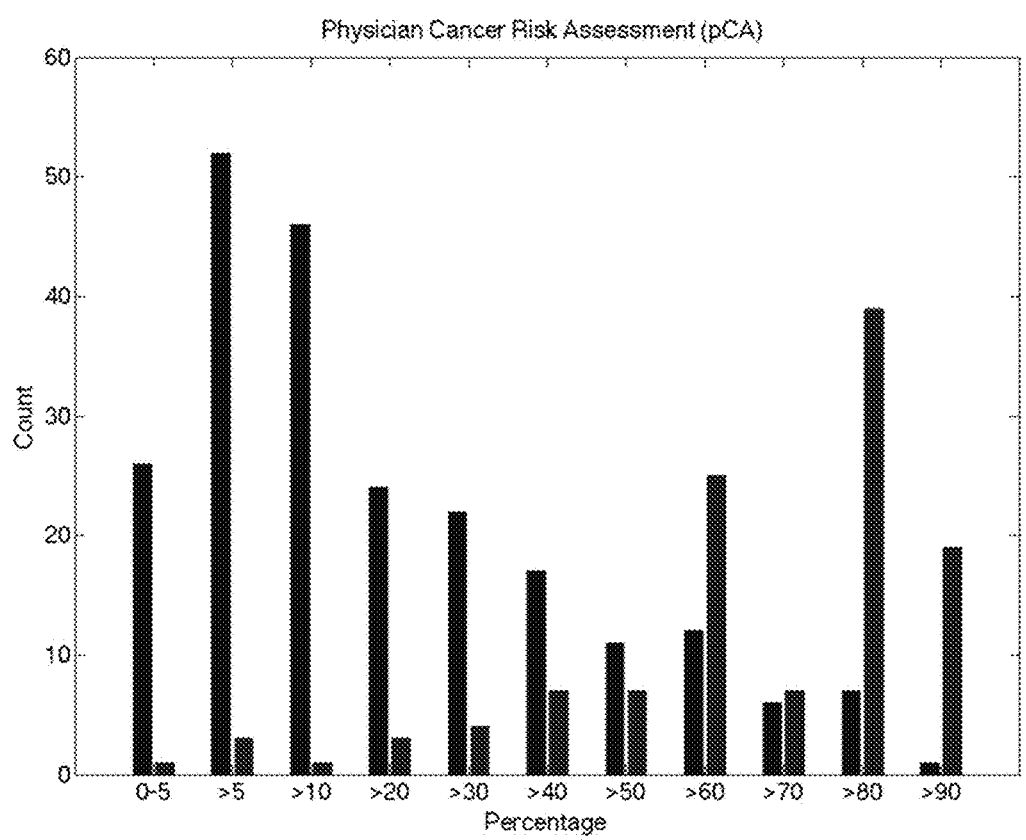

The pCA with all samples in the PANOPTIC study are shown in FIG. 1A; the pCA with all samples in the PANOPTIC study at stage 1$a$ is shown in FIG. 1B.

Performance on All Risk Categories: Guideline Analysis

One objective of XL2 is to integrate molecular markers with physician's assessment of cancer risk to improve risk stratification.

Summary of Results

Figure 2A:
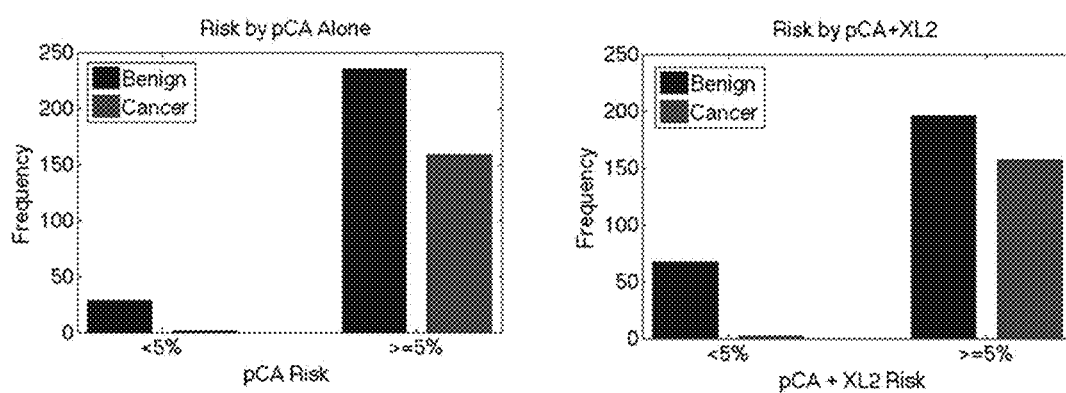
FIGS. 2A and 2B is a series of bar graphs that depict performance on all cancer risk categories. The graphs depict cancer risk as assessed by pCA alone or pCA+XL2.

Combining pCA with XL2 increases specificity by a factor of 2.4. See FIG. 2A, 2B and Tables 11, 12, 13.

If Guidelines are followed then 2.4-fold more benign nodules are correctly routed to CT surveillance. McNemar's statistical test was used to demonstrate that pCA+XL2 is significantly better than pCA alone.

TABLE 11

Analysis Performance

| | TP | FP | FN | TN | Sens | Spec | PPV | NPV |
|---|---|---|---|---|---|---|---|---|
| pCA | 158 | 235 | 1 | 28 | 99% | 11% | 40% | 97% |
| pCA + XL2 | 157 | 196 | 2 | 67 | 99% | 26% | 45% | 97% |
| XL2 | 126 | 185 | 33 | 78 | 79% | 30% | 41% | 70% |

TABLE 12

Performance Restricted to Stage 1a only (n = 340)

| | TP | FP | FN | TN | Sens | Spec | PPV | NPV |
|---|---|---|---|---|---|---|---|---|
| pCA | 115 | 198 | 1 | 26 | 99% | 12% | 37% | 96% |
| pCA + XL2 | 114 | 167 | 2 | 57 | 98% | 25% | 41% | 97% |

Note that restriction to Stage 1a does not change conclusions.

Both pCA+XL1 and pCA+XL2 are significantly better at classifying subjects as compared to pCA alone (p value=2.2e-5).

Figure 2B:
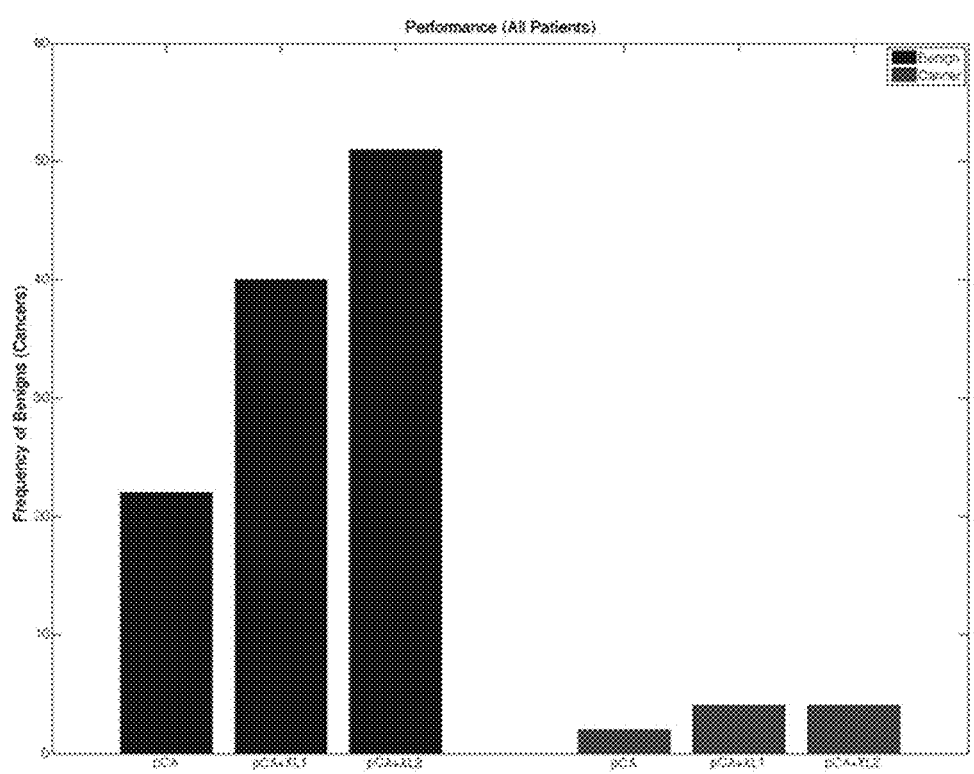

FIG. 2B shows the number of benigns and cancers with cancer risk at or below 5%. Without increasing the number of cancers significantly, the number of benigns routed by pCA+XL1 and pCA+XL2 are substantially higher than pCA alone.

The assumption: pCA is reduced by 50% if XL1 (XL2) returns "Likely Benign", otherwise no change.

Table 13 below shows the individual performances of pCA, XL1 and XL2 on all samples of the interim analysis as well as the combined (and more representative in practice) performance of pCA+XL1 and pCA+XL2.

TABLE 13

Analysis Performance—all samples

| Model | Sens | Spec | PPV | NPV | PPV* | NPV* | LBR* |
|---|---|---|---|---|---|---|---|
| pCA | 97 | 22 | 48 | 92 | 29 | 96 | 17 |
| XL1** | 77 | 26 | 43 | 60 | 26 | 77 | 26 |
| XL2 | 89 | 31 | 49 | 79 | 30 | 90 | 26 |
| pCA + XL1 | 95 | 40 | 54 | 91 | 35 | 96 | 32 |
| pCA + XL2 | 95 | 52 | 59 | 93 | 39 | 97 | 40 |

*Adjusted to population cancer prevalence of 25%.
**XL1 on own has optimized threshold of 0.40; In combination with pCA threshold is 0.43

The primary comparison is practice without XL (i.e. pCA) and with XL (i.e. pCA+XL1, pCA+XL2):

The key measures are NPV* which is the probability that a Rule Out is correct and LBR* which is the diagnostic yield.

While pCA+XL1 (96%) and pCA+XL2 (97%) have the same Rule Out confidence of pCA alone (96%).

pCA+XL1 (32%) and pCA+XL2 (40%) have significantly more benign nodules Rule Out compared to pCA alone (17%).

Performance on All Samples: Procedure Use

Figure 3:
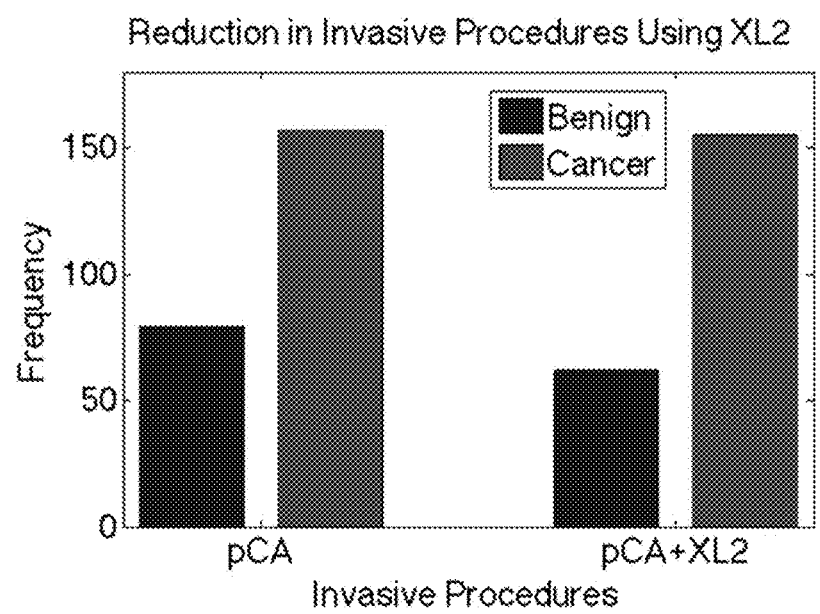
FIG. 3 is a bar graph that depicts the reduction in invasive procedures on all cancer risk categories obtained through the use of pCA+XL2 in comparison to the use of pCA alone.

For this analysis, the number of samples tested as "Likely Benign" by pCA+XL2 and originally routed to Invasive Procedures was identified (FIG. 3). This determines the potential impact of XL2 on reducing invasive procedures on benign nodules:

Benign nodules routed from invasive procedures to CT Surveillance: 17/79=22%

Malignant nodules routed from invasive procedures to CT Surveillance: 2/157=1%

Performance on Low-Moderate Risk Samples: Guideline Analysis

Figure 4:
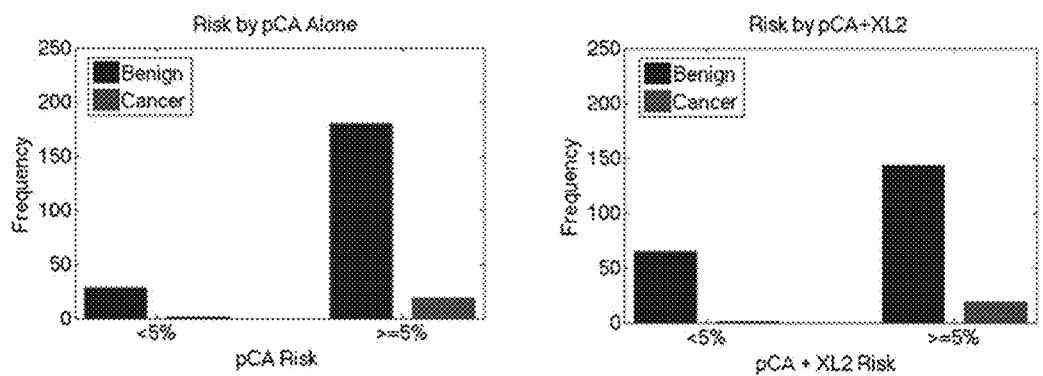
FIG. 4 is a series of graphs that depict performance on low-to-moderate risk subject samples. The graphs depict cancer risk as assessed by either pCA alone or pCA+XL2.
Figure 4:
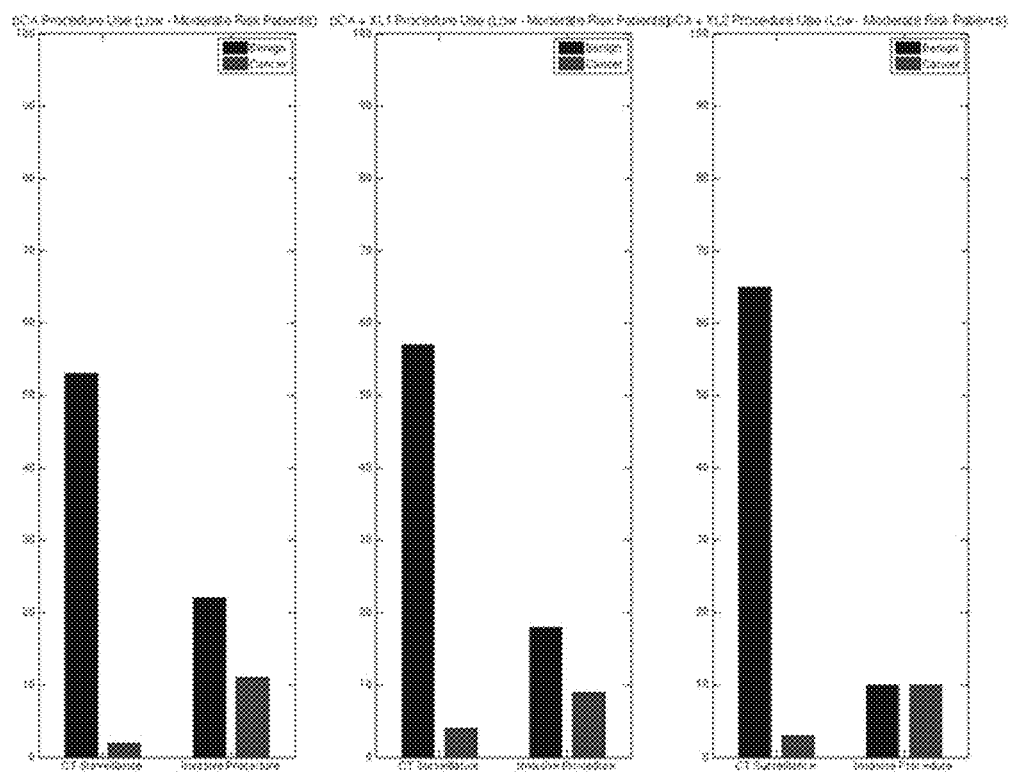

For this analysis, the performance of pCA alone, XL2 alone and the integration of pCA with XL2 are assessed around the 5% cancer risk threshold (FIG. 4A and Tables 14, 15 and 16). FIG. 4 depicts the change in procedure use when XL1 (XL2) is applied to low to moderate risk patients. In some aspects, the rule is "If Likely Benign then place in CT Surveillance".

For XL1 the number of benign invasive procedures is reduced from 22 to 18 (18% reduction). 2 additional cancer patients are routed to CT Surveillance over pCA.

For XL2 the number of benign invasive procedures is reduced from 22 to 10 (55% reduction). 1) additional cancer patient are routed to CT Surveillance over pCA.

If applied to all patients, disregarding pCA then the reductions are 12% and 36%, respectively. 2) additional cancer patients are routed to CT Surveillance over pCA.

FIG. 7 depicts an XL2 ROC curve obtained from subject samples having low-moderate risk.

Summary

Combining pCA with XL2 increases specificity by a factor of 2.4. If Guidelines are followed, then 2.4-fold more benign nodules are correctly routed to CT surveillance.

TABLE 14

Analysis Performance—Low-Moderate Risk Samples

|  | TP | FP | FN | TN | Sens | Spec | PPV | NPV |
|---|---|---|---|---|---|---|---|---|
| pCA | 19 | 180 | 1 | 28 | 95% | 13% | 10% | 97% |
| XL2 | 19 | 157 | 1 | 51 | 95% | 25% | 11% | 98% |
| pCA + XL2 | 19 | 143 | 1 | 65 | 95% | 31% | 12% | 98% |

TABLE 15

Performance Restricted to Stage 1a only (n = 306)

|  | TP | FP | FN | TN | Sens | Spec | PPV | NPV |
|---|---|---|---|---|---|---|---|---|
| pCA | 18 | 161 | 1 | 26 | 95% | 14% | 10% | 96% |
| pCA + XL2 | 18 | 131 | 1 | 56 | 95% | 30% | 12% | 98% |

Note that Restriction to Stage 1a does not change conclusions.

TABLE 16

Analysis Performance—Low-Moderate Risk Samples

| Model | Sens | Spec | PPV | NPV | PPV* | NPV* | LBR* |
|---|---|---|---|---|---|---|---|
| pCA | 85 | 29 | 17 | 92 | 9 | 96 | 28 |
| XL1 | 85 | 24 | 16 | 90 | 8 | 95 | 23 |
| XL2 | 92 | 29 | 18 | 96 | 9 | 98 | 28 |
| pCA + XL1 | 69 | 53 | 20 | 91 | 10 | 96 | 52 |
| pCA + XL2 | 69 | 68 | 27 | 93 | 14 | 97 | 65 |

*Adjusted to population cancer prevalence of 25%.

Table 16 shows the individual performances of pCA, XL1 and XL2 on all samples of the interim analysis as well as the combined (and more representative in practice) performance of pCA+XL1 and pCA+XL2.

The primary comparison is practice without XL (i.e. pCA) and with XL (i.e. pCA+XL1, pCA+XL2):

The key measures are NPV* which is the probability that a Rule Out is correct and LBR* which is the diagnostic yield.

While pCA+XL1 (96%) and pCA+XL2 (97%) have the same Rule Out confidence of pCA alone (96%).

pCA+XL1 (52%) and pCA+XL2 (65%) have significantly more benign nodules Rule Out compared to pCA alone (28%).

Performance on Low-Moderate Risk Samples: Procedure Use

Figure 5:
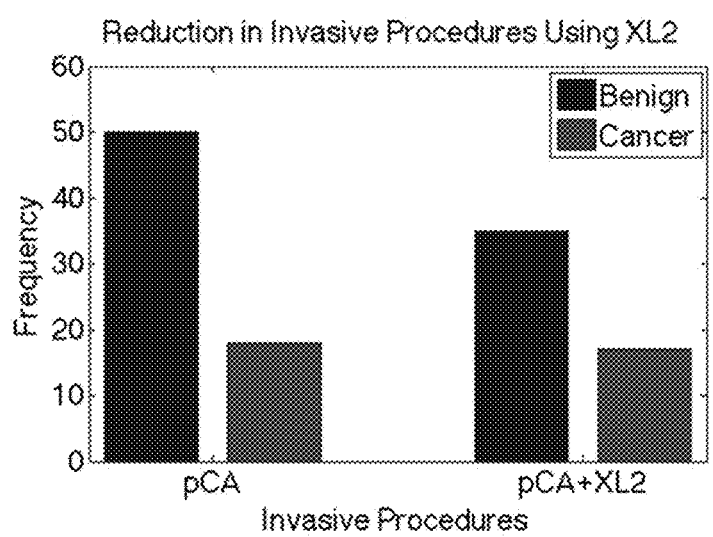
FIG. 5 is a bar graph that depicts the reduction in invasive procedures on low-to-moderate risk categories obtained through the use of pCA+XL2 in comparison to the use of pCA alone.
Figure 6:
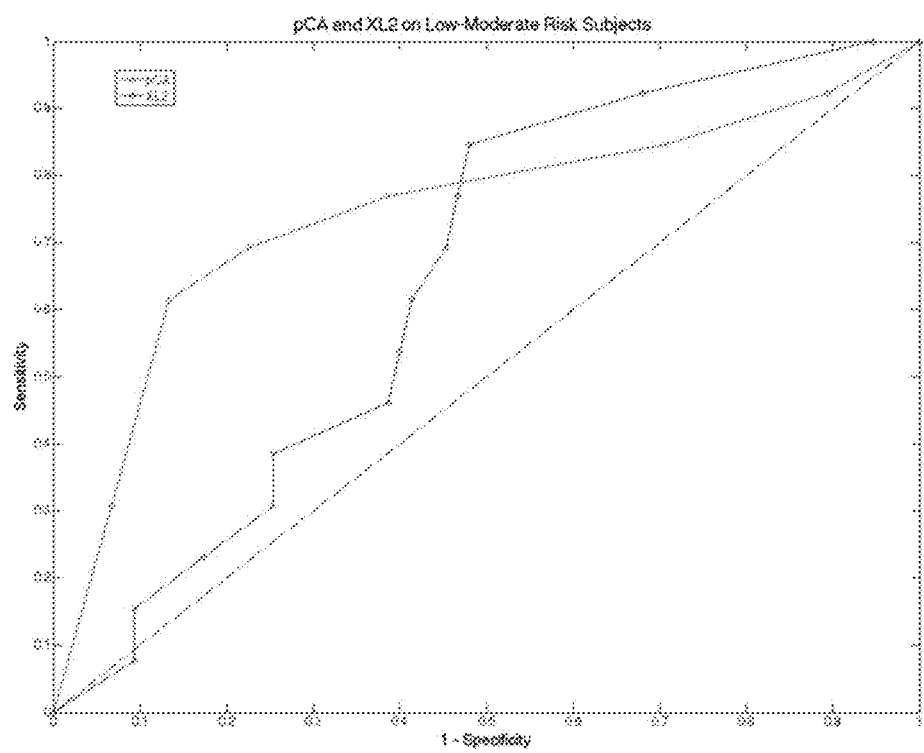
FIG. 6 depicts an XL2 ROC curve obtained from subject samples having low-moderate risk.

For this analysis, the number of samples tested as "Likely Benign" by pCA+XL2 and originally routed to Invasive Procedures was identified to determine the potential impact of XL2 on reducing invasive procedures on benign nodules (FIG. 5). The data indicate Benign nodules routed from invasive procedures to CT surveillance: 15/50=30%

Malignant nodules routed from invasive procedures to CT surveillance: 1/18=6%

Note that the progression for the malignant nodules routed from invasive to CT surveillance was as follows:

15 benign; 1 cancer 21 benign; 4 cancer 32 benign; 4 cancer

Total benign in invasive procedures were 79 for all risk categories, and the total cancer nodules in invasive procedures were 157.

Risk Assessment

Figure 7A:
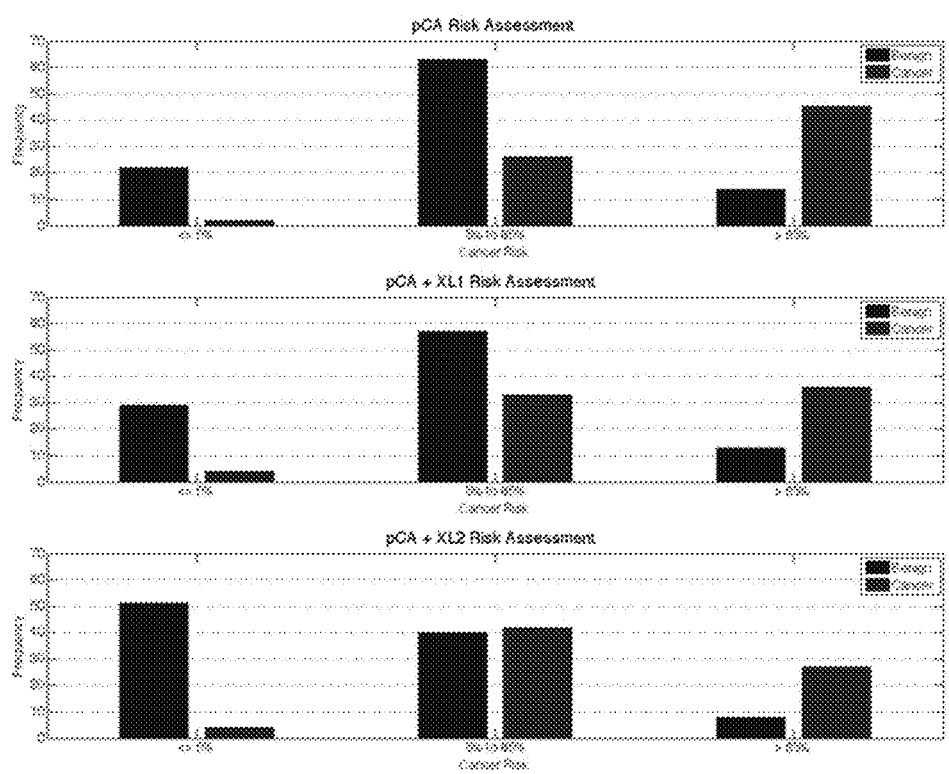
FIGS. 7A and 7B are a series of graphs that depict cancer risk assessment as indicated by pCA, pCA+XL1, or pCA+XL2.
Figure 7B:
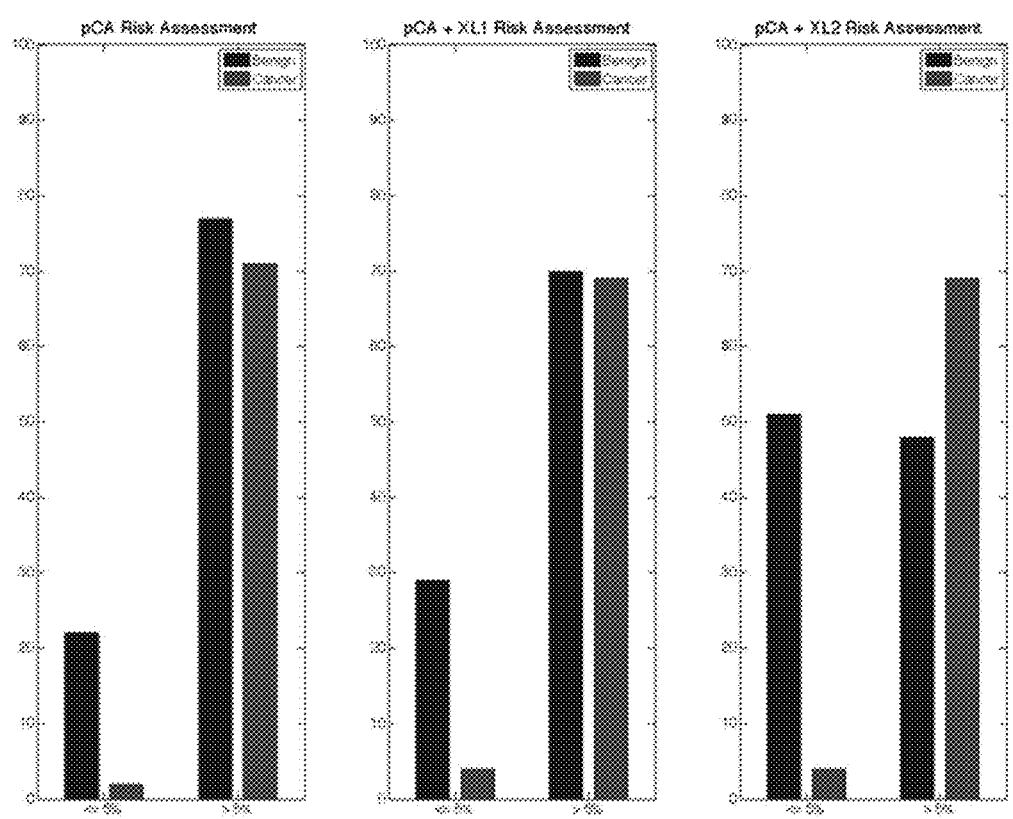
Figure 8:
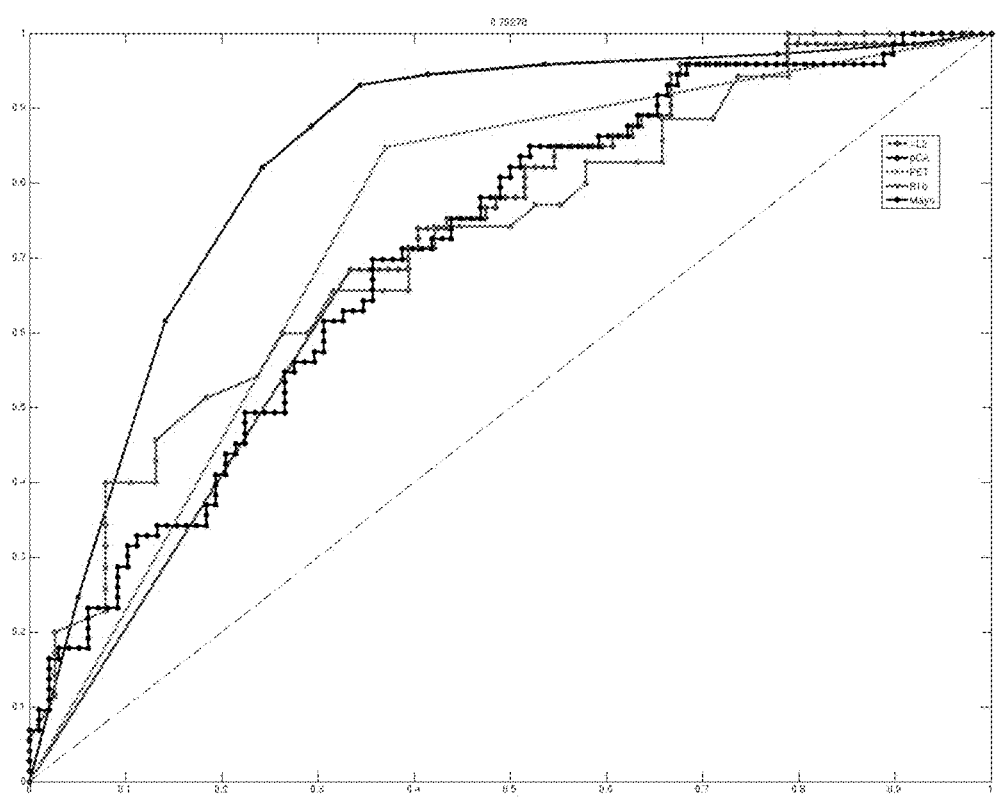
FIG. 8 is a series of graphs that depict performance of various assessment methods. The methods presented in FIG. 8 are XL2, pCA, PET, B1b and Mayo.
Figure 8:
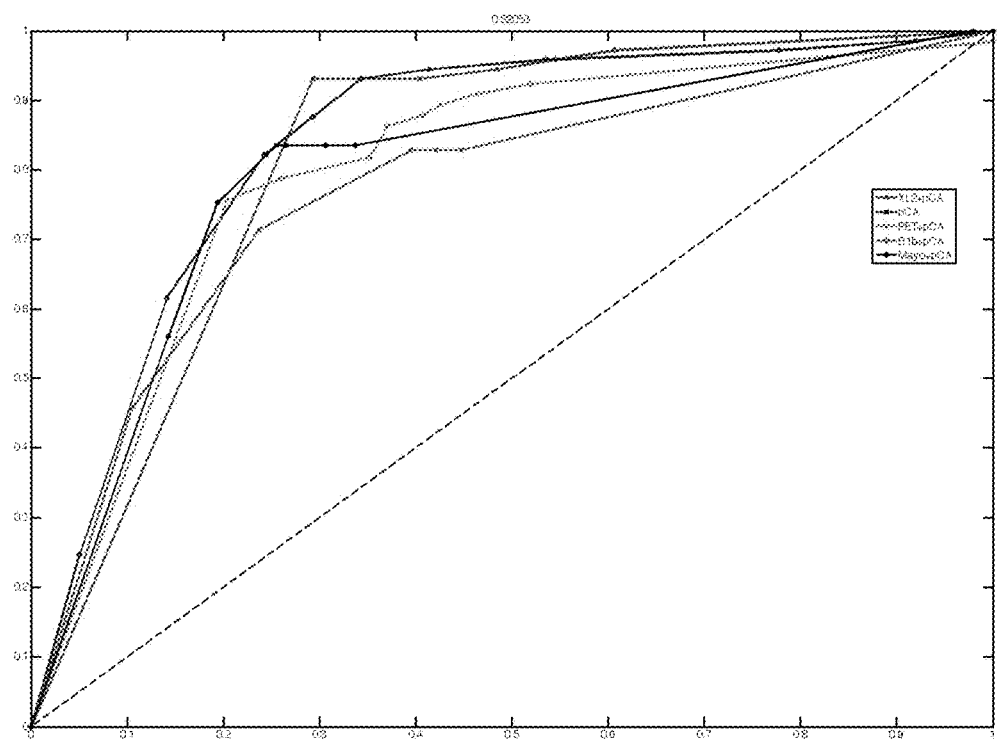

FIG. 7A depicts risk assessment and risk distribution bins into the Guideline recommended risk groups. FIG. 7B depicts risk assessment as interpreted by Guidelines. FIG. 8 shows "below 5%" and above 5% bins.

Comparative Analysis

Comparative analyses were performed for pCA, XL2, PET, and clinical models (FIG. 8). In the first analysis, the performance of each predictor in isolation on all of the interim samples is assessed.

The data indicate the following:

For a rule out test with 95% sensitivity, pCA, XL2 and Mayo are effectively equivalent, followed by Brock 1b and PET.

However, due to low sample number (n<=172), the variability on these estimates is high.

In addition, the decision threshold used for PET is SUV>=2.5, resulting in a single point on its ROC.

The VA and B1a algorithms are omitted as they are slightly inferior in performance and muddy the plot.

Note that in this analysis XL2 does not use pCA (only NS<=15 mm) as it might be considered unfair to utilize pCA in the XL2 predictor (since PET and B1b do not).

Since the pCA result is a combination of different factors, the question is not whether or not pCA is superior to the other predictors, but which of the other predictors adds the most incremental value to the physician's risk assessment. That is, which has best performance: pCA+XL2, pCA+PET, or pCA+clinical model.

The predictors were combined with pCA using the same rules:

If both pCA and the predictor have low risk then decrease the pCA Risk.

If both pCA and the predictor have high risk then increase the pCA Risk.

If pCA and the predictor disagree use the pCA Risk.

The data indicate the following: The Brock model does not increase performance when combined with pCA. This is perhaps not surprising as the pCA uses all of the factors used by the Brock model (and others).

The Mayo model does not increase performance when combined with pCA. Note that the pCA uses all of the factors used by the Mayo model (and others).

PET does not improve physician risk assessment. Especially in the area of 'Rule Out'.

XL2 improves physician risk assessment. In particular, in the area of the curve for high confidence 'Rule Out' (>95% sensitivity), XL2+pCA is almost twice as good as pCA alone (specificity of ~40% vs ~23%).

XL2+pCA is far superior to PET+pCA, B1b+pCA and Mayo+pCA as a Rule Out test.

Reversal Performance

Table 15 indicates the performance of various reversals assayed.

TABLE 15

Reversal Performance

| Ratio | Protein1 | Protein2 | Study | Median | AUC | RuleIn | RuleOut |
|---|---|---|---|---|---|---|---|
| BGH3/C163A | BGH3 | C163A | 1013_Orig | B < C | 0.574074074 | 0.048567435 | 0.028022362 |
| BGH3/C163A | BGH3 | C163A | 1013_Rerun | B < C | 0.641025641 | 0.03048433 | 0.062108262 |
| LG3BP/C163A | LG3BP | C163A | 1013_Orig | B < C | 0.588749126 | 0.013906359 | 0.041998602 |
| LG3BP/C163A | LG3BP | C163A | 1013_Rerun | B < C | 0.618233618 | 0.011111111 | 0.067236467 |
| LG3BP/GELS | LG3BP | GELS | 1013_Orig | B < C | 0.585255066 | 0.013626834 | 0.053808526 |
| LG3BP/GELS | LG3BP | GELS | 1013_Rerun | B < C | 0.555555556 | 0.000569801 | 0.050997151 |
| LG3BP/IBP3 | LG3BP | IBP3 | 1013_Orig | B < C | 0.536687631 | 0.001048218 | 0.031586303 |
| LG3BP/IBP3 | LG3BP | IBP3 | 1013_Rerun | B < C | 0.588319088 | 0.001994302 | 0.066096866 |
| LUM/C163A | LUM | C163A | 1013_Orig | B < C | 0.630328442 | 0.052760307 | 0.041509434 |
| LUM/C163A | LUM | C163A | 1013_Rerun | B < C | 0.595441595 | 0.054985755 | 0.060968661 |
| MASP1/C163A | MASP1 | C163A | 1013_Orig | B < C | 0.57092942 | 0.024877708 | 0.042278127 |
| MASP1/C163A | MASP1 | C163A | 1013_Rerun | B < C | 0.650997151 | 0.033618234 | 0.072079772 |
| MASP1/IBP3 | MASP1 | IBP3 | 1013_Orig | B < C | 0.483927324 | 0.015303983 | 0.016561845 |
| MASP1/IBP3 | MASP1 | IBP3 | 1013_Rerun | B < C | 0.626780627 | 0.018518519 | 0.06011396 |
| PEDF/C163A | PEDF | C163A | 1013_Orig | B > C | 0.554856744 | 0.028301887 | 0.044304682 |
| PEDF/C163A | PEDF | C163A | 1013_Rerun | B < C | 0.592592593 | 0.013675214 | 0.068945869 |
| S10A6/C163A | S10A6 | C163A | 1013_Orig | B < C | 0.546820405 | 0.013067785 | 0.029839273 |
| S10A6/C163A | S10A6 | C163A | 1013_Rerun | B < C | 0.595441595 | 0.006837607 | 0.061823362 |
| S10A6/ENPL | S10A6 | ENPL | 1013_Orig | B < C | 0.582110412 | 0.020405311 | 0.041928721 |
| S10A6/ENPL | S10A6 | ENPL | 1013_Rerun | B < C | 0.623931624 | 0.015384615 | 0.06011396 |
| LUM/GELS | LUM | GELS | 1013_Orig | B < C | 0.644304682 | 0.032215234 | 0.054018169 |
| LUM/GELS | LUM | GELS | 1013_Rerun | B < C | 0.568376068 | 0.00997151 | 0.022222222 |

| Ratio | Evaluate | Consistency_Median | Consistency_RuleIn | Consistency_RuleOut | Consistency |
|---|---|---|---|---|---|
| BGH3/C163A | 1 | 1 | 1 | 1 | 3 |
| BGH3/C163A | 0 | 0 | 0 | 0 | 0 |
| LG3BP/C163A | 1 | 1 | 1 | 1 | 3 |
| LG3BP/C163A | 0 | 0 | 0 | 0 | 0 |
| LG3BP/GELS | 1 | 1 | 1 | 1 | 3 |
| LG3BP/GELS | 0 | 0 | 0 | 0 | 0 |
| LG3BP/IBP3 | 1 | 1 | 1 | 1 | 3 |
| LG3BP/IBP3 | 0 | 0 | 0 | 0 | 0 |
| LUM/C163A | 1 | 1 | 1 | 1 | 3 |
| LUM/C163A | 0 | 0 | 0 | 0 | 0 |
| MASP1/C163A | 1 | 1 | 1 | 1 | 3 |
| MASP1/C163A | 0 | 0 | 0 | 0 | 0 |
| MASP1/IBP3 | 1 | 1 | 1 | 0 | 2 |
| MASP1/IBP3 | 0 | 0 | 0 | 0 | 0 |
| PEDF/C163A | 1 | 0 | 0 | 1 | 1 |
| PEDF/C163A | 0 | 0 | 0 | 0 | 0 |
| S10A6/C163A | 1 | 1 | 1 | 1 | 3 |
| S10A6/C163A | 0 | 0 | 0 | 0 | 0 |
| S10A6/ENPL | 1 | 1 | 0 | 1 | 2 |
| S10A6/ENPL | 0 | 0 | 0 | 0 | 0 |
| LUM/GELS | 1 | 1 | 0 | 1 | 2 |
| LUM/GELS | 0 | 0 | 0 | 0 | 0 |

The data in Table 20 above indicates that one of the best performing reversals is LG3BP/C163A.

Performance of pCA, XL1, XL2, pCA+XL1, and pCA+XL2

Table 16 depicts the performance on all interim subjects. Table 17 depicts the performance on low-moderate risk subjects. The data indicate that pCA+XL1 results in a 12% reduction in invasive procedures on benign nodules. The data further indicate that pCA+XL2 results in a 36% reduction in invasive procedures on benign nodules.

TABLE 16

Performance on All interim Subjects (n = 172)

| Model | Sens | Spec | PPV* | NPV* | LBR** |
|---|---|---|---|---|---|
| pCA | 97 | 22 | 29 | 96 | 17 |
| pCA + XL1 | 95 | 40 | 35 | 96 | 32 |
| pCA + XL2 | 95 | 52 | 39 | 97 | 40 |

*Prevalence adjusted to expected cancer prevalence of 23%
**LBR = likely benign rate = % of test reports stating "likely benign"

TABLE 17

Performance on Low-Moderate Risk Subjects (n = 88)

| Model | Sens | Spec | PPV* | NPV* | LBR** |
|---|---|---|---|---|---|
| pCA | 85 | 29 | 9 | 96 | 28 |
| pCA + XL1 | 69 | 53 | 10 | 96 | 52 |
| pCA + XL2 | 69 | 68 | 14 | 97 | 65 |

*Prevalence adjusted to expected cancer prevalence of 23%
**LBR = likely benign rate = % of test reports stating "likely benign"

The data indicate that performance of pCA+XL1 and pCA+XL2 is significantly better than pCA alone. The data further indicate that pCA+XL2 has superior performance to pCA+XL1.

The peptides assayed in XL1 are presented below. Also presented below is a high performing reversal of XL2, LG3BP/C163A.

$$XL1 = \frac{TSP1 + ALDOA + COIA1 + FRIL + LG3BP}{norm(GELS + PEDF + LUM + PTPRJ + MASP1 + C163A)}$$

$$XL2 = \frac{LG3BP}{C163A}$$

Table 18 below compares the performance of XL1 and XL2 to PET and the VA, Mayo and Brock clinical models.

Provided below are performance results of the original Xpresys Lung (XL-1) with 11 proteins comprising the diagnostic signal as well as Xpresys Lung 2 (XL-2) an improved version of the Xpresys that measures 2 proteins from the original Xpresys product and deploys a different mathematical analysis: Ratio vs. logistic regression.

Although PET is widely used, we note that less than 20% of the participating sites used clinical models.

TABLE 18

|       | XL2 | XL1 | PET | VA | Mayo | Brock |
|-------|-----|-----|-----|-----|------|-------|
| AUC   | 82% | 79% | 74% | 73% | 71%  | 72%   |
| LR+   | 3.18| 2.80| 2.29| 1.65| 1.63 | 1.30  |
| LR−   | 0.10| 0.14| 0.24| 0.31| 0.31 | 0.42  |
| PPV   | 49% | 46% | 41% | 33% | 33%  | 28%   |
| NPV   | 97% | 96% | 93% | 92% | 91%  | 89%   |
| Sens* | 93% | 90% | 85% | 85% | 85%  | 86%   |
| Spec  | 71% | 68% | 63% | 48% | 48%  | 34%   |

Provided below are performance results of the original XL-2 integrated with Mayo compared to other various clinical models alone.

TABLE 19

|            | NPV_adj | LR−  | LBR | AUC |
|------------|---------|------|-----|-----|
| XL2 + Mayo | 97%     | .08  | 54% | 77% |
| Mayo       | 97%     | .10  | 46% | 71% |
| B1a        | 95%     | .15  | 31% | 70% |
| pCA        | 89%     | .37  | 13% | 73% |
| VA         | 88%     | .40  | 12% | 60% |
| PET        | 81%     | .71  | 75% | 61% |

In every metric XL2+Mayo has optimal performance with the one exception being the LBR for PET. However, PET's confidence in the LBR is very low.

The performance of Mayo drops quickly. To achieve the same LBR as XL2+Mayo (54%), the NPV_adj and LR− of Mayo are 87% and 0.44, respectively.

Another approach is to fix a SPR (screen positive rate) across studies and look at performance.

TABLE 20

|            | SPR  | NPV_adj | LR−  | AUC |
|------------|------|---------|------|-----|
| XL2 + Mayo | 46%  | 97%     | .08  | 77% |
| Mayo       | 46%  | 87%     | .44  | 71% |
| B1a        | 45%  | 85%     | .52  | 70% |
| pCA        | 61%* | 86%     | .50  | 73% |
| VA         | 46%  | 81%     | .72  | 60% |
| PET        | 25%* | 81%     | .71  | 61% |

*closest values

An explanation of the abbreviations used in used in the tables presented herein are provided below.

AUC: this statistic represents the area under the curve. It is defined by a Receiver (R) Operator (O) Curve (C). The ROC curve is a standard measure of diagnostic performance and is obtained by plotting the test's sensitivity or true positive rate (ability to detect cancer) vs. the test's false negative rate (1-specificity) at various test threshold settings.

LR: "likelihood ratio" is used for assessing the value of performing a diagnostic test. The sensitivity and specificity of the test is used to determine whether a patient's test result usefully changes the probability that a condition is present compared to a patient without disease. This statistic is considered independent of disease prevalence. A positive likelihood ratio (LR+) of 3 is considered a moderate increase in the risk of cancer whereas a negative likelihood ratio (LR−) of 0.1 is considered a large decrease in the risk of cancer.

PPV: "positive predictive value" refers to the probability that a positive result correctly identifies a patient who has the disease.

NPV: "negative predictive value" refers to the probability that a negative result correctly identifies a patient who does not have the disease.

Sens: "sensitivity of a test" refers to the probability that a patient with the disease will have a positive test result.

Spec: "specificity of a test" refers to the probability that a patient without the disease will have a negative test result.

XL-1: Xpresys® Lung 1: A lung cancer risk stratification test that monitors five diagnostic proteins and six normalizing proteins.

XL-2: Xpresys® Lung 2: A lung cancer risk stratification test that monitors 2 diagnostic proteins. A refinement of XL-1.

PET: positron emission tomography.

CT: Computed tomography.

VA, Mayo, Brock: refers to different models to calculate lung cancer risk.

Summary

The data indicate that measured in terms of AUC, the tests group clearly into two performance groups with XL2 and XL1 having superior AUC to all other diagnostic modalities measured: PET and clinical models.

The data further indicate 2. Measured in terms of Likelihood Ratios, XL-2 and XL-1 are superior to PET in both the positive (LR+) and negative (LR−) results. Xpresys Lung and PET are superior to all clinical models.

The data particularly indicate that XL1 and XL2 are particularly strong, by design, as a rule out test. The LR− performance of XL1 and XL2 would be considered a statistical "large decrease" in the post-test probability of disease whereas the PET (and clinical models) have a "slight" to "moderate" impact on the post-test probability of disease.

Example 4

PANOPTIC Performance of Guideline/Practical Benchmarks

Table 21 describes the Xpresys Lung Product Profile.

TABLE 21

| Xpresys Lung Product Profile | |
|---|---|
| Intended Use | To Rule Out lung cancer. Identify, with high probability, those lung nodules that are benign. |
| Intended Use Population | Patients 40 years or older with a lung nodule between 8-30 mm in diameter. |
| Test Report | "Likely Benign" if there is a high probability that the lung nodule is benign, otherwise, "Indeterminate". |

TABLE 21-continued

Xpresys Lung Product Profile

| | |
|---|---|
| Test Performance | "A 'Likely Benign' test report has a 97% probability of being correct" "54% of test reports will be 'Likely Benign'" |
| Clinical Utility | Reduce unnecessary risky and costly invasive procedures, such as biopsy and surgery, on benign lung nodules. |

Xpresys Lung migration from version 1 (XL1) to version 2 (XL2):

$$XL1 = \frac{TSP1 + ALDOA + COIA1 + FRIL + LG3BP}{norm(GELS + PEDF + LUM + PTPRJ + MASP1 + C163A)}$$

$$XL2 = \frac{LG3BP}{C163A}$$

XL1 was developed and validated on moderately-sized archival biobanks with multiple collection protocols. XL2 was developed and validated on large prospective studies under a single protocol. XL2 allows for conversion to an antibody (Ab)-based platform (market expansion, reduction in COGS). All clinical and commercial data collected for XL1 were also collected for XL2. XL2 integrates clinical factor information with molecular information.

Table 22 provides a development/evidence plan for Xpresys Lung.

TABLE 22

| | Design | Samples/Sites | Publication | XL1 | XL2 |
|---|---|---|---|---|---|
| Discovery | Retrospective (multiple protocols) | 143/3 | Science Translational Medicine; | Discovery | Discovery |
| Verification | Retrospective (multiple protocols) | 104/4 | Clinical Proteomics | Validation | |
| Validation | Retrospective (multiple protocols) | 141/4 | J. Thoracic Oncology | | |
| Study 1013 | Prospective-Retrospective (single protocol) | 353/12 | Lung | | |
| Study 1001 'PANOPTIC' | Prospective-Retrospective (single protocol) | 604/33 | JAMA (intent) ATS Oral Presentation | | Validation |
| TBD | Prospective-Retrospective (single protocol) | 500-700/IDN | TBD | Clinical Utility | Clinical Utility |

XL1 was discovered on ~10% of samples (~10% of sites); all retrospective and multiple protocol. XL2 was discovered on ~55% of samples (~40% of sites); most prospective and single protocol. XL2 is the top performing classifier on both Study 1013 and Study 1001.

PANOPTIC is an all-comer study within the intended use population of Xpresys Lung. PANOPTIC has highly generalizable results due to its scale both in terms of samples and number of sites. PANOPTIC collected the initial physician's assessment (pCA) of lung cancer risk for each lung nodule. PANOPTIC allows for assessing the incremental benefit of Xpresys Lung in actual practice. PANOPTIC collected sufficient clinical data to compare the performance of Xpresys Lung with benchmarks such as PET and established clinical factor models (VA, Mayo and Brock). pCA, PET, VA and Mayo are all referenced in the ACCP Guidelines for lung nodule management. PANOPTIC allows for the assessment of integrating Xpresys Lung with pCA and clinical factor models such as VA, Mayo and Brock. PANOPTIC allows for a prospective-retrospective analysis of the clinical utility of Xpresys Lung.

The performance of Xpresys Lung was compared to the tools used both in practice and defined in the ACCP guidelines for lung nodule management:

pCA: Physician Cancer Risk Assessment
PET: Positron Emission Tomography
VA: Clinical Factor Model (developed within VA system)
Mayo: Clinical Factor Model (developed at Mayo)
Brock: Clinical Factor Model (not in guidelines)
Performance measures of relevance for Ruling Out:
NPV: Negative Predictive Value (Probability that a lung nodule is benign).
LBR: Likely Benign Rate (1-SPR) (Percentage of test reports that are "Likely Benign")

Key Observatoins: Within the targeted high performance zone, pCA performs poorly. There is an opportunity to improve upon physician risk assessment because physicians, without additional tools, may tend to over treat. Within the targeted high performance zone, PET performs poorly. This is not surprising as PET is typically used to Rule In (not rule out) lung cancer. Among the clinical factor algorithms, Mayo and Brock have promising performance while VA performs poorly. XL2, when combined with any one of pCA, Mayo, Brock and VA, improves performance.

Table 23 provides a performance comparison.

TABLE 23

| | 1-SPR | NPV | LR- | AUC |
|---|---|---|---|---|
| XL2 + Mayo | 54% | 97% | .08 | 77% |
| Mayo | 54% | 87% | .44 | 71% |
| B1a | 55% | 85% | .52 | 70% |
| pCA | 39%* | 86% | .50 | 73% |
| VA | 54% | 81% | .72 | 60% |
| PET | 75%* | 81% | .71 | 61% |

The comparison attempts to fix the 1-SPR parameter (diagnostic yield). Only XL2 integrated with Mayo achieves an actionable NPV. The Negative Likelihood Ratio (LR-) is also provided.

Up to risk threshold of 15%, no malignant nodules are erroneously routed to invasive procedures. 40% of benign nodules are rescued from invasive procedures. This represents significant improvement over current practice.

Example 5

PANOPTIC Trial Continued

Introduction

Lung nodules are an increasing opportunity and challenge with a recent estimate of 1.6 million nodules in the United States yearly as an incidental imaging finding [Gould M K, Tang T, Liu I A, Lee J, Zheng C, Danforth K N, Kosco A E, Di Fiore J L, and Suh D E. Recent Trends in the Identification of Incidental Pulmonary Nodules. Am J Resp Crit Care Med 2015; 192:1208-1214]. With implementation of lung cancer screening, this exponential increase in nodules is anticipated to continue [Aberle D R, Adams A M, Berg C D, et al. Reduced lung cancer mortality with low-dose computed tomographic screening. N Engl J Med 2011; 365:395-409]. Computed tomography (CT) analysis of nodules can identify features to distinguish benign from malignant but most nodules remain indeterminate and require a decision regarding diagnostic testing and biopsy.

The evaluation of an indeterminate nodule≥8 mm in diameter should be guided by a physician estimate of the pre-test probability of cancer (pCA) [Gould M K, Donington J, Lynch W R, et al. Evaluation of individuals with pulmonary nodules: when is it lung cancer? Diagnosis and management of lung cancer, 3rd ed: American College of Chest Physicians evidence-based clinical practice guidelines. Chest 2013; 143: e93S-e120s]. A low pCA estimate, ≤5%, is the threshold generally used to observe a nodule with further CT surveillance. This observation threshold goal is to balance the risk of unnecessary procedures against the chance that an observation period will cause harm for a malignant nodule. The impact of this low threshold is limited because only 9.5% of indeterminate nodules are low risk in pulmonary practices [Tanner N T, Aggarwal J, Gould M K, Kearny P, Diette G, Vachani A, Fang K C, Silvestri G A. Management of Pulmonary Nodules by Community Pulmonologists: A Multicenter Observational Study. Chest 2015; 148: 1405-1414].

In pulmonary practices, 80% of nodules are categorized as intermediate risk with a pCA between 5% and 65%. [Tanner N T, Aggarwal J, Gould M K, Kearny P, Diette G, Vachani A, Fang K C, Silvestri G A. Management of Pulmonary Nodules by Community Pulmonologists: A Multicenter Observational Study. Chest 2015; 148:1405-1414]. In that broad intermediate category, 75% of the nodules are benign and 25% are malignant so differentiation of these nodules will have the greatest impact on the tests and procedures in current use. For example, in community pulmonary practices, 65% of the benign nodules had at least one biopsy and 36% went to surgery. With better tools, these are avoidable invasive procedures.

Since the largest proportion of nodules are benign, a blood test that can distinguish a benign nodule would benefit patient care. A survey of experienced pulmonologists found that a hypothetical blood test resulted in significant alterations in a decision to pursue invasive testing [Vachani A, Tanner N T, Aggarwal J, Mathews C, Kearney P, Fang K C, Silvestri G, Diette G B. Factors that influence physician decision making for indeterminate pulmonary nodules. Ann Am Thorac Soc 2014; 11:1586-1591]. A proteomics based blood test was developed using multiple reaction mass spectrometry [Gould M K, Tang T, Liu I A, Lee J, Zheng C, Danforth K N, Kosco A E, Di Fiore J L, and Suh D E. Recent Trends in the Identification of Incidental Pulmonary Nodules. Am J Resp Crit Care Med 2015; 192:1208-1214] where protein candidates (n=388) were evaluated on archived blood samples resulting in a 13 protein classifier [Li X J, Hayward C, Fong P Y, et al. A blood-based proteomic classifier for the molecular characterization of pulmonary nodules. Sci Transl Med 2013; 5:207ra142]. The classifier provided improved performance in comparison to a four-parameter clinical model and was independent of patient age, tobacco use, nodule size, and a diagnosis of chronic obstructive pulmonary disease [Vachani A, Pass H I, Rom W N, Midthun D E, Edell E S, Laviolette M, Li X J, Fong P Y, Hunsucker S W, Hayward C, Mazzone P J, Madtes D K, Miller Y E, Walker M G, Shi J, Kearney P, Fang K C, Massion P P. Validation of a multiprotein plasma classifier to identify benign lung nodules. J Thorac Oncol 2015; 10:629-637]. Clinical utility of the test was evaluated using prospectively collected plasma (n=353) with a 32% reduction in patients with benign nodules receiving invasive procedures was estimated [Tanner N T, Aggarwal J, Gould M K, Kearny P, Diette G, Vachani A, Fang K C, Silvestri G A. Management of Pulmonary Nodules by Community Pulmonologists: A Multicenter Observational Study. Chest 2015; 148: 1405-1414].

The plasma test was further refined to combine with five clinical factors to differentiate benign from malignant lung nodules and was evaluated in a large prospective trial. Details about clinician estimated pre-test probabilities, procedure use, and guideline adherence are published [Vachani A, Hammoud Z, Springmeyer S, Cohen N, Nguyen D, Williamson C, Starnes S, Hunsucker S, Law S, Li X J, Porter A, Kearney P. Clinical Utility of a Plasma Protein Classifier for Indeterminate Lung Nodules. Lung 2015; 193:1023-27].

Methods

Study Design

The PANOPTIC trial is a prospective, multicenter, observational trial with retrospective evaluation of the performance of the proteomic test. Patient care was not directed or influenced by the protocol. A blinding protocol was strictly followed. All sites had local (n=24) or central (9) Institutional Review Board approval.

Site Selection

Academic health centers, teaching hospitals, and large pulmonary practices (generally part of an integrated network) were approached for participation. Of 40 sites in North America, 33 sites (31 U.S., and two Canadian) were selected based on geographic location, interest, and qualification.

Patient Selection

Inclusion Criteria included: 8-30 mm diameter nodule, age≥40 years, undergoing a diagnostic evaluation within 60 days of the baseline CT by a pulmonologist, and/or a thoracic surgeon.

Exclusion Criteria included: no prior attempted or completed diagnostic biopsy procedure, such as transthoracic needle aspiration, bronchoscopic biopsy or surgery, no prior CT scan available that previously identified the same lung nodule under consideration, no current diagnosis of any cancer, no prior diagnosis of any cancer within 2 years of lung nodule detection (except for non-melanoma skin cancer), and no administration of blood products within 30 days of subject enrollment.

Data Collection

At enrollment and before additional testing, the physician pre-test probability of cancer (pCA) was recorded (0-5%, 6-10%, 11-20%, 21-30%, 31-40%, etc.). Blood samples were obtained and processed for proper storage and shipment per protocol. The nodule location, size, and contour were collected at baseline and all subsequent CT scans. Data on imaging and procedures was collected until definitive diagnosis, nodule resolution, or at least one year of radiographic stability. PET or PET/CT scans results were recorded as an SUV value of ≥2.5 mSv or not. Data on procedures including bronchoscopy, transthoracic needle biopsy, and surgery were recorded.

Proteomic Plasma Test

The test (Xpresys Lung, Integrated Diagnostics, Seattle, Wash.) is based on mass spectroscopy MRM-MS as previously described [Vachani A, Pass H I, Rom W N, Midthun D E, Edell E S, Laviolette M, Li X J, Fong P Y, Hunsucker S W, Hayward C, Mazzone P J, Madtes D K, Miller Y E, Walker M G, Shi J, Kearney P, Fang K C, Massion PP. Validation of a multiprotein plasma classifier to identify benign lung nodules. J Thorac Oncol 2015; 10:629-637, Li X J, Hayward C, Fong P Y, et al. A blood-based proteomic classifier for the molecular characterization of pulmonary nodules. Sci Transl Med 2013; 5:207ra142] and was developed following National Academy of Medicine guidelines [IOM (Institutes of Medicine), Evolution of Translational 'Omics: Lessons Learned and the Path Forward, Washington D.C. The National Academies Press, 2012]. Development was prospectively performed starting with samples from a prior prospective study (NCT01752101) [Vachani A, Hammoud Z, Springmeyer S, Cohen N, Nguyen D, Williamson C, Starnes S, Hunsucker S, Law S, Li X J, Porter A, Kearney P. Clinical Utility of a Plasma Protein Classifier for Indeterminate Lung Nodules. Lung 2015; 193:1023-27]. Details of discovery, verification, and validation are published separately [In preparation: Mazzone P P, Kearney P, Hunsucker S, Law S, Li X J, Porter A. Development of a Proteomic Test Combined with Clinical Risk Factors. 2016]. A previous version of the test was based on 11 proteins [Vachani A, Hammoud Z, Springmeyer S, Cohen N, Nguyen D, Williamson C, Starnes S, Hunsucker S, Law S, Li X J, Porter A, Kearney P. Clinical Utility of a Plasma Protein Classifier for Indeterminate Lung Nodules. Lung 2015; 193:1023-27]. We assessed whether test performance could be improved based on three factors; focus on the best performing protein markers, refinement of the intended use population to a lower risk group (pCA≤50%), and combining the test with clinical risk factors. For details see the supplemental materials. The test uses the relative abundance of two plasma proteins (LG3BP and C163A), integration with five clinical risk factors (age, smoking status, nodule diameter, nodule spiculation status, and nodule location), and a prescribed decision threshold to differentiate lung nodules that are likely benign from those that remain indeterminate.

Data Analysis

A nodule was determined to be benign by pathology, resolution or absence of enlargement by CT imaging. Malignancy determination was based on histology. The period of observation was at least one year and up to two years. Statistical analyses were performed using MATLAB, version 8.3.0.532 (MathWorks) and MedCalc, version 16.4 (MedCalc Software bvba). Chi squared of analysis of variance testing was used to compare groups, and a p value of ≤0.05 is considered significant. For comparison of cancer risk predictors, the McNemar statistical test was used at a fixed sensitivity or specificity [McNemar Q. Note On the Sampling Error of the Difference Between Correlated Proportions or Percentages. Psycometrika, 1947; 12:153-157]. Results presented are based on the median negative predictive value (NPV) unless otherwise specified.

Physicians, patients, along with laboratory and statistical personnel were blinded to the results of the protein classifier and clinical information.

Technical Definition and Equation for Xpresys Lung (XL)

XL integrates the relative abundance of two plasma proteins (LG3BP and C163A) with five clinical risk factors (age, smoking status, nodule diameter, nodule spiculation status and nodule location). Functional details on these proteins can be found in [Granville C A, Dennis P A. An overview of lung cancer genomics and proteomics. Am J Respir Cell Mol Biol 2005; 32:169-176]. XL provides a numerical value, XL_2(k), for a subject k, as defined below:

$$XL\_2(k) = \begin{cases} \max(0, p(k) - 0.5), & \log_2\left(\frac{LG3BP}{C163A}\right) \leq .38 \\ p(k), & \log_2\left(\frac{LG3BP}{C163A}\right) > .38 \end{cases}$$

$$p(k) = \frac{e^X}{1 + e^X}$$

$$X = -6.8272 + 0.0391*Age + 0.7917*Smoker +$$
$$0.1274*Diameter + 1.0407*Spiculation + 0.7838*Location$$

where Age is the age of the subject in years, Smoker is 1 if the subject is a former or current smoker (otherwise 0), Diameter is the size of the lung nodule in mm, Spiculation is 1 if the lung nodule is spiculated (otherwise 0) and Location is 1 if the lung nodule is located in an upper lung lobe (otherwise 0). The linear function X that integrates the clinical risk factors is a simplification of the Mayo clinical risk predictor [Gould M K, Ananth L, Barnett P G. Veterans Affairs SNAP Cooperative Study Group. A clinical model to estimate the pretest probability of lung cancer in patients with solitary pulmonary nodules. Chest 2007; 131:383-388].

XL_2(k) ranges between 0 and 1. The closer XL_2(k) is to 0, the more likely subject k has a very high NPV which is calculated using PANOPTIC data. The ranges of the XL_2(k) function for the NPV values of 90% to 98% are shown in Table 2s, along with the other performance indicators.

Results

Figure 18:
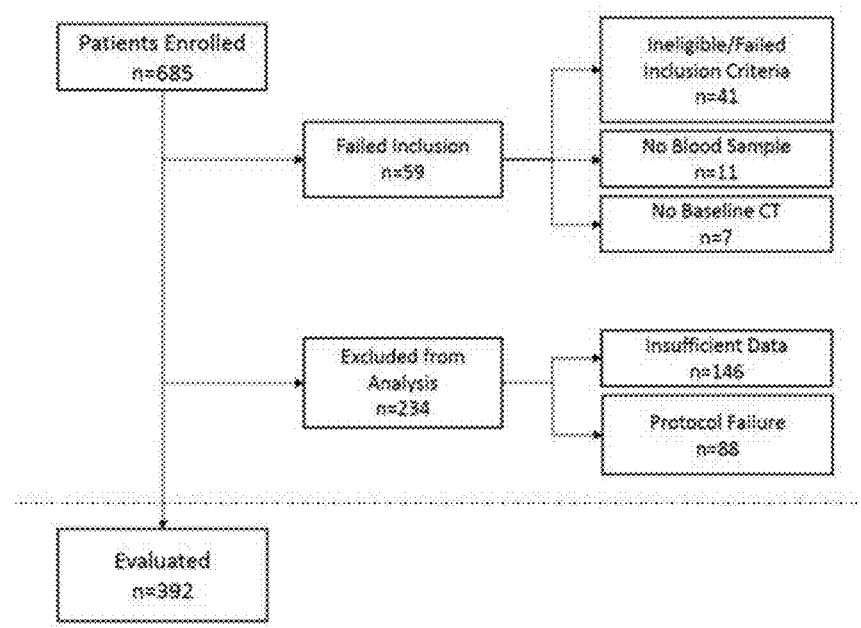
FIG. 18 is a diagram of patients enrolled and excluded. The Insufficient Data category includes patients with no physician pCA, patients lost to follow-up or without a second procedure, and no final diagnosis or treatment without a final diagnosis. Protocol failure included if blood sample couldn't be tested, the diagnosis couldn't be confirmed, or insufficient CT follow-up to establish a benign diagnosis.

A total of 685 patients were enrolled prospectively from November 2012 to December 2015 and 392 were eligible for analysis. Not meeting inclusion/exclusion criteria, no blood sample or baseline CT occurred in 59 patients. An additional 234 were not eligible as detailed in FIG. 18. All 392 patients had complete data beyond one year and 350 had complete data to 2 years. Benign nodules were present in 195 (49.7%) of patients and malignant nodules in 197 (50.3%), a prevalence of 50%. Baseline demographics, stratified by benign or malignant nodule are included in Table 24.

TABLE 24

Patient demographics, smoking history, and lung nodule characteristics for all patients, malignant nodules (cancer), and benign nodules. N/A is not available.

|  | All Patients | Cancer | Benign | p value |
|---|---|---|---|---|
| Patients | 392 | 197 | 195 |  |
| Age | 66.43 (±0.98) | 67.37 (±1.25) | 65.47 (±1.52) | 0.057 |
| Gender |  |  |  |  |
| Male | 202 (51.53%) | 91 (46.19%) | 111 (56.92%) | 0.034 |
| Female | 190 (48.47%) | 106 (53.81%) | 84 (43.08%) |  |
| Smoking History |  |  |  |  |
| Never | 60 (15.31%) | 20 (10.15%) | 40 (20.51%) | 0.009 |
| Former | 223 (56.89%) | 112 (56.85%) | 111 (56.92%) | 0.993 |
| Current | 109 (27.81%) | 65 (32.99%) | 44 (22.56%) | 0.050 |
| Pack Year Mean | 48.26 (+/−3.66) | 51.67 (+/−4.68) | 44.37 (+/−5.70) | 0.051 |
| Lung Nodule |  |  |  |  |
| Size (mm) | 16.82 (±0.61) | 19.24 (±0.80) | 14.38 (±0.79) | <0.001 |
| Nodule Location |  |  |  |  |
| Upper Lobe |  | 135 (68.53%) | 91 (46.67%) | 0.004 |
| Lower Lobes |  | 62 (31.47%) | 104 (53.33%) | <0.001 |
| Benign Nodule Diagnosis |  |  |  |  |
| Granuloma |  |  | 18 (9.23%) |  |
| Hamartoma |  |  | 7 (3.59%) |  |
| CT Stable/Resolution |  |  | 137 (70.26%) |  |
| Other |  |  | 25 (12.82%) |  |
| N/A |  |  | 8 (4.10%) |  |
| Malignant Nodule Histology |  |  |  |  |
| Adenocarcinoma |  | 117 (59.39%) |  |  |
| Squamous Cell |  | 35 (17.77%) |  |  |
| Large Cell |  | 2 (1.02%) |  |  |
| Mixed/non-specified NSCLC |  | 16 (8.12%) |  |  |
| Small Cell |  | 13 (6.60%) |  |  |
| Carcinoid |  | 6 (3.05%) |  |  |
| Other |  | 8 (4.06%) |  |  |

Cancer patients were more likely to be female (p=0.03) and current smokers (p=0.05), but the difference in mean pack-years of smoking was borderline significant (p=0.051). Patients with benign nodules (20%) were more likely to be never smokers (p<0.01). The nodules were significantly larger (19.2 mm) in the cancer group compared to the benign group (14.4 mm) and upper lobe location was more likely to be a malignant nodule (p<0.01).

Figure 19:
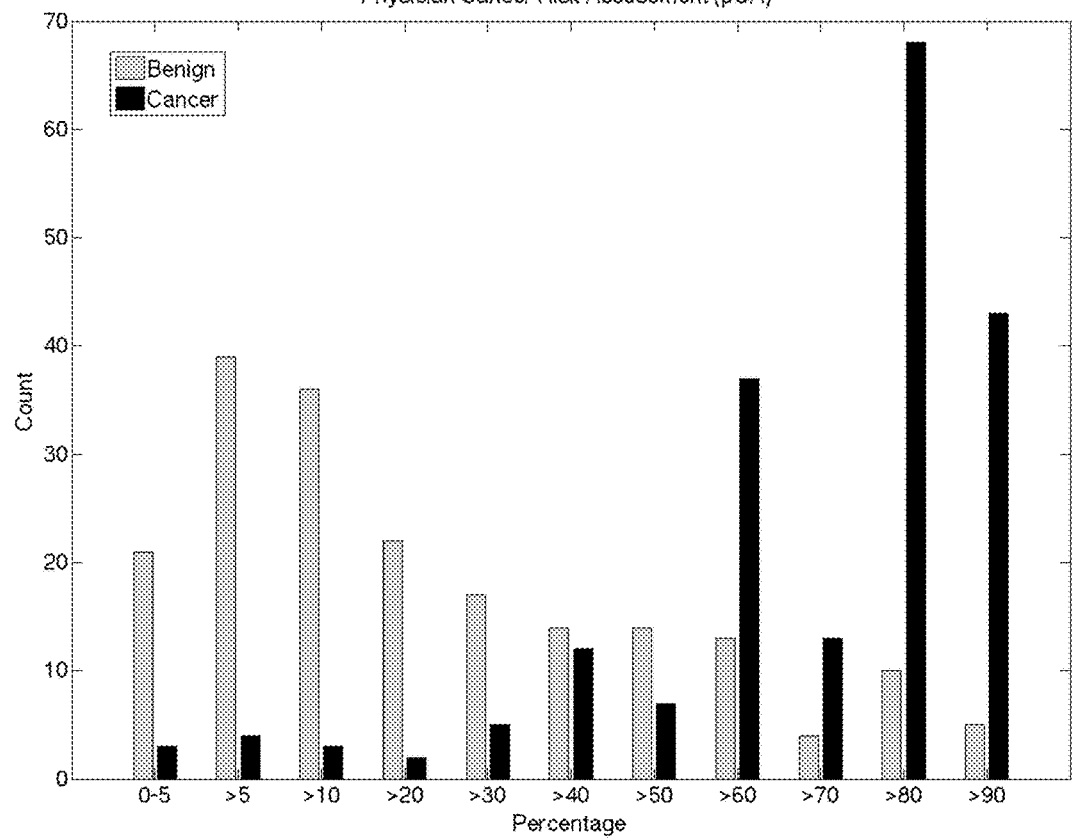
FIG. 19 is a graph showing physician pretest probability of malignancy (pCA) displayed by deciles (the first two columns are 5% increments). Shown are 197 cancer nodules and 195 benign nodules.

The physician pre-test probability of cancer (pCA) results compared to the diagnosis is shown in FIG. 19. This figure demonstrates that physicians are good at a general separation of benign nodules into lower risk (<50%) and malignant nodules into higher risk (>50%). An AUC of these results is 0.85±0.02. As expected, only 6% of the nodules are in the low risk group of 0-5%, but the majority of the benign nodules have a risk of less than 50%. This lower risk group (pCA<50%) is the intended use for this proteomic test. Table 25 shows the demographics, smoking, and nodule information for the 178 patients in the lower risk group with 149 benign and 29 malignant nodules, a prevalence of 16%.

TABLE 25

Patient demographics, smoking history, lung nodule characteristics, and diagnosis or histotype for all, malignant (cancer) nodules, and benign nodules in the 178 lower risk patients. N/A means not available.

|  | All Patients | Cancer | Benign |
|---|---|---|---|
| Patients | 178 | 29 | 149 |
| Age | 65.52 (+/−155) | 66.05 (+/−3.05) | 65.42 (+/−1.76) |
| Gender |  |  |  |
| Male | 95 (53.37%) | 12 (41.38%) | 83 (55.70%) |
| Female | 83 (46.63%) | 17 (58.62%) | 66 (44.30%) |
| Smoking History Status |  |  |  |
| Never | 42 (23.60%) | 6 (20.69%) | 36 (24.16%) |
| Former | 99 (55.62%) | 16 (55.17%) | 83 (55.70%) |
| Current | 37 (20.79%) | 7 (24.14%) | 30 (20.13%) |
| Pack Year Mean | 43.56 (+/−6.17) | 43.66 (+/−11.73) | 43.54 (+/−7.06) |
| Lung Nodule |  |  |  |
| Size | 13.95 (+/−0.76) | 16.48 (+/−2.18) | 13.46 (+/−0.78) |

TABLE 25-continued

Patient demographics, smoking history, lung nodule characteristics, and diagnosis or histotype for all, malignant (cancer) nodules, and benign nodules in the 178 lower risk patients. N/A means not available.

| | All Patients | Cancer | Benign |
|---|---|---|---|
| Nodule Location | | | |
| Upper Lobe | | 20 (68.97%) | 70 (46.98%) |
| Lower Lobes | | 9 (31.03%) | 79 (53.02%) |
| Benign Nodule Diagnosis | | | |
| Granuloma | | | 9 (6.04%) |
| Hamartoma | | | 6 (4.03%) |
| CT Stable/Resolution | | | 116 (77.85%) |
| Other | | | 15 (10.07%) |
| N/A | | | 3 (2.01%) |
| Malignant Nodule Histology | | | |
| Adenocarcinoma | | 17 (58.62%) | |
| Squamous Cell | | 4 (13.79%) | |
| Large Cell | | 0 (0.00%) | |
| Mixed/non-specified NSCLC | | 1 (3.45%) | |
| Small Cell | | 2 (6.90%) | |
| Carcinoid | | 3 (10.34%) | |
| Other | | 2 (6.90%) | |

The median performance of the proteomic test on the 178 patients is an NPV of 98% (95% CI 92%-100%) at a sensitivity of 97% (82%-100%). Performance at other NPV is shown in Table 26.

TABLE 26

Xpresys Lung Performance and Test Report at multiple negative predictive values for Likely Benign results (n = 178 patients) and the threshold for Indeterminate results.

| XL_2(k) Value | NPV (95% CI) | Sensitivity (95% CI) | Specificity (95% CI) | PPV (95% CI) | Test Report |
|---|---|---|---|---|---|
| 0 to 0.131 | 98% (92%-100%) | 97% (82%-100%) | 44% (36%-52%) | 25% (17%-34%) | Likely Benign |
| >0.131 to 0.1613 | 97% (91%-100%) | 93% (77%-99%) | 49% (41%-57%) | 26% (18%-36%) | Likely Benign |
| >0.1613 to 0.172 | 96% (90%-99%) | 90% (73%-98%) | 54% (45%-62%) | 27% (19%-37%) | Likely Benign |
| >0.172 to 0.176 | 95% (89%-99%) | 86% (68%-96%) | 55% (47%-63%) | 27% (18%-37%) | Likely Benign |
| >0.176 to 0.1785 | 94% (87%-98%) | 83% (64%-94%) | 56% (47%-64%) | 27% (18%-37%) | Likely Benign |
| >0.1785 to 0.193 | 93% (86%-98%) | 79% (60%-92%) | 57% (44%-65%) | 26% (18%-37%) | Likely Benign |
| >0.193 to 0.195 | 92% (85%-97%) | 76% (56%-90%) | 58% (49%-66%) | 26% (17%-37%) | Likely Benign |
| >0.195 to 0.2306 | 91% (84%-96%) | 69% (49%-85%) | 64% (56%-72%) | 27% (18%-39%) | Likely Benign |
| >0.2306 to 0.354 | 90% (84%-95%) | 55% (36%-74%) | 83% (75%-88%) | 38% (24%-54%) | Likely Benign |
| >0.354 | — | — | — | — | Indeterminate |

Figure 20:
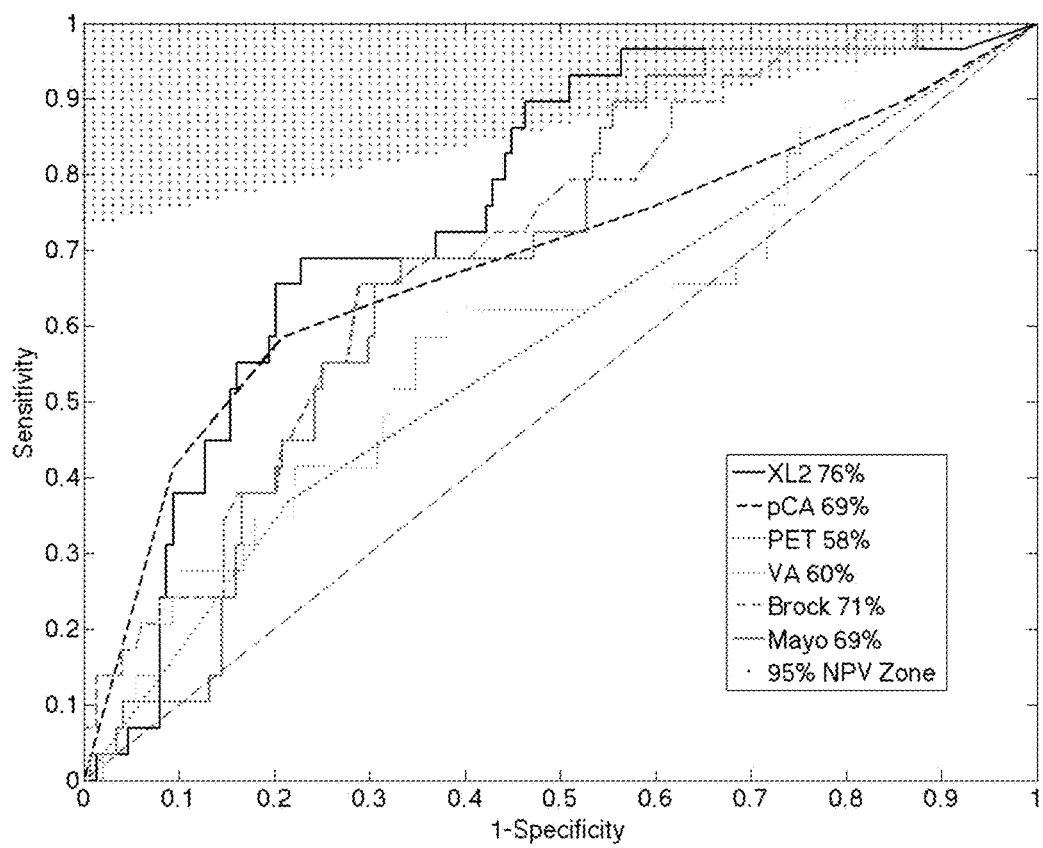
FIG. 20 is a graph showing ROC plot comparisons of the proteomic test (XL2) to physician pCA, PET, and the VA and Mayo cancer risk equations. This performance is with 178 lower risk patients. The shaded area is the zone where performance is ≥95% NPV. The percentages shown are the AUC values for the proteomic test (XL2), physician pCA, PET, and three risk equations (VA, Brock, and Mayo).

Comparisons of the proteomic test to physician pCA, PET, and three cancer risk equations are shown in FIG. 20. The cancer risk equations for comparison are those used for nodule evaluations [Gould M K, Ananth L, Barnett P G. Veterans Affairs SNAP Cooperative Study Group. A clinical model to estimate the pretest probability of lung cancer in patients with solitary pulmonary nodules. Chest 2007; 131: 383-388; McWilliams A, Tammemagi M C, Mayo J R, et al. Probability of cancer in pulmonary nodules detected on first screening CT. N Engl J Med 2013; 369:910-919; Nair V S, Sundaram V, Gould M K, Desai M. Utilization of [18F] FDG PET imaging in the National Lung Screening Trial. Chest 2016; 150:621-630]. The proteomic test has the best performance with the highest AUC of all the comparators. In contrast to physician pCA, with an AUC of 85% for all nodules, the AUC for lower risk nodules is 69%, doesn't reach the 95% NPV zone, and significantly underperforms compared to the proteomic test (p<0.001). Similarly, the PET AUC is only 58% and the highest NPV for PET is 79% (95% CI:66%-88%). When the NPV are directly compared the proteomic test with an NPV of 95% (95% CI:89%-99%) is significantly better than PET. The three clinical risk equations enter the 95% NPV zone, but the proteomic test is significantly better with p values≤0.002.

Discussion

The PANOPTIC trial evaluates a proteomic blood test and shows excellent performance by identifying a high proportion of benign nodules that can be safely followed with CT surveillance.

The performance is based on the negative predictive value (NPV) where the median value is 98% (95% CI 92%-110%). This high NPV will provide confidence that the post-test probability of cancer is less than 5% and CT surveillance can be recommended. Compared to the current tools available, this proteomic test is significantly better. With the current tools, physicians cannot determine which intermediate risk, indeterminate nodules are benign so they proceed with further evaluation. Since the largest proportion of nodules are in this intermediate risk group, the need for new tools is sizable.

When confronted with a pulmonary nodule, the clinician has an array of diagnostic tools to consider. Each of these options have benefits and risks. One option is a PET-CT scan, which is non-invasive, but has considerable expense and a high radiation exposure [Brix G, Lechel U, Glatting G, Ziegler S I, Munzing W, Muller S P, Beyer T. Radiation exposure of patients undergoing whole-body dual-modality $^{18}$F-FDG PET/CT examinations. J Nucl Med 2005; 46:608-613; Rivera M P, Mehta A C, Wahidi M M. Establishing the diagnosis of lung cancer: diagnosis and management of lung cancer, 3rd ed: American College of Chest Physicians evidence-based clinical practice guidelines. Chest 2013; 143: Suppl 5:e142S-e165S]. Nodules can be biopsied via a bronchoscope, which is minimally invasive, but only yields a diagnosis 34 to 88% of the time [Wiener R S, Schwartz L M, Woloshin S, Welch H G. Population-Based Risk for Complications after Transthoracic Needle Lung Biopsy of a Pulmonary Nodule: An Analysis of Discharge Records. Ann Intern Med 2011; 155:137-144]. CT guided transthoracic needle biopsy of nodules has better diagnostic yield but comes with a 15% risk of a pneumothorax complication [Lokhandwala T, Dann T R, Johnson M, D' Souza A O. Costs of the Diagnostic Workup for Lung Cancer: A Medicare Claims Analysis. International Journal of Radiation Oncology 2014;90(5):S9- S10]. Surgical biopsy comes with a complication rate of 5% [Gould M K, Donington J, Lynch W R, et al. Evaluation of individuals with pulmonary nodules: when is it lung cancer? Diagnosis and management of lung cancer, 3rd ed: American College of Chest Physicians evidence-based clinical practice guidelines. Chest 2013; 143: e93S-e120S]. A large Medicare claims analysis found that of the total diagnostic costs, 43.1% was due to biopsy of patients without lung cancer [Lung-RADS. American College of Radiology. Accessed 25 Sep. 2016]. Therefore, avoidance of unnecessary additional evaluation of benign pulmonary nodules will be good for patient care and the health care system.

The proteomic test was not compared to Lung-RADS. Lung-RADS was developed for nodules found with lung cancer screening with LDCT. Lung-RADS structures reporting and management recommendations based primarily on the size of nodules and has a goal of reducing false-positives by increasing the size of nodules considered positive [Yip R, Henschke C I, Yankelevitz D F, Smith J P. CT Screening for Lung Cancer: Alternative Definitions of Positive Test Result Based on the National Lung Screening Trial and International Early Lung Cancer Action Program Databases. Radiology 2014; 273:591-596]. Lung-RADS was evaluated with the data from the National Lung Screening Trial and there was a reduction in the false-positive rate from 27% to 13% at baseline [Pinsky P F, Gierada D S, Black W, Munden R, Nath H, Aberle D, Kazerooni E. Performance of Lung-RADS in the National Lung Screening Trial: A Retrospective Assessment. Ann Intern Med 2015; 162:485-491]. However, sensitivity decreased from 94% in the NLST to 85% in this retrospective, secondary analysis.

The strengths of this trial include its extensibility: a large, well-defined and geographically diverse population, in addition to a study design with a high level of evidence [10]. Collection of physician pre-test probability of cancer was an important component of the trial and confirmed the value of focusing the proteomic test on the lower risk population. A limitation of the trial is that the effect of the plasma protein test was retrospectively analyzed so a prospective interventional trial with the proteomic test is warranted. Also, community practices are under represented among study sites.

In conclusion, physicians are adept at categorizing nodules into lower and higher risk groups. When this robust proteomic test is applied to the lower risk group, it can be anticipated that significantly more patients with benign nodules will be correctly routed into CT surveillance. These patients will then be able to avoid unnecessary invasive procedures, saving the anxiety and costs of procedures, and procedure complications.

Example 6

Continued Clinical Assessment

Introduction

We have previously validated a blood-based risk predictor that used 11 molecular factors (A. K. Brady et al., Survival outcome according to KRAS mutation status in newly diagnosed patients with stage IV non-small cell lung cancer treated with platinum doublet chemotherapy. *Oncotarget* 6, 30287 (Oct. 6, 2015)) and established its potential clinical utility on a prospectively collected biobank (A. Vachani et al., Clinical Utility of a Plasma Protein Classifier for Indeterminate Lung Nodules. *Lung* 193, 1023 (December 2015)). Separately, several risk predictors composed purely of clinical risk factors have been validated (M. K. Gould, L. Ananth, P. G. Barnett, S. C. S. G. Veterans Affairs, A clinical model to estimate the pretest probability of lung cancer in patients with solitary pulmonary nodules. *Chest* 131, 383 (February 2007); A. McWilliams et al., Probability of cancer in pulmonary nodules detected on first screening CT. *The New England journal of medicine* 369, 910 (Sep. 5, 2013); S. J. Swensen, M. D. Silverstein, D. M. Ilstrup, C. D. Schleck, E. S. Edell, The probability of malignancy in solitary pulmonary nodules. Application to small radiologically indeterminate nodules. *Arch Intern Med* 157, 849 (Apr. 28, 1997)). Here we explore two end points:

First, molecular markers are comparable in performance to clinical factors for risk prediction, and Second, the integration of molecular and clinical risk factors results in a better risk prediction.

The most reliable clinical tools are those that undergo multiple validations of performance on independent sample sets (C. Micheel, S. J. Nass, G. S. Omenn, Institute of Medicine (U.S.). Committee on the Review of Omics-Based Tests for Predicting Patient Outcomes in Clinical Trials., *Evolution of translational omics: lessons learned and the path forward*. (National Academies Press, Washington, D.C., 2012), pp. xv, 338 p). Consequently, the focus of this analysis is not the discovery of new molecular or clinical risk factors, but the evaluation of previously validated markers and factors, both individually and integrated, on a prospectively collected sample set. The molecular markers evaluated are those previously discovered and validated as being predictive for cancer risk in lung nodules (X. J. Li et al., A blood-based proteomic classifier for the molecular characterization of pulmonary nodules. *Science translational medicine* 5, 207ra142 (Oct. 16, 2013); A. Vachani et al., Validation of a multiprotein plasma classifier to identify benign lung nodules. *Journal of thoracic oncology: official publication of the International Association for the Study of Lung Cancer* 10, 629 (April 2015)). The clinical risk factors, also previously validated as being predictive for cancer risk in lung nodules, include age, nodule size, smoking history, nodule location and nodule speculation (S. J. Swensen, M. D. Silverstein, D. M. Ilstrup, C. D. Schleck, E. S. Edell, The probability of malignancy in solitary pulmonary nodules. Application to small radiologically indeterminate nodules. *Arch Intern Med* 157, 849 (Apr. 28, 1997)). Finally, the endpoints are explored using samples acquired from a prospective trial (NCT01752101) of lung nodule management previously reported (A. Vachani et al., Clinical Utility of a Plasma Protein Classifier for Indeterminate Lung Nodules. *Lung* 193, 1023 (December 2015)). All subjects in this trial underwent an invasive procedure (biopsy and/or surgery). We chose to focus on these subjects as it allows for the assessment of how accurately risk prediction tools could identify benign lung nodules that undergo unnecessary invasive procedures.

Methods

Study Design

Trial NCT01752101 was a prospective, multicenter, observational trial with retrospective evaluation of the performance of molecular and clinical markers. Patient care was not directed or influenced by the protocol. A blinding protocol was strictly followed. All sites had local or central Institutional Review Board approval.

Patient Selection

Patients with an indeterminate pulmonary nodule were enrolled at 12 geographically diverse sites in the U.S. Eligible patients were those with a lung nodule between 8-30 mm in diameter, minimum 40 years of age, and had recently completed a CT guided needle aspiration (TTNA) or bronchoscopic biopsy with an established diagnosis or were scheduled for a surgical lung biopsy. Exclusion criteria included a prior malignancy within 5 years of lung nodule identification or a clinical tumor stage≥T2, nodal stage≥N2, or evidence of metastatic disease.

All TTNA and bronchoscopy procedures were categorized as either diagnostic (provided a specific malignant or benign pathological diagnosis), or non-diagnostic (the specific etiology of the lung nodule remained unknown). All surgical procedures were categorized into either diagnostic (i.e. no specific prior diagnosis) or therapeutic (i.e. surgery preceded by a TTNA or bronchoscopy that yielded a malignant diagnosis).

Finally, the analysis here focused on those subjects with lung nodules between 8 and 20 mm in diameter. These were of interest as lung nodules below 20 mm are more challenging to classify as malignant or benign Data Collection Blood samples were obtained and processed for proper storage and shipment per protocol (11). The nodule location, size, and contour were collected at baseline and all subsequent CT scans. Data on imaging and procedures was collected until definitive diagnosis which occurred within 21 days of Informed Consent. Data on procedures including bronchoscopy, transthoracic needle biopsy, and surgery were recorded.

Molecular and Clinical Markers

The assay (Xpresys Lung™, Integrated Diagnostics, Seattle, Wash.) is based on mass spectroscopy MRM-MS as previously described (X. J. Li et al., A blood-based proteomic classifier for the molecular characterization of pulmonary nodules. *Science translational medicine* 5, 207ra142 (Oct. 16, 2013); A. K. Brady et al., Survival outcome according to KRAS mutation status in newly diagnosed patients with stage IV non-small cell lung cancer treated with platinum doublet chemotherapy. *Oncotarget* 6, 30287 (Oct. 6, 2015); A. Vachani et al., Clinical Utility of a Plasma Protein Classifier for Indeterminate Lung Nodules. *Lung* 193, 1023 (December 2015); X. J. Li et al., An integrated quantification method to increase the precision, robustness, and resolution of protein measurement in human plasma samples. *Clinical proteomics* 12, 3 (2015)) it was developed following National Academy of Medicine guidelines (C. Micheel, S. J. Nass, G. S. Omenn, Institute of Medicine (U.S.). Committee on the Review of Omics-Based Tests for Predicting Patient Outcomes in Clinical Trials., *Evolution of translational omics: lessons learned and the path forward*. (National Academies Press, Washington, D.C., 2012), pp. xv, 338 p) and monitors 11 proteins. Clinical factors collected included age, smoking status, nodule diameter, nodule spiculation and nodule location.

Data Analysis

All statistical analyses were performed using Matlab (Mathworks inc., version 8.3.0.532) and MedCalc, version 16.4 (MedCalc Software bvba). Chi-squared of analysis of variance testing was used to compare groups, and a p-value of ≤0.05 is considered significant. Physicians, patients, along with laboratory and statistical personnel were blinded to the results of the protein classifier and clinical information. Continuous and categorical variables were assessed using Mann-Whitney and Fisher's exact tests, respectively. All confidence intervals are reported as two-sided binomial 95% confidence intervals (CIs).

Results

A total of 475 subjects were enrolled prospectively from April 2012 to December 2014 in the registered study, NCT01752101. Of these, 50 subjects violated the inclusion/exclusion criteria; 43 additional subjects had a lung cancer other than NSCLC; 26 additional subjects had missing data; and 3 additional subjects violated the blood sample collection protocol. This left 353 patients eligible for analysis (see (A. Vachani et al., Clinical Utility of a Plasma Protein Classifier for Indeterminate Lung Nodules. *Lung* 193, 1023 (December, 2015).) for more details). Of the 353 eligible subjects, 222 had nodule size 8-20 mm. Baseline demographics are shown in Table 27.

TABLE 27

Patient demographics and lung nodule characteristics for all 222 subjects.

| Characteristics | All Patients | | Cancer | | Benign | | p-value |
|---|---|---|---|---|---|---|---|
| Patients | 222 | | 180 | | 42 | | |
| Age (years) [mean (range)] | 66.69 | (44.68-95.46) | 67.12 | (45.31-95.46) | 64.82 | (44.68-87.47) | 0.177 |
| Gender (n, %) | | | | | | | 0.071 |
| Male | 89 | 40% | 67 | 37% | 22 | 52% | |
| Female | 133 | 60% | 113 | 63% | 20 | 48% | |
| Smoking History | | | | | | | |
| Status (n, %) | | | | | | | 0.392 |
| Never | 33 | 15% | 25 | 14% | 8 | 19% | |
| Former | 135 | 61% | 110 | 61% | 25 | 60% | |

TABLE 27-continued

Patient demographics and lung nodule characteristics for all 222 subjects.

| Characteristics | All Patients | | Cancer | | Benign | | p-value |
|---|---|---|---|---|---|---|---|
| Current | 48 | 22% | 42 | 23% | 6 | 14% | |
| Passive Exposure | 6 | 3% | 3 | 2% | 3 | 7% | |
| Lung Nodules | | | | | | | |
| Size (mm) [mean (range)] | 14.59 | (8-20) | 14.72 | (8-20) | 14.07 | (8-20) | 0.289 |

In this population of subjects, the cancer prevalence was 81% (180 out of 222 subjects). The average age of subjects with a malignant nodule (67.1 years) was not significantly different from subjects with a benign nodule (64.8 years). Smoking history binned into the categories of 'never', 'former' and 'current' were similar for subjects with malignant and benign nodules. Nodule size was not significantly different between subjects with a malignant nodule (14.7 mm) and subjects with a benign nodule (14.1 mm).

Of the 11 proteomic markers evaluated five were previously reported as being diagnostic (ALDOA, COIA1, TSP1, FRIL and LG3BP) and 6 reported as being endogenous normalizers (C163A, PEDF, LUM, GELS, MASP and PTPRJ) (A. Vachani et al., Validation of a multiprotein plasma classifier to identify benign lung nodules. *Journal of thoracic oncology: official publication of the International Association for the Study of Lung Cancer* 10, 629 (April, 2015); X. J. Li et al., An integrated quantification method to increase the precision, robustness, and resolution of protein measurement in human plasma samples. *Clinical proteomics* 12, 3 (2015)). In this analysis, we focus on ratio pairs P1/P2 were P1 is a diagnostic protein and P2 is a normalizer. Among all such protein ratio pairs, LG3BP/C163A had the maximal AUC of 60% for classifying the 222 subjects as being malignant or benign. This is significantly better than random by the Mann-Whitney test (p-value 0.025). The ratio of these two proteins, LG3BP/C163A, will be used to assess the stated study hypotheses. Table 28 presents the AUC performance of all ratio pairs.

TABLE 28

AUC performance of all proteomic ratio pairs P1/P2 where P1 is one of the five diagnostic proteins (ALDOA, COIA1, TSP1, FRIL and LG3BP) and P2 is one of the six normalization proteins (C163A, PEDF, LUM, GELS, MASP and PTPRJ).

| P1 | P2 | AUC |
|---|---|---|
| LG3BP | C163A | 0.60 |
| LG3BP | GELS | 0.60 |
| COIA1 | GELS | 0.59 |
| COIA1 | LUM | 0.56 |
| COIA1 | PEDF | 0.56 |
| ALDOA | C163A | 0.56 |
| FRIL | LUM | 0.56 |
| FRIL | PEDF | 0.55 |
| LG3BP | MASP1 | 0.55 |
| LG3BP | PTPRJ | 0.55 |
| ALDOA | GELS | 0.54 |
| FRIL | MASP1 | 0.54 |
| TSP1 | C163A | 0.54 |
| TSP1 | GELS | 0.53 |
| COIA1 | C163A | 0.53 |
| ALDOA | PTPRJ | 0.53 |
| ALDOA | PEDF | 0.53 |
| FRIL | PTPRJ | 0.52 |
| COIA1 | MASP1 | 0.52 |
| TSP1 | LUM | 0.52 |
| TSP1 | PTPRJ | 0.52 |
| TSP1 | PEDF | 0.51 |
| FRIL | GELS | 0.51 |
| LG3BP | PEDF | 0.51 |
| ALDOA | LUM | 0.51 |
| FRIL | C163A | 0.51 |
| COIA1 | PTPRJ | 0.51 |
| TSP1 | MASP1 | 0.50 |
| LG3BP | LUM | 0.50 |
| ALDOA | MASP1 | 0.50 |

Study Endpoint #1

Figure 21:
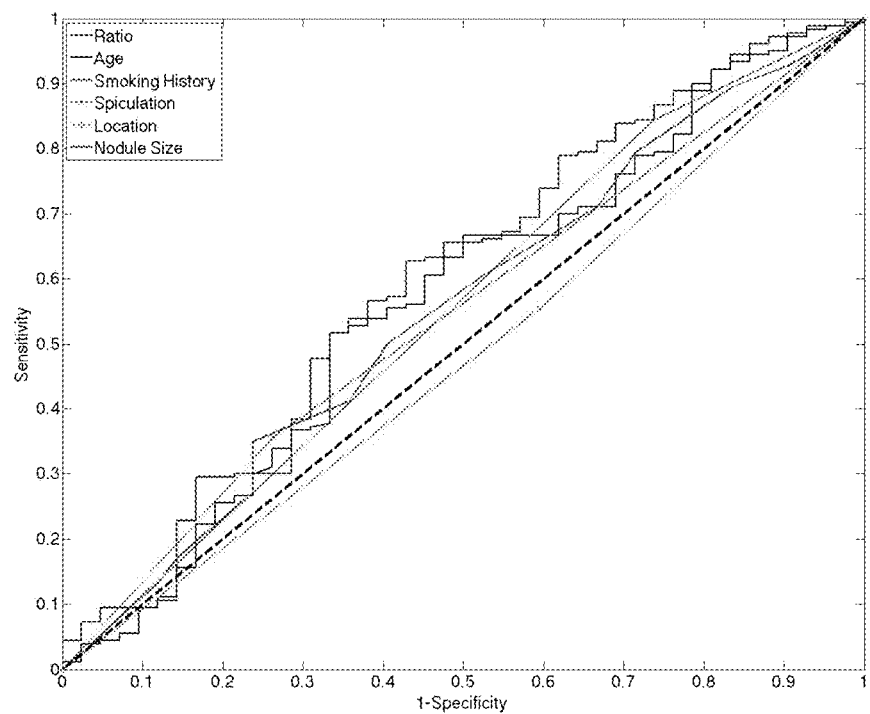
FIG. 21 is a graph showing the comparison of five clinical risk factors and the proteomic ratio LG3BP/C163A

We assess the individual performance of five clinical risk factors (nodule size, subject age, subject smoking history, nodule location and nodule spiculation) and the proteomic ratio LG3BP/C163A. FIG. 21 presents the performance of the five clinical risk factors and the molecular marker LG3BP/C163A using a ROC plot. In comparing these six factors, the proteomic ratio has the highest AUC (60%) and is significantly better than random (pvalue=0.025). In contrast, none of the clinical risk factors have an AUC significantly better than random (AUC appears in parentheses): nodule size (55%), age (57%), smoking history (55%), nodule location (48%) and nodule spiculation (55%).

Study Endpoint #2

To address the second study endpoint, we need to integrate the five clinical risk factors with the proteomic ratio. This integration was conducted using a decision tree approach (L. Breiman, *Classification and regression trees*. Wadsworth statistics/probability series (Chapman & Hall, Boca Raton, Fla., 1993), pp. x, 358 p). The proteomic ratio LG3BP/C163A is used first to classify a lung nodule as lower or higher risk based on a decision threshold "t" (see formula below where "k" denotes a lung nodule under evaluation). Secondly, a cancer risk score, "ClinFact", is calculated over the five clinical risk factors. Note that the ClinFact risk algorithm is a simplification of the 'Mayo' algorithm with the cancer history factor omitted (5). If the lung nodule is lower risk, as determined by the proteomic ratio LG3BP/C163A, then the Mayo risk prediction is reduced by a fixed amount "T", otherwise, it is left unchanged. We call this integrated model "IntMod". Effectively, the proteomic ratio LG3BP/C163A is used to identify lower risk lung nodules in order to rule out lung cancer.

$$IntMod(k) = \begin{cases} \max(0, ClinFact(k) - T), & \log_2\left(\frac{LG3BP}{C163A}\right) \le t \\ ClinFact(k), & \log_2\left(\frac{LG3BP}{C163A}\right) > t \end{cases}$$

$$ClinFact(k) = \frac{e^X}{1 + e^X}$$

$$X = -6.8272 + 0.0391 * Age + 0.7917 * Smoker + 0.1274 * Diameter + 1.0407 * Spiculation + 0.7838 * Location$$

We note that this integrated model has two parameters, namely, "t" and "T" which need to be learned.

Optimal Values of Parameters t and T

In this analysis we learn the optimal values for the integrating parameters t and T. All possible pairs of values for t (−1.1 to 3.3 in increments of 0.1) and for T (0 to 1 in increments of 0.1) are assessed and the AUC of the resulting IntMod predictor calculated. We make the following observations:

The longest continuous stretch of values fort where the highest AUC values occur is from t=0.14 to 0.39, regardless of the value of parameter T. In this range the AUC values are all at least 62%. That is, this is the range of values for parameter t with both high and stable performance for IntMod.

Within the range t=0.14 to 0.39, the vast majority oft values (23 out of 29) achieve maximal AUC when T=0.5. In particular, the maximum AUC achieved is 63.1% for t=0.29 and T=0.5.

Within the entire range t=0.14 to 0.39, the AUC achieved is significantly different from 0.5 with p-values all less than 0.008 (Mann-Whitney test) when T=0.5.

Figure 22:
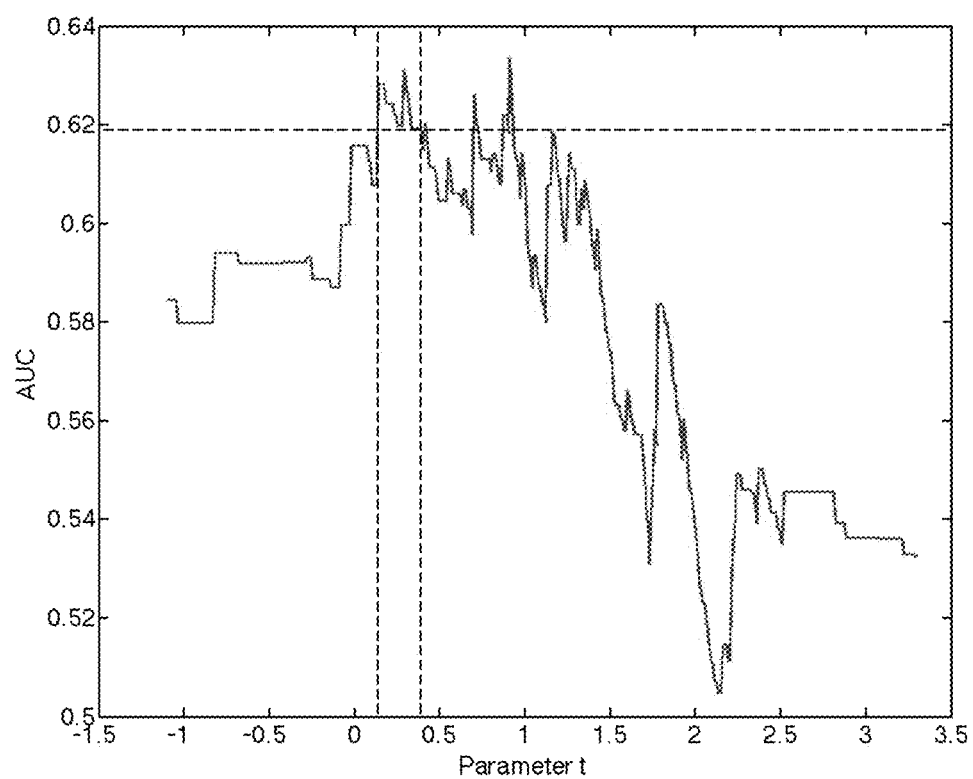
FIG. 22 is a graph showing the performance of the Integrated Model (IntMod) for different values of parameter t and T=0.5. Optimal sustained performance occurs for values of t between 0.14 and 0.39 where AUC values are all at least 62% and with p-values all below 0.008 (Mann-Whitney).

For further discussion, we select t=0.29 and T=0.5 as this is within the longest continuous range of values with strong performance. However, it is important to point out that the performance of the integrated model is essentially the same for any value oft in this range (0.14 to 0.39). FIG. 22 presents the AUC performance of IntMod for all values of the parameter t and for T=0.5.

Comparative Performance of the Proteomic Ratio, Mayo and the Integrated Model

Figure 23:
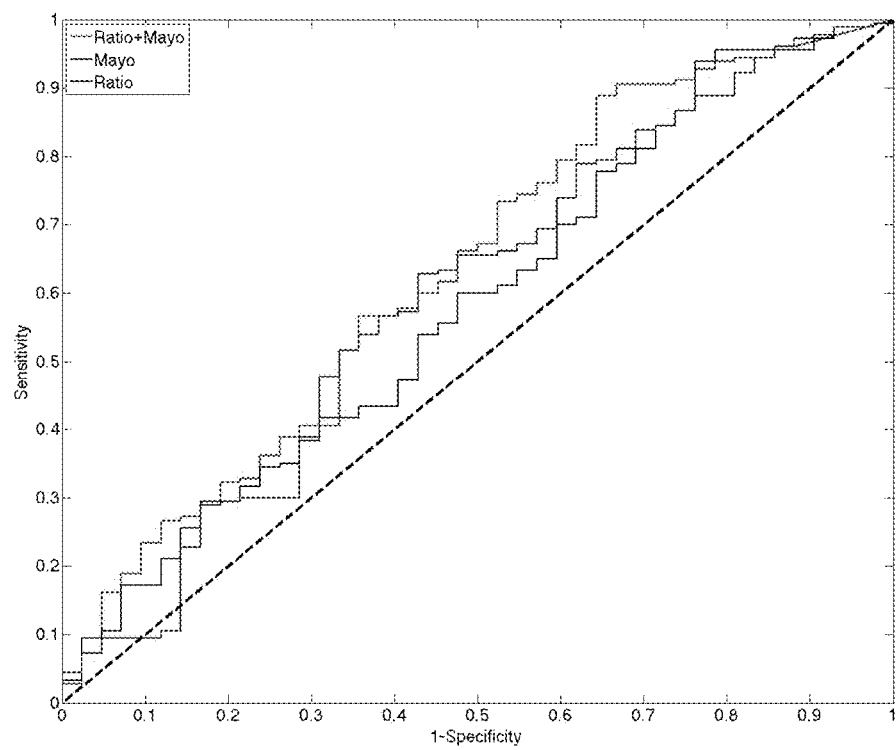
FIG. 23 is a graph showing a comparison of proteomic ratio, Mayo algorithm and the Integrated Model (Ratio+Mayo. At sensitivity 90% and specificity 33% the integrated model has statistically significant better performance than both the Mayo model and the proteomic ratio.

On these subjects the AUC performance of the proteomic ratio, the simplified Mayo algorithm and the integrated model IntMod are, respectively, 60%, 58% and 63%. These are illustrated in FIG. 23. Although these AUC values demonstrate an improved performance for the integrated model over the proteomic ratio and Mayo alone, we focus on the clinically relevant point on the IntMod ROC curve (sensitivity=90%, specificity=33%) to statistically compare performance at the same sensitivity and specificity, using the McNemar test, to the proteomic ratio and the Mayo model. High sensitivity is typically required to rule out lung cancer confidently.

Using the McNemar test, the integrated model has significantly better specificity (when sensitivity is fixed at 90%) to both the proteomic ratio (p-value 0.031) and the Mayo model (p-value 0.008). Similarly, using the McNemar test, the integrated model has significantly better sensitivity (when specificity is fixed at 33%) to both the proteomic ratio (p-value<0.001) and the Mayo model (p-value<0.001).

Discussion

The two endpoints tested in this study were confirmed. First, the proteomic marker LG3BP/C163A has comparable (in fact superior) performance to five commonly used clinical risk factors. Second, the integration of this proteomic marker with the five clinical risk factors resulted in a risk predictor statistically superior to both the proteomic marker and to the clinical risk factors separately. This result affirms that integrated risk predictors can enable better risk prediction for lung nodule management.

This analysis assessed five previously reported clinical risk factors and 11 proteomic markers on a new set of prospectively collected samples from 12 sites. The evaluation of risk markers on multiple sample sets helps to establish their performance and appropriate use in clinical use. In this study, we focused on the subpopulation of lung nodules between 8 and 20 mm in diameter and having undergone an invasive procedure. This subpopulation is important as it contains benign lung nodules that are overtreated, and so, enables the evaluation of clinical risk factors and proteomic markers for the purpose of identifying those benign lung nodules that can avoid unnecessary invasive procedures. It is important to note that the performance values observed in this study are definitely lower than those previously reported on other populations of lung nodules using the same clinical risk factors and proteomic markers; the population that is tested matters.

The design of the integrated model warrants a few comments. First, proteomic ratios were assessed instead of individual protein markers. The reason for this is that ratios are particular useful as they normalize for pre-analytical and analytical variation (X. J. Li et al., An integrated quantification method to increase the precision, robustness, and resolution of protein measurement in human plasma samples. *Clinical proteomics* 12, 3 (2015)). Furthermore, to reduce the possibility of overfitting we avoided utilizing more than two proteomic markers. Second, there are many other valid methodologies to integrate the clinical and proteomic risk factors including logistic regression (D. Freedman, *Statistical models: theory and practice*. (Cambridge University Press, Cambridge; New York, 2009), pp. xiv, 442 p), support vector machines (N. Cristianini, J. Shawe-Taylor, *An introduction to support vector machines: and other kernel-based learning methods*. (Cambridge University Press, Cambridge; New York, 2000), pp. xiii, 189 p) and random forests (T. Hastie, R. Tibshirani, J. H. Friedman, *The elements of statistical learning: data mining, inference, and prediction*. Springer series in statistics (Springer, New York, 2001), pp. xvi, 533 p), among others, in addition to the decision tree approach used here.

Example 7

Xpresys Lung version 2 (XL2) is a blood test with the intended use of identifying lung nodules that are likely benign so those nodules can safely avoid risky and costly invasive procedures such as biopsy and surgery. See Section 2.1 for details.

It is estimated that over three million lung nodules will be detected either incidentally or through lung cancer screening programs annually in the US. The majority of individuals with lung nodules are of Medicare age. See Section 2.2 for details.

Although the majority of lung nodules detected annually are benign (75%-85%), 62% undergo an unnecessary biopsy and 35% undergo an unnecessary surgery, or both. See Section 2.2 for details.

The key performance metric for XL2 is its negative predictive value (NPV) as XL2 is a cancer rule out test. The median NPV for XL2 is 98% (CI: 92%-100%) based on the prospective PANOPTIC study that spanned 33 sites and enrolled 685 subjects. The American College of Chest Physician's (ACCP) guidelines recommend a 95% NPV to observe a lung nodule over time. See Section 3.2 for details.

Xpresys Lung version 2 (XL2) is superior to Xpresys Lung version 1 (XL1) in several ways, most notably (see Section 3.7 for details): (1) XL2 was developed and validated on two large prospective studies; XL1 was developed and validated on two moderate-size retrospective studies; (2) XL2 utilizes a subset of the XL1 protein biomarkers most accurate in identifying benign lung nodules; (3) XL2 integrates protein biomarkers with five clinical factors previously validated (and endorsed by the ACCP Guidelines) as having utility for evaluating the cancer/benign status of a lung nodule.

XL2 has statistically superior performance to PET. Specifically, in the PANOPTIC study, where XL2 and PET can be directly compared on the same subjects, the NPV of XL2 is 98% (CI: 92%-100%) whereas the NPV of PET is 79% (CI: 66%-88%). See Section 3.3 for details.

XL2 has statistically superior performance to the four most common clinical risk factor algorithms (Mayo, VA, Brock and Herder) where XL2 and the clinical risk factor algorithms are compared on the same subjects. See Section 3.3 for details.

XL2 has statistically superior performance to physicians where XL2 and physician cancer risk assessment are compared on the same subjects. See Section 3.3 for details.

If XL2 were used in PANOPTIC then 36% of unnecessary invasive procedures (biopsies and/or surgeries) could have been avoided. XL2 has the potential to avoid over 36,000 surgeries, 1,600 hospitalizations, and almost 750 deaths per year. The majority of these occurring in the Medicare population of patients. See Sections 2.2 and 3.4 for details.

XL2 is very safe to use as compared to current practice. Specifically, if XL2 were used in PANOPTIC then only 3% of malignant nodules would have been erroneously routed to CT surveillance. In comparison, 45% of patients with malignant lung nodules in the PANOPTIC trial intended use population were erroneously routed to CT surveillance. See Section 3.4 for details.

To ensure that the intended use population is objectively defined as lower risk for use in the Medicare population, a patient must satisfy the following: (1) have a newly detected lung nodule between 8 mm and 30 mm in diameter; (2) not currently be a smoker; and (3) have a Mayo clinical risk prediction of 40% or less.

The Mayo clinical risk predictor is a validated formula, identified in the ACCP guidelines, for lung nodule risk assessment. The Mayo formula incorporates the following clinical risk factors: nodule size, smoking history, age, nodule location, nodule spiculation and cancer history.

1. Xpresys Lung Introductory Summary

Xpresys Lung has been developed to differentiate benign from malignant lung nodules. Xpresys Lung is a blood test for proteins that combines expertise in proteomics and computer science using large data sets. Mass spectrometry has been employed as a technology for molecular diagnostics for decades and recent advances in instrumentation allows measurement of hundreds of proteins at a time. Cancers secrete and shed proteins that are different from normal cells and some of these proteins circulate in the blood. InDi started with 388 protein candidates and blood samples stored from both patients with benign and malignant lung nodules. The initial analyses discovered and validated a predictor for benign nodules using a combination of 11 proteins. Xpresys Lung version one (XL1) provided significant performance over clinical risk factors physicians use to differentiate benign from malignant lung nodules. InDi has now completed further work with protocol-collected blood samples to refine a second version of Xpresys Lung (XL2) which is a robust test for determining which nodules are benign.

This new version, XL2, improves on XL1 in four ways as described in Section 3.7. These are: 1) a refined intended use population; 2) the identification of 2 of the prior 11 proteins that are most accurate in identifying benign lung nodules; 3) the incorporation of five clinical risk factors; and 4) discovery and validation based on two large prospective studies where samples were collected using a uniform protocol rather than archival biobanks.

XL2 achieves high performance for identifying benign nodules. At a 98% negative predictive value (NPV), the sensitivity is 97% (Table 34, Section 3.6). This improved test performs significantly better than PET (NPV of 79%, with a 95% CI of 66%-88%) (Section 3.3.4.3). XL2 also performs significantly better than four clinical risk predictors (Mayo, VA, Brock and Herder) (Section 3.3.4.2). XL2 will provide physicians the best available evidence to determine which nodules are benign.

XL2 will be positioned before PET, bronchoscopy, needle biopsy, and surgery (Section 2.4.2). The confidence from the high NPV values with XL2 will guide more patients with benign nodules into CT surveillance. That will achieve the goal of Xpresys Lung: avoid unnecessary further evaluation of benign nodules, especially invasive procedures.

The projected clinical utility of XL2 is a 36% reduction of invasive procedures (Section 2.4.1). These reductions in invasive procedures will reduce surgeries, surgical mortality, and hospitalizations from biopsy complications (Section 2.4.3).

After the coverage determination, InDi intends to proceed with a prospective interventional trial. This trial will confirm XL2 produces results that have clinical utility in health care delivery settings. This trial is summarized in Section 4.

2. Clinical Aspects of Xpresys Lung and Lung Nodules 2.1 Xpresys Lung Intended Use and Description 2.1.1 Intended Use Xpresys Lung version 2 (XL2) is intended for the evaluation of 8-30 mm lung nodules in patients 40 years or older where the physician estimates a lower cancer risk (pretest probability of cancer is 0 to 50%). To be defined as lower risk in the Medicare population the patient must have a pretest probability of cancer of <40% based on the Mayo model and not be a current smoker. The goal for Xpresys Lung is to identify those nodules that are likely benign so those nodules can be safely observed by CT surveillance rather than undergo costly and risky invasive procedures such as biopsy and surgery.

2.1.2 Description of Xpresys Lung

XL2 is a risk predictor that integrates molecular (proteomic) measurements with clinical risk factors. Proteins associated with cancers or benign processes are measured. These proteins are secreted or shed from cells in the lung and measured in a blood plasma sample. The XL2 result will be reported as Likely Benign (90-98% negative predictive value) or Indeterminate (post-test cancer risk not significantly lower than the pre-test risk of cancer). For details see Section 3.6.

2.2 The Unmet Need for Lung Nodules is Significant and Growing 2.2.1 Lung Nodules 2.2.1.1 Definitions Lung nodules are rounded densities seen by x-ray imaging. X-ray imaging can be a chest radiograph (CXR) or computer-assisted tomography (CAT scan). Nodules are mostly surrounded by lung tissue and are also called coin lesions, solitary pulmonary nodules or lesions, or a "spot" on the lung. Rounded densities larger than 30 mm in diameter are lung masses, not nodules. The edges of the nodules can be described as smooth or irregular (stellate or spiculated), and irregular edges somewhat more indicative for cancer. Heavily calcified nodules with smooth edges are generally benign and solid nodules that have not shown growth over time are considered benign. With improved CT imaging subsolid nodules, ground-glass opacities or part-solid nodules, are now seen and have different guidelines. The focus of this application is 8-30 mm solid nodules and not subsolid nodules.

For a comprehensive review of nodules and their evaluation see the 2-part series by V. K. Patel, et al., "A Practical Algorithmic Approach to the Diagnosis and Management of Solitary Pulmonary Nodules. Part 1: Radiologic Characteristics and Imaging Modalities," Chest, vol. 143, no. 3, pp. 825-339, 2013; and V. K. Patel, et al., "A Practical Algorithmic Approach to the Diagnosis and Management of Solitary Pulmonary Nodules. Part 2: Pretest Probabiity and Algorithm," Chest, vol. 143, no. 3, pp. 840-846, 2013.

2.2.1.2 Numbers of Nodules Detected Annually

The estimated number of new lung nodules detected annually in the US is 1.57 million [7]. The number of new lung nodules has been increasing due to a combination of factors including CT scan technology improvements and more CT scans being done. The 1.57 million estimate is for nodules that are 4-30 mm diameter; the estimate for 8-30 mm nodules is 800,000 per year.

2.2.1.3 Incidental and Screen-Detected Nodules

The above estimate of 1.57 million nodules per year is only for incidentally found nodules and does not include another 1.5 million screen-detected nodules. Incidental means the imaging was done for reasons other than nodule detection. For example, imaging of the heart, upper abdomen, and even mammography includes lung tissue so a lung nodule is an incidental finding.

Lung cancer screening now has coverage in the United States. As of Apr. 26, 2016 there were 806 sites registered for screening. Initial estimates are that another 1.5 million nodules per year will be found once screening programs are in place. The National Lung Screening Trial (NSLT) had a screen positive rate of 24% and estimated there are 7 million persons in the United States that meet NSLT enrollment criteria.

2.2.1.4 Lung Nodule "Epidemic" and Health Care

Early detection of lung nodules is a great opportunity to reduce lung cancer mortality but it comes with significant risks. These risks are both for patients and health care delivery. For patients a major problem is the risk of unnecessary invasive procedures to find the minority of nodules that are cancer. XL2 addresses these avoidable procedures.

For health care delivery, the risks are both costs and overloading the health care system. The majority of patients with nodules will be over 65 years of age. In the NLST, over 57% of enrollees in the NSLT were over 65 years of age. Also the rates of nodule detection increased dramatically with age, at least until age 89. So Medicare enrollees are more likely to meet lung cancer screening criteria and have more nodules detected. If the nodules are ≥8 mm, then further testing is indicated, XL2 addresses these avoidable procedures.

2.2.1.5 Relevance to Medicare Population

Of the expected 3 million nodules per year found incidentally or by lung cancer screening, the majority will be Medicare age. Four recent studies underscore the importance of lung cancer evaluations to the Medicare population: (1) The mean age of 377 eligible patients in an 18 site retrospective chart review study was 65. All patients had nodules 8-20 mm in diameter. (2) A prospective study across 12 sites and 475 patients found 62.5% of patients were 65 years of age or older. All patients had nodules 8-30 mm in diameter. (3) Over 50% of patients in a prospective study across 33 sites and 685 patients were 65 years of age or older (PANOPTIC Study). All patients had nodules 8-30 mm in diameter. (4) A recent study reported that between January 2009 and December 2011, 8,979 Medicare patients from a random sampling of 5% of Medicare claims, underwent lung cancer evaluations because of an abnormal chest CT scan.

2.2.2 Lung Nodule Evaluation: Current Practice and Need for Improvement 2.2.2.1 Guidelines Groups have published guidelines for the evaluation of lung nodules. A set of guidelines regarding lung cancer is published and updated by the American College of Chest Physicians (ACCP). The ACCP guidelines for lung nodules, updated in 2013, is the primary reference used by pulmonologists in the United States. It is important to focus on ACCP section 4.0 for ≥8 mm nodules, the intended use for Xpresys Lung.

2.2.2.2 General Approach to 8-30 mm "Indeterminant" Nodules

Nodules are found with imaging other than chest CT scans (Section 2.2.1.3). Thus a chest CT with high-resolution imaging of the nodule is often needed. The CT findings alone or prior images may indicate a nodule is benign. The details of imaging and differential diagnosis of nodules has been reviewed by Patel and colleagues. When CT imaging alone is not definitive, the nodule is described as "indeterminant".

CT imaging accuracy was studied using expert reviewers in a retrospective study of 344 nodules before any nodules were determined to be benign. CT results (after excluding 128 [27%] without a "reference standard" or an "inconclusive result") showed a sensitivity of 95.6% (95% CI, 91.3%-97.9%), and a specificity of 40.6% (95% CI, 33.0%-48.7%). The results with CT interpretation of indeterminate nodules with general radiologists will be expected to be inferior.

Most 8-30 mm nodules are indeterminant. The ACCP Guidelines state: "Although clinical and radiographic [CT scans] characteristics cannot reliably distinguish between benign and malignant nodules in most individuals, it is nevertheless important to estimate the clinical probability of malignancy before ordering imaging tests or biopsy procedures". The pretest probability of malignancy (pCA) is estimated by using clinical judgment or with a quantitative risk model (see Section 2.2.4). Establishing a pCA creates three groupings (excluding patients at high surgical risk), Low, Intermediate, and High probability. The exact numbers changed between guideline revisions but are similar, with <5% pCA being Low and >65% pCA being High. The general concept is that Low risk patients will be observed with further CT surveillance to watch for growth if a nodule is malignant.

Conversely, the guidelines suggest those patients in the High risk group go directly to surgery. The logic is that the probability of cancer is high enough that a negative biopsy will not change the care pathway.

The Intermediate risk group (5-65% pCA) are recommended to enter the diagnostic odyssey with PET scanning often the next step. A negative PET suggests a benign nodule, so the patient is followed with CT scans. A positive PET scan goes on to surgery or biopsy. This is the overall concept, but PET has sensitivity and specificity problems, but PET has sensitivity and specificity problems as discussed in Section 2.2.6.

2.2.2.3 The Problems with Guidelines and Current Practice

The guidelines are conceptually good, but are based on mostly weak evidence and there is evidence that they are not followed.

The guidelines are based on weak evidence. The ACCP guidelines use the GRADE system and most recommendations regarding ≥8 mm nodules are 2C, a weak recommendation with low quality evidence. There are 3 recommendations that are level 1C, a strong recommendation with low quality evidence, which are: soliciting patient preference, going to further evaluation if there's evidence of malignant growth, and a preference for thorascopic rather than open biopsy.

There is abundant evidence that suggest the guidelines are not followed. A retrospective cohort study of 15 Veterans hospitals and 300 patients found that only 45% of the patient care for nodules was in concordance with guidelines. A pulmonary community practice observational record review of 18 practices and 377 patients found a wide variation in management of nodules. The surgery for benign nodules rate was 35% and the rate of surgery was the same for Low, Intermediate and High risk patients. The risk categories were calculated by the study and despite a Low risk, 28% had biopsies and 17% had surgery. Furthermore, the rate of malignant nodules observed with CT surveillance was 24.5%, resulting in a risk of delayed diagnosis.

The rates of surgery for benign nodules range between 10% and 55% as summarized by Vachani, et al. in their publication of a survey from 196 pulmonologists that supports the potential of a non-invasive biomarker to strongly and independently affect management decisions [18]. High rates of surgery for benign nodules are problematic because of the morbidity and mortality associated with surgery. Surgical risk figures are dependent on the population and the procedures used. The surgical mortality estimate after lobectomy in a Medicare age patient is 2-3% (Section 2.4.3.2).

Therefore, there is a clear opportunity for improvement in current practice. The rates of avoidable surgery for benign nodules was 35% in community practices and reported as high as 55%. The high rates for avoidable PET scans, biopsies, and surgeries are addressed in Sections 2.4.1.2, 2.4.3.1, and 2.4.3.2 respectively.

2.2.3 Physician Pretest Probability of Cancer (pCA), Lower Cancer Risk Group, and the Unmet Need The guidelines recommend a determination of the pretest probability of malignancy (pCA) by clinical judgment or with a model such as the Mayo equation. Pulmonologists uniformly used their clinical judgment for assigning pCA, and other physicians do not determine a pCA.

The PANOPTIC trial (Section 2.3) collected pCA results upon clinical presentation, after a CT scan, and before other testing. The physicians in the study used their clinical judgment 80% of the time and were significantly better than the two quantitative risk models used most often, the VA and Mayo, (AUC 0.85 vs 0.75 (VA) p<0.001 and vs 0.78 (Mayo) p=0.011). This indicates that physician pCA may be best for separation of patients with nodules into higher and lower cancer risk groups such as a pCA of 50% or less risk of cancer. But not all physicians may be confident in determining a pCA so an alternative method to define the lower risk population is to use the Mayo model with a pCA<40% combined with not being a current smoker.

Figure 31:
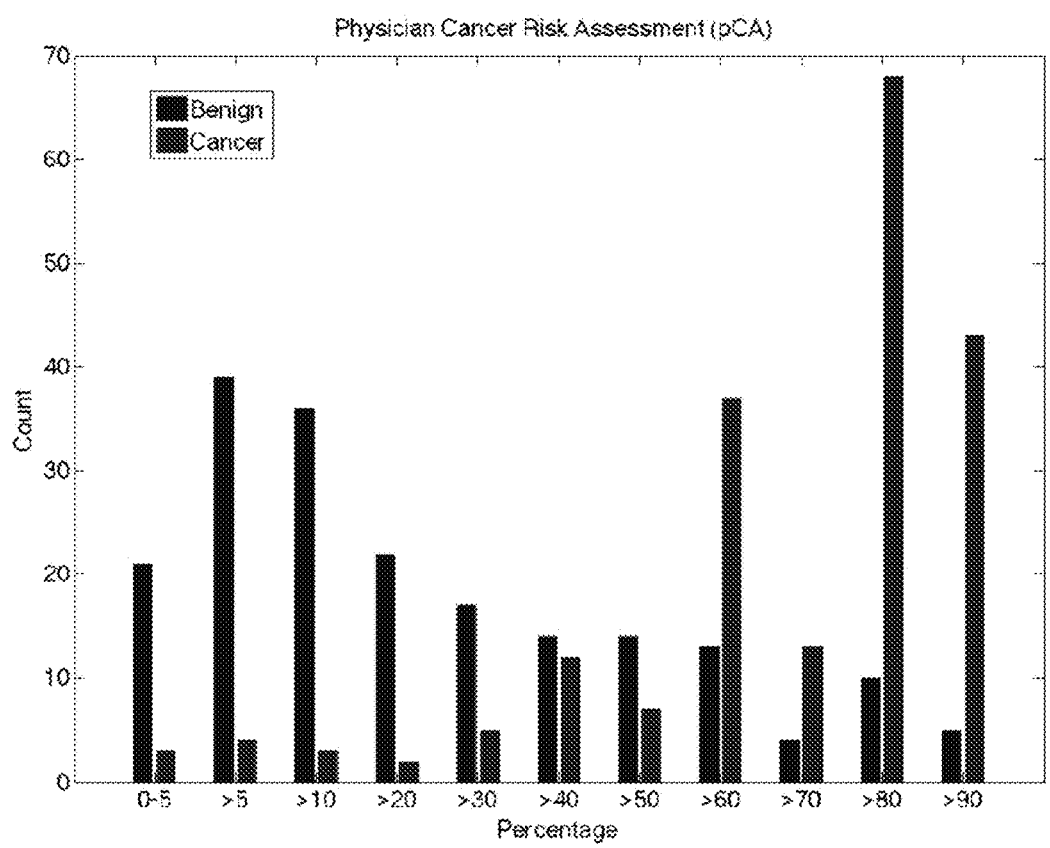
FIG. 31 is a graph showing PANOPTIC trial physician pretest probability (pCA) counts displayed by deciles (the first two columns are 5% increments). Shown are 196 cancer nodules and 196 benign nodules.

Further analyses of physician pCA data elucidates the need for XL2. As shown in FIG. 31, physicians are good at placing most cancerous nodules into pCA greater than 50% and most benign nodules into pCA of 50% or less. However, most benign nodules are not in the Low risk (0-5% pCA) category where CT surveillance is recommended. Most benign nodules are in the Intermediate risk category where further evaluation is recommended. These evaluations lead to many benign nodules undergoing risky and expensive procedures. In PANOPTIC, the 33 research sites were nearly all academic centers and integrated health networks yet the rates for surgery on benign nodules was 18% and biopsy of benign nodules was 30%. The comparable figures for community pulmonary practices (where most patients receive their care) are 35% of surgeries were performed on benign nodules and 62% of biopsies were performed on benign nodules.

Therefore, the unmet need is to provide the treating physician with a test for a Lower Risk nodule (pCA of 50% or less). This test should have a high Negative Predictive Value (NPV) result for a benign nodule. The post-test result then indicates the nodule is Low risk (0-5% pCA) and CT surveillance is recommended.

2.2.3.1 Physician pCA for Lower Risk Patients

As shown in FIG. 31, physicians were quite good establishing risk for all nodules (the entire risk population) with an AUC of 85%. However, they were not as good with lower risk (pCA 50% or less) patients (n=178 with 29 cancer and 149 benign nodules). In those lower risk patients, the physician AUC is 0.69 and is shown graphically in FIG. 35.

Most of these benign nodules are within the Intermediate risk population where the guidelines recommend further evaluation. If the guidelines are followed, most of those 149 patients with benign nodules will undergo avoidable imaging and biopsy. This underscores the need for XL2 and is discussed further in Sections 2.4 and 3.4 on Clinical Utility.

2.2.4 Quantitative Cancer Risk Models

Figure 32:
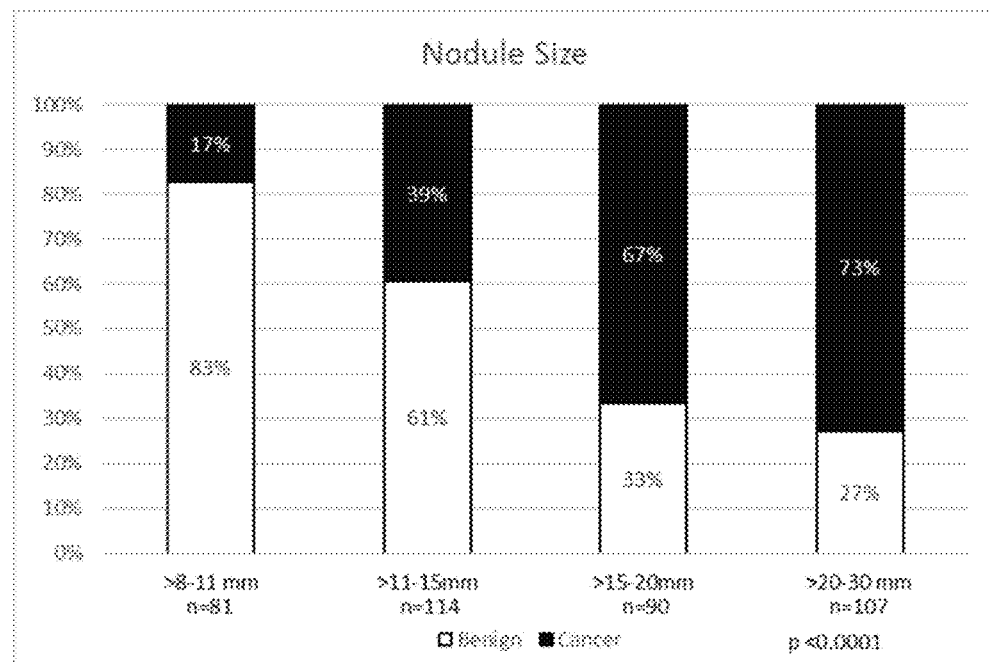
FIG. 32 is a graph showing lung nodules in the PANOPTIC trial separated by size with proportions of cancer and benign nodules. Shown are 392 nodules: 196 cancer nodules and 196 benign nodules.

The PANOPTIC results show that physicians are better than quantitative models at assigning pretest probability of cancer risk (pCA). The major factor for cancer risk in a pulmonary nodule is size. FIG. 32 shows the increasing prevalence of cancer associated with size. Other major factors are smoking history and age. Since CT screening is just being implemented in the United States, most risk models were developed for incidental nodules rather than screen detected nodules.

2.2.4.1 Incidental Nodule Models

The Mayo Clinic and a Veterans Administration (VA) Hospital group have developed prediction models that are based on similar but not identical factors. The prevalence of cancer in the VA model is considerably higher so it performs differently. These and other models have been summarized in the ACCP 2013 guidelines with support given to the Mayo model. The first sentence of the Guidelines reads: "Although clinical and radiographic characteristics cannot reliably distinguish between benign and malignant nodules in most individuals, it is nevertheless important to estimate the clinical probability of malignancy before ordering tests or biopsy procedures."

2.2.4.2 Screen-Detected Nodules

Using two Canadian lung cancer screening trials, McWilliams published a set of quantitative equations with AUC>0.90. The equations are available through Brock University.

The combined data includes 2,961 patients, but only 144 (<5%) of the nodules were malignant. They included subsolid nodules, but 79% were solid. The mean nodule size was 4.1 mm and median was 3.4 mm consistent with a low proportion of cancers. Predictors of cancer in the model included older age, female sex, family history of lung cancer, emphysema, larger nodule size, location of the nodule in the upper lobe, part-solid nodule type, lower nodule count, and spiculation.

The McWilliams paper recommends their equations be used for nodules from a baseline screening, low-dose CT scan (rather than incidentally found nodules).

2.2.5 Guidelines for Radiologists and CT Scan Nodule Reporting; Lung-RADS and Fleishner There are guidelines for radiologists regarding reporting lung nodules and the intervals for follow-up imaging. The guidelines for incidental nodules<8 mm come from the Fleishner Society. Fleishner guidelines were developed for incidentally found nodules.

Guidance from the American College of Radiology for lung cancer screening programs is Lung-RADS. Lung-RADS was developed to improve reporting and management recommendations to clinicians. One goal was to reduce the number of false positive reports needing further evaluation without increasing the false negatives. Based on the literature, they changed the size of nodules considered "positive" to 6 mm from 4 mm as used in the NLST. Another goal for Lung-RADS is a structured reporting system for lung cancer screening programs based on nodule size, CT imaging density, and whether the nodule was present at baseline, enlarging, or new at follow-up. Lung-RADS does not include other clinical factors that clinicians use such as smoking history, age, nodule location, or exposures (e.g. asbestos).

2.2.6 PET Scans

Positron Emission Tomography with contrast agents (PET) is useful in lung cancer staging, but PET has significant limitations for the diagnosis of lung nodules. These limitations are a lack of sensitivity, especially for smaller nodules, non-standardized reading and reporting, and false positive scans for inflammatory and infectious nodules.

2.2.6.1 PET sensitivity

Smaller nodules are difficult to image and PET was initially limited to nodules>10 mm. Small nodules and low-uptake of contrast in low-metabolic malignancies are major limits to sensitivity for PET imaging. The initial sensitivities reported from single-center experience with PET were estimated to be 95%. The estimate dropped to 87% when reviewed by the ACCP in 2007. Current estimates range from 72% to 94% and are reviewed in the 2013 ACCP Guidelines below. A 2014 meta-analysis reports a pooled sensitivity of 89% (95% CI, 86%-91%) and high heterogeneity when areas of infectious lung disease are included.

Early publications of PET about nodules were encouraging such that the 2007 ACCP guidelines gave PET an evidence Grade of 2A, but concerns about the quality of evidence and risk of bias decreased the recommendation to Grade 2C. The review articles by Patel initially state that PET is "very accurate" but after a summary of more recent data they emphasize the shortcomings of PET, and add a limitation that PET is best suited for nodules with an "intermediate" pCA. A recent study using NLST data showed PET use for nodules was 11% of 14,195 patients, but there was still inappropriate PET use in 21% of cases which suggested overutilization with small nodules and concern about contributing to excess healthcare costs.

Recently PET has been combined with CT to improve resolution so the size limitation has been re-stated to 8-10 mm. The combination is anticipated to improve the results but with increased cost and much higher radiation exposure.

2.2.6.2 PET Reporting

The reporting of PET has variation and is often only reported subjectively. Since the isotope in the contrast agent degrades (~110 min half-life for fluorine-18), the dose administered to a patient depends on the proximity in time to when the isotope was created. So the degree of a positive or negative PET depends on comparison of uptake in a normal high metabolic area with the area in question. This comparison is often just reported subjectively but can be measured. A measured value, the Standard Uptake Value (SUV) is produced. A SUV value greater than 2.5 is considered positive. Some publications, such as Herder only reported subjective results on a four-point descriptive scale, without SUV values. Subsequent publications must guess at a similar scale using SUV values. For example, one of these publications (Al-Ameri) used a 3 division scale of SUV with good results. However, this paper did not report mean or median sizes of nodules nor numbers of nodules evaluated in their 139 patients with PET scans. Of the total of 244 patients, they report that 188 had a solitary nodule (presumably the remainder had multiple nodules), and the largest nodule was ≤10 mm in 103 patients and PET sensitivity was not addressed in the study which appears to have a lot of smaller nodules. Consequently, it is difficult to derive conclusions or compare to other studies where basic nodule characteristics (such as nodule size) are disclosed.

So these example publications, Herder and Al-Ameri, highlight the lack of standardization across sites and physicians in PET interpretation and reporting.

2.2.6.3 False Positives by PET

False positive scans for nodules are an additional problem. The Tanner chart review of community practices found a false positive PET scan rate of 39%. Also notable is that a PET scan was performed in 37% of patients and was associated with increased intensity of biopsy and surgery compared to surveillance (P<0.0001).

Deppen reported a meta-analysis which included endemic areas for infectious lung disease [S. A. Deppen, et al., "Accuracy of FDG-PET to Diagnose Lung Cancer in Areas With Infectious Lung Disease. A Meta-analysis," JAMA, vol. 312, no. 12, pp. 1227-1236, 2014]. Besides extreme heterogeneity regarding accuracy for diagnosis of lung nodules, the specificity in endemic regions was only 61% compared to 77% in nonendemic regions. They concluded their data did not support the use of FDP-PET to diagnose lung cancer in endemic regions. These endemic regions in the United States include the Mississippi, Ohio, and Missouri river valley regions along with the southwestern United States including the Central Valley of California.

2.2.6.4 PET Risks

PET is non-invasive but not risk free. The radiation dose from PET alone is significant at 14 mSv. When combined with CT, as is now usual, the dose increases to 24 mSv. For comparison, a low-dose CT for screening is 1.4 mSv.

2.3 InDi Clinical Research to Support Xpresys Lung

Integrated Diagnostics (InDi) has worked with leading physicians and scientists to produce peer-review publications and presentations in major journals and meetings. This research has been conceived, designed, and conducted with collaboration of major leaders in the fields of molecular diagnosis, lung cancer, and pulmonary nodules. These efforts will be summarized here with details of results in the appended publications. The results of XL2 and comparisons with existing evaluation tools are presented below.

2.3.1 Discovery, Verification, and Validation of XL1

The initial discovery for Xpresys Lung started with 388 candidate proteins and an assay was developed for 371 of them. The first samples were frozen plasma from 3 sites (n=143) and 36 cooperative proteins were identified for a classifier. Verification was with 13 proteins from 4 sites (n=104) and along with discovery work was published in Science Translational Medicine [X.-J. Li, C. et al., "A Blood-Based Proteomic Classifier for the Molecular Characterization of Pulmonary Nodules," Science Translational Medicine, vol. 5, no. 207, p. 207ra142, 2013]. At this time, it was determined that this systems biology and proteomics approach was most suited for excluding malignancy in nodules between 8 and 30 mm in size. Validation for XL1 was done with 11 proteins, of which 5 were diagnostic and 6 were used for normalization, with new archival samples from 4 sites (n=141) and published in the Journal of Thoracic Oncology [A. Vachani, et al., "Validation of a Multiprotein Plasma Classifier to Identify Benign Lung Nodules," Journal of Thoracic Oncology, vol. 10, no. 4, pp. 629-637, 2015].

2.3.2 Survey and Chart Review

InDi contracted with Boston Healthcare for a survey of pulmonary physicians to determine their practice patterns and potential acceptance of a biomarker for pulmonary nodules. The need and acceptance was confirmed and published in 2014.

Boston Healthcare also collected data for a comprehensive chart review of community pulmonary practices to understand practice patterns where most of pulmonary nodules are managed. Nodule management of 377 patients from 18 geographically diverse sites were assessed. The results have been presented at national meetings and published in 2015 [A. Vachani, et al., "Clinical Utility of a Plasma Protein Classifier for Indeterminate Lung Nodules," Lung, vol. 193, no. 6, pp. 1023-1027, 2015]. Of particular note was the finding that benign nodules had a 61% biopsy and 35% surgery rate.

2.3.3 Analytic Validation

Analytic validation has been performed and published in 2015 [X.-J. Li, et al., "An Integrated Quantification Method to Increase the Precision, Rocustness, and Resolution of Protein Measurement in Human Plasma Samples," Clinical Proteomics, vol. 12, no. 3, 2015].

2.3.4 Clinical Utility and Discovery/Verification of XL2

Study 1013 is a prospective study started in 2012 and enrolled 475 patients from 12 sites. This study was unique since it included patients who were undergoing procedures to determine if a lung nodule is benign or cancerous. Therefore a tissue diagnosis was available and a potential change in the use of invasive procedures could be assessed if Xpresys Lung would have been used. The main finding was a 32% decrease if XL1 result was followed, but 24% of malignant nodules would have been routed to CT surveillance.

Study 1013 results were also used for the discovery of XL2.

2.3.5 PANOPTIC and XL2 Validation

Study 1001 (PANOPTIC) was also started in 2012 and enrolled 685 patients from 33 sites. This study included all intended use nodules before any diagnostic testing had been initiated. The study is unique because physician pretest probability of cancer (pCA) was collected. Data was used to validate XL2 and present the performance and comparison data in this document.

2.4 Clinical Utility, Anticipated Clinical Use of XL2, and XL2 Impact on Invasive Procedures

2.4.1 Clinical Utility

XL2 is a robust test for determining which lower risk nodules are benign. The clinical need that XL2 addresses is to appropriately place more patients with benign nodules into CT surveillance. This will avoid unnecessary imaging and invasive procedures which is the primary clinical utility goal for XL2. Results from the PANOPTIC trial can be used to estimate the effect of XL2 at many Negative Predictive Values (NPV) (Table 34). Here we will use the 98% NPV values and discuss the clinical context. The 98% NPV is used as the majority of likely benign reports have a NPV of 98% (Table 34).

2.4.1.1 Clinical Utility at 98% NPV

At a NPV of 98%, the sensitivity of XL2 is 97%, with a specificity of 44% (Table 30, Section 3.2). If XL2 was used in all lower risk nodules (n=178), the reduction of invasive procedures in PANOPTIC on benign nodules would be 36% (15 of 42) (Section 3.4).

The number of patients tested would be 178 patients, 69 (39%) would receive a "Likely Benign" test result with a 98% probability (NPV) of being benign. That very high NPV would likely lead to CT surveillance alone.

There were 29 malignant nodules in the lower risk group and 13 of 29 (45%) were routed to CT surveillance by the clinicians. The use of XL2 at the 98% NPV level, would route 1 patient (3%) to CT surveillance (Table 33, Section 3.4).

2.4.1.2 Clinical Utility and PET Scans

At the 98% NPV level, 21 of 56 (36%) PET scans that were obtained in patients with benign nodules would have been avoided with the use of XL2. In the same group there were 19 PET scans done on malignant nodules which were then incorrectly routed to CT surveillance. XL2 use would have reduced that to only 1 PET scan followed by CT surveillance.

2.4.2 Anticipated Clinical Use and Timing of XL2 Testing

Integrated Diagnostics (InDi) plans to promote XL2 to pulmonologists, both academic and community. The primary goal of XL2 is to reduce avoidable imaging and invasive procedures on benign nodules in the intended use population. The test result document (Section 3.6) will report negative predictive values of 90-98% as both the actual value, and as "Likely Benign". The ordering physician can then decide with the patient what level of risk is appropriate. If a patient is adverse to procedures, a lower NPV result such as 95% may be chosen. Conversely, if a patient is very adverse to an observation period with a surveillance CT, then a 98% NPV result may be needed to decide for CT surveillance.

2.4.2.1 Timing of XL2 Testing

Xpresys Lung 2 will be used at one of several points in the evaluation of patients with nodules. Most often, XL2 will be used on lower risk indeterminate nodules (Section 2.2.2.2) after a CT scan and before any other imaging, such as PET. XL2 in PANOPTIC, showed favorable clinical utility if done before PET scanning (Section 2.4.1.2). This use would avoid both the expense of PET and the risk from high radiation (Section 2.2.6.4).

XL2 can also be used in patients with contraindications to invasive procedures or surgery before deciding about CT surveillance or empiric treatments such as irradiation.

2.4.3 XL2 Impact on Invasive Procedures for Indeterminate Nodules

In this section, InDi will estimate the effects of XL2 on invasive procedures and the morbidity and mortality associated with these procedures.

There are two types of invasive diagnostic procedures: biopsies and surgical resection.

2.4.3.1 Biopsies of Nodules

Biopsies can be obtained through a bronchoscope or a needle passed through the chest wall with CT image guidance. A community practice chart review found 38% of patients had a form of biopsy. Complications with biopsies or surgery are increased with age, smoking history, and other lung disease.

Biopsy through the bronchoscope has the lowest risk with a 2-4% risk of bleeding or pneumothorax. The disadvantage of this procedure is inaccurate sampling of the nodule. Correct sampling averages about 50%. The correct sampling rate may improve with modern navigation techniques that are being adopted. Bronchoscopic biopsy use for nodules is currently about 20% of nodules.

Needle biopsies are done in about 15% of patients with nodules with a 1% risk of bleeding, and a 15-19% risk of pneumothorax. About half (7%) of patients with a pneumothorax require chest tube placement with a significant period of hospitalization. Most needles biopsies are diagnostic but the risk of a non-diagnostic result with a malignant nodule is about 20%.

Biopsies (combined bronchoscopy and needle) are performed in about 25% of nodules (200,000) and the procedures are for benign nodules in 42-62% (104,000). Complications from biopsies result in hospitalization in 2-7% (range of bronchoscopy and needle biopsy complications, median 4.5%). That translates into 4,680 excess hospitalizations (104,000×0.045) per year that are potentially avoidable.

2.4.3.2 Surgery for Nodules

Eventually most malignant nodules go to surgery for resection and about 15-25% of patients have biopsy attempts before surgery (not included in XL2 Impact estimates). The overall surgery rate is about 34% (270,000 per year) for benign and malignant nodules in the nodule population (InDi data). Complications include death (2% in CMS population), prolonged lung air leak (3-5%), and pneumonia (1-8%).

Published rates for surgery for benign nodules range from 31-44%. That translates into about 102,000 surgeries (270,000×0.38 [mid-range]) and 2,052 deaths (270,000×0.38×0.02) per year that are avoidable for patients that don't have lung cancer.

2.4.3.3 XL2 Impact Estimates

Using the figures for potential avoidable invasive procedures calculated above, and assuming XL2 has broad use after reimbursement then XL2 has the potential to save over 36,000 surgeries, over 1,600 hospitalizations, and almost 750 deaths per year. The majority of these occurring in the CMS population of patients (Section 2.2.1.5).

3. Technical and Performance Summary of XL2

This section presents the following details of the XL2 test:
Development and Validation (Section 3.1):
XL2 was developed and validated on two large and generalizable prospective studies including the PANOPTIC study, which enrolled 685 subjects across 33 sites.

XL2 was developed and validated following the National Academy of Medicine's guidelines for rigorous test development.

XL2 development and validation achieves the highest level of evidence being both prospective and conducted on a large number of independent sites.

Performance (Section 3.2):
XL2 has a negative predictive value, sensitivity and specificity of 98% (CI: 92%-100%), 97% (CI: 82%-100%) and 44% (CI: 36%-52%).

Comparative Performance (Section 3.3):
XL2 compares favorably relative to current practice, PET and four clinical risk predictor models and demonstrates statistically significant superior performance.

Potential Clinical Utility of XL2: Benefit and Harm (Section 3.4):

Two prospective studies allow calculation of the potential clinical utility of XL2.

If XL2 were used in PANOPTIC then 36% of invasive procedures on benign lung nodules would have been eliminated.

Importantly, XL2 is also safer than current practice. If XL2 were used in PANOPTIC then only 3% of malignant lung nodules would have been erroneously routed away from invasive procedures. In comparison, the physicians erroneously routed 45% of malignant lung nodules away from invasive procedures.

This section closes with the formal specification of XL2 (Section 3.5), the reporting of XL2 results (Section 3.6), and a description of the primary differences between XL1 and XL2 (Section 3.7).

3.1 Development and Validation of XL2

XL2 was developed on Study 1013 (NCT01752101) and then verified and validated on the PANOPTIC study (NCT01752114). Study 1013 and PANOPTIC are both prospective studies of lung nodules, designed and sponsored by Integrated Diagnostics, for the primary purpose of developing and validating Xpresys Lung. These studies are summarized in Table 29.

TABLE 29

Study 1013 and PANOPTIC showing development phases and numbers of sites and patients.

|  | Study 1013 | PANOPTIC |
|---|---|---|
| Development Phase | Discovery | Verification & Validation |
| Number of Sites | 12 | 33 |
| Patients Enrolled | 475 | 685 |
| Intended Use Patients | 22 | 178 |

Development and validation of XL2 adhered to the best practices for test development as defined by the National Academy of Medicine (NAM) Guidelines for best practices in test development and validation. In particular, discovery and validation were both prospective and conducted on a large number of independent sites. Additionally, verification and validation were conducted under a strict blinding protocol and utilized a 3rd party statistician. This is the highest level of clinical validation achievable by the NAM. Details of the early development of XL2 and discovery on Study 1013 are available for review. The validation protocol and results are also available for review.

3.2 Performance of XL2 in the PANOPTIC Trial 3.2.1 Performance Measures and Results with XL2

The performance of XL2 is based on the 178 PANOPTIC subjects in the intended use population. The four standard performance measures for a diagnostic test are sensitivity, specificity, positive predictive value (PPV) and negative predictive value (NPV).

Sensitivity: The percentage of malignant lung nodules correctly predicted as malignant by XL2.

Specificity: The percentage of benign lung nodules correctly predicted as benign by XL2.

Negative Predictive Value (NPV): The percentage of lung nodules predicted to be benign by XL2 that are benign.

Positive Predictive Value (PPV): The percentage of lung nodules predicted to be malignant by XL2 that are malignant.

XL2 is designed to be a lung cancer rule out test, that is, it identifies lung nodules that are likely benign so that CT surveillance is used and invasive procedures can be avoided. Consequently, the accuracy at which it reports a lung nodule to be likely benign is of paramount clinical importance. This performance measure is the NPV.

What NPV will be best for deciding the pathway? It depends on patient preference and the physician's advice (Section 2.2.2.2). The ACCP guidelines recommend that a lung nodule can be observed with CT surveillance if the probability of cancer is under 5%. This is equivalent to NPV values over 95%. XL2 has been validated for NPV values of 90% and higher. Table 30 presents the performance of XL2 for NPV values of 90% to 98% along with 95% confidence intervals (CI). We note that the largest proportion of Likely Benign reports in the study have a NPV of 98%.

The 90% NPV value is the lowest to be considered "Likely Benign". This is because NPV values below 90% are not statistically different from the pre-test probability of a lung nodule being benign. The pre-test probability of a benign lung nodule within the intended use population of PANOPTIC is 83.7%, which is below the 95% lower CI of all NPV values in Table 30. For XL2 results where the NPV is below 90%, the post-test probability of being benign is not statistically different than the pre-test probability of being benign. In these cases the test result is considered "Indeterminate". See section 3.6 for full details on XL2 test reporting.

TABLE 30

Performance and Likely Benign reports for XL2 on 178 patients from the PANOPTIC study at NPV values of 90% to 98% ('Likely Benign') and for below 90% ('Indeterminate').

| NPV (95% CI) | Sensitivity (95% CI) | Specificity (95% CI) | PPV (95% CI) | % of Reports |
|---|---|---|---|---|
| 98% (92%-100%) | 97% (82%-100%) | 44% (36%-52%) | 25% (17%-34%) | 39% |
| 97% (91%-100%) | 93% (77%-99%) | 49% (41%-57%) | 26% (18%-36%) | 5% |
| 96% (90%-99%) | 90% (73%-98%) | 54% (45%-62%) | 27% (19%-37%) | 4% |
| 95% (89%-99%) | 86% (68%-96%) | 55% (47%-63%) | 27% (18%-37%) | 2% |
| 94% (87%-98%) | 83% (64%-94%) | 56% (47%-64%) | 27% (18%-37%) | 1% |
| 93% (86%-98%) | 79% (60%-92%) | 57% (44%-65%) | 26% (18%-37%) | 2% |
| 92% (85%-97%) | 76% (56%-90%) | 58% (49%-66%) | 26% (17%-37%) | 1% |
| 91% (84%-96%) | 69% (49%-85%) | 64% (56%-72%) | 27% (18%-39%) | 6% |
| 90% (84%-95%) | 55% (36%-74%) | 83% (75%-88%) | 38% (24%-54%) | 18% |
| <90% | — | — | — | 22% |

3.2.2 Graphical Performance of XL2

Figure 33:
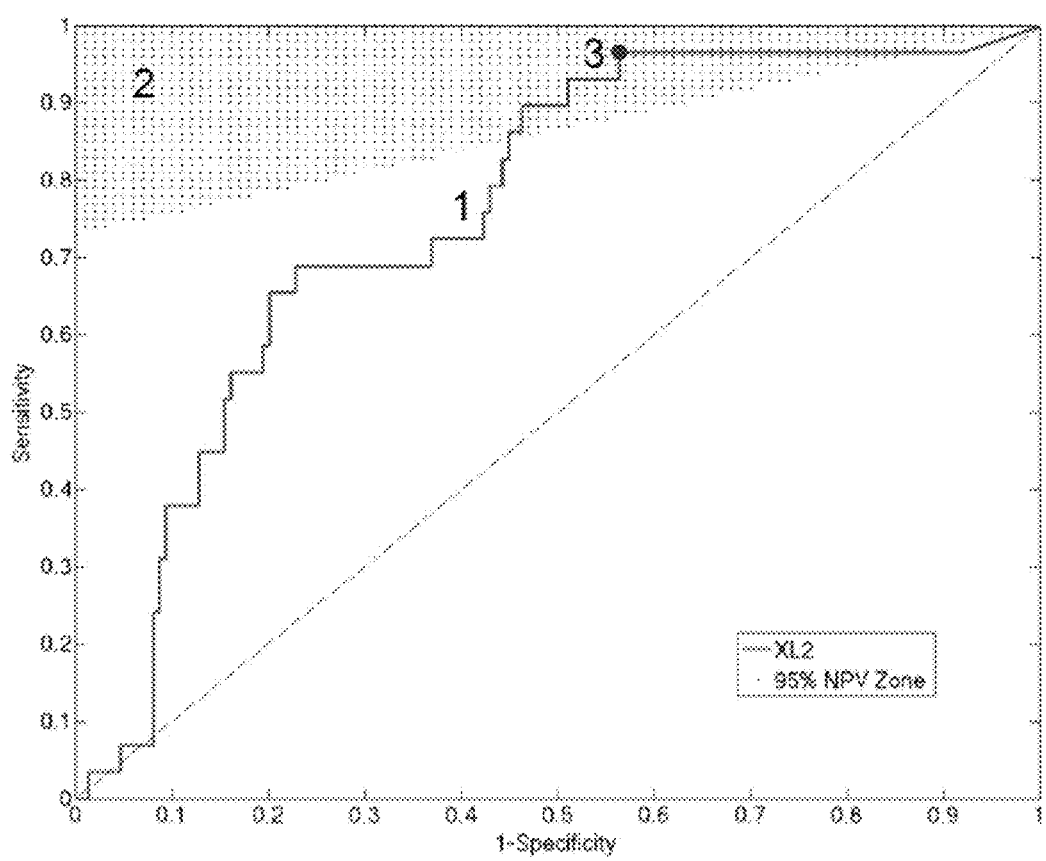
FIG. 33 is a graph showing performance of XL2 on the PANOPTIC intended use group (n=178). The solid curve is the Receiver Operator Characteristic (ROC) curve for XL2 (#1) which has an AUC of 76% (95% CI 69%-82%) and significantly better than random (p-value 9.4E-5). The grey area (#2) represents all sensitivity and specificity pairs that yield a NPV of 95% and greater. The blue dot (#3) represents the point at which XL2 has a sensitivity of 97%, specificity of 44% and a NPV of 98%.

The performance of a diagnostic test is often depicted graphically using a receiver operating characteristic (ROC) curve. FIG. 33 presents the ROC curve for XL2 alone on the 178 PANOPTIC subjects within the intended use population. This same graphical format will be used for multiple figures.

There are three landmarks on this ROC plot worth noting for the subsequent graphics.

Landmark #1 is the ROC curve itself for XL2. The further away from random, shown as the dashed diagonal line, this curve is the better the overall performance of the diagnostic test. This is typically measured by the area under the curve (AUC).

Landmark #2 is the '95% NPV zone'. The NPV of a diagnostic test depends entirely on its sensitivity, specificity and disease prevalence. This dependency is captured by the following formula:

$$NPV = \frac{\text{specificity} * (1 - \text{prevalence})}{(1 - \text{sensitivity}) * \text{prevalence} + \text{specificity} * (1 - \text{prevalence})}$$

In the PANOPTIC study the cancer prevalence in the intended use population is 16.3%. The implication is that we can determine those sensitivity and specificity values that result in a clinically relevant NPV of at least 95%. These sensitivity and specificity values are depicted in FIG. 33 as the '95% NPV zone'. A robust diagnostic test for ruling out cancer in lung nodules should have sensitivity and specificity within this zone.

Another important aspect of the 95% NPV zone is that this is where XL2 will be compared to other cancer risk predictors (Section 3.3.3).

Landmark #3 is the point on the ROC curve where XL2 reaches maximum NPV. At this point XL2 has sensitivity of 97%, specificity of 44% and NPV of 98%. The NPV is emphasized because this area of the graphic is most relevant for a rule-out test such as XL2.

3.3 Comparative Performance of XL2

3.3.1 Current Risk Predictor Selections for Comparison to XL2

This section compares the performance XL2 to six other cancer risk predictors for lung nodules. All comparisons are made using the same 178 PANOPTIC patients in the lower risk, intended use population. This allows for an 'apples-to-apples' comparison. These six predictors fall into three categories as follows.

Current Practice: Current practice for estimating the cancer risk of a lung nodule is the initial physician cancer risk assessment (pCA) based on physician clinical judgement. This also represents how cancer risk was estimated for over 80% of lung nodules evaluated in PANOPTIC and is also a practice recommended in the ACCP Guidelines (Section 2.2.4.1).

PET: PET is referenced in the ACCP Guidelines for use as a tool for assessing cancer risk. PET was used in 75 of 178 (42%) of intended use subjects in the PANOPTIC study.

Clinical Risk Predictors: Four clinical risk predictors have been discussed (Section 2.2.4) and are assessed: Mayo, VA, Brock and Herder. Mayo and VA are referenced in the ACCP Guidelines, however, they were used by under 20% of physicians in the PANOPTIC study. The Brock and Herder models are included for completeness but were not utilized by physicians in the PANOPTIC study as discussed in Sections 2.2.4.2 and 2.2.6.2, respectively. We note that because the Herder model requires a PET to be performed, only 75 of 178 (42%) of the intended use subjects in the PANOPTIC study have a Herder result.

3.3.2 Comparison Methodology

In section 3.3.3, XL2 and six other cancer risk predictors are presented as ROC curves. This will give an overall impression of the performance of these risk predictors in terms of AUC and performance in the important '95% NPV zone'. However, no statistical claims are intended. Full statistical treatment is reserved for Section 3.3.4.

In Section 3.3.4, XL2 is compared 'apples-to-apples' to the six other cancer risk predictors in a strict statistical manner. Except in the case of PET, all of these comparisons are based on the following methodology:

Comparisons are made based on performance in the 95% NPV zone.

The McNemar statistical test is utilized. The McNemar test is most appropriate when comparing predictors on the same set of samples and at a fixed sensitivity (or fixed specificity).

In the case of PET, a McNemar comparison is not possible due to the poor performance of PET in the '95% NPV zone'. Instead, direct NPV performance comparisons are made.

3.3.3 Graphical Comparison of XL2 to All Other Risk Predictors

Before proceeding to a formal statistical comparison of XL2 to the other risk predictors, we begin with an overall picture of the performance of six risk predictors relative to XL2. For this purpose, we visualize performance using a ROC plot (FIG. 34) and measure the entire AUC. We do not make statistical comparisons based on the entire AUC as this is not the relevant metric for a rule-out test (despite XL2 having the highest AUC). Section 3.3.4 contains results from formal statistical comparisons.

Figure 34:
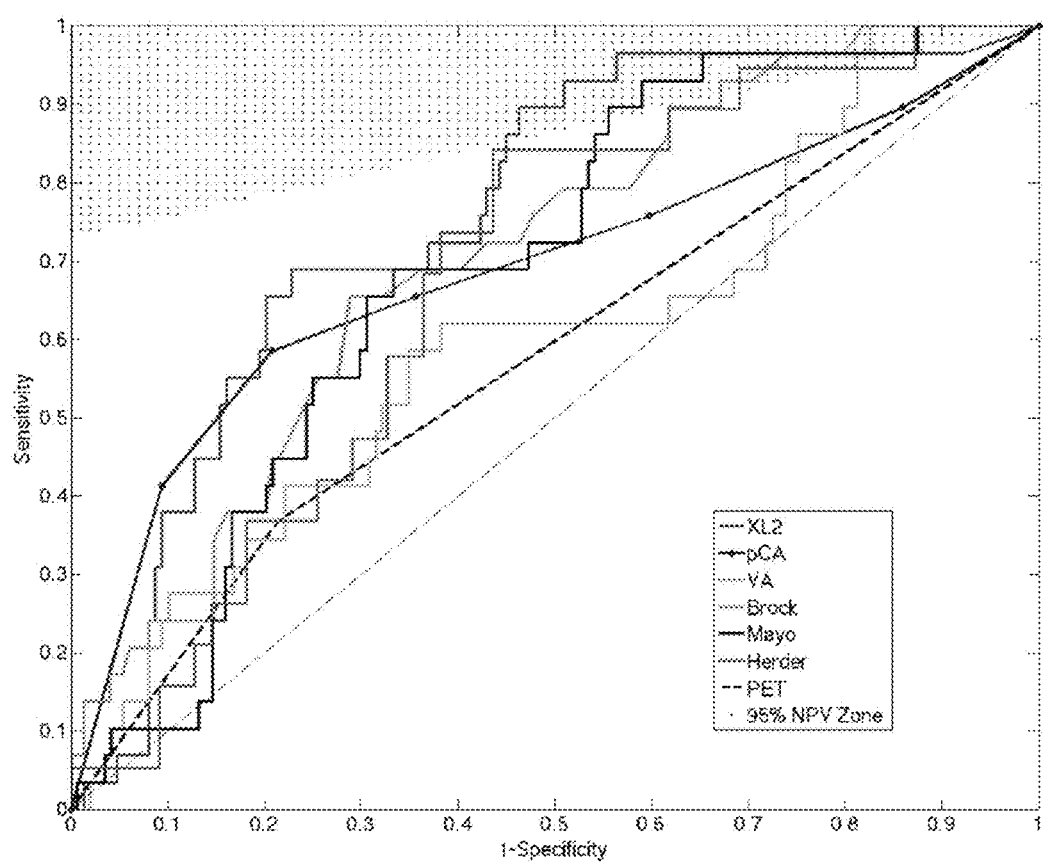
FIG. 34 is a graph showing comparison of XL2 to six cancer risk predictors.

FIG. 34 presents XL2 and six other risk predictors in a single ROC plot. The AUCs for all of the predictors in FIG. 34 are presented in Table 31. We make three immediate remarks on this head-to-head comparison in this intended use population with a cancer risk of 50% or less:

1. XL2 has superior performance overall (highest AUC), but more importantly, the best performance in the '95% NPV Zone'.

2. Current practice (pCA) performs very poorly overall (AUC=69%) but particularly poorly within '95% NPV zone'.

3. PET has the worst performance both overall (AUC=58%) and also within the '95% NPV zone'.

Although the most important factor is the superior performance of XL2 in the 95% NPV zone, it is notable that even outside the 95% NPV zone, the performance of XL2 continues to be superior, or equivalent, to all other cancer risk predictors, PET and pCA.

TABLE 31

Overall AUC and 95% CI of the Cancer Risk Predictors

| Cancer Risk Predictor | AUC | 95% CI |
| --- | --- | --- |
| XL2 | 76% | 69%-82% |
| pCA | 69% | 62%-76% |
| VA | 60% | 53%-67% |
| Brock | 71% | 63%-77% |
| Mayo | 69% | 62%-76% |
| Herder | 67% | 56%-78% |
| PET | 58% | 46%-69% |

3.3.4 Statistical Comparisons

In this section, XL2 is compared, in a formal statistical sense, to current practice (pCA), four clinical risk predictors, and then PET.

3.3.4.1 Comparison of XL2 to Current Practice (pCA)

Figure 35:
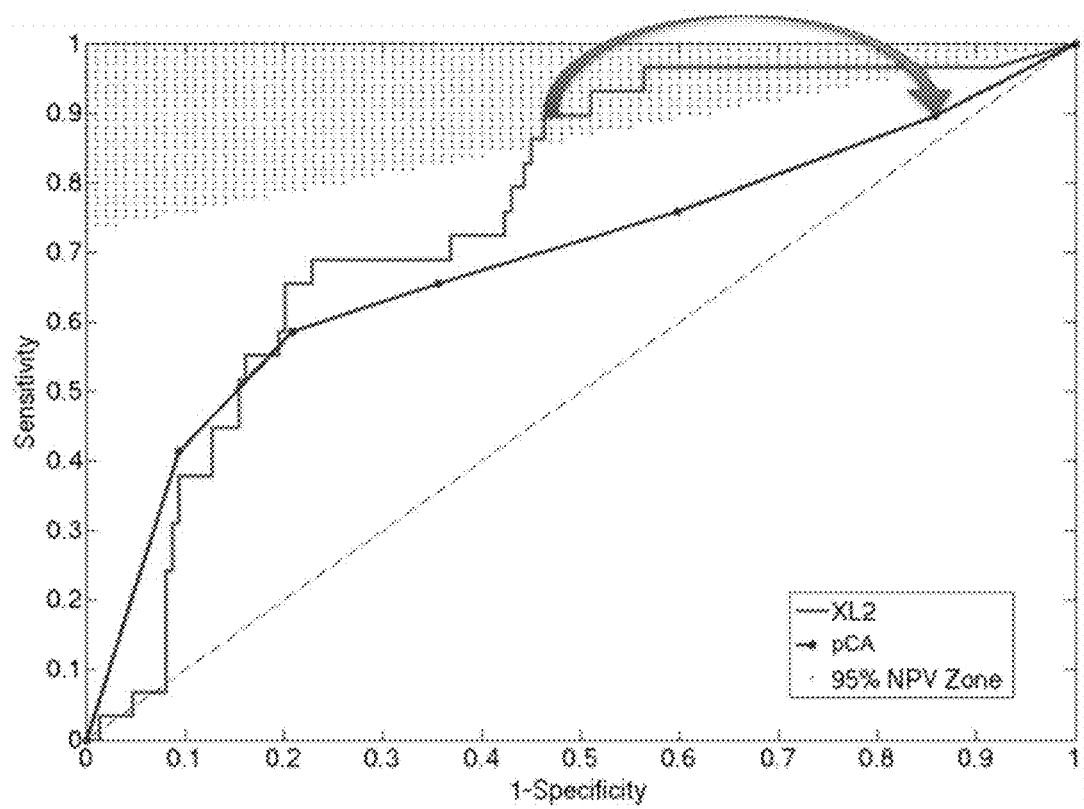
FIG. 35 is a graph showing comparison of XL2 to pCA in the intended use group. Comparison of XL2 to pCA is made at 90% sensitivity, the highest sensitivity achieved by pCA. The blue arching arrow depicts the two points on the respective ROC curves being compared.

XL2 is compared to current practice, physician clinical judgment for the pretest probability of cancer (pCA) in the lower risk group (pCA 50% or less). As shown in FIG. 35, pCA never reaches the desired 95% NPV level. Since the highest sensitivity attained by pCA is 90%, this level is used to compare the performance of XL2 to pCA.

Using the McNemar test (Section 3.3.2), at the same sensitivity of 90%, XL2 has significantly greater specificity with p-value of 2.12E-11.

3.3.4.2 Comparison of XL2 to Clinical Risk Predictors

Figure 36:
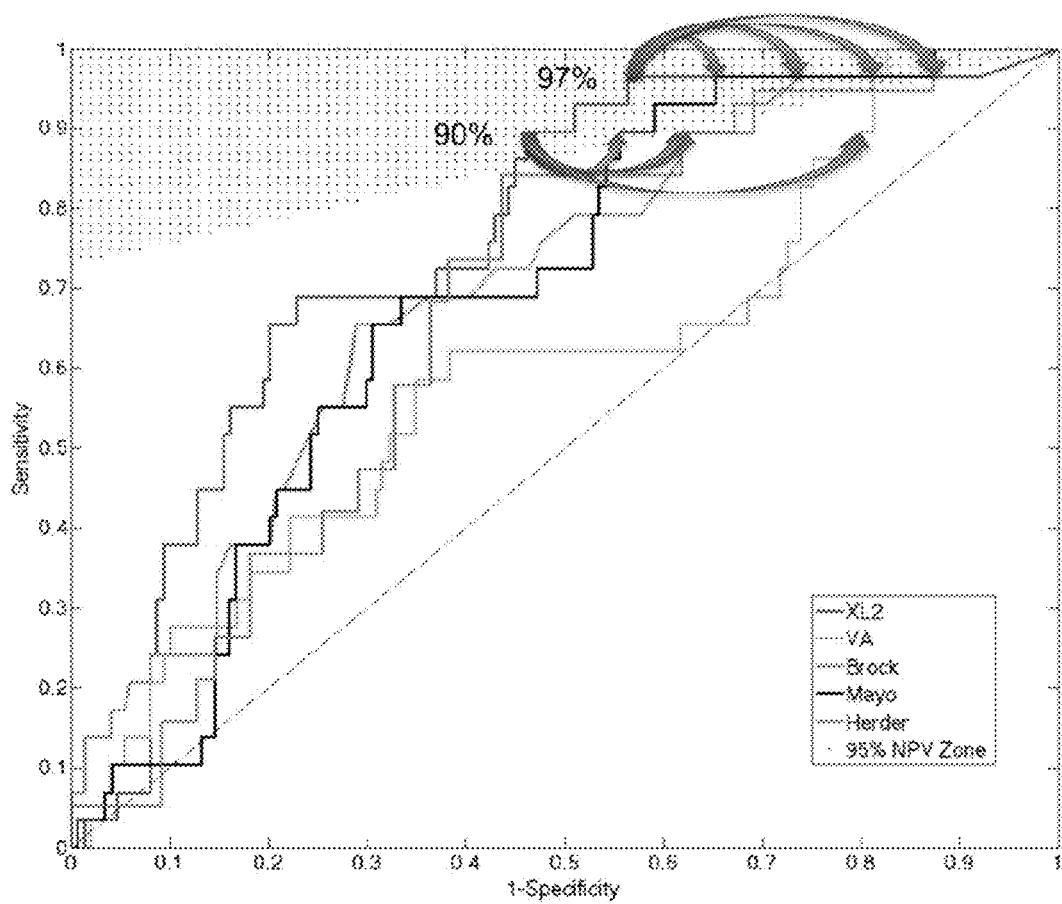
FIG. 36 is a graph showing comparison of XL2 to four clinical risk predictors. Comparison is made at 90% and also at 97% sensitivity. The blue arrows depict the respective points on the four clinical risk predictor curves being compared to XL2.
Figure 37:
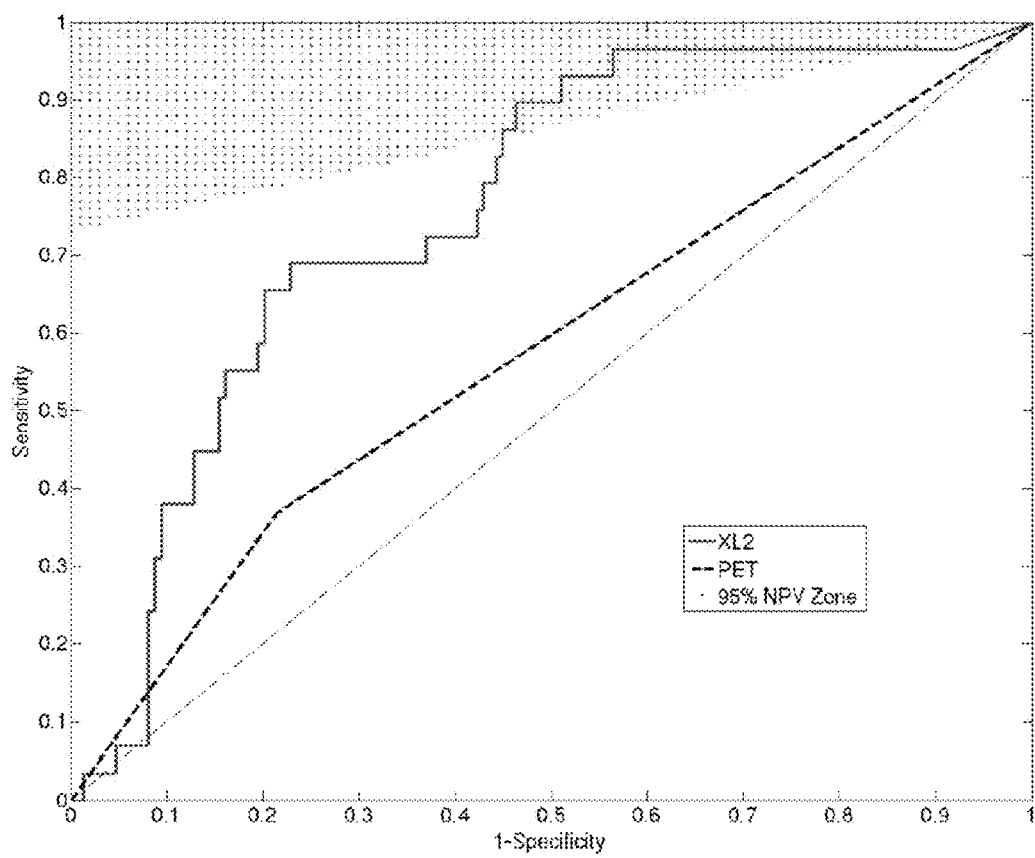
FIG. 37 is a graph showing comparison of XL2 and PET with 75 patients in the intended use group that had a PET scan.

We compare XL2 to four clinical risk predictors (Mayo, VA, Brock and Herder) in FIG. 36. The comparison is made at sensitivities of 90% and 97% which XL2 and all four clinical risk predictors attain. We include these two sensitivities for a robust comparison.

Using the McNemar test (Section 3.3.2), at sensitivities of 90% and 97%, XL2 has significantly greater specificity than the four clinical risk predictors with p-values reported in Table 32. We note that comparisons between XL2 and all models except Herder are made on all 178 PANOPTIC patients. For Herder (which requires a PET to be performed) only 75 patients could be compared. This lower sample number resulted in higher (but still significant) p-values.

TABLE 32

Comparison of XL2 to Clinical Risk Predictors for incidental (Mayo & VA) and screen-detected (Brock) nodules. Herder combines clinical factors with PET.

| Comparison | 90% Sensitivity p-value | 97% Sensitivity p-value |
| --- | --- | --- |
| XL2 vs. Mayo | 0.0009 | 0.0009 |
| XL2 vs. VA | 1.562e-11 | 2.71E-7 |
| XL2 vs. Brock | 0.0021 | 0.0051 |
| XL2 vs. Herder | 0.0455 | 0.0233 |

3.3.4.3 Comparison of XL2 to PET

Of the 178 PANOPTIC patients within the intended use of XL2, 75 had a diagnostic PET performed. The comparison below is based on these 75 patients.

Because PET never reaches the 95% NPV zone or a sufficiently high sensitivity, the McNemar test cannot be applied. Instead, we compare the NPV of PET directly to the NPV of XL2.

The highest NPV for PET is 79% (95% CI:66%-88%) so this is compared to when XL2 reaches a NPV of 95% (95% CI:89%-99%). These two CI do not overlap, and so, XL2 has significantly better NPV as compared to PET.

3.4 Potential Clinical Utility of XL2: Benefit and Harm

PANOPTIC was a non-interventional study, however, the potential clinical utility of XL2 can be estimated from PANOPTIC by answering the following question:

"If XL2 were used in PANOPTIC to identify lung nodules likely to be benign, how many benign (benefit) and malignant (harm) nodules would have been routed away from invasive procedures into CT surveillance?"

At NPV=98% (see Table 33), XL2 has the following potential clinical utility in PANOPTIC: (a) 15 of 42 (36%) of benign nodules would have been saved from unnecessary invasive procedures (benefit); and (b) 1 of 29 (3%) of malignant nodules would have been erroneously routed to CT surveillance (harm).

At an NPV of 95% (see Table 33), XL2 has the following potential clinical utility in PANOPTIC: (a) 20 of 42 (48%) of benign nodules would have been saved from unnecessary invasive procedures (benefit); and (b) 2 of 29 (7%) of malignant nodules would have been erroneously routed to CT surveillance (harm).

TABLE 33

Potential Clinical Utility of XL2

| NPV | Reduction in Invasive Procedures on Benign Nodules (95% CI) | Malignant Nodules Sent to CT Surveillance (95% CI) |
|---|---|---|
| 98% | 15/42 = 36% (22%-52%) | 1/29 = 3% (0%-18%) |
| 97% | 17/42 = 40% (26%-57%) | 2/29 = 7% (1%-23%) |
| 96% | 19/42 = 45% (30%-61%) | 2/29 = 7% (1%-23%) |
| 95% | 20/42 = 48% (32%-64%) | 2/29 = 7% (1%-23%) |
| 94% | 20/42 = 48% (32%-64%) | 2/29 = 7% (1%-23%) |
| 93% | 22/42 = 52% (36%-68%) | 3/29 = 10% (2%-27%) |
| 92% | 22/42 = 52% (36%-68%) | 4/29 = 14% (4%-32%) |
| 91% | 25/42 = 60% (43%-74%) | 4/29 = 14% (4%-32%) |
| 90% | 32/42 = 76% (61%-88%) | 7/29 = 24% (10%-44%) |

How safe is XL2? We observe that in the intended use population in PANOPTIC, 13 of 29 (45%) of malignant nodules were routed to CT surveillance (then having a risk of delayed diagnosis). Comparing this to the estimates shown in Table 33 illustrates that XL2 will provide a safe test for both reducing unnecessary invasive procedures while simultaneously sending fewer malignant nodules to CT surveillance.

3.5 Technical Definition of XL2

XL2 integrates the relative abundance of two plasma proteins (LG3BP and C163A) with five clinical risk factors (age, smoking status, nodule diameter, nodule spiculation status and nodule location). XL2 provides a numerical value, XL_2(k), for a subject k, as defined below:

$$XL\_2(k) = \begin{cases} \max(0, p(k) - 0.5), & \log_2\left(\frac{LG3BP}{C163A}\right) \leq .38 \\ p(k), & \log_2\left(\frac{LG3BP}{C163A}\right) > .38 \end{cases}$$

$$p(k) = \frac{e^X}{1 + e^X}$$

$$X = -6.8272 + 0.0391 * Age + 0.7917 * Smoker + 0.1274 * Diameter + 1.0407 * Spiculation + 0.7838 * Location$$

where Age is the age of the subject in years, Smoker is 1 if the subject is a former or current smoker (otherwise 0), Diameter is the size of the lung nodule in mm, Spiculation is 1 if the lung nodule is spiculated (otherwise 0) and Location is 1 if the lung nodule is located in an upper lung lobe (otherwise 0). The linear function X that integrates the clinical risk factors is a simplification of the Mayo clinical risk predictor that eliminates the cancer risk history factor.

XL_2(k) ranges between 0 and 1. The closer XL_2(k) is to 0, the more likely subject k has a very high NPV which is calculated using PANOPTIC data.

The ranges of the XL_2(k) function for the NPV values of 90% to 98% are shown in Table 34, along with the other key performance indicators.

3.6 Reporting XL2 Results

XL2 results will be reported as Likely Benign or Indeterminate, with the NPV value and confidence intervals shown in the Likely Benign reports. Example the XL2 test request form and Test Report forms are presented as [DOC-000107] and [DOC-000106] in the XL2 dossier submission.

The separation of Likely Benign and Indeterminate is based on the cancer prevalence of the study population and statistical comparisons. The cancer prevalence in the intended use population in the PANOPTIC study was 16.3% which corresponds to a benign prevalence of 83.7%. In other words, the pre-test probability of a lung nodule being benign is 83.7% before any clinical judgment or testing. XL2 reports "Likely Benign" when the post-test probability of being benign (i.e. the NPV) is 90% or higher as shown in Table 34.

Note that when the "k" value exceeds 0.354, the lower confidence interval of an NPV of less than 90% will overlap with the prevalence of 83.7% for the population. Therefore, this will be when the test report changes from Likely Benign to Indeterminant.

TABLE 34

XL2 Performance, Test Report, and Percentage of Reports at multiple negative predictive values for Likely Benign results (n = 178 patients)

| XL 2(k) Value | NPV (95% CI) | Sensitivity (95% CI) | Specificity (95% CI) | PPV (95% CI) | Test Report | Percentage of Tests Reported |
|---|---|---|---|---|---|---|
| 0 to 0.131 | 98% (92%-100%) | 97% (82%-100%) | 44% (36%-52%) | 25% (17%-34%) | Likely Benign | 39% |
| >0.131 to 0.1613 | 97% (91%-100%) | 93% (77%-99%) | 49% (41%-57%) | 26% (18%-36%) | Likely Benign | 5% |
| >0.1613 to 0.172 | 96% (90%-99%) | 90% (73%-98%) | 54% (45%-62%) | 27% (19%-37%) | Likely Benign | 4% |
| >0.172 to 0.176 | 95% (89%-99%) | 86% (68%-96%) | 55% (47%-63%) | 27% (18%-37%) | Likely Benign | 2% |
| >0.176 to 0.1785 | 94% (87%-98%) | 83% (64%-94%) | 56% (47%-64%) | 27% (18%-37%) | Likely Benign | 1% |
| >0.1785 to 0.193 | 93% (86%-98%) | 79% (60%-92%) | 57% (44%-65%) | 26% (18%-37%) | Likely Benign | 2% |
| >0.193 to 0.195 | 92% (85%-97%) | 76% (56%-90%) | 58% (49%-66%) | 26% (17%-37%) | Likely Benign | 1% |
| >0.195 to 0.2306 | 91% (84%-96%) | 69% (49%-85%) | 64% (56%-72%) | 27% (18%-39%) | Likely Benign | 6% |

TABLE 34-continued

XL2 Performance, Test Report, and Percentage of Reports at multiple
negative predictive values for Likely Benign results (n = 178 patients)

| XL 2(k) Value | NPV (95% CI) | Sensitivity (95% CI) | Specificity (95% CI) | PPV (95% CI) | Test Report | Percentage of Tests Reported |
|---|---|---|---|---|---|---|
| >0.2306 to 0.354 | 90% (84%-95%) | 55% (36%-74%) | 83% (75%-88%) | 38% (24%-54%) | Likely Benign | 18% |
| >0.354 | — | — | — | — | Indeterminate | 22% |

3.7 Primary Differences of Xpresys Lung 1 (XL1) and Xpresys Lung 2 (XL2)

XL2 is a second generation version of XL1 that has four significant improvements over XL1:

3.7.1 Intended Use Population

The intended use population of XL2 are patients with a lower cancer risk, whereas the intended use population of XL1 included all patient risk groups (0%-100%). Under guidance from KOLs and commercial experience with XL1, it became clear that physicians needed a test to differentiate benign from malignant nodules and that need is greatest in patients with lower risk rather than higher risk (Section 2.2.3). Thus, focusing of the intended use population has led to performance improvements.

3.7.2 Reduction in Molecular Factors

Discovery work on Study 1013 identified two proteins (LG3BP and C163A) that were more accurate than the five diagnostic proteins of XL1 at identifying benign nodules for patients with a lower cancer risk. The likely reason for this is that protein expression differs between lower and higher risk nodules [DOC-000114].

3.7.3 Addition of Clinical Risk Factors

XL1 is purely a molecular test whereas XL2 incorporates molecular markers with known clinical risk factors (Section 3.5). This not only enhances the performance of XL2 over XL1, but is appealing to physicians as these are the clinical risk factors they currently use to assess cancer risk. That is, XL2 is not attempting to replace the current practice of using clinical risk factors but augments current practice with molecular factors.

3.7.4 Quality of Clinical Evidence

XL1 was developed and validated on five archival biobanks. In contrast, XL2 was developed and validated in two prospective studies with samples collected using a uniform protocol. The first, Study 1013' spanned 12 sites and enrolled 475 subjects. The second, 'PANOPTIC' spanned 33 sites and enrolled 685 subjects. Consequently, XL2 is more generalizable to clinical practice. Furthermore, PANOPTIC collected physician probabilities of cancer risk and clinical factors to allow XL2 to be directly compared to current practice in lung nodule evaluation.

4. Proposed Prospective Interventional Study

A prospective interventional study is required to establish the clinical utility of XL2. Specifically, to establish that the incorporation of XL2 into clinical practice results in improved and measureable clinical outcomes. It is not enough to show change in physician behavior, rather, significant improvements in measurable clinical endpoints are needed, such as reduced invasive procedures on benign nodules. Key aspects of the prospective interventional study are detailed below. We note that the intent is to engage MolDx in the design of this study to ensure alignment.

Goal: To establish in a prospective study that the use of XL2 in a treatment protocol results in statistically significant improved clinical outcomes relative to current practice.

Clinical Endpoints: To measure both the benefit and harm of XL2, the primary endpoints measured will be: (a) Benefit: Significant reduction in the use of PET and invasive procedures (biopsy or surgery) on benign lung nodules using XL2 relative to current practice; and (b) Harm: No significant increase in the rate of malignant nodules routed to CT surveillance using XL2 relative to current practice (without use of XL2).

Study Design: The prospective interventional study will have an intervention arm where XL2 will be used to guide treatment. Enrolled patients with a sufficiently high probability of a benign lung nodule would enter CT surveillance, otherwise, be treated with usual care. The control arm will either be historical controls from the same participating sites, or, a contemporary randomized arm. The decision to proceed with a historically controlled study or a RCT will be made based on resources and participating sites.

Control and Treatment Arms: The control and treatment (XL2) arms will have identical inclusion/exclusion criteria as well as outcome adjudication. If the control arm is historical then subjects will be selected from the same participating sites using the same usual care protocols to control for bias.

Effect Size and Sample Size: Under the assumptions that the reduction in invasive procedures on benign lung nodules is 36% and current practice has a benign lung nodule surgery rate of 35%, it is estimated that the intervention arm of the study will require 548 subjects.

Study Sites: Ideally the prospective interventional study will be conducted within an Integrated Delivery Network (IDN). The benefit of conducting the study within an IDN is access the multiple sites, implementation of a standard protocol and access to an Electronic Medical Record (EMR) system. If for some reason an IDN is not feasible then the study can be executed on a subset of the 33 PANOPTIC study sites.

Data Analysis: A prospective data analysis plan will be created that may include the following elements:

Prospectively defined interim looks at the data and any resulting adaptive adjustments, if necessary.

Fully defined statistical treatment of comparisons between treatment and control arms. A methodology for intent to treat analysis will be included.

A predefined protocol for addressing multiplicity testing in the event of testing multiple claims in the study.

Example 8

Rule-In Application

The classifier described herein provides a cancer risk estimate XL_2 as defined below:

For a subject k, XL_2(k) is as defined below:

$$XL\_2(k) = \begin{cases} \max(0, p(k) - 0.5), & \log_2\left(\frac{LG3BP}{C163A}\right) \leq .38 \\ p(k), & \log_2\left(\frac{LG3BP}{C163A}\right) > .38 \end{cases}$$

$$p(k) = \frac{e^X}{1 + e^X}$$

$$X = -6.8272 + 0.0391 * \text{Age} + 0.7917 * \text{Smoker} + 0.1274 * \text{Diameter} + 1.0407 * \text{Spiculation} + 0.7838 * \text{Location}$$

where Age is the age of the subject in years, Smoker is 1 if the subject is a former or current smoker (otherwise 0), Diameter is the size of the lung nodule in mm, Spiculation is 1 if the lung nodule is spiculated (otherwise 0) and Location is 1 if the lung nodule is located in an upper lung lobe (otherwise 0).

XL_2(k) ranges between 0 and 1. The closer XL_2(k) is to 0, the more likely subject k has a benign lung nodule and the closer XL_2(k) is to 1 the more likely subject k has a malignant lung nodule.

As illustrated in Table 35, as the XL_2 value increases, the Positive Predictive Value (PPV) increases, which is equivalent to increased probability of malignancy. For example, when XL_2(k) is above 0.354 then the probability of malignancy is at least 38%. In the PANOPTIC study the pre-test risk of cancer is 16%, and so, this represents a 38/16=2.4 fold increase in cancer risk.

TABLE 35

| Integrated Classifier Cutpoint (XL_2) | NPV (95% CI) | Sensitivity (95% CI) | Specificity (95% CI) | PPV (95% CI) |
|---|---|---|---|---|
| 0 to 0.131 | 98% (92%-100%) | 97% (82%-100%) | 44% (36%-52%) | 25% (17%-34%) |
| >0.131 to 0.1613 | 97% (91%-100%) | 93% (77%-99%) | 49% (41%-57%) | 26% (18%-36%) |
| >0.1613 to 0.172 | 96% (90%-99%) | 90% (73%-98%) | 54% (45%-62%) | 27% (19%-37%) |
| >0.172 to 0.176 | 95% (89%-99%) | 86% (68%-96%) | 55% (47%-63%) | 27% (18%-37%) |
| >0.176 to 0.1785 | 94% (87%-98%) | 83% (64%-94%) | 56% (47%-64%) | 27% (18%-37%) |
| >0.1785 to 0.193 | 93% (86%-98%) | 79% (60%-92%) | 57% (44%-65%) | 26% (18%-37%) |
| >0.193 to 0.195 | 92% (85%-97%) | 76% (56%-90%) | 58% (49%-66%) | 26% (17%-37%) |
| >0.195 to 0.2306 | 91% (84%-96%) | 69% (49%-85%) | 64% (56%-72%) | 27% (18%-39%) |
| >0.2306 to 0.354 | 90% (84%-95%) | 55% (36%-74%) | 83% (75%-88%) | 38% (24%-54%) |

Consequently, the XL_2 is a risk predictor for both ruling in and ruling out cancer.

The invention claimed is:

1. A method of determining the likelihood that a pulmonary nodule in a subject is not lung cancer, comprising:
   (a) contacting a blood sample obtained from the subject with a proteolytic enzyme to produce peptide fragments from a panel of proteins present in the blood sample, wherein the panel comprises C163A and LG3BP;
   (b) combining the produced peptide fragments from the panel from step (a) with labeled, synthetic peptide fragments which correspond to the produced peptide fragments from the panel;
   (c) performing selected reaction monitoring mass spectrometry to measure the abundance of the peptide fragments from step (b);
   (d) calculating a probability of lung cancer score based on the peptide fragment measurements of step (c) and clinical risk factors comprising age, smoking status, nodule diameter, nodule spiculation status and nodule location; and
   (e) ruling out lung cancer for the subject if the score in step (d) is lower than a pre-determined score; wherein the said score is determined as XL 2(k), for a subject k, wherein $$XL\_2(k) = \begin{cases} \max(0, p(k) - 0.5), & \log_2\left(\frac{LG3BP}{C163A}\right) \le .38 \\ p(k), & \log_2\left(\frac{LG3BP}{C163A}\right) > .38 \end{cases}$$

$$p(k) = \frac{e^X}{1 + e^X}$$

X=6.8272+0.0391* Age+0.7917* Smoker+0.1274* Diameter+1.0407* Spiculation+0.7838* Location
wherein Age is the age of the subject in years, Smoker is 1 if the subject is a former or current smoker otherwise 0, Diameter is the size of the lung nodule in mm, Spiculation is 1 if the lung nodule is spiculated otherwise 0 and Location is 1 if the lung nodule is located in an upper lung lobe otherwise 0.

2. The method of claim 1, wherein when lung cancer is ruled out, the subject is monitored periodically.

3. The method of claim 1, wherein the subject has low to moderate cancer risk.

4. The method of claim 1, further comprising a physician's assessment of cancer risk.

5. The method of claim 4, wherein the subject is assigned a physician's assessment of cancer risk from between 0 to 1.

6. The method of claim 2, wherein the periodic monitoring is a pulmonary function test (PFT), pulmonary imaging, a biopsy or any combination thereof.

7. The method of claim 6, wherein said pulmonary imaging is an x-ray, a chest computed tomography (CT) scan, or a positron emission tomography (PET) scan.

8. The method of claim 1, wherein said pulmonary nodule has a diameter of less than or equal to 3 cm.

9. The method of claim 1, wherein said pulmonary nodule has a diameter of about 0.8 cm up to 3.0 cm.

10. The method of claim 1, wherein the selected reaction monitoring mass spectrometry is performed using an antibody that specifically binds the peptide fragments being detected.

11. A method of determining the likelihood that a pulmonary nodule in a subject is lung cancer, comprising:
(a) contacting a blood sample obtained from the subject with a proteolytic enzyme to produce peptide fragments from a panel of proteins present in the blood sample, wherein the panel comprises C163A and LG3BP;
(b) combining the produced peptide fragments from the panel from step (a) with labeled, synthetic peptide fragments which correspond to the produced peptide fragments from the panel;
(c) performing selected reaction monitoring mass spectrometry to measure the abundance of the peptide fragments from step (b);
(d) calculating a probability of lung cancer score based on the peptide fragment measurements of step (c) and clinical risk factors comprising age, smoking status, nodule diameter, nodule spiculation status and nodule location; and
(e) ruling in lung cancer for the subject if the score in step (d) is equal to or higher than a pre-determined score;
wherein the said score is determined as XL 2(k), for a subject k, wherein $$XL\_2(k) = \begin{cases} \max(0, p(k) - 0.5), & \log_2\left(\frac{LG3BP}{C163A}\right) \le .38 \\ p(k), & \log_2\left(\frac{LG3BP}{C163A}\right) > .38 \end{cases}$$

$$p(k) = \frac{e^X}{1 + e^X}$$

X=6.8272+0.0391* Age+0.7917* Smoker+0.1274* Diameter+1.0407* Spiculation+0.7838* Location
wherein Age is the age of the subject in years, Smoker is 1 if the subject is a former or current smoker otherwise 0, Diameter is the size of the lung nodule in mm, Spiculation is 1 if the lung nodule is spiculated otherwise 0 and Location is 1 if the lung nodule is located in an upper lung lobe otherwise 0.

12. The method of claim 11, wherein when lung cancer is ruled in, the subject is monitored periodically.

13. The method of claim 11, wherein the subject has low to moderate cancer risk.

14. The method of claim 11, further comprising a physician's assessment of cancer risk.

15. The method of claim 14, wherein the subject is assigned a physician's assessment of cancer risk from between 0 to 1.

* * * * *

SEQUENCE LISTING

<160> NUMBER OF SEQ ID NOS: 8

<210> SEQ ID NO 1
<211> LENGTH: 6
<212> TYPE: PRT
<213> ORGANISM: Homo sapiens

<400> SEQUENCE: 1

Val Glu Ile Phe Tyr Arg
1               5

<210> SEQ ID NO 2
<211> LENGTH: 15
<212> TYPE: PRT
<213> ORGANISM: Homo sapiens

<400> SEQUENCE: 2

Thr Gly Val Ile Thr Ser Pro Asp Phe Pro Asn Pro Tyr Pro Lys
1               5                   10                  15

<210> SEQ ID NO 3
<211> LENGTH: 12

```
<212> TYPE: PRT
<213> ORGANISM: Homo sapiens

<400> SEQUENCE: 3

Leu Gln Ser Leu Phe Asp Ser Pro Asp Phe Ser Lys
1               5                   10

<210> SEQ ID NO 4
<211> LENGTH: 12
<212> TYPE: PRT
<213> ORGANISM: Homo sapiens

<400> SEQUENCE: 4

Leu Thr Leu Leu Ala Pro Leu Asn Ser Val Phe Lys
1               5                   10

<210> SEQ ID NO 5
<211> LENGTH: 7
<212> TYPE: PRT
<213> ORGANISM: Homo sapiens

<400> SEQUENCE: 5

Glu Leu Thr Ile Gly Ser Lys
1               5

<210> SEQ ID NO 6
<211> LENGTH: 11
<212> TYPE: PRT
<213> ORGANISM: Homo sapiens

<400> SEQUENCE: 6

Ser Leu Glu Asp Leu Gln Leu Thr His Asn Lys
1               5                   10

<210> SEQ ID NO 7
<211> LENGTH: 8
<212> TYPE: PRT
<213> ORGANISM: Homo sapiens

<400> SEQUENCE: 7

Ile Asn Pro Ala Ser Leu Asp Lys
1               5

<210> SEQ ID NO 8
<211> LENGTH: 8
<212> TYPE: PRT
<213> ORGANISM: Homo sapiens

<400> SEQUENCE: 8

Phe Leu Asn Val Leu Ser Pro Arg
1               5
```